United States Patent
Flinn et al.

(12) 
(10) Patent No.: US 6,451,604 B1
(45) Date of Patent: Sep. 17, 2002

(54) COMPOSITIONS AFFECTING PROGRAMMED CELL DEATH AND THEIR USE IN THE MODIFICATION OF FORESTRY PLANT DEVELOPMENT

(75) Inventors: Barry Flinn; Annette Lasham, both of Auckland (NZ)

(73) Assignees: Genesis Research & Development Corporation Limited, Auckland (NZ); Fletcher Challenge Forests Limited, Auckland (NZ)

(*) Notice: Subject to any disclaimer, the term of this patent is extended or adjusted under 35 U.S.C. 154(b) by 0 days.

(21) Appl. No.: 09/325,932

(22) Filed: Jun. 4, 1999

(51) Int. Cl.[7] .......................... C12N 15/82; C12N 5/14; C12N 15/63; A01H 1/00; A01H 5/00; C07H 21/04

(52) U.S. Cl. .................. 435/468; 435/320.1; 435/410; 536/23.6; 800/278; 800/295

(58) Field of Search ...................... 536/23.6; 435/320.1, 435/410, 468; 800/278, 295

(56) References Cited

PUBLICATIONS

Eric P. Beers, et al. "Plant proteolytic enzymes; possible roles during programmed cell death"; *Plant Molecular Biology*, 48: 399–413, 2000.

PCT International Search Report; In re Genesis Research and Development Corporation, Ltd.; International Application No. PCT/NZ00/00086, filed Jun. 2, 2000.

Martinez–Garcie, M. et al.; EMBL Accession No. L76926, submitted Aug. 27, 1997.

Perry, D.J., et al., EMBL Accession No. AF051247, submitted Mar. 25, 1998.

Perez–Amador, M.A., et al., EMBL Accession No. U90265, submitted Jan. 6, 1999.

Perez–Amador, M.A., et al., EMBL Accession No. U90266, submitted Jan. 6, 1999.

Gray, J. et al., EMBL Accession No. U77345, submitted Apr. 18, 1997.

Newman, T. et al., EMBL Accession No. U77347, submitted Jun. 19, 1997.

Shin, H. et al., EMBL Accession No. U89609, submitted Sep. 4, 1998.

Seals, D.F. et al., EMBL Accession No. AF113545, submitted Apr. 12, 1999.

Sun, L. et al., EMBL Accession No. U66593, submitted Jan. 6, 1999.

Delmer, D.P. et al., EMBL Accession No. S79309, submitted Dec. 4, 1995.

Hassanain, H.H. et al., EMBL Accession No. AF126055, submitted Jun. 3, 1999.

Winge, P. et al., EMBL Accession No. AF115476, submitted Apr. 26, 1999.

Park, J.M. et al., Swiss–Prot Accession No. Q42808 submitted Jul. 15, 1998.

Holdsworth, M.J. et al., Swiss–Prot Accession No. P26357, submitted May 1, 1992.

Dou, Q. Ping and Bing An. "RB and Apoptotic Cell Death," *Frontiers in Bioscience 3*, d419–430, (24 pages) Apr. 6, 1981, reprinted online through www.bioscience.org/1998/v3/d/dou/d419–430.htm.

Greenberg, Jean T. "Programmed Cell Death in Plant–Pathogen Interactions," *Annu. Rev. Plant Physiol. Plant Mol. Biol.* 48: 525–545, 1997.

Hammond–Kosack, Kim E. and Jonathan D.G. Jones. "Plant Disease Resistance Genes," *Annu. Rev. Plant Physiol. Plant Mol. Biol.* 48: 575–607, 1997.

Jones, Alan M. and Jeffery L. Dangl. "Logjam at the Styx: programmed cell death in plants," *Trends in Plant Science*, v.1, No. 4: pp. 114–119, Apr. 1996.

Wilson, Iain Wilson, John Vogel, and Shauna Somerville. "A common theme in plants and animals?" *Current Biology*, v. 7, No. 3: R175–R178, 1997.

Yang, Yinong, Jyoti Shah, and Daniel F. Klessig. "Signal perception and transduction in plant defense responses," *Genes & Development*, pp. 1621–1639.

*Primary Examiner*—Terry McKelvey
(74) *Attorney, Agent, or Firm*—Ann W. Speckman; Janet Sleath

(57) ABSTRACT

Novel isolated polynucleotides associated with programmed cell death and various plant developmental mechanisms are provided, together with genetic constructs comprising such sequences. Methods for the modulation of the content, structure and metabolism of forestry plants, and particularly for the modulation of PCD and various plant developmental mechanisms in forestry plants, are also disclosed, the methods comprising incorporating one or more of the polynucleotides or genetic constructs of the present invention into the genome of a forestry plant.

19 Claims, 3 Drawing Sheets

SEQUENCE LISTING

```
<160> NUMBER OF SEQ ID NOS: 206

<210> SEQ ID NO 1
<211> LENGTH: 860
<212> TYPE: DNA
<213> ORGANISM: Pinus radiata

<400> SEQUENCE: 1
aatgcgtcct cgcagcgttt ttcaccttcg aaaaccattg cgtgttgtaa aagcaagctg      60
cgcccggacg gatttcgtcg gaactcagaa gcttttttgag ttttcggatt catatattca    120
tcggaagtgc ttcccactgg aggaaattga aaccacgttg cagcctggca tttttgcagg    180
gcatgatagg gctgaggagc tcagaacggc taattgaaag agatttcaga ggataaattc    240
tgtggtttca atttgataca ggatgaaaat gagtagtttt aattaccctc ctcaggacga    300
tggcgagccc caatatgcta gctcgggcag tggtgagaat cacatgcctg atgatgatga    360
ccccaactgg ggcgatggtt ataaagttta cccacagcca aatcaaggtg aggcccaaga    420
tcagcccgaa tatgcaggct tcaatgagga ttaccaggag cagaaaaatg acatctatgg    480
taaaatcatg ctatctggca tactagtgtt tatttttatt attttgttag ccattttgct    540
gcacgtttat gccagatggt tttggaggcg gtctgctcga ttccccaacc ggaatcgacg    600
gagatcatct tctatccgtc atcggtttaa tttttatagaa gaagaaccgg tatggctgcg    660
gaacgtgggg ttgcaatctg ccgtattaga gacacttccc atctttgtgt ataaatcaca    720
ggatttcaca gatgggctgg agtgcgcagt gtgtctgtgc gaattcgagg agaatgagat    780
agctcggctt ctgcccaatt gcaggcacaa ttttcatgtc gagtgtattg acatgtggtt    840
tcgttcgcat tccacttgcc                                                860

<210> SEQ ID NO 2
<211> LENGTH: 367
<212> TYPE: DNA
<213> ORGANISM: Pinus radiata

<400> SEQUENCE: 2
ccggctggtg ggcgactgca acgccatggg cgacgactac ggcggcggct atcccaacac      60
caaattcccc gacgacgggt cgtccaacgc ctacgccctc aacggcagga tcatgctcgc    120
cgccatcatc gtcctcttct tcgtcgtcat catcatgatc tccctccacc tctacgcccg    180
ctggttcctc ctccgccgcc agcagcgccg ccgcttcctc cgccgcaacc gcctcaaccg    240
ccgcacccag atcgtcttct acgccgactt ccccgccccc caggcctccc gcggcctcga    300
ctcctccgtc ctcaagtccc tccccgtctt caccttctcc tcctccgccg ccgccgccgc    360
cgccgcc                                                              367

<210> SEQ ID NO 3
<211> LENGTH: 330
<212> TYPE: DNA
<213> ORGANISM: Pinus radiata
```

<400> SEQUENCE: 3

```
gcaacgccat gggcgacgac tacggcttcg gcgatcccaa caccgaattc cgcggcaacg      60
ggcagtccaa cgcctacgcc ctcaacggca ggatcatgct cgccgccatc atcgtcctct     120
tcttcgtcgt catcatcatg atctccctcc acctctacgc ccgctggttc ctcctccgcc     180
gccagcagcg ccgccgcttc ctccgccgca accgcctcaa ccgccgcacc cagatcgtct     240
tctacgccga cttccccgcc ccccaggcct cccgcggcct cgactcctcc gtcctcaagt     300
ccctcccccgt cttcaccttc tcctcctccg                                     330
```

<210> SEQ ID NO 4
<211> LENGTH: 315
<212> TYPE: DNA
<213> ORGANISM: Pinus radiata

<400> SEQUENCE: 4

```
gaacaagact gtgattgagt ccctcccttt cttcaggttc tcctcgctca agggatcgaa      60
acaagggcta gagtgcgcgg tgtgcttgtc caagttcgaa gacattgaga ttctccggtt     120
actccccaag tgcaggcatg cattccacat cgattgcatc gattattggc ttgagaagca     180
ctcaagctgc ccgctctgcc ggcacaaagt cagtgccgag gacccagcaa atttcaccta     240
tacgaatagc atgaggctga tgagccaatc tgatatgaga caagattcca acttggagct     300
gttcgttcag agaga                                                      315
```

<210> SEQ ID NO 5
<211> LENGTH: 483
<212> TYPE: DNA
<213> ORGANISM: Pinus radiata

<400> SEQUENCE: 5

```
agctagcagt gctctgccat atttgcagag taggctatca aataatttga gggccgagac      60
caacccatt tgaaaggaaa tttctgtggc ttcaacatga gttcggttag cgaaacccat     120
gaaccgcctc agtatgggag cgcgcagggt tatgtcatca gtggcaaaat catgttgtcg     180
gcaataatat gtcttttgt tgtggtgttg ctcatgtttt tgctgcacct ttatgccaga     240
tggatttggc gacactctgc taggttttcc cgacggaatc gacgcagatc agcttctagg     300
cgtcgccggc ttcgtttctc gggacaagta ccggcgagtc tccagaatac ggggttggat     360
tcttcgatat tgcagactct gcccatgttt gtgtataaat cccaagattt catcgatggt     420
ctggagtgcg cagtctgtct gtgcgagttg gaggagaatg agaaagcccg gcttctgcca     480
aat                                                                   483
```

<210> SEQ ID NO 6
<211> LENGTH: 600
<212> TYPE: DNA
<213> ORGANISM: Pinus radiata

<400> SEQUENCE: 6

```
caagacgaag acgacgacga cgacgagggt cgagaagcga agcaagggtt gcagcaggaa      60
gaaagaatgg cgagatcgag cggcgacgac gctcaggctc tgttccactc gctccgatcc     120
gcttacgccg ccactcccaa gaacctcaag atcatcgatc tgtacgtggc cttcgccgtc     180
ttcacagcac tgattcaggt tgtttatatg gctctggttg gctctttccc tttcaattcg     240
ttcctggctg ggggcctttc ttgtattgga acggccgtcc tggctgtttg tctccgtatc     300
```

```
caagtcaaca aggagaacaa ggagttcaag gatttaccac ctgagcgtgc tttcgcagat    360
tttgttctct gcaatttggt gcttcacttg gtgattatga atttccttgg ttaagctgga    420
gccacgggtt ttgcaggatc tacatagctt gaggagtgat cgaatagtag taaaataact    480
agttgccaat tcattttgct ttactggact gtgaggtgca aagctagtga tatgtgctga    540
atgataggat tttgtggatt gactggggag cccaaattta tgttcttgtt tgaggtacac    600

<210> SEQ ID NO 7
<211> LENGTH: 778
<212> TYPE: DNA
<213> ORGANISM: Pinus radiata

<400> SEQUENCE: 7
caagacgaag acgacgacga cgacgagggt cgagaagcga agcaagggtt gcagcaggaa     60
gaaagaatgg cgagatcgag cggcgacgac gctcaggctc tgttccactc gctccgatcc    120
gcttacgccg ccactcccaa gaacctcaag atcatcgatc tgtacgtggc cttcgccgtc    180
ttcacagcac tgattcaggt tgtttatatg gctctggttg gctctttccc tttcaattcg    240
ttcctggctg ggggcctttc ttgtattgga acggccgtcc tggctgtttg tctccgtatc    300
caagtcaaca aggagaacaa ggagttcaag gatttaccac ctgagcgtgc tttcgcagat    360
tttgttctct gcaatttggt gcttcacttg gtgattatga atttccttgg ttaagctgga    420
gccacgggtt ttgcaggatc tacatagctt gaggagtgat cgaatagtag taaaataact    480
agttgccaat tcattttgct ttactggact gtgaggtgca aagctagtga tatgtgctga    540
atgataggat tttgtggatt gactggggag cccaaattta tgttcttgtt tgaggtacac    600
caagaaaaga atgattttc ttctgccgaa aaaaaaaaa aaacctttat ttgattagct    660
tagttttgta tcatggttgt gcttagtctg ccgacatttg gtcctgtcaa ggatgtcaat    720
gggctgtggc atgtcggatt ttataagtaa tccaaaattt tctgttcaaa aaaaaaaa    778

<210> SEQ ID NO 8
<211> LENGTH: 771
<212> TYPE: DNA
<213> ORGANISM: Pinus radiata

<400> SEQUENCE: 8 atttttgtgac cgaaggccgg ggtgatcgaa acaagttgag agatccaagc gaaaatggga     60
acctcaacag ctaaggatgc acaagttctc gttgcatcac ttcgatctgc atattctgca    120
actcctacca agctgaagat catcgatctg tatgtggtct acgcagttct cacggcagtt    180
gtgcaggttg tctacatggc aatagttgga tcatttcctt tcaatgcttt tctttcagga    240
gttctatctt gcacggggtc agctgtgctt gcagtttgtt tgcggatgca agtcaacaaa    300 gaaacaagg aattcaagga tctccctcca gaaagagcat ttgcagattt tgttttgtgc    360
aatcttgtac ttcacttggt gataatgaac ttcctaggtt agtggacaag gacttgcaga    420
tttggaatga gagggtaccc atcacaaagc aacaaaagaa gaattggcta cttgcctttc    480
cttgaaatat gtcgttgcta aggatttagt ggtagtcaaa tacacaaatg cctgaaattg    540
gctcttcttg gttaatgtag ctcccttaat tttctcgtgc ttttgattct ggcgtagaa     600 gacattgtac tcttacatat tgcaaacata aatataagct attgcattat tataccttcg    660
tattgatcat ttcataatgt ggttcaggtc tttgaactct gttgtatggt ttgactcttg    720
agaatcagtg ctgtcaataa gtatcaagca gaagtgatga gaaaaaaaaa a            771
```

<210> SEQ ID NO 9
<211> LENGTH: 424
<212> TYPE: DNA
<213> ORGANISM: Pinus radiata

<400> SEQUENCE: 9

```
gccaaggcca gggccggaga gaaatatcca atcaaggatg ggaagttcaa cagccaagga      60
tgcgcacgta ctcgttgcct cgcttcgatc tgcatattct gcaactccca ccaaacttaa     120
gattattgat ctgtatgtgg tttacgccat tctcacggca gttgtgcagg ttgtgtacat     180
ggcaatagtt ggatcgtttc cttttaatgc ttttctttca ggagttctat catgcacagg     240
gacagctgtg cttgcagttt gtttgaggat gcaagtgaac aaagaaaaca aggaattcaa     300
ggatcttcct ccagaaagag catttgcaga tttttgtattg tgcaatcttg tacttcactt     360
ggtgataatg aatttcctag gttaatggat aagcatttgt aaaaccggaa tcagagggtg     420
gcat                                                                  424
```

<210> SEQ ID NO 10
<211> LENGTH: 689
<212> TYPE: DNA
<213> ORGANISM: Pinus radiata

<400> SEQUENCE: 10

```
cagaagcgct catgtttctc tctcatttca ttggagacat tcatcagcct ttgcatgtag      60
gcttcactac agacagaggg gccaacgaaa ttgaggtccg ctggtacacc cggaaacaaa     120
accttcacca tgtttgggat agtaatataa ttgagaccgc tgaagagaga tactacagct     180
cagacacaga cggccttgtt gatgctatcc agcagaacat cacgaatgat tgggcagaag     240
aagttaaagg ctgggagacc tgcagttcta ccaagccacc ttgcccagac atatatgcat     300
ccgaaagtat cgccgcggcc tgtcagtggg catacaaagg tgtcagtgaa ggttcggtat     360
tagaagatcc atatttcctg tcccgtttac ctactgttaa tcttcggtta gctaaagggg     420
gagttcgact tgcagccact ctaaaccgca ttttcatgtg agtggcttca agttctggtt     480
gaaaatatgg gactaaaagg aggacaaggt gaagatttaa ggcatattgg agtgacagag     540
agctactcac agactacaat tgcagttcat gcttgtatag gtagtcatat gttcataccc     600
tactgctttc catcttcttg aattgcccaa ctgttcagtg cgttgtcact aaataaagac     660
attctgtcta ttaaaaaaaa aaaaaaaaa                                      689
```

<210> SEQ ID NO 11
<211> LENGTH: 484
<212> TYPE: DNA
<213> ORGANISM: Pinus radiata

<400> SEQUENCE: 11

```
acttcctgtt gttggagatc aaaaatgggt tatatggatc tgctccttca acgtaccaat      60
ggcccctggg aagactcgtt ccatcgtttg cagtgctcga aacttctttc agttcacaat     120
gccagggcca gcttggtggc aggtgatccc gaggtggcat gagcactgga cttcgaataa     180
agtttatgat ggagatatga ttgtccttca gggacaggag aagatcttcc tctccaagtc     240
gatggagggt caggaagacg taaatgagca atacacaaag atcacattta cacccactca     300
agccgatcgg tttgtcctgg cattccgcaa ttggctaaga cggcacggga acagccaacc     360
cgaatggttt ggctcgagca gtcaaaagcc tttgccatct accgtcttgt cgaaacgtca     420
gatgcttgat cggttcgagc aacatactct caagtgctcg tcatgcagaa aagcctacga     480
```

```
agca                                                                      484

<210> SEQ ID NO 12
<211> LENGTH: 769
<212> TYPE: DNA
<213> ORGANISM: Pinus radiata

<400> SEQUENCE: 12
atacaaatgg acgcattaac tcatggaact tctgtcggat tcatcacttt ctcgcccaaa       60
attggcagcc aatgtaataa taaatccaag ggagactgca atttctcgtt cttgacagct      120
aaagaacaat ctataagaag aagaagaaat aattttgcta caaggaggcg ggatttacat      180
gtggtttctg caactgtagc tccgcccacc attcctggct cttcttccgc tgaagatttt      240
gacaaagatc gtgaagcaga ggaggagagt gggaaattta tatggagaga tcattggtat      300
cccgtttctt taattgaaga cctggacccc aagattccta cgccttttcca gctcttgggt      360 cgcgagattg ttctctggca agatgccgag ggaaattgga aagccttcga ggacaagtgc      420
ccccacagac ttgctcctct ctcggaaggg agattggatg agaatggatg gcttcaatgc      480
tcctaccatg gctggtcttt caaggcagat gggtcatgtg ctcgaatccc gcaggccgca      540
tccgaaggac ctgaatctcg ggccgcaagg tcacctcgag cttgtgcagt gagtttcccg      600
acaacagtct ctcagggttt gctgttcgtg tggcccgacg agaatggctg ggaaagggcc      660
tcaaagttcg agccccccatt gctacctgat gcatttagtg atccacgctt ctcaacggtc      720
acaatacaaa gagatctgtt ctatggttat gatacattga tggaaaacg                  769

<210> SEQ ID NO 13
<211> LENGTH: 482
<212> TYPE: DNA
<213> ORGANISM: Pinus radiata

<400> SEQUENCE: 13
gttcaaagcg ggtggtgatt tagccgaggg cgaagaggag gacgaagaag ggcttcgtaa       60
caaacgtggc gattgatcct accttagcct gaaaatgctg tcaggaggct acgcaaccag      120
atccgacact actactgtca acaacggatc cgctaatggc ccaataggaa gtgctccccc      180
aagaattaac tcgatacaaa ataataatcc aggagctgtc aggcctggct ggggaaccat      240
gccccttcac atgaatcctt atcatcccca atcaatgcct cttccgcccc ccaatggtat      300
gcagggtcag cttgtgtgca gtggatgtag aactcttctt gtttatccgc aaggtgcacc      360
aaatgtttgc tgtgcagtat gcaacacagt cactccagtt ccacctcctg ggacagaaat      420
ggctcagcta atctgtggac gttgtcgtac attgctaatg tatgttcgtg gagcaactag      480
tg                                                                     482

<210> SEQ ID NO 14
<211> LENGTH: 456
<212> TYPE: DNA
<213> ORGANISM: Pinus radiata

<400> SEQUENCE: 14
tttctgttcc accacaaaga atcgatggac caccgtcagg acaacaccg tctacttcaa        60 cgtcaatgcc ccaatctact caaactgtag tggttgaaaa ccccatgtcc gttgacgaga      120
gtggcaaact ggtgactaat gtcgtcgtcg gcgtcacaac agagaaaagg tgatctattg      180
ccaacagttg aatatggata tggagattgg ttgtgcatac cttgtgagaa agacattcac      240
atcagtactg gagtccccag tacattcaga ttcctgtcgc tgtattgagg atcttgtaaa      300
```

```
acttcgtcttt catttgtttg gccctatggt acttgtagag tgaataaaag tcttgatatt      360
cctacatgag cttggacaaa aaaggttatc tactttatc agttgaatat ggagatggat        420
gttggtttgt atatgatgtg gataatagca tttttat                                456
```

<210> SEQ ID NO 15
<211> LENGTH: 1014
<212> TYPE: DNA
<213> ORGANISM: Pinus radiata

<400> SEQUENCE: 15

```
accaccagaa ataatgtgtc acctgcaact tctaccagtt cttctactgc ttttacaatc       60
caaggcaatg tctatccaga tggactttat tatgtgtcaa tgctcattgg gaacccacca      120
aagccctatc accttgatgt tgacacaggg agtgatttga cttggatcca gtgtgatgct     180
ccttgcagaa gttgtgccaa gggaccacac gctctgtaca acccaagaa aagccaactt      240 gtatcctgca tggcgcctat gtgtgtgaat gtgcaagcag gtcacagcca tgaatgcaca     300
agtacctctg aacagtgtga ctatgagata gagtatgctg atctgggatc ctctatggga    360
gttcttgcga gagacaatat tagagtgtta ctgacaaatg gctctatagc tcgaacaaat    420
tttgtgtttg gatgtgcata tgaccagcag ggttctcttg cagtttcacc tgcagtgaca   480
gatggagtat tgggccttag cagtgctcag gttagtttgc catcacaatt agcaagtcaa    540
ggtctgacta gaatgtgat tggtcattgt attgctggag atgaaagaga tgaaagaagt     600
gggggttata tgttctttgg caatgatctt gtacctgtgt ggggaatgac atgggttccc    660
atgtttggca agcctgcaat gaaattatat tccgtgggca gtgcaaatat gaacttgga    720 aacaggccgc ttgtttctaa tgacctaaaa acaaattag gaggggtggt ttttgatagt     780
ggtagctcct ttacatatct cacacagaca gcttacttcg catttgtctc agcagttaaa    840
gagaatcttt ttggaggagg gttagtacag gattgtcag ataaaacttt accgctgtgt     900
tggcgggcaa gacatcctat caggtctata gcagatgtga aacctttctt caaaccattg   960
actctggatt ttgggggcaa cccatggctt attaagacca aacagtttga catt          1014
```

<210> SEQ ID NO 16
<211> LENGTH: 530
<212> TYPE: DNA
<213> ORGANISM: Pinus radiata

<400> SEQUENCE: 16

```
ttcggcacga gattaagacc aaacagtttg acattccccc agaaggttac ttggtcatca       60
gttctcatgg taatgtttgt ctgggaatcc tcaatgcag tgaagtgaac gatggcgcca      120
caaatataat tggagacatt tcttttgcaag gacaccttat tgtttatgac aatgtcaaga    180
accagattgg ctgggtccat gcagattgcc acaagccacc taagatgatg aaggccttcc   240 cctttttttaa gtaaaacaat gcagcaggaa ctggttcatg ctttgtaatg agcgatgcaa    300
aattttgaac atttttgtcaa atatacagaa gacagttgtt aatgtgcaaa tcgtattatt    360
agtgttggtt atagcttata tgtacattat ttacatccac attttctcat atttggggat    420
ctgtcgagct atcaacgagt cctttcacat atttaagtga aatcactatt ttaatatgtt   480
tgtattgtat atattgcatc gatagtagaa tattatcata aaaaaaaaa                530
```

<210> SEQ ID NO 17
<211> LENGTH: 1293
<212> TYPE: DNA

<213> ORGANISM: Pinus radiata

<400> SEQUENCE: 17

| | | | | | |
|---|---|---|---|---|---|
| ctgactctct | ctctctctgt | tttgtctcct | ccctcctctc | tctcgttttc | gcttcgtcgt | 60
| gaacgcaccc | acacgatctt | ccattccctc | aacaatgtcg | actctcaccg | tcccgcagcc | 120
| actgccccct | gtagccgatg | actgcgagca | gctccggaca | gccttcgcag | gatggggaac | 180
| aaatgagaag | ctgatcatat | ccatattggg | tcataggaat | gcggcgcaga | ggaagctgat | 240
| tcggcaaacc | tatgccgaga | cttacggcga | ggacctcctc | aaggcattgg | acagagaact | 300
| taccaatgat | ttcgagaggc | tggtggtcct | ttggtcactt | gatccggctg | aacgtgatgc | 360
| gtacttggcg | aatgaagcga | cgaaaagatg | gacttcaagc | aaccaggttc | tcatggaaat | 420
| agcctgcacg | aggtctccgc | agcagttgct | tatggcaaga | caagcatatc | atgcccgata | 480
| caagaagtca | atggaagagg | acgtcgctca | ccacacaact | ggagattttc | gtaagttgct | 540
| ggtacctctt | gggagctcct | accgtaatga | tggagatgag | gtgaatatga | ctttggcaaa | 600
| agcagaggct | aagatactcc | acgagaagat | ctcagagaag | gcttatggcc | atgaggatct | 660
| cataaggatt | ttggctacta | ggagcaaagc | acaggtcaat | gctacgctga | atcactacaa | 720
| aaatgagttt | ggaaatgata | tcaacaagga | tttgaaaact | gatccaaaag | acgcgttcct | 780
| tactatactg | agagctacag | taaagtgcct | gactcgccct | gagaagtatt | ttgaaaaggt | 840
| tcttcgtcta | gccatcaata | gcgaggaac | agatgaaggg | gctctgacca | gagtagttgc | 900
| taccagggcc | gaggttgaca | tgaagtttat | aagtgaggag | taccagagga | ggaatagcat | 960
| ccctctcgat | cgtgccattg | tcaaggacac | tactggagac | tatgaaaaaa | tgcttctggc | 1020
| attgattggc | cacgtcgagg | cttgatttac | aagtactcat | gaagctatcc | tggtggaggc | 1080
| aatatctctg | tttttggtgt | ggtttgaggc | atttctattt | tccttgcttt | ccaacaacgt | 1140
| gtagttacca | acatgcctcc | ccagttgtca | gttgtagcta | tgcgaagcaa | atacacttct | 1200
| tataatggcg | ttggtttatg | tacttatgag | aagtctttga | ttttgatctt | taatcaagac | 1260
| tgctagtaag | tgatcgtgaa | aaaaaaaaaa | aaa | | | 1293

<210> SEQ ID NO 18
<211> LENGTH: 484
<212> TYPE: DNA
<213> ORGANISM: Pinus radiata

<400> SEQUENCE: 18

| | | | | | |
|---|---|---|---|---|---|
| ggaagctgat | tcggcaaacc | tatgccgaga | cttacggcga | ggacctcctc | aaggcattgg | 60
| acagagaact | taccaatgat | tttgaggtct | gatcttcttt | aattatttgt | attcatccca | 120
| tggagacgcg | tccctctttc | tctcagatta | atccatattc | attccgtatc | gtcagaggct | 180
| ggtggtcctt | tggtcgcttg | atccggctga | acgtgatgcg | tacttggcga | atgaagcgac | 240
| gaaaagatgg | acttcaagca | accaggttct | catggaaata | gcctgcacga | ggtctccaca | 300
| gcagttgctc | atggcaagac | aagcatatca | tgctcgatac | aagaagtcgc | tggaagagga | 360
| cgtcgctcac | cacacaactg | gagattttcg | taagttgctg | gtacctcttg | tgagctccta | 420
| ccattatgat | ggagatgagg | tgaatatgac | tttggcaaaa | gcagaggcta | agatactcca | 480
| cgag | | | | | | 484

<210> SEQ ID NO 19
<211> LENGTH: 221
<212> TYPE: DNA
<213> ORGANISM: Pinus radiata

<400> SEQUENCE: 19

```
cgtacttggc gaatgaagcg acgaaaagat ggacttcaag caaccaggtt ctaatggaaa    60
tagcctgcac gaggtctccg cagcagttgc ttatggcaag acaagcatat catgcccgat   120
acaagaagtc gctggaagag gacgtcggtc accacacaac tggagatttt cgtaagttgc   180
tggtacctct tgtgagctcc taccgttatg atggagatga g                      221
```

<210> SEQ ID NO 20
<211> LENGTH: 789
<212> TYPE: DNA
<213> ORGANISM: Pinus radiata

<400> SEQUENCE: 20

```
atcgtcttcg gctcctcgcg atatcaccaa cttgcttccg cacagagaga gagagagaga    60
gagagagaga gaatgcgac tatcgcggtg ccaccgtcgg ttccgtctcc ggctgaggat   120
gccgagcagc tccaaaaagc tttcgcagga tggggacga atgaagatct gatcatatcc   180
atactgcctc acagaaacgc agcgcagcgg aaagtaatcc gacaaacata tgccgagaca   240
tatggggaag atcttctcaa agcgcttgac aaggaactct ctagtgactt tgagagatct   300
gtgcttctgt ggaccctgga tcctgcggag cgtgatgcat tcttgtccaa tgaagctacc   360
aagagattga cttcgagcaa ctgggttctc atggaaattg cttgcacgag gtcttcaatg   420
gagttattca tggtgaggca ggcctatcat gctcgttata agaaatctct tgaagaagac   480
atcgcatatc acactactgg ggatttccgc aagctgcttg ttcctctggc aagtaccttt   540
cggtatgagg ggcctgaggt gaacatgaca ttggcgagat cagaggctaa gatacttcat   600
gagaagattc acgagaaggc ttacaatcat gatgagctca tcagaattgt tactacaaga   660
agtaaagctc agcttaatgc aaccctcaat tactacaaca atgagtttgg gaatgccatc   720
aacaaggatc tgaaggctga tccaaatgat gaatttctga aactgctgag atcagcaatt   780
aagtgcttg                                                           789
```

<210> SEQ ID NO 21
<211> LENGTH: 704
<212> TYPE: DNA
<213> ORGANISM: Pinus radiata

<400> SEQUENCE: 21

```
gttttgttga gctactagat tttagtaaat caagaattca tcagctataa attgaggcat    60
tcgatttcag ttttagttac attttggtga agttggtcga cctgcattgc tgaagatatc   120
gtgcgaagta tgtgatttgt cgagaagatg tcaacaatta tagtgccagt tccaataccg   180
accccatctg aagactctga acgcctgagg aaggcttttg aagggtgggg cacaaatgag   240
aagtcaatca tacaaatatt aggacataga actgcagcac aacgcaaagt aatccgtcaa   300
agttattttc aactgtacga agaggatctc ttgaagcgat tagaatctga ctttcaagt   360
gactttgaga aagctgtatt cctttgggta ctagatccag ctgaacgtga tgcggtcata   420
tctcatggtg caataaagaa gtggaatgca aagaatatat cgcttttaga aatttccagt   480
gctcgatctt cggctgaact attgatggtg aggcaagcat atcatattcg gtacaaaaag   540
tccctcgaag aagacgtggc tgcacataca agtggaaact tccgtaagtt gctggtagca   600
cttgtaagtt catatcggta tgaaggtccg gaagtggata tgcatttggc aagttatgaa   660
gcaaagaagc taagtgaatc tataaccgag caaaaaagat aatt                    704
```

<210> SEQ ID NO 22
<211> LENGTH: 1235
<212> TYPE: DNA
<213> ORGANISM: Pinus radiata

<400> SEQUENCE: 22

| | | | | | |
|---|---|---|---|---|---|
| cacagctttc | cttaaccgga | gaagccatag | atatgttttg | aggttctggg | ttttgtgtga | 60 |
| agcataacac | tgcgataatc | gagaagagag | agagcaatgt | ctgtacaaag | agcgttatca | 120 |
| aacatagctg | cgctagccat | cagcgttgga | acgggagtcg | gcctcctaaa | cgcgtcgctg | 180 |
| tataccgtgg | atggggggca | caaagcggtc | cttttcgaca | gattcagagg | cgtcctggac | 240 |
| accaccgtgg | gggaaggcac | ccacttcctc | attccatggc | ttcagaaacc | ctacatattc | 300 |
| gagatcagaa | cgaaaccccg | ctccatcagc | accatcacgg | gcaccaagga | cctccagatg | 360 |
| gtgaacatct | ctctgaggat | acttgccagg | cccaaagagg | actcgttacc | cgacatattc | 420 |
| cagaggctcg | gcctcgatta | cgacgagaga | gtgttgccct | ccattgggaa | tgaggtcttg | 480 |
| aaggccgtcg | tggcgcagtt | caacgctgac | cagctcttga | ccgagaggcc | aacggtttct | 540 |
| gctctggtca | gggaggctct | gctgcatcgc | gccaaagatt | ttaacatttt | gttggacgac | 600 |
| gtggccatca | cccatctgtc | ctatggcccc | gagttctcaa | aagcagtgga | gcagaagcag | 660 |
| gtggcgcagc | aggaagccga | gaggtcgaag | tttgtggttg | ccaaagctga | gcaggagagg | 720 |
| agagctgccg | tggtgagagc | agaggggag | agtgaggctg | ctaagcttat | ttctctggcc | 780 |
| acgtctgctc | cgggactagg | gctaattgag | ctcaggcgta | tcgaggctgc | caaggagatt | 840 |
| gcttccaccc | tttctcggag | ccctaatgtg | gtctacttgc | cctctggcaa | caacatgctc | 900 |
| tgggcttga | acccttcgca | ttgaacacga | ggttactgat | ccatcttaga | tggtaaggag | 960 |
| ttgatgatga | gcccaagtca | cggatgcgat | cagcatgtcc | agtgtttctt | gataaatata | 1020 |
| caagaaatta | tttctgtata | tttttttatgc | ggtggaggtt | ttttgggcaa | agaatattca | 1080 |
| tattaccgat | ttagaactcg | acaatatttc | aaatatcaag | atgcagagaa | ataacatgct | 1140 |
| taagccttct | aggaaaaaat | aagctttccg | aaaaacggct | ttgctcggat | atatatgtta | 1200 |
| ttaatttatc | aaggttggga | cgtcgacgcg | gccgc | | | 1235 |

<210> SEQ ID NO 23
<211> LENGTH: 497
<212> TYPE: DNA
<213> ORGANISM: Pinus radiata

<400> SEQUENCE: 23

| | | | | | |
|---|---|---|---|---|---|
| ctctctctct | atctccgctc | gtcgatctgc | gcttcgagga | ggaagggagg | cggggagaat | 60 |
| ggggagcagc | caggcggcgg | tctcgttcct | gacgaacgtg | gcgcgggcgg | cgttcggcct | 120 |
| cggcgccgcc | gggacggcgc | tgaacgcgtc | gctgtacacg | gtcgacggcg | gccagcgggc | 180 |
| ggtgatcttc | gaccggctcc | gcggggtcat | ggatgagacg | gtcggggagg | ggacccactt | 240 |
| cctcgtcccc | tggctccaga | agcccttcat | tttcgacatc | cggacgaggc | cgcacacctt | 300 |
| ctcttccgtc | tccgggacca | aggatctcca | gatggtcaac | cttactctcc | gagttctctc | 360 |
| tcggcctcag | gtctctcgtt | tgccatatat | cttccggcac | ctgggtctcg | agtatgatga | 420 |
| gaaggtcctt | ccgtcaatcg | ggaatgaggt | tttgaaagct | gttgtcgccc | aattcaatgc | 480 |
| ggattcagct | tcttact | | | | | 497 |

<210> SEQ ID NO 24
<211> LENGTH: 527

<212> TYPE: DNA
<213> ORGANISM: Pinus radiata

<400> SEQUENCE: 24

```
gagtgttgcc ttcaatcatc cacgagacac tgaaagctgt ggtagcacag tacaatgcaa      60
gtcaacttat cactcagaga gaggcagtaa gcagagaaat aaggagaatt ttgacggaga     120
gagctgctaa ttttttacatt gcattggacg acgtctctat aacaagcctt actttcggaa    180
gagagttcac agctgccatt gaagcaaagc aagttgctgc tcaagaagca gaacgtgcca    240
agtttgttgt cgagaaggca gaacaagata aaaagagtgc tatcattaga gctcagggag    300
aagccacaag tgctcagctt attggtgaag ctatttctaa taatccagct ttcatcacgt    360
tgagaaagat tgaggccagc cgggaaatag cacacactct ctctaactca actaatagga    420
tcttcttgag ttctgattca ttactgctaa accttcagga tatgagcctg gacgatgcac    480
acaagccacc acctaagcct aaaaagtgat gaacacaata aattatt                 527
```

<210> SEQ ID NO 25
<211> LENGTH: 483
<212> TYPE: DNA
<213> ORGANISM: Pinus radiata

<400> SEQUENCE: 25

```
agattcggca cgagagcggt agctgcagcc ttccatcaaa tcaaggagac agagctcaac      60
agatcagaga ttctatacaa gaagccgaga gaaacgggt tgggtagtca gagcaagaga     120
aggaagatga attttaacaa tgtgagggtg cctggagggg gaggagctgc atgggcgcta    180
actaaagccg tagtacttgg tggggctggg ctttacggtg cactcaacag tctctacaat    240
gtcgagggag gtcacagggc cattgtcttc aataggatcg ttggtgtcaa ggataaggta    300
tatcctgaag gcacacatct tatgattccc tggtttgata ggcctgtcat ctatgatgtc    360
agagcacgtc ctcaccttgt agaaagcact tcaggcagcc gtgaccttca gatggttaag    420
attggtctcc gagttcttac aagaccaatg ccagatcagt taccaacaat ttacaggccc    480
ttg                                                                   483
```

<210> SEQ ID NO 26
<211> LENGTH: 384
<212> TYPE: DNA
<213> ORGANISM: Pinus radiata

<400> SEQUENCE: 26

```
cggcacgagt ctctctcccc cccccccccc cctccctcgc tcggtaggtt ccggctggtt      60
cagttcagcg tcgactacga cccatttctc cgattcctcc gaccggtcgg cgagttctct    120
cggggaatgg attttagaaa tgtcaaagtt ccaaaagtgc caggaggagg ggctacttct    180
gctttgctca aactgggagt cataggtggc atagccctct atgcagccac aaacagtctc    240
tacaacgttg agggaggtca tcgagccatt gtattcaatc ggctagttgg tgtaaaggac    300
aaggtttatc ctgaagggac gcacataatg atcccgtggt ttgagaggcc agttatctac    360
gatgtccgtg caagacctca ttta                                            384
```

<210> SEQ ID NO 27
<211> LENGTH: 768
<212> TYPE: DNA
<213> ORGANISM: Pinus radiata

<400> SEQUENCE: 27

-continued

```
gacggattct agcgagaagt cgtctgcctg ccggaatccg gtgactccga acgccctctg      60
ccctgccgtg gtcttccgcg tcggcgcttc ttctcttctt ctgcgataag cggggtttgg     120
agcgggaact ttccgttagg cttgccgttg agggtttggc agagcttgat ttcagtgaag     180
tgaattatcg tctaaacggg aatacaacat gcgtcggttt ttttgctgta cttgctcaac     240
agagggtgct cctgaacaac ctgaggccca tttcttgaat gcagctaaga acaatggaaa     300
cgggttccag ggagactata agatgtctga gggtgcaaag agtggtccgc cacagaaaat     360
agcacctatt gaagcacctg ctttgtcatt agaagaactg aaggaagcaa ctgataactt     420
tggggcaaag gctttgattg gggaggggtc ctacggaaga gtttactatg caatgttaag     480
tgatggtcaa cctgcagcaa tcaagaaatt ggatgtcaac agccagccag aggcaaattc     540
cgaattctta gctcagattt caatggtctc aaggctgaag catgaccata tagttgagct     600
ggtgggttac tgtgttgagg gaactctccg tgtattggct tatgagtttg caacaatggg     660
ctctttacat gacattttac atggacggaa aggagtgcag ggggctcaac caggtccagt     720
tctggattgg atgcaaaggg tgaaaattgc tgttggtgca gcaaaggg                  768

<210> SEQ ID NO 28
<211> LENGTH: 932
<212> TYPE: DNA
<213> ORGANISM: Pinus radiata

<400> SEQUENCE: 28
gcaccgacgc caatcggtgc gctgccaaat tgaatgtggg actggaggct tacaagataa      60
aaatgataat agatcagatg attggggtct ctgtaagctc tggaaaatat gagcatttgc     120
aggtttatca agtgcgttac agtgggggat ggagctgtgg ggaagacatg cttgctcatc     180
tcatatacaa gcaacacatt cccaactgac tacgtaccca cagtgttcga taacttcagt     240
gcaaatgtgg tagttgatgg taacaatgtc aatctcggcc tctgggatac tgcagggcaa     300
gaagactaca ataggttgag accactgagt tacaggggga cagacgtgtt cctcttggcg     360
ttttccctga tcagcaaagc cagttatgaa atgtttccca agaagtggat tcctgaactc     420
aaacattatg tgccatctgt gccaattgtt ctcgtgggaa ccaaactaga tttacgagat     480
gacaagcagt tttttagtga tcatcctggt gcagccccta taacaacagc ccagggagaa     540
gagctaaaga accagattgg ggctgtagca tatattgagt gcagttctaa aacacagcag     600
aacgtcaagg cagttttttga tgctgcaatc aattcggtcc ttcaactacc taaacctgtg     660
aaacctcgaa agaaaaggca aacttgtgct gttctttgag gggaagttgg ggacttcttg     720
aaaatatggt acctggaatc tggcttaaga tttcttgctt acatgtaatt tgatacattt     780
tcttgaatct taacacagtt gccaatatct gcaaacacat tcagcttcag tgtttgctgt     840
gtaaaaaaaa cagctgtatc tagatatcat ggatttggaa gtttatatta ttttttaatc     900
attcggacag gtgattaaca aaatgtaatg tc                                   932

<210> SEQ ID NO 29
<211> LENGTH: 603
<212> TYPE: DNA
<213> ORGANISM: Pinus radiata

<400> SEQUENCE: 29
gctctggaaa atatgagcat ttgcaggttt atcaagtgcg ttacagtggg ggatggagct      60
gtggggaaga catgcttgct catctcatat acaagcaaca cattcccaac tgactacgta     120
cccacagtgt tcgataactt cagtgcaaat gtggtagttg atggtaacaa tgtcaatctc     180
```

-continued

```
ggcctctggg atactgcagg gcaagaagac tacaataggt tgagaccact gagttacagg      240
gggacagacg tgttcctctt ggcgttttcc ctgatcagca aagccagtta tgaaaatgtt      300
tccaagaagt ggattcctga actcaaacat tatgtgccat ctgtgccaat tgttctcgtg      360
ggaaccaaac tagatttacg agatgacaag cagtttttta gtgatcatcc tggtgcagcc      420
cctataacaa cagcccaggg agaagagcta agaaccaga ttggggctgt agcatatatt      480
gagtgcagtt ctaaaacaca gcagaacgtc aaggcagttt tgatgctgc aatcaattcg       540 gtccttcaac tacctaaacc tgtgaaacct cgaaagaaaa ggcaaacttg tgctgttctt      600
tga                                                                   603
```

<210> SEQ ID NO 30
<211> LENGTH: 472
<212> TYPE: DNA
<213> ORGANISM: Pinus radiata

<400> SEQUENCE: 30

```
caaccaaata taacccccaaa agcaggaaaa taaagaagt tcacaagacc cagaattcca      60
gaatttctgc tttttagatt caaggaaagc ttctttgttc ctttcttcct gggggtgttt      120
cttcaatggc tgcgagtgcg tcaagattca tcaaatgtgt gacagttggt gatggggctg      180
tgggcaagac ttgcatgctg atctgctaca ccagcaacaa gtttccaact gattatatac      240
caacagtatt cgataacttc agtgcaaatg tagtagttga aggtaccact gttaacctgg      300
gactctggga taccgctggg caagaagatt acaatagatt aagacccctg agctacagag      360
gtgcagatgt ctttgtcttg gctttctctt tagttagtcg agctagttac gagaacatac      420
ttaaaaagtg gatccctgaa ctccagcatt atgcaccagg aaatccctct gg             472
```

<210> SEQ ID NO 31
<211> LENGTH: 614
<212> TYPE: DNA
<213> ORGANISM: Pinus radiata

<400> SEQUENCE: 31

```
ccgagctccg cttttttataa aatccttta tcgcaagctg gcaagagttg tctctctcat       60
tccagcccct cctccgtaaa gaaaatcaag aaagaaaatc cctctctctc tctagttcgc      120
tctctctctc tctctctctc tctctcttgt gggtagtcag agtacgtttc cctccgcgga      180
cgacttgctt ttcgctgcct ttccctggtt tcaatgcgcc ccatttcgcg gccacagagt      240
ttcgccgtct ccgttcaaga ctagccggtg aagaggggcg gacgtttccg aagttcttgg      300
gggggcaaga ggaggaggag gaggaggagg atatgagcgc gtcgaggttc atcaagtgcg      360
tcaccgtcgg cgacggggcc gtcggcaaga cttgcatgct catctcctac actagcaaca      420
ccttccccac ggactatgta ccaactgtgt tcgacaattt cagtgcaaat gtcgttgtgg      480
atggaagcac tgttaacctg ggtttgtggg atacagctgg acaggaagac tataatagac      540
taagacctct tagctaccgt ggggctgatg ttttcctgct cactttctct ctcattagca      600
aggccagcta tgaa                                                       614
```

<210> SEQ ID NO 32
<211> LENGTH: 408
<212> TYPE: DNA
<213> ORGANISM: Pinus radiata

<400> SEQUENCE: 32

-continued

| | |
|---|---|
| atcaagtgcg tcaccgtcgg cgacggtgcc gtcggcaaaa cctgcctgtt gatttcttat | 60 |
| accagcaaca ctttccccac ggactatgtg cccacggtgt ttgacaattt tagtgcaaat | 120 |
| gtggtggtta atggaagtac tgttaatctg ggattgtggg atactgctgg acaagaggat | 180 |
| tataacagat taagacctct aagttaccgt ggagcagatg ttttttatact tgctttctct | 240 |
| ctcataagca aggccagtta tgaaaacgtt tcaaagaagt ggattccaga attaaagcat | 300 |
| tatgcacctg gtgtgccaat aattctcgtg gaacaaagc tggatttgcg ggatgataag | 360 |
| cagttcttta tagaccatcc tggtgcagtg cctattacga cccagcag | 408 |

<210> SEQ ID NO 33
<211> LENGTH: 331
<212> TYPE: DNA
<213> ORGANISM: Pinus radiata

<400> SEQUENCE: 33

| | |
|---|---|
| aagtgcgtga cggtcggcga cggggcggtg ggcaagactt gcttgctcat tcctacacc | 60 |
| agcaacacct tccccacgga ttatgtgccc accgtcttcg acaacttcag tgctaatgtg | 120 |
| gttgtcaacg aagcactgt gaacctggga ctgtgggata ctgcaggaca ggaggattac | 180 |
| aacagactaa gacctttgag ttatcggggg gcagatgttt tcattctagc attctctctc | 240 |
| atcagcaagg ccagctatga aaatgtctct aagaagtgga ttccggtgtt gaagcattat | 300 |
| gcacctggtg tcccaattgt tcttgttggg a | 331 |

<210> SEQ ID NO 34
<211> LENGTH: 466
<212> TYPE: DNA
<213> ORGANISM: Pinus radiata

<400> SEQUENCE: 34

| | |
|---|---|
| gagttttct gaagagtcag agcaaccatg agtactgcca gatttattaa gtgtgtgact | 60 |
| gtggggggatg gtgctgtggg aaagacttgc atgcttattt cctacacgag caacacattt | 120 |
| ccaacggact atgtaccaac agtgtttgat aacttcagtg caaatgtagt ggtggatgga | 180 |
| agtacagtga atcttggcct ctgggacacg gcggggcaag aggattacaa caggctcagg | 240 |
| cccctgagtt acagaggtgc agatgtcttc tcctggcctt tctccttgat cagcaaggcc | 300 |
| agttatgaaa acatttcaa aaattggatt ccagaattga gacactacgc accatctgtg | 360 |
| cctatcattt tggtgggaac aaaattagat ttacgagaag acaaacagtt ttttgcggat | 420 |
| catcccggag cagccccaat ctcgacagct caaggtgaaa atttga | 466 |

<210> SEQ ID NO 35
<211> LENGTH: 367
<212> TYPE: DNA
<213> ORGANISM: Pinus radiata

<400> SEQUENCE: 35

| | |
|---|---|
| ctcgtgccgc gattgtctca ttcctcatca aatagttaaa accagcagga caatctgtag | 60 |
| cagtgtagcc tggctgtttt ctcctacctc ctcttcaacc tcttctcttc tctctttctc | 120 |
| ctccttcaaa gtgtccatca gtttcaactg tggctggaga gcttctcgca tagttccact | 180 |
| ggggttttct tgtggggaag aaagatgagc gcctccaagt tcatcaagtg cgtcactgtc | 240 |
| ggagatggag ctgtgggcaa gacttgcatg ctcatttgct acaccagcaa caagttccct | 300 |
| actgattaca tacccacagt gttttgataac ttcagtgcaa atgtggctgt ggatgggaac | 360 |
| atagtca | 367 |

<210> SEQ ID NO 36
<211> LENGTH: 549
<212> TYPE: DNA
<213> ORGANISM: Pinus radiata

<400> SEQUENCE: 36

```
agagttaaag gatattgaca cagacactttt ctcctatttt gagggtctca tggaagagag      60
ttcacttgta tcaagcattc aaatcctaga aaaagattat gaagatgcaa tatatgatag     120
aggggaactt gacgagcgca tgtttgtgaa tgaagaggat agtttgtttg gttcagcaag     180
caactcggga ggttctgtca ctgtgtctgg agtgaagaga aaatttgata gtatttcctc     240
acctacaaag acaataacaa gtccaccatc tccacgagge tctcctgttg catccectgt     300
gaaagagagc tctgccactg ccagtactaa gatgccaccc cctacaccag tgagcacagc     360
aatgacaact gcaaagtggc ttcgaactgt tatagctcca cttcctccaa aaccttcttc     420
agagcttggg cattttcttt catcatgtga cagggacatt accgcagatg taagtcaccg     480
agcaagaata gtactagaag caattttcct agtagtcacc tggggaaaga tgtgttgtgg     540
agcccagag                                                             549
```

<210> SEQ ID NO 37
<211> LENGTH: 433
<212> TYPE: DNA
<213> ORGANISM: Pinus radiata

<400> SEQUENCE: 37

```
cacagatggt tttagctatt ttgagggtct catggaggaa acctccctga attcaagcat      60
aagaattta gagagtaact acatgaatgc aattcatgat agaggagaac tggatgagag     120
gatgtttgtg aatgatgagg atagtttgtt tggttctgtc catgcatctg ttgattctgt     180
caatatattg ggggcaaagc gaaagtatga ggctatctcc tctccaatga agagaataac     240
aagtccatta tcttccccag tctctccatc agcttcagga acaatatatt caaatgtcaa     300
gatgttgcca cctacaccag tgagcacaac aatgactact gcgaagtggc ttcggactgt     360
catagcacct cttccagctg aaccttgtaa agagcttaac agttttttgc ttcttgtgac     420
agagatgtaa ctg                                                        433
```

<210> SEQ ID NO 38
<211> LENGTH: 383
<212> TYPE: DNA
<213> ORGANISM: Pinus radiata

<400> SEQUENCE: 38

```
cactggaggc aatggtcgga aactgatttg gcatggggtt cctcgaagca tcagagattg      60
tcacaggaaa gttcatgaca gtagtgacgg actaattata caaagagatg tggcactctc     120
tttctcaggt ggtgacataa atgaattgaa tcttagattg acaggacaca tattgaagga     180
acaataatat atgcactttt caaagatcta tggactagga aaagtaagtc atatctcctg     240
ttatttatct tctccttttgc tgctgattaa tattgtaaag gttcagatcc tttcagtagc     300
aagctgtcat tgccagaaca acgagagaga aaaatcatat ctagaaagtg tataggttga     360
ccacggcaca ggtgtatgcc att                                             383
```

<210> SEQ ID NO 39
<211> LENGTH: 1036
<212> TYPE: DNA

<213> ORGANISM: Pinus radiata

<400> SEQUENCE: 39

| | | | | | |
|---|---|---|---|---|---|
| gctcatcatt | ttgtgtgaaa | ataagcgatg | ggttggttcc | acaggtgttt | tggattcatt | 60 |
| agaaagaaga | agaagcagaa | aagcccaaaa | tctgagcctc | cgtctcgtga | acatttactg | 120 |
| aagtccacac | aagaagaatt | cgagaataca | aagggagctc | aatacaaata | tcaccgcaga | 180 |
| tttcctgctg | ttagggataa | aaccgagcag | gttgcgacgc | gatcatttgg | ggatttggat | 240 |
| ggagcttcac | taatagaaac | tcctggcaga | gaaaccctcc | aaattgttat | aacagagtgc | 300 |
| ccaaatactc | gtacagtatg | ttctggatgt | aaatccaggt | taagcaactg | gtgtccgtcc | 360 |
| tgcagatgca | accttggaaa | ttttaggtgc | ttagctcctg | aaacggagac | atcatctcaa | 420 |
| gaacttactt | gcatgtatca | aagctatggt | tgtgaggata | tgtatcctta | ctacagtgaa | 480 |
| ttaagacatg | aagctcagtg | caattttagg | ccatacaact | gtccctatgc | tggctccgaa | 540 |
| tgcaagctag | ttggagatat | tccctttttg | gtggctcatt | taagagatga | tcacaaagtt | 600 |
| tatatgcata | atagttgcac | ctttgatcat | cgatatgtaa | agtcaaatcc | actcgaggtt | 660 |
| gagaatgcta | tttggatgcc | aactgtaatc | aattgttttg | ggcaattctt | ttgtctacat | 720 |
| tttgaagcgt | ttctattaga | catggcccct | gtatatatag | cttttctgat | tttcatggga | 780 |
| gatgataatg | aagctaaaaa | ctttagctat | tgcctcgaga | ctggaggcaa | tggtcggaaa | 840 |
| ctgatttggc | atgggttcc | tcgaagcatc | agagattgtc | acaggaaagt | tcatgacagt | 900 |
| agtgacggac | taattataca | aagagatgtg | gcactctttt | tctcaggtgg | tgacataaat | 960 |
| gaattgaatc | ttagattgac | aggacacata | ttgaaggaac | aataatatat | gctggatcct | 1020 |
| ctagagtcct | gcttta | | | | | 1036 |

<210> SEQ ID NO 40
<211> LENGTH: 563
<212> TYPE: DNA
<213> ORGANISM: Pinus radiata

<400> SEQUENCE: 40

| | | | | | |
|---|---|---|---|---|---|
| tttaaaggg | cgcaatagtg | atcaagtttc | ggttgatctc | caggtttta | gatgccttgg | 60 |
| tcagtatttt | tgcctgcact | tcgaggcctt | tcagctcgga | atggcaccag | tctacatagc | 120 |
| attccttcgg | tttatgggtg | atgcaacga | ggcgaaaaac | tacagttaca | gcctcgaggt | 180 |
| tggtgggaac | gggagaaaga | tgatctggca | aggtgtgcct | cggagcataa | gggacagcca | 240 |
| ccgcaaagtc | cgcgatagtt | tcgatggtct | catcatccaa | cgcaacatgg | ctctcttctt | 300 |
| ctctggtggc | gaccggaagg | aactgaagct | tagggtgact | ggtaggatct | ggaaagaaca | 360 |
| gtgacgacag | ggtacttccg | tctcatgctc | ctttagatta | tcctgctctt | aaaaatcaga | 420 |
| atagttcgtc | cgcgtagtga | tcaccacgtc | ttcttgggca | tgtattttt | gggaatttta | 480 |
| ggggggggcaa | tgtctctttg | cttgaactat | gcatcgaata | catgaatggg | aagacagcaa | 540 |
| aaatgtcgta | tattccaagc | aaa | | | | 563 |

<210> SEQ ID NO 41
<211> LENGTH: 868
<212> TYPE: DNA
<213> ORGANISM: Pinus radiata

<400> SEQUENCE: 41

| | | | | | |
|---|---|---|---|---|---|
| ctctctctct | ctctccctct | acctccctcc | ctccctcctt | ctccctcatc | cctctctcat | 60 |
| ttttaagcct | ccagatacaa | atctttcatc | tataaacata | taaagacgc | gccttttcga | 120 |

```
acttttggcg ctccacccgc ccgttttctt cccttgattc tgctcggatc tgtccctct      180 gagccgatcc caacggtcaa aaccccgggt ttcgaagaaa aggtggacag gggtttctgt      240
gttggattgt gtgtggagat tggagcgac gagtcatggc ggatcaggcc ttggagggaa      300
gccaaccggt tgatctgtcc aagcatcctt caggaatcgt tcccactctt cagaacatag      360
tctcaacagt gaatttggac tgcaaattgg atcttaaggc cattgctttg caagctagaa      420
atgctgagta taatcccaag cgttttgctg ctgtaattat gagaataagg gagccaaaga      480
caacggcatt gatatttgct tcagggaaaa tggtttgtac tggagccaag agtgaacaac      540
aatcaaagtt agcagcgcgg aagtatgctc gaatcattca gaaacttgga ttcccggcta      600
aatttaagga tttcaaaatt caaatattg tgggttcttg tgatgtgaaa ttccccatca      660
ggcttgaagg tcttgcatat tcacatggtg ctttctcaag ttatgaacca gagctgttcc      720
ctggattgat atatcggatg aaacagccaa aaatcgtgct gctaatcttt gtgtcaggaa      780
aaattgtcct cactggggca aaggtgcgag atgagacgta cactgccttt gagaacatat      840
accctgtgct cactgagttc aggaaaaat                                       868

<210> SEQ ID NO 42
<211> LENGTH: 722
<212> TYPE: DNA
<213> ORGANISM: Pinus radiata

<400> SEQUENCE: 42 tttcttcga gactcctctg ccgcagcagc tctctcctcg cccttttgag gatttacaat      60
ccacatactc tataaaaacc gggacaaatc aaatcaactc aattcaaaca ccacctataa      120
atacaaaagc taaccagatt caagagattc tctcaggatt tagtataaga aggatcgaga      180
tttcattttc cgagggcatt ataaaagctt ttctgtttca ttcgatttcg attgtgtagt      240
gaagagcatg gccgaacagg tcttggaagg gagtcagcca gtggatctcg agaagcatcc      300
ttcaggcatc gttcccaccc tccagaatat agtgtccact gtaaacttgg attgcaaatt      360
ggacttgaaa gccattgctc ttcaagctcg aaatgcagag tacaatccca agcgttttgc      420
agcagtcata atgagaataa gggagcccaa aactacagca ctgatatttg catcagggaa      480
gatggtttgc acaggtgcaa aaagtgaaca acagtcaaaa cttgctgcaa gaaagtatgc      540
tcgtattatc caaaaattgg gctttcctgc tcatttcaag gattttaaga tccagaatat      600
cgtggggtct tgtgatgtta aatttcctat tagattggaa gggcttgcat actcccatgg      660
tgctttctca agctatgaac cagaattgtt tccaggccta atttatcgaa tgaaacagcc      720
ca                                                                   722

<210> SEQ ID NO 43
<211> LENGTH: 884
<212> TYPE: DNA
<213> ORGANISM: Pinus radiata

<400> SEQUENCE: 43
aagggtttat tgtcgcctta gctgtgccct cgtaacagca gcgatcggtg tttatttgca      60
tcttctgttg aatattggag ggctcctcac ggggctcgct tgcattggtt ctgtaatcgg      120
gctcttatcc gtccctactt cctcgaacaa tgagggtaag agagctgcgc tgctcctggc      180
agctgctgcg ttcaagggag ctactctggg accgctcatc gacgcggtca ttaatattga      240
ctccagtata ctggtgagtg cgtttgttgg gacctctttg gccttcgctt gcttttcggc      300
```

-continued

```
agcagcaatc acagccagga gacgggaata cctattttg ggaggattat tgggctcggg    360
aatcagcata ttgatgtggc tgcaactagc atcctcgatt tttggtggtt cttcggcgat    420
ttacacattt gagatctact tcggtctgct agttttcctt gggtatatta tatttgacac    480
acagatgatc atcgagaaag cggaccatgg agactatgat tatttaaaac attcactgga    540
cctcttcatt gacttcgttg ctgtatttgt tcgcctgatg gtcataatgg caaagaatgc    600
agacagtaaa tccagggaag ggaaaaagaa gagaagggct tgaactagtg atgtaatgag    660
gcgtctttgg atacaaaaat agaagcactg gttcttgatg caatatggc cgtttaggtt      720
gttttcagtt gtaaatacaa catctctctg aacattttgt tttgtttgga tatttcaaat    780
agtggttccg taaaatcttg tagcgatgct ctttcttttt gtgtatggtg ttctatggac    840
agatataaat ataaatagcc tttgtcatta aaaaaaaaaa aaaa                    884
```

<210> SEQ ID NO 44
<211> LENGTH: 527
<212> TYPE: DNA
<213> ORGANISM: Pinus radiata

<400> SEQUENCE: 44

```
ccgatttcga agaacgagtt tggtcgacga tttcgcgatc cgcccgcctg cgaaaaaagt     60
tcatcttcct cccaatcgat cgtttctcgc cgagcatcga atcgacatgg acgcgttcgc    120
ttccctgttc cagtcgagcg gcaaggggtg gagccacgat tccctcaaga acttccgcca    180
gatatctccc gccgtccaat ctcacctcaa gaatgtttat ctgtccttat gctgtgcctt    240
gatggcttcg gccggtggtg cttacctgca tctgatgctg aacatcggcg ggctcctcac    300
gacaattgct tgcatcggaa gcatcgtgtg gctgctttcg attcctccac atgaagagca    360
aaagaggttt ggtctgctca tggcggcggc tctctttgaa ggagcgtgta tcggtcctct    420
catcgaagcg gccattaagg tcgacccgag cattgtgata agcgcatttg tgggatctgc    480
gctggccttc gcttgtttct cgggcgcagc atgttggcta ggcggag                  527
```

<210> SEQ ID NO 45
<211> LENGTH: 864
<212> TYPE: DNA
<213> ORGANISM: Pinus radiata

<400> SEQUENCE: 45

```
aaagttacta gcaggaaatc caactaggta tcatgaagac taccaacgca ggctcgataa     60
tgttggtgct cattattttt gggtgctgtt tcattggggt catagctaca tcttttgatt    120
tctattactt cgttcaacag tggcctggtt catactgcga tactcgtaga ggatgctgtt    180
accctcgcac gggaaggcct gcttccgaat tttccattca tggcctctgg cccaactaca    240
agaccggtaa atggccacag ttctgtggtt cctccgaaga attcgactac tcaaagatct    300
cagatctgga ggaggagctg aacaggtatt ggggttcgtt aagctgtcca agcagcgatg    360
gacaggaatt tgggacac gagtgggaga acatggcac ttgctctctc aatcttgatg       420
agcattcata ctttgagaag gctctctcct tgagacaaaa tatagacatt cttggggctc    480
ttaaaactgc aggtattaaa cccgatgaa gccaatacag tttgagcgat atcaaggaag     540
ccattaaaca aaacactggg cagctcccag gaatcgattg caacacgagc gcagagggag    600
agcatcaact atatcaggtg tatgtgtgtg ttgataaatc cgatgcttcc actgttattg    660
aatgccccat ttatccacac agcaattgcc catccatggt tgtgtttcct ccttttgggg    720
aggatcagga ggaccgagat ggttacacag aaggaatgta cgagctgtag atctggacaa    780
```

```
acagcatttc ttctctccgc atttgatttt tatcaatgaa atttccgatt ccaacattttt   840 gtaaaaaaaa aaaaaaaaac tcga                                            864
```

<210> SEQ ID NO 46
<211> LENGTH: 199
<212> TYPE: PRT
<213> ORGANISM: Pinus radiata

<400> SEQUENCE: 46

```
Met Lys Met Ser Ser Phe Asn Tyr Pro Pro Gln Asp Asp Gly Glu Pro
1               5                   10                  15

Gln Tyr Ala Ser Ser Gly Ser Gly Glu Asn His Met Pro Asp Asp Asp
            20                  25                  30

Asp Pro Asn Trp Gly Asp Gly Tyr Lys Val Tyr Pro Gln Pro Asn Gln
        35                  40                  45

Gly Glu Ala Gln Asp Gln Pro Glu Tyr Ala Gly Phe Asn Glu Asp Tyr
    50                  55                  60

Gln Glu Gln Lys Asn Asp Ile Tyr Gly Lys Ile Met Leu Ser Gly Ile
65                  70                  75                  80

Leu Val Phe Ile Phe Ile Ile Leu Ala Ile Leu Leu His Val Tyr
                85                  90                  95

Ala Arg Trp Phe Trp Arg Arg Ser Ala Arg Phe Pro Asn Arg Asn Arg
            100                 105                 110

Arg Arg Ser Ser Ser Ile Arg His Arg Phe Asn Phe Ile Glu Glu Glu
        115                 120                 125

Pro Val Trp Leu Arg Asn Val Gly Leu Gln Ser Ala Val Leu Glu Thr
    130                 135                 140

Leu Pro Ile Phe Val Tyr Lys Ser Gln Asp Phe Thr Asp Gly Leu Glu
145                 150                 155                 160

Cys Ala Val Cys Leu Cys Glu Phe Glu Glu Asn Glu Ile Ala Arg Leu
                165                 170                 175

Leu Pro Asn Cys Arg His Asn Phe His Val Glu Cys Ile Asp Met Trp
            180                 185                 190

Phe Arg Ser His Ser Thr Cys
        195
```

<210> SEQ ID NO 47
<211> LENGTH: 116
<212> TYPE: PRT
<213> ORGANISM: Pinus radiata

<400> SEQUENCE: 47

```
Asn Ala Met Gly Asp Asp Tyr Gly Gly Gly Tyr Pro Asn Thr Lys Phe
1               5                   10                  15

Pro Asp Asp Gly Ser Ser Asn Ala Tyr Ala Leu Asn Gly Arg Ile Met
            20                  25                  30

Leu Ala Ala Ile Ile Val Leu Phe Phe Val Val Ile Ile Met Ile Ser
        35                  40                  45

Leu His Leu Tyr Ala Arg Trp Phe Leu Leu Arg Arg Gln Gln Arg Arg
    50                  55                  60

Arg Phe Leu Arg Arg Asn Arg Leu Asn Arg Arg Thr Gln Ile Val Phe
65                  70                  75                  80

Tyr Ala Asp Phe Pro Ala Pro Gln Ala Ser Arg Gly Leu Asp Ser Ser
                85                  90                  95

Val Leu Lys Ser Leu Pro Val Phe Thr Phe Ser Ser Ser Ala Ala Ala
```

-continued

```
                    100                 105                 110

Ala Ala Ala Ala
            115

<210> SEQ ID NO 48
<211> LENGTH: 109
<212> TYPE: PRT
<213> ORGANISM: Pinus radiata

<400> SEQUENCE: 48

Asn Ala Met Gly Asp Asp Tyr Gly Phe Gly Asp Pro Asn Thr Glu Phe
  1               5                  10                  15

Arg Gly Asn Gly Gln Ser Asn Ala Tyr Ala Leu Asn Gly Arg Ile Met
             20                  25                  30

Leu Ala Ala Ile Ile Val Leu Phe Phe Val Val Ile Ile Met Ile Ser
         35                  40                  45

Leu His Leu Tyr Ala Arg Trp Phe Leu Arg Arg Gln Gln Arg Arg
     50                  55                  60

Arg Phe Leu Arg Arg Asn Arg Leu Asn Arg Arg Thr Gln Ile Val Phe
 65                  70                  75                  80

Tyr Ala Asp Phe Pro Ala Pro Gln Ala Ser Arg Gly Leu Asp Ser Ser
                 85                  90                  95

Val Leu Lys Ser Leu Pro Val Phe Thr Phe Ser Ser Ser
            100                 105

<210> SEQ ID NO 49
<211> LENGTH: 104
<212> TYPE: PRT
<213> ORGANISM: Pinus radiata

<400> SEQUENCE: 49

Asn Lys Thr Val Ile Glu Ser Leu Pro Phe Phe Arg Phe Ser Ser Leu
  1               5                  10                  15

Lys Gly Ser Lys Gln Gly Leu Glu Cys Ala Val Cys Leu Ser Lys Phe
             20                  25                  30

Glu Asp Ile Glu Ile Leu Arg Leu Leu Pro Lys Cys Arg His Ala Phe
         35                  40                  45

His Ile Asp Cys Ile Asp Tyr Trp Leu Glu Lys His Ser Ser Cys Pro
     50                  55                  60

Leu Cys Arg His Lys Val Ser Ala Glu Asp Pro Ala Asn Phe Thr Tyr
 65                  70                  75                  80

Thr Asn Ser Met Arg Leu Met Ser Gln Ser Asp Met Arg Gln Asp Ser
                 85                  90                  95

Asn Leu Glu Leu Phe Val Gln Arg
            100

<210> SEQ ID NO 50
<211> LENGTH: 129
<212> TYPE: PRT
<213> ORGANISM: Pinus radiata

<400> SEQUENCE: 50

Met Ser Ser Val Ser Glu Thr His Glu Pro Pro Gln Tyr Gly Ser Ala
  1               5                  10                  15

Gln Gly Tyr Val Ile Ser Gly Lys Ile Met Leu Ser Ala Ile Ile Cys
             20                  25                  30

Leu Phe Val Val Val Leu Leu Met Phe Leu Leu His Leu Tyr Ala Arg
         35                  40                  45
```

```
Trp Ile Trp Arg His Ser Ala Arg Phe Ser Arg Asn Arg Arg Arg
    50                  55                  60

Ser Ala Ser Arg Arg Arg Leu Arg Phe Ser Gly Gln Val Pro Ala
65                  70                  75                  80

Ser Leu Gln Asn Thr Gly Leu Asp Ser Ile Leu Gln Thr Leu Pro
                85                  90                  95

Met Phe Val Tyr Lys Ser Gln Asp Phe Ile Asp Gly Leu Glu Cys Ala
                100                 105                 110

Val Cys Leu Cys Glu Leu Glu Glu Asn Glu Lys Ala Arg Leu Leu Pro
                115                 120                 125

Asn

<210> SEQ ID NO 51
<211> LENGTH: 115
<212> TYPE: PRT
<213> ORGANISM: Pinus radiata

<400> SEQUENCE: 51

Met Ala Arg Ser Ser Gly Asp Asp Ala Gln Ala Leu Phe His Ser Leu
1               5                   10                  15

Arg Ser Ala Tyr Ala Ala Thr Pro Lys Asn Leu Lys Ile Ile Asp Leu
                20                  25                  30

Tyr Val Ala Phe Ala Val Phe Thr Ala Leu Ile Gln Val Val Tyr Met
                35                  40                  45

Ala Leu Val Gly Ser Phe Pro Phe Asn Ser Phe Leu Ala Gly Gly Leu
        50                  55                  60

Ser Cys Ile Gly Thr Ala Val Leu Ala Val Cys Leu Arg Ile Gln Val
65                  70                  75                  80

Asn Lys Glu Asn Lys Glu Phe Lys Asp Leu Pro Pro Glu Arg Ala Phe
                85                  90                  95

Ala Asp Phe Val Leu Cys Asn Leu Val Leu His Leu Val Ile Met Asn
                100                 105                 110

Phe Leu Gly
        115

<210> SEQ ID NO 52
<211> LENGTH: 115
<212> TYPE: PRT
<213> ORGANISM: Pinus radiata

<400> SEQUENCE: 52

Met Ala Arg Ser Ser Gly Asp Asp Ala Gln Ala Leu Phe His Ser Leu
1               5                   10                  15

Arg Ser Ala Tyr Ala Ala Thr Pro Lys Asn Leu Lys Ile Ile Asp Leu
                20                  25                  30

Tyr Val Ala Phe Ala Val Phe Thr Ala Leu Ile Gln Val Val Tyr Met
                35                  40                  45

Ala Leu Val Gly Ser Phe Pro Phe Asn Ser Phe Leu Ala Gly Gly Leu
        50                  55                  60

Ser Cys Ile Gly Thr Ala Val Leu Ala Val Cys Leu Arg Ile Gln Val
65                  70                  75                  80

Asn Lys Glu Asn Lys Glu Phe Lys Asp Leu Pro Pro Glu Arg Ala Phe
                85                  90                  95

Ala Asp Phe Val Leu Cys Asn Leu Val Leu His Leu Val Ile Met Asn
                100                 105                 110
```

-continued

Phe Leu Gly
        115

<210> SEQ ID NO 53
<211> LENGTH: 115
<212> TYPE: PRT
<213> ORGANISM: Pinus radiata

<400> SEQUENCE: 53

Met Gly Thr Ser Thr Ala Lys Asp Ala Gln Val Leu Val Ala Ser Leu
1               5                   10                  15

Arg Ser Ala Tyr Ser Ala Thr Pro Thr Lys Leu Lys Ile Ile Asp Leu
            20                  25                  30

Tyr Val Val Tyr Ala Val Leu Thr Ala Val Val Gln Val Val Tyr Met
        35                  40                  45

Ala Ile Val Gly Ser Phe Pro Phe Asn Ala Phe Leu Ser Gly Val Leu
    50                  55                  60

Ser Cys Thr Gly Ser Ala Val Leu Ala Val Cys Leu Arg Met Gln Val
65                  70                  75                  80

Asn Lys Glu Asn Lys Glu Phe Lys Asp Leu Pro Pro Glu Arg Ala Phe
                85                  90                  95

Ala Asp Phe Val Leu Cys Asn Leu Val Leu His Leu Val Ile Met Asn
            100                 105                 110

Phe Leu Gly
        115

<210> SEQ ID NO 54
<211> LENGTH: 115
<212> TYPE: PRT
<213> ORGANISM: Pinus radiata

<400> SEQUENCE: 54

Met Gly Ser Ser Thr Ala Lys Asp Ala His Val Leu Val Ala Ser Leu
1               5                   10                  15

Arg Ser Ala Tyr Ser Ala Thr Pro Thr Lys Leu Lys Ile Ile Asp Leu
            20                  25                  30

Tyr Val Val Tyr Ala Ile Leu Thr Ala Val Val Gln Val Val Tyr Met
        35                  40                  45

Ala Ile Val Gly Ser Phe Pro Phe Asn Ala Phe Leu Ser Gly Val Leu
    50                  55                  60

Ser Cys Thr Gly Thr Ala Val Leu Ala Val Cys Leu Arg Met Gln Val
65                  70                  75                  80

Asn Lys Glu Asn Lys Glu Phe Lys Asp Leu Pro Pro Glu Arg Ala Phe
                85                  90                  95

Ala Asp Phe Val Leu Cys Asn Leu Val Leu His Leu Val Ile Met Asn
            100                 105                 110

Phe Leu Gly
        115

<210> SEQ ID NO 55
<211> LENGTH: 152
<212> TYPE: PRT
<213> ORGANISM: Pinus radiata

<400> SEQUENCE: 55

Glu Ala Leu Met Phe Leu Ser His Phe Ile Gly Asp Ile His Gln Pro
1               5                   10                  15

Leu His Val Gly Phe Thr Thr Asp Arg Gly Ala Asn Glu Ile Glu Val

```
            20                  25                  30

Arg Trp Tyr Thr Arg Lys Gln Asn Leu His His Val Trp Asp Ser Asn
            35                  40                  45

Ile Ile Glu Thr Ala Glu Arg Tyr Tyr Ser Ser Asp Thr Asp Gly
            50                  55                  60

Leu Val Asp Ala Ile Gln Gln Asn Ile Thr Asn Asp Trp Ala Glu Glu
 65                  70                  75                  80

Val Lys Gly Trp Glu Thr Cys Ser Ser Thr Lys Pro Pro Cys Pro Asp
                    85                  90                  95

Ile Tyr Ala Ser Glu Ser Ile Ala Ala Ala Cys Gln Trp Ala Tyr Lys
                    100                 105                 110

Gly Val Ser Glu Gly Ser Val Leu Glu Asp Pro Tyr Phe Leu Ser Arg
                    115                 120                 125

Leu Pro Thr Val Asn Leu Arg Leu Ala Lys Gly Gly Val Arg Leu Ala
                    130                 135                 140

Ala Thr Leu Asn Arg Ile Phe Met
145                 150

<210> SEQ ID NO 56
<211> LENGTH: 161
<212> TYPE: PRT
<213> ORGANISM: Pinus radiata

<400> SEQUENCE: 56

Leu Pro Val Val Gly Asp Gln Lys Trp Val Trp Ile Cys Ser Phe
 1               5                  10                  15

Asn Val Pro Met Ala Pro Gly Lys Thr Arg Ser Ile Val Cys Ser Ala
                    20                  25                  30

Arg Asn Phe Phe Gln Phe Thr Met Pro Gly Pro Ala Trp Trp Gln Val
                    35                  40                  45

Ile Pro Arg Trp His Glu His Trp Thr Ser Asn Lys Val Tyr Asp Gly
                    50                  55                  60

Asp Met Ile Val Leu Gln Gly Gln Glu Lys Ile Phe Leu Ser Lys Ser
 65                  70                  75                  80

Met Glu Gly Gln Glu Asp Val Asn Glu Gln Tyr Thr Lys Ile Thr Phe
                    85                  90                  95

Thr Pro Thr Gln Ala Asp Arg Phe Val Leu Ala Phe Arg Asn Trp Leu
                    100                 105                 110

Arg Arg His Gly Asn Ser Gln Pro Glu Trp Phe Gly Ser Ser Ser Gln
                    115                 120                 125

Lys Pro Leu Pro Ser Thr Val Leu Ser Lys Arg Gln Met Leu Asp Arg
                    130                 135                 140

Phe Glu Gln His Thr Leu Lys Cys Ser Cys Arg Lys Ala Tyr Glu
145                 150                 155                 160

Ala

<210> SEQ ID NO 57
<211> LENGTH: 256
<212> TYPE: PRT
<213> ORGANISM: Pinus radiata

<400> SEQUENCE: 57

Ile Gln Met Asp Ala Leu Thr His Gly Thr Ser Val Gly Phe Ile Thr
 1               5                  10                  15

Phe Ser Pro Lys Ile Gly Ser Gln Cys Asn Asn Lys Ser Lys Gly Asp
                    20                  25                  30
```

```
Cys Asn Phe Ser Phe Leu Thr Ala Lys Glu Gln Ser Ile Arg Arg Arg
            35                  40                  45

Arg Asn Asn Phe Ala Thr Arg Arg Asp Leu His Val Val Ser Ala
        50                  55                  60

Thr Val Ala Pro Pro Thr Ile Pro Gly Ser Ser Ala Glu Asp Phe
65                  70                  75                  80

Asp Lys Asp Arg Glu Ala Glu Glu Ser Gly Lys Phe Ile Trp Arg
                85                  90                  95

Asp His Trp Tyr Pro Val Ser Leu Ile Glu Asp Leu Asp Pro Lys Ile
                100                 105                 110

Pro Thr Pro Phe Gln Leu Leu Gly Arg Glu Ile Val Leu Trp Gln Asp
            115                 120                 125

Ala Glu Gly Asn Trp Lys Ala Phe Glu Asp Lys Cys Pro His Arg Leu
        130                 135                 140

Ala Pro Leu Ser Glu Gly Arg Leu Asp Glu Asn Gly Trp Leu Gln Cys
145                 150                 155                 160

Ser Tyr His Gly Trp Ser Phe Lys Ala Asp Gly Ser Cys Ala Arg Ile
                165                 170                 175

Pro Gln Ala Ala Ser Glu Gly Pro Glu Ser Arg Ala Ala Arg Ser Pro
            180                 185                 190

Arg Ala Cys Ala Val Ser Phe Pro Thr Thr Val Ser Gln Gly Leu Leu
        195                 200                 205

Phe Val Trp Pro Asp Glu Asn Gly Trp Glu Arg Ala Ser Lys Phe Glu
                210                 215                 220

Pro Pro Leu Leu Pro Asp Ala Phe Ser Asp Pro Arg Phe Ser Thr Val
225                 230                 235                 240

Thr Ile Gln Arg Asp Leu Phe Tyr Gly Tyr Asp Thr Leu Met Glu Asn
                245                 250                 255

<210> SEQ ID NO 58
<211> LENGTH: 129
<212> TYPE: PRT
<213> ORGANISM: Pinus radiata

<400> SEQUENCE: 58

Met Leu Ser Gly Gly Tyr Ala Thr Arg Ser Asp Thr Thr Val Asn
1               5                   10                  15

Asn Gly Ser Ala Asn Gly Pro Ile Gly Ser Ala Pro Arg Ile Asn
            20                  25                  30

Ser Ile Gln Asn Asn Pro Gly Ala Val Arg Pro Gly Trp Gly Thr
        35                  40                  45

Met Pro Leu His Met Asn Pro Tyr His Pro Gln Ser Met Pro Leu Pro
    50                  55                  60

Pro Pro Asn Gly Met Gln Gly Gln Leu Val Cys Ser Gly Cys Arg Thr
65                  70                  75                  80

Leu Leu Val Tyr Pro Gln Gly Ala Pro Asn Val Cys Cys Ala Val Cys
                85                  90                  95

Asn Thr Val Thr Pro Val Pro Pro Gly Thr Glu Met Ala Gln Leu
            100                 105                 110

Ile Cys Gly Arg Cys Arg Thr Leu Leu Met Tyr Val Arg Gly Ala Thr
        115                 120                 125

Ser

<210> SEQ ID NO 59
```

```
<211> LENGTH: 56
<212> TYPE: PRT
<213> ORGANISM: Pinus radiata

<400> SEQUENCE: 59

Ser Val Pro Pro Gln Arg Ile Asp Gly Pro Pro Ser Gly Thr Thr Pro
1               5                   10                  15

Ser Thr Ser Thr Ser Met Pro Gln Ser Thr Gln Thr Val Val Val Glu
            20                  25                  30

Asn Pro Met Ser Val Asp Glu Ser Gly Lys Leu Val Thr Asn Val Val
        35                  40                  45

Val Gly Val Thr Thr Glu Lys Arg
    50                  55

<210> SEQ ID NO 60
<211> LENGTH: 338
<212> TYPE: PRT
<213> ORGANISM: Pinus radiata

<400> SEQUENCE: 60

Thr Thr Arg Asn Asn Val Ser Pro Ala Thr Ser Thr Ser Ser Ser Thr
1               5                   10                  15

Ala Phe Thr Ile Gln Gly Asn Val Tyr Pro Asp Gly Leu Tyr Tyr Val
            20                  25                  30

Ser Met Leu Ile Gly Asn Pro Pro Lys Pro Tyr His Leu Asp Val Asp
        35                  40                  45

Thr Gly Ser Asp Leu Thr Trp Ile Gln Cys Asp Ala Pro Cys Arg Ser
    50                  55                  60

Cys Ala Lys Gly Pro His Ala Leu Tyr Lys Pro Lys Ser Gln Leu
65                  70                  75                  80

Val Ser Cys Met Ala Pro Met Cys Val Asn Val Gln Ala Gly His Ser
            85                  90                  95

His Glu Cys Thr Ser Thr Ser Glu Gln Cys Asp Tyr Glu Ile Glu Tyr
        100                 105                 110

Ala Asp Leu Gly Ser Ser Met Gly Val Leu Ala Arg Asp Asn Ile Arg
    115                 120                 125

Val Leu Leu Thr Asn Gly Ser Ile Ala Arg Thr Asn Phe Val Phe Gly
130                 135                 140

Cys Ala Tyr Asp Gln Gln Gly Ser Leu Ala Val Ser Pro Ala Val Thr
145                 150                 155                 160

Asp Gly Val Leu Gly Leu Ser Ser Ala Gln Val Ser Leu Pro Ser Gln
                165                 170                 175

Leu Ala Ser Gln Gly Leu Thr Lys Asn Val Ile Gly His Cys Ile Ala
            180                 185                 190

Gly Asp Glu Arg Asp Glu Arg Ser Gly Gly Tyr Met Phe Phe Gly Asn
        195                 200                 205

Asp Leu Val Pro Val Trp Gly Met Thr Trp Val Pro Met Phe Gly Lys
    210                 215                 220

Pro Ala Met Lys Leu Tyr Ser Val Gly Ser Ala Asn Met Lys Leu Gly
225                 230                 235                 240

Asn Arg Pro Leu Val Ser Asn Asp Leu Lys Asn Lys Leu Gly Gly Val
                245                 250                 255

Val Phe Asp Ser Gly Ser Ser Phe Thr Tyr Leu Thr Gln Thr Ala Tyr
            260                 265                 270

Phe Ala Phe Val Ser Ala Val Lys Glu Asn Leu Phe Gly Gly Gly Leu
    275                 280                 285
```

```
Val Gln Asp Leu Ser Asp Lys Thr Leu Pro Leu Cys Trp Arg Ala Arg
    290                 295                 300

His Pro Ile Arg Ser Ile Ala Asp Val Lys Pro Phe Phe Lys Pro Leu
305                 310                 315                 320

Thr Leu Asp Phe Gly Gly Asn Pro Trp Leu Ile Lys Thr Lys Gln Phe
                325                 330                 335

Asp Ile

<210> SEQ ID NO 61
<211> LENGTH: 83
<212> TYPE: PRT
<213> ORGANISM: Pinus radiata

<400> SEQUENCE: 61

Arg His Glu Ile Lys Thr Lys Gln Phe Asp Ile Pro Pro Glu Gly Tyr
  1               5                  10                  15

Leu Val Ile Ser Ser His Gly Asn Val Cys Leu Gly Ile Leu Asn Gly
               20                  25                  30

Ser Glu Val Asn Asp Gly Ala Thr Asn Ile Ile Gly Asp Ile Ser Leu
           35                  40                  45

Gln Gly His Leu Ile Val Tyr Asp Asn Val Lys Asn Gln Ile Gly Trp
       50                  55                  60

Val His Ala Asp Cys His Lys Pro Pro Lys Met Met Lys Ala Phe Pro
65                  70                  75                  80

Phe Phe Lys

<210> SEQ ID NO 62
<211> LENGTH: 316
<212> TYPE: PRT
<213> ORGANISM: Pinus radiata

<400> SEQUENCE: 62

Met Ser Thr Leu Thr Val Pro Gln Pro Leu Pro Pro Val Ala Asp Asp
  1               5                  10                  15

Cys Glu Gln Leu Arg Thr Ala Phe Ala Gly Trp Gly Thr Asn Glu Lys
               20                  25                  30

Leu Ile Ile Ser Ile Leu Gly His Arg Asn Ala Ala Gln Arg Lys Leu
           35                  40                  45

Ile Arg Gln Thr Tyr Ala Glu Thr Tyr Gly Glu Asp Leu Leu Lys Ala
       50                  55                  60

Leu Asp Arg Glu Leu Thr Asn Asp Phe Glu Arg Leu Val Val Leu Trp
65                  70                  75                  80

Ser Leu Asp Pro Ala Glu Arg Asp Ala Tyr Leu Ala Asn Glu Ala Thr
                85                  90                  95

Lys Arg Trp Thr Ser Ser Asn Gln Val Leu Met Glu Ile Ala Cys Thr
               100                 105                 110

Arg Ser Pro Gln Gln Leu Leu Met Ala Arg Gln Ala Tyr His Ala Arg
           115                 120                 125

Tyr Lys Lys Ser Met Glu Glu Asp Val Ala His His Thr Thr Gly Asp
       130                 135                 140

Phe Arg Lys Leu Leu Val Pro Leu Gly Ser Ser Tyr Arg Asn Asp Gly
145                 150                 155                 160

Asp Glu Val Asn Met Thr Leu Ala Lys Ala Glu Ala Lys Ile Leu His
                165                 170                 175

Glu Lys Ile Ser Glu Lys Ala Tyr Gly His Glu Asp Leu Ile Arg Ile
```

```
                   180                 185                 190
Leu Ala Thr Arg Ser Lys Ala Gln Val Asn Ala Thr Leu Asn His Tyr
            195                 200                 205

Lys Asn Glu Phe Gly Asn Asp Ile Asn Lys Asp Leu Lys Thr Asp Pro
        210                 215                 220

Lys Asp Ala Phe Leu Thr Ile Leu Arg Ala Thr Val Lys Cys Leu Thr
225                 230                 235                 240

Arg Pro Glu Lys Tyr Phe Glu Lys Val Leu Arg Leu Ala Ile Asn Lys
                245                 250                 255

Arg Gly Thr Asp Glu Gly Ala Leu Thr Arg Val Val Ala Thr Arg Ala
            260                 265                 270

Glu Val Asp Met Lys Phe Ile Ser Glu Glu Tyr Gln Arg Arg Asn Ser
        275                 280                 285

Ile Pro Leu Asp Arg Ala Ile Val Lys Asp Thr Thr Gly Asp Tyr Glu
        290                 295                 300

Lys Met Leu Leu Ala Leu Ile Gly His Val Glu Ala
305                 310                 315

<210> SEQ ID NO 63
<211> LENGTH: 111
<212> TYPE: PRT
<213> ORGANISM: Pinus radiata

<400> SEQUENCE: 63

Ser Ile Phe Ile Pro Tyr Arg Gln Arg Leu Val Val Leu Trp Ser Leu
 1               5                  10                  15

Asp Pro Ala Glu Arg Asp Ala Tyr Leu Ala Asn Glu Ala Thr Lys Arg
            20                  25                  30

Trp Thr Ser Ser Asn Gln Val Leu Met Glu Ile Ala Cys Thr Arg Ser
        35                  40                  45

Pro Gln Gln Leu Leu Met Ala Arg Gln Ala Tyr His Ala Arg Tyr Lys
    50                  55                  60

Lys Ser Leu Glu Glu Asp Val Ala His His Thr Thr Gly Asp Phe Arg
65                  70                  75                  80

Lys Leu Leu Val Pro Leu Val Ser Ser Tyr His Tyr Asp Gly Asp Glu
                85                  90                  95

Val Asn Met Thr Leu Ala Lys Ala Glu Ala Lys Ile Leu His Glu
            100                 105                 110

<210> SEQ ID NO 64
<211> LENGTH: 73
<212> TYPE: PRT
<213> ORGANISM: Pinus radiata

<400> SEQUENCE: 64

Tyr Leu Ala Asn Glu Ala Thr Lys Arg Trp Thr Ser Ser Asn Gln Val
 1               5                  10                  15

Leu Met Glu Ile Ala Cys Thr Arg Ser Pro Gln Gln Leu Leu Met Ala
            20                  25                  30

Arg Gln Ala Tyr His Ala Arg Tyr Lys Lys Ser Leu Glu Glu Asp Val
        35                  40                  45

Gly His His Thr Thr Gly Asp Phe Arg Lys Leu Leu Val Pro Leu Val
    50                  55                  60

Ser Ser Tyr Arg Tyr Asp Gly Asp Glu
65                  70
```

```
<210> SEQ ID NO 65
<211> LENGTH: 239
<212> TYPE: PRT
<213> ORGANISM: Pinus radiata

<400> SEQUENCE: 65

Met Ala Thr Ile Ala Val Pro Pro Ser Val Pro Ser Pro Ala Glu Asp
 1               5                  10                  15

Ala Glu Gln Leu Gln Lys Ala Phe Ala Gly Trp Gly Thr Asn Glu Asp
            20                  25                  30

Leu Ile Ile Ser Ile Leu Pro His Arg Asn Ala Ala Gln Arg Lys Val
        35                  40                  45

Ile Arg Gln Thr Tyr Ala Glu Thr Tyr Gly Glu Asp Leu Leu Lys Ala
50                  55                  60

Leu Asp Lys Glu Leu Ser Ser Asp Phe Glu Arg Ser Val Leu Leu Trp
65                  70                  75                  80

Thr Leu Asp Pro Ala Glu Arg Asp Ala Phe Leu Ser Asn Glu Ala Thr
                85                  90                  95

Lys Arg Leu Thr Ser Ser Asn Trp Val Leu Met Glu Ile Ala Cys Thr
            100                 105                 110

Arg Ser Ser Met Glu Leu Phe Met Val Arg Gln Ala Tyr His Ala Arg
        115                 120                 125

Tyr Lys Lys Ser Leu Glu Glu Asp Ile Ala Tyr His Thr Thr Gly Asp
    130                 135                 140

Phe Arg Lys Leu Leu Val Pro Leu Ala Ser Thr Phe Arg Tyr Glu Gly
145                 150                 155                 160

Pro Glu Val Asn Met Thr Leu Ala Arg Ser Glu Ala Lys Ile Leu His
                165                 170                 175

Glu Lys Ile His Glu Lys Ala Tyr Asn His Asp Glu Leu Ile Arg Ile
            180                 185                 190

Val Thr Thr Arg Ser Lys Ala Gln Leu Asn Ala Thr Leu Asn Tyr Tyr
        195                 200                 205

Asn Asn Glu Phe Gly Asn Ala Ile Asn Lys Asp Leu Lys Ala Asp Pro
    210                 215                 220

Asn Asp Glu Phe Leu Lys Leu Leu Arg Ser Ala Ile Lys Cys Leu
225                 230                 235

<210> SEQ ID NO 66
<211> LENGTH: 184
<212> TYPE: PRT
<213> ORGANISM: Pinus radiata

<400> SEQUENCE: 66

Met Ser Thr Ile Ile Val Pro Val Pro Ile Pro Thr Pro Ser Glu Asp
 1               5                  10                  15

Ser Glu Arg Leu Arg Lys Ala Phe Glu Gly Trp Gly Thr Asn Glu Lys
            20                  25                  30

Ser Ile Ile Gln Ile Leu Gly His Arg Thr Ala Ala Gln Arg Lys Val
        35                  40                  45

Ile Arg Gln Ser Tyr Phe Gln Leu Tyr Glu Glu Asp Leu Leu Lys Arg
50                  55                  60

Leu Glu Ser Glu Leu Ser Ser Asp Phe Glu Lys Ala Val Phe Leu Trp
65                  70                  75                  80

Val Leu Asp Pro Ala Glu Arg Asp Ala Val Ile Ser His Gly Ala Ile
                85                  90                  95

Lys Lys Trp Asn Ala Lys Asn Ile Ser Leu Leu Glu Ile Ser Ser Ala
```

-continued

```
                    100                 105                 110
Arg Ser Ser Ala Glu Leu Leu Met Val Arg Gln Ala Tyr His Ile Arg
            115                 120                 125
Tyr Lys Lys Ser Leu Glu Glu Asp Val Ala Ala His Thr Ser Gly Asn
130                 135                 140
Phe Arg Lys Leu Leu Val Ala Leu Val Ser Ser Tyr Arg Tyr Glu Gly
145                 150                 155                 160
Pro Glu Val Asp Met His Leu Ala Ser Tyr Glu Ala Lys Lys Leu Ser
                    165                 170                 175
Glu Ser Ile Thr Glu Gln Lys Arg
            180
```

<210> SEQ ID NO 67
<211> LENGTH: 275
<212> TYPE: PRT
<213> ORGANISM: Pinus radiata

<400> SEQUENCE: 67

```
Met Ser Val Gln Arg Ala Leu Ser Asn Ile Ala Ala Leu Ala Ile Ser
1                   5                   10                  15
Val Gly Thr Gly Val Gly Leu Leu Asn Ala Ser Leu Tyr Thr Val Asp
            20                  25                  30
Gly Gly His Lys Ala Val Leu Phe Asp Arg Phe Arg Gly Val Leu Asp
            35                  40                  45
Thr Thr Val Gly Glu Gly Thr His Phe Leu Ile Pro Trp Leu Gln Lys
        50                  55                  60
Pro Tyr Ile Phe Glu Ile Arg Thr Lys Pro Arg Ser Ile Ser Thr Ile
65                  70                  75                  80
Thr Gly Thr Lys Asp Leu Gln Met Val Asn Ile Ser Leu Arg Ile Leu
                85                  90                  95
Ala Arg Pro Lys Glu Asp Ser Leu Pro Asp Ile Phe Gln Arg Leu Gly
            100                 105                 110
Leu Asp Tyr Asp Glu Arg Val Leu Pro Ser Ile Gly Asn Glu Val Leu
            115                 120                 125
Lys Ala Val Val Ala Gln Phe Asn Ala Asp Gln Leu Leu Thr Glu Arg
130                 135                 140
Pro Thr Val Ser Ala Leu Val Arg Glu Ala Leu Leu His Arg Ala Lys
145                 150                 155                 160
Asp Phe Asn Ile Leu Leu Asp Asp Val Ala Ile Thr His Leu Ser Tyr
                165                 170                 175
Gly Pro Glu Phe Ser Lys Ala Val Glu Gln Lys Gln Val Ala Gln Gln
            180                 185                 190
Glu Ala Glu Arg Ser Lys Phe Val Val Ala Lys Ala Glu Gln Glu Arg
            195                 200                 205
Arg Ala Ala Val Val Arg Ala Glu Gly Glu Ser Glu Ala Ala Lys Leu
        210                 215                 220
Ile Ser Leu Ala Thr Ser Ala Ala Gly Leu Gly Leu Ile Glu Leu Arg
225                 230                 235                 240
Arg Ile Glu Ala Ala Lys Glu Ile Ala Ser Thr Leu Ser Arg Ser Pro
                245                 250                 255
Asn Val Val Tyr Leu Pro Ser Gly Asn Asn Met Leu Leu Gly Leu Asn
            260                 265                 270
Pro Ser His
        275
```

```
<210> SEQ ID NO 68
<211> LENGTH: 146
<212> TYPE: PRT
<213> ORGANISM: Pinus radiata

<400> SEQUENCE: 68

Met Gly Ser Ser Gln Ala Ala Val Ser Phe Leu Thr Asn Val Ala Arg
 1               5                  10                  15

Ala Ala Phe Gly Leu Gly Ala Ala Gly Thr Ala Leu Asn Ala Ser Leu
                20                  25                  30

Tyr Thr Val Asp Gly Gly Gln Arg Ala Val Ile Phe Asp Arg Leu Arg
            35                  40                  45

Gly Val Met Asp Glu Thr Val Gly Glu Gly Thr His Phe Leu Val Pro
        50                  55                  60

Trp Leu Gln Lys Pro Phe Ile Phe Asp Ile Arg Thr Arg Pro His Thr
65                  70                  75                  80

Phe Ser Ser Val Ser Gly Thr Lys Asp Leu Gln Met Val Asn Leu Thr
                85                  90                  95

Leu Arg Val Leu Ser Arg Pro Gln Val Ser Arg Leu Pro Tyr Ile Phe
                100                 105                 110

Arg His Leu Gly Leu Glu Tyr Asp Glu Lys Val Leu Pro Ser Ile Gly
            115                 120                 125

Asn Glu Val Leu Lys Ala Val Val Ala Gln Phe Asn Ala Asp Ser Ala
        130                 135                 140

Ser Tyr
145

<210> SEQ ID NO 69
<211> LENGTH: 168
<212> TYPE: PRT
<213> ORGANISM: Pinus radiata

<400> SEQUENCE: 69

Val Leu Pro Ser Ile Ile His Glu Thr Leu Lys Ala Val Val Ala Gln
 1               5                  10                  15

Tyr Asn Ala Ser Gln Leu Ile Thr Gln Arg Glu Ala Val Ser Arg Glu
                20                  25                  30

Ile Arg Arg Ile Leu Thr Glu Arg Ala Ala Asn Phe Tyr Ile Ala Leu
            35                  40                  45

Asp Asp Val Ser Ile Thr Ser Leu Thr Phe Gly Arg Glu Phe Thr Ala
        50                  55                  60

Ala Ile Glu Ala Lys Gln Val Ala Ala Gln Glu Ala Glu Arg Ala Lys
65                  70                  75                  80

Phe Val Val Glu Lys Ala Glu Gln Asp Lys Lys Ser Ala Ile Ile Arg
                85                  90                  95

Ala Gln Gly Glu Ala Thr Ser Ala Gln Leu Ile Gly Glu Ala Ile Ser
                100                 105                 110

Asn Asn Pro Ala Phe Ile Thr Leu Arg Lys Ile Glu Ala Ser Arg Glu
            115                 120                 125

Ile Ala His Thr Leu Ser Asn Ser Thr Asn Arg Ile Phe Leu Ser Ser
        130                 135                 140

Asp Ser Leu Leu Leu Asn Leu Gln Asp Met Ser Leu Asp Ala His
145                 150                 155                 160

Lys Pro Pro Pro Lys Pro Lys Lys
                165
```

```
<210> SEQ ID NO 70
<211> LENGTH: 119
<212> TYPE: PRT
<213> ORGANISM: Pinus radiata

<400> SEQUENCE: 70

Met Asn Phe Asn Asn Val Arg Val Pro Gly Gly Gly Ala Ala Trp
1               5                   10                  15

Ala Leu Thr Lys Ala Val Val Leu Gly Gly Ala Gly Leu Tyr Gly Ala
                20                  25                  30

Leu Asn Ser Leu Tyr Asn Val Glu Gly Gly His Arg Ala Ile Val Phe
            35                  40                  45

Asn Arg Ile Val Gly Val Lys Asp Lys Val Tyr Pro Glu Gly Thr His
    50                  55                  60

Leu Met Ile Pro Trp Phe Asp Arg Pro Val Ile Tyr Asp Val Arg Ala
65                  70                  75                  80

Arg Pro His Leu Val Glu Ser Thr Ser Gly Ser Arg Asp Leu Gln Met
                85                  90                  95

Val Lys Ile Gly Leu Arg Val Leu Thr Arg Pro Met Pro Asp Gln Leu
                100                 105                 110

Pro Thr Ile Tyr Arg Pro Leu
            115

<210> SEQ ID NO 71
<211> LENGTH: 86
<212> TYPE: PRT
<213> ORGANISM: Pinus radiata

<400> SEQUENCE: 71

Met Asp Phe Arg Asn Val Lys Val Pro Lys Val Pro Gly Gly Gly Ala
1               5                   10                  15

Thr Ser Ala Leu Leu Lys Leu Gly Val Ile Gly Ile Ala Leu Tyr
                20                  25                  30

Ala Ala Thr Asn Ser Leu Tyr Asn Val Glu Gly His Arg Ala Ile
            35                  40                  45

Val Phe Asn Arg Leu Val Gly Val Lys Asp Lys Val Tyr Pro Glu Gly
    50                  55                  60

Thr His Ile Met Ile Pro Trp Phe Glu Arg Pro Val Ile Tyr Asp Val
65                  70                  75                  80

Arg Ala Arg Pro His Leu
                85

<210> SEQ ID NO 72
<211> LENGTH: 186
<212> TYPE: PRT
<213> ORGANISM: Pinus radiata

<400> SEQUENCE: 72

Met Arg Arg Phe Phe Cys Cys Thr Cys Ser Thr Glu Gly Ala Pro Glu
1               5                   10                  15

Gln Pro Glu Ala His Phe Leu Asn Ala Ala Lys Asn Asn Gly Asn Gly
                20                  25                  30

Phe Gln Gly Asp Tyr Lys Met Ser Glu Gly Ala Lys Ser Gly Pro Pro
            35                  40                  45

Gln Lys Ile Ala Pro Ile Glu Ala Pro Ala Leu Ser Leu Glu Glu Leu
    50                  55                  60

Lys Glu Ala Thr Asp Asn Phe Gly Ala Lys Ala Leu Ile Gly Glu Gly
```

```
                65                  70                  75                  80
        Ser Tyr Gly Arg Val Tyr Ala Met Leu Ser Asp Gly Gln Pro Ala
                        85                  90                  95

Ala Ile Lys Lys Leu Asp Val Asn Ser Gln Pro Glu Ala Asn Ser Glu
                        100                 105                 110

Phe Leu Ala Gln Ile Ser Met Val Ser Arg Leu Lys His Asp His Ile
                        115                 120                 125

Val Glu Leu Val Gly Tyr Cys Val Glu Gly Thr Leu Arg Val Leu Ala
                        130                 135                 140

Tyr Glu Phe Ala Thr Met Gly Ser Leu His Asp Ile Leu His Gly Arg
        145                 150                 155                 160

Lys Gly Val Gln Gly Ala Gln Pro Gly Pro Val Leu Asp Trp Met Gln
                        165                 170                 175

Arg Val Lys Ile Ala Val Gly Ala Ala Lys
                        180                 185

<210> SEQ ID NO 73
<211> LENGTH: 196
<212> TYPE: PRT
<213> ORGANISM: Pinus radiata

<400> SEQUENCE: 73

Met Ser Ile Cys Arg Phe Ile Lys Cys Val Thr Val Gly Asp Gly Ala
        1               5                   10                  15

Val Gly Lys Thr Cys Leu Leu Ile Ser Tyr Thr Ser Asn Thr Phe Pro
                        20                  25                  30

Thr Asp Tyr Val Pro Thr Val Phe Asp Asn Phe Ser Ala Asn Val Val
                        35                  40                  45

Val Asp Gly Asn Asn Val Asn Leu Gly Leu Trp Asp Thr Ala Gly Gln
        50                  55                  60

Glu Asp Tyr Asn Arg Leu Arg Pro Leu Ser Tyr Arg Gly Thr Asp Val
        65                  70                  75                  80

Phe Leu Leu Ala Phe Ser Leu Ile Ser Lys Ala Ser Tyr Glu Asn Val
                        85                  90                  95

Ser Lys Lys Trp Ile Pro Glu Leu Lys His Tyr Val Pro Ser Val Pro
                        100                 105                 110

Ile Val Leu Val Gly Thr Lys Leu Asp Leu Arg Asp Asp Lys Gln Phe
                        115                 120                 125

Phe Ser Asp His Pro Gly Ala Ala Pro Ile Thr Thr Ala Gln Gly Glu
                        130                 135                 140

Glu Leu Lys Asn Gln Ile Gly Ala Val Ala Tyr Ile Glu Cys Ser Ser
        145                 150                 155                 160

Lys Thr Gln Gln Asn Val Lys Ala Val Phe Asp Ala Ala Ile Asn Ser
                        165                 170                 175

Val Leu Gln Leu Pro Lys Pro Val Pro Arg Lys Lys Arg Gln Thr
                        180                 185                 190

Cys Ala Val Leu
                        195

<210> SEQ ID NO 74
<211> LENGTH: 115
<212> TYPE: PRT
<213> ORGANISM: Pinus radiata

<400> SEQUENCE: 74

Met Ala Ala Ser Ala Ser Arg Phe Ile Lys Cys Val Thr Val Gly Asp
```

```
                1               5                  10                  15
Gly Ala Val Gly Lys Thr Cys Met Leu Ile Cys Tyr Thr Ser Asn Lys
                    20                  25                  30

Phe Pro Thr Asp Tyr Ile Pro Thr Val Phe Asp Asn Phe Ser Ala Asn
                35                  40                  45

Val Val Val Glu Gly Thr Thr Val Asn Leu Gly Leu Trp Asp Thr Ala
        50                  55                  60

Gly Gln Glu Asp Tyr Asn Arg Leu Arg Pro Leu Ser Tyr Arg Gly Ala
65                  70                  75                  80

Asp Val Phe Val Leu Ala Phe Ser Leu Val Ser Arg Ala Ser Tyr Glu
                    85                  90                  95

Asn Ile Leu Lys Lys Trp Ile Pro Glu Leu Gln His Tyr Ala Pro Gly
                100                 105                 110

Asn Pro Ser
        115
```

<210> SEQ ID NO 75
<211> LENGTH: 94
<212> TYPE: PRT
<213> ORGANISM: Pinus radiata

<400> SEQUENCE: 75

```
Met Ser Ala Ser Arg Phe Ile Lys Cys Val Thr Val Gly Asp Gly Ala
1               5                   10                  15

Val Gly Lys Thr Cys Met Leu Ile Ser Tyr Thr Ser Asn Thr Phe Pro
                    20                  25                  30

Thr Asp Tyr Val Pro Thr Val Phe Asp Asn Phe Ser Ala Asn Val Val
                35                  40                  45

Val Asp Gly Ser Thr Val Asn Leu Gly Leu Trp Asp Thr Ala Gly Gln
        50                  55                  60

Glu Asp Tyr Asn Arg Leu Arg Pro Leu Ser Tyr Arg Gly Ala Asp Val
65                  70                  75                  80

Phe Leu Leu Thr Phe Ser Leu Ile Ser Lys Ala Ser Tyr Glu
                    85                  90
```

<210> SEQ ID NO 76
<211> LENGTH: 136
<212> TYPE: PRT
<213> ORGANISM: Pinus radiata

<400> SEQUENCE: 76

```
Ile Lys Cys Val Thr Val Gly Asp Gly Ala Val Gly Lys Thr Cys Leu
1               5                   10                  15

Leu Ile Ser Tyr Thr Ser Asn Thr Phe Pro Thr Asp Tyr Val Pro Thr
                    20                  25                  30

Val Phe Asp Asn Phe Ser Ala Asn Val Val Val Asn Gly Ser Thr Val
                35                  40                  45

Asn Leu Gly Leu Trp Asp Thr Ala Gly Gln Glu Asp Tyr Asn Arg Leu
        50                  55                  60

Arg Pro Leu Ser Tyr Arg Gly Ala Asp Val Phe Ile Leu Ala Phe Ser
65                  70                  75                  80

Leu Ile Ser Lys Ala Ser Tyr Glu Asn Val Ser Lys Lys Trp Ile Pro
                    85                  90                  95

Glu Leu Lys His Tyr Ala Pro Gly Val Pro Ile Ile Leu Val Gly Thr
                100                 105                 110

Lys Leu Asp Leu Arg Asp Asp Lys Gln Phe Phe Ile Asp His Pro Gly
```

```
                    115                 120                 125

Ala Val Pro Ile Thr Gln Gln
    130             135

<210> SEQ ID NO 77
<211> LENGTH: 110
<212> TYPE: PRT
<213> ORGANISM: Pinus radiata

<400> SEQUENCE: 77

Lys Cys Val Thr Val Gly Asp Gly Ala Val Gly Lys Thr Cys Leu Leu
  1               5                  10                  15

Ile Ser Tyr Thr Ser Asn Thr Phe Pro Thr Asp Tyr Val Pro Thr Val
             20                  25                  30

Phe Asp Asn Phe Ser Ala Asn Val Val Val Asn Gly Ser Thr Val Asn
         35                  40                  45

Leu Gly Leu Trp Asp Thr Ala Gly Gln Glu Asp Tyr Asn Arg Leu Arg
     50                  55                  60

Pro Leu Ser Tyr Arg Gly Ala Asp Val Phe Ile Leu Ala Phe Ser Leu
 65                  70                  75                  80

Ile Ser Lys Ala Ser Tyr Glu Asn Val Ser Lys Lys Trp Ile Pro Val
                 85                  90                  95

Leu Lys His Tyr Ala Pro Gly Val Pro Ile Val Leu Val Gly
             100                 105                 110

<210> SEQ ID NO 78
<211> LENGTH: 146
<212> TYPE: PRT
<213> ORGANISM: Pinus radiata

<400> SEQUENCE: 78

Met Ser Thr Ala Arg Phe Ile Lys Cys Val Thr Val Gly Asp Gly Ala
  1               5                  10                  15

Val Gly Lys Thr Cys Met Leu Ile Ser Tyr Thr Ser Asn Thr Phe Pro
             20                  25                  30

Thr Asp Tyr Val Pro Thr Val Phe Asp Asn Phe Ser Ala Asn Val Val
         35                  40                  45

Val Asp Gly Ser Thr Val Asn Leu Gly Leu Trp Asp Thr Ala Gly Gln
     50                  55                  60

Glu Asp Tyr Asn Arg Leu Arg Pro Leu Ser Tyr Arg Gly Ala Asp Val
 65                  70                  75                  80

Phe Leu Leu Ala Phe Ser Leu Ile Ser Lys Ala Ser Tyr Glu Asn Ile
                 85                  90                  95

Phe Lys Asn Trp Ile Pro Glu Leu Arg His Tyr Ala Pro Ser Val Pro
             100                 105                 110

Ile Ile Leu Val Gly Thr Lys Leu Asp Leu Arg Glu Asp Lys Gln Phe
         115                 120                 125

Phe Ala Asp His Pro Gly Ala Ala Pro Ile Ser Thr Ala Gln Gly Glu
     130                 135                 140

Asn Leu
145

<210> SEQ ID NO 79
<211> LENGTH: 54
<212> TYPE: PRT
<213> ORGANISM: Pinus radiata

<400> SEQUENCE: 79
```

-continued

```
Met Ser Ala Ser Lys Phe Ile Lys Cys Val Thr Val Gly Asp Gly Ala
 1               5                  10                 15

Val Gly Lys Thr Cys Met Leu Ile Cys Tyr Thr Ser Asn Lys Phe Pro
            20                 25                 30

Thr Asp Tyr Ile Pro Thr Val Phe Asp Asn Phe Ser Ala Asn Val Ala
            35                 40                 45

Val Asp Gly Asn Ile Val
            50
```

<210> SEQ ID NO 80
<211> LENGTH: 182
<212> TYPE: PRT
<213> ORGANISM: Pinus radiata

<400> SEQUENCE: 80

```
Glu Leu Lys Asp Ile Asp Thr Asp Thr Phe Ser Tyr Phe Glu Gly Leu
 1               5                  10                 15

Met Glu Glu Ser Ser Leu Val Ser Ser Ile Gln Ile Leu Glu Lys Asp
            20                 25                 30

Tyr Glu Asp Ala Ile Tyr Asp Arg Gly Glu Leu Asp Glu Arg Met Phe
            35                 40                 45

Val Asn Glu Glu Asp Ser Leu Phe Gly Ser Ala Ser Asn Ser Gly Gly
            50                 55                 60

Ser Val Thr Val Ser Gly Val Lys Arg Lys Phe Asp Ser Ile Ser Ser
65                  70                 75                 80

Pro Thr Lys Thr Ile Thr Ser Pro Pro Ser Pro Arg Gly Ser Pro Val
            85                 90                 95

Ala Ser Pro Val Lys Glu Ser Ser Ala Thr Ala Ser Thr Lys Met Pro
            100                105                110

Pro Pro Thr Pro Val Ser Thr Ala Met Thr Thr Ala Lys Trp Leu Arg
            115                120                125

Thr Val Ile Ala Pro Leu Pro Pro Lys Pro Ser Ser Glu Leu Gly His
            130                135                140

Phe Leu Ser Ser Cys Asp Arg Asp Ile Thr Ala Asp Val Ser His Arg
145                 150                155                160

Ala Arg Ile Val Leu Glu Ala Ile Phe Leu Val Val Thr Trp Gly Lys
            165                170                175

Met Cys Cys Gly Ala Gln
            180
```

<210> SEQ ID NO 81
<211> LENGTH: 142
<212> TYPE: PRT
<213> ORGANISM: Pinus radiata

<400> SEQUENCE: 81

```
Thr Asp Gly Phe Ser Tyr Phe Glu Gly Leu Met Glu Glu Thr Ser Leu
 1               5                  10                 15

Asn Ser Ser Ile Arg Ile Leu Glu Ser Asn Tyr Met Asn Ala Ile His
            20                 25                 30

Asp Arg Gly Glu Leu Asp Glu Arg Met Phe Val Asn Asp Glu Asp Ser
            35                 40                 45

Leu Phe Gly Ser Val His Ala Ser Val Asp Ser Val Asn Ile Leu Gly
            50                 55                 60

Ala Lys Arg Lys Tyr Glu Ala Ile Ser Ser Pro Met Lys Arg Ile Thr
65                  70                 75                 80
```

Ser Pro Leu Ser Ser Pro Val Ser Pro Ser Ala Ser Gly Thr Ile Tyr
                85                  90                  95

Ser Asn Val Lys Met Leu Pro Pro Thr Pro Val Ser Thr Thr Met Thr
            100                 105                 110

Thr Ala Lys Trp Leu Arg Thr Val Ile Ala Pro Leu Pro Ala Glu Pro
        115                 120                 125

Cys Lys Glu Leu Asn Ser Phe Leu Leu Leu Val Thr Glu Met
130                 135                 140

<210> SEQ ID NO 82
<211> LENGTH: 61
<212> TYPE: PRT
<213> ORGANISM: Pinus radiata

<400> SEQUENCE: 82

Thr Gly Gly Asn Gly Arg Lys Leu Ile Trp His Gly Val Pro Arg Ser
1               5                   10                  15

Ile Arg Asp Cys His Arg Lys Val His Asp Ser Ser Asp Gly Leu Ile
            20                  25                  30

Ile Gln Arg Asp Val Ala Leu Phe Ser Gly Gly Asp Ile Asn Glu
        35                  40                  45

Leu Asn Leu Arg Leu Thr Gly His Ile Leu Lys Glu Gln
    50                  55                  60

<210> SEQ ID NO 83
<211> LENGTH: 325
<212> TYPE: PRT
<213> ORGANISM: Pinus radiata

<400> SEQUENCE: 83

Met Gly Trp Phe His Arg Cys Phe Gly Phe Ile Arg Lys Lys Lys Lys
1               5                   10                  15

Gln Lys Ser Pro Lys Ser Glu Pro Pro Ser Arg Glu His Leu Leu Lys
            20                  25                  30

Ser Thr Gln Glu Glu Phe Glu Asn Thr Lys Gly Ala Gln Tyr Lys Tyr
        35                  40                  45

His Arg Arg Phe Pro Ala Val Arg Asp Lys Thr Glu Gln Val Ala Thr
    50                  55                  60

Arg Ser Phe Gly Asp Leu Asp Gly Ala Ser Leu Ile Glu Thr Pro Gly
65              70                  75                  80

Arg Glu Thr Leu Gln Ile Val Ile Thr Glu Cys Pro Asn Thr Arg Thr
            85                  90                  95

Val Cys Ser Gly Cys Lys Ser Arg Leu Ser Asn Trp Cys Pro Ser Cys
            100                 105                 110

Arg Cys Asn Leu Gly Asn Phe Arg Cys Leu Ala Pro Glu Thr Glu Thr
        115                 120                 125

Ser Ser Gln Glu Leu Thr Cys Met Tyr Gln Ser Tyr Gly Cys Glu Asp
    130                 135                 140

Met Tyr Pro Tyr Tyr Ser Glu Leu Arg His Glu Ala Gln Cys Asn Phe
145                 150                 155                 160

Arg Pro Tyr Asn Cys Pro Tyr Ala Gly Ser Glu Cys Lys Leu Val Gly
                165                 170                 175

Asp Ile Pro Phe Leu Val Ala His Leu Arg Asp His Lys Val Tyr
            180                 185                 190

Met His Asn Ser Cys Thr Phe Asp His Arg Tyr Val Lys Ser Asn Pro
        195                 200                 205

-continued

```
Leu Glu Val Glu Asn Ala Ile Trp Met Pro Thr Val Ile Asn Cys Phe
    210                 215                 220

Gly Gln Phe Phe Cys Leu His Phe Glu Ala Phe Leu Leu Asp Met Ala
225                 230                 235                 240

Pro Val Tyr Ile Ala Phe Leu Ile Phe Met Gly Asp Asp Asn Glu Ala
                245                 250                 255

Lys Asn Phe Ser Tyr Cys Leu Glu Thr Gly Asn Gly Arg Lys Leu
                260                 265                 270

Ile Trp His Gly Val Pro Arg Ser Ile Arg Asp Cys His Arg Lys Val
                275                 280                 285

His Asp Ser Ser Asp Gly Leu Ile Ile Gln Arg Asp Val Ala Leu Phe
    290                 295                 300

Phe Ser Gly Gly Asp Ile Asn Glu Leu Asn Leu Arg Leu Thr Gly His
305                 310                 315                 320

Ile Leu Lys Glu Gln
                325

<210> SEQ ID NO 84
<211> LENGTH: 120
<212> TYPE: PRT
<213> ORGANISM: Pinus radiata

<400> SEQUENCE: 84

Phe Lys Gly Arg Asn Ser Asp Gln Val Ser Val Asp Leu Gln Val Phe
1               5                   10                  15

Arg Cys Leu Gly Gln Tyr Phe Cys Leu His Phe Glu Ala Phe Gln Leu
                20                  25                  30

Gly Met Ala Pro Val Tyr Ile Ala Phe Leu Arg Phe Met Gly Asp Asp
                35                  40                  45

Asn Glu Ala Lys Asn Tyr Ser Tyr Ser Leu Glu Val Gly Gly Asn Gly
            50                  55                  60

Arg Lys Met Ile Trp Gln Gly Val Pro Arg Ser Ile Arg Asp Ser His
65                  70                  75                  80

Arg Lys Val Arg Asp Ser Phe Asp Gly Leu Ile Ile Gln Arg Asn Met
                85                  90                  95

Ala Leu Phe Phe Ser Gly Gly Asp Arg Lys Glu Leu Lys Leu Arg Val
                100                 105                 110

Thr Gly Arg Ile Trp Lys Glu Gln
            115                 120

<210> SEQ ID NO 85
<211> LENGTH: 197
<212> TYPE: PRT
<213> ORGANISM: Pinus radiata

<400> SEQUENCE: 85

Met Ala Asp Gln Ala Leu Glu Gly Ser Gln Pro Val Asp Leu Ser Lys
1               5                   10                  15

His Pro Ser Gly Ile Val Pro Thr Leu Gln Asn Ile Val Ser Thr Val
                20                  25                  30

Asn Leu Asp Cys Lys Leu Asp Leu Lys Ala Ile Ala Leu Gln Ala Arg
                35                  40                  45

Asn Ala Glu Tyr Asn Pro Lys Arg Phe Ala Ala Val Ile Met Arg Ile
            50                  55                  60

Arg Glu Pro Lys Thr Thr Ala Leu Ile Phe Ala Ser Gly Lys Met Val
65                  70                  75                  80
```

```
Cys Thr Gly Ala Lys Ser Glu Gln Gln Ser Lys Leu Ala Ala Arg Lys
                85                  90                  95

Tyr Ala Arg Ile Ile Gln Lys Leu Gly Phe Pro Ala Lys Phe Lys Asp
            100                 105                 110

Phe Lys Ile Gln Asn Ile Val Gly Ser Cys Asp Val Lys Phe Pro Ile
        115                 120                 125

Arg Leu Glu Gly Leu Ala Tyr Ser His Gly Ala Phe Ser Ser Tyr Glu
    130                 135                 140

Pro Glu Leu Phe Pro Gly Leu Ile Tyr Arg Met Lys Gln Pro Lys Ile
145                 150                 155                 160

Val Leu Leu Ile Phe Val Ser Gly Lys Ile Val Leu Thr Gly Ala Lys
                165                 170                 175

Val Arg Asp Glu Thr Tyr Thr Ala Phe Glu Asn Ile Tyr Pro Val Leu
            180                 185                 190

Thr Glu Phe Arg Lys
        195

<210> SEQ ID NO 86
<211> LENGTH: 158
<212> TYPE: PRT
<213> ORGANISM: Pinus radiata

<400> SEQUENCE: 86

Met Ala Glu Gln Val Leu Glu Gly Ser Gln Pro Val Asp Leu Glu Lys
1               5                   10                  15

His Pro Ser Gly Ile Val Pro Thr Leu Gln Asn Ile Val Ser Thr Val
            20                  25                  30

Asn Leu Asp Cys Lys Leu Asp Leu Lys Ala Ile Ala Leu Gln Ala Arg
        35                  40                  45

Asn Ala Glu Tyr Asn Pro Lys Arg Phe Ala Ala Val Ile Met Arg Ile
    50                  55                  60

Arg Glu Pro Lys Thr Thr Ala Leu Ile Phe Ala Ser Gly Lys Met Val
65                  70                  75                  80

Cys Thr Gly Ala Lys Ser Glu Gln Gln Ser Lys Leu Ala Ala Arg Lys
                85                  90                  95

Tyr Ala Arg Ile Ile Gln Lys Leu Gly Phe Pro Ala His Phe Lys Asp
            100                 105                 110

Phe Lys Ile Gln Asn Ile Val Gly Ser Cys Asp Val Lys Phe Pro Ile
        115                 120                 125

Arg Leu Glu Gly Leu Ala Tyr Ser His Gly Ala Phe Ser Ser Tyr Glu
    130                 135                 140

Pro Glu Leu Phe Pro Gly Leu Ile Tyr Arg Met Lys Gln Pro
145                 150                 155

<210> SEQ ID NO 87
<211> LENGTH: 213
<212> TYPE: PRT
<213> ORGANISM: Pinus radiata

<400> SEQUENCE: 87

Arg Val Tyr Leu Ser Leu Ser Cys Ala Leu Val Thr Ala Ala Ile Gly
1               5                   10                  15

Val Tyr Leu His Leu Leu Leu Asn Ile Gly Gly Leu Leu Thr Gly Leu
            20                  25                  30

Ala Cys Ile Gly Ser Val Ile Gly Leu Leu Ser Val Pro Thr Ser Ser
        35                  40                  45
```

-continued

Asn Asn Glu Gly Lys Arg Ala Ala Leu Leu Ala Ala Ala Phe
    50                  55                  60

Lys Gly Ala Thr Leu Gly Pro Leu Ile Asp Ala Val Ile Asn Ile Asp
65                  70                  75                  80

Ser Ser Ile Leu Val Ser Ala Phe Val Gly Thr Ser Leu Ala Phe Ala
                85                  90                  95

Cys Phe Ser Ala Ala Ala Ile Thr Ala Arg Arg Arg Glu Tyr Leu Phe
                100                 105                 110

Leu Gly Gly Leu Leu Gly Ser Gly Ile Ser Ile Leu Met Trp Leu Gln
            115                 120                 125

Leu Ala Ser Ser Ile Phe Gly Gly Ser Ser Ala Ile Tyr Thr Phe Glu
    130                 135                 140

Ile Tyr Phe Gly Leu Leu Val Phe Leu Gly Tyr Ile Ile Phe Asp Thr
145                 150                 155                 160

Gln Met Ile Ile Glu Lys Ala Asp His Gly Asp Tyr Asp Tyr Leu Lys
                165                 170                 175

His Ser Leu Asp Leu Phe Ile Asp Phe Val Ala Val Phe Val Arg Leu
                180                 185                 190

Met Val Ile Met Ala Lys Asn Ala Asp Ser Lys Ser Arg Glu Gly Lys
            195                 200                 205

Lys Lys Arg Arg Ala
    210

<210> SEQ ID NO 88
<211> LENGTH: 140
<212> TYPE: PRT
<213> ORGANISM: Pinus radiata

<400> SEQUENCE: 88

Met Asp Ala Phe Ala Ser Leu Phe Gln Ser Ser Gly Lys Gly Trp Ser
1               5                   10                  15

His Asp Ser Leu Lys Asn Phe Arg Gln Ile Ser Pro Ala Val Gln Ser
                20                  25                  30

His Leu Lys Asn Val Tyr Leu Ser Leu Cys Cys Ala Leu Met Ala Ser
            35                  40                  45

Ala Gly Gly Ala Tyr Leu His Leu Met Leu Asn Ile Gly Gly Leu Leu
    50                  55                  60

Thr Thr Ile Ala Cys Ile Gly Ser Ile Val Trp Leu Leu Ser Ile Pro
65                  70                  75                  80

Pro His Glu Glu Gln Lys Arg Phe Gly Leu Leu Met Ala Ala Ala Leu
                85                  90                  95

Phe Glu Gly Ala Cys Ile Gly Pro Leu Ile Glu Ala Ala Ile Lys Val
                100                 105                 110

Asp Pro Ser Ile Val Ile Ser Ala Phe Val Gly Ser Ala Leu Ala Phe
            115                 120                 125

Ala Cys Phe Ser Gly Ala Ala Cys Trp Leu Gly
    130                 135                 140

<210> SEQ ID NO 89
<211> LENGTH: 245
<212> TYPE: PRT
<213> ORGANISM: Pinus radiata

<400> SEQUENCE: 89

Met Lys Thr Thr Asn Ala Gly Ser Ile Met Leu Val Leu Ile Ile Phe
1               5                   10                  15

```
Gly Cys Cys Phe Ile Gly Val Ile Ala Thr Ser Phe Asp Phe Tyr Tyr
                20                  25                  30

Phe Val Gln Gln Trp Pro Gly Ser Tyr Cys Asp Thr Arg Arg Gly Cys
            35                  40                  45

Cys Tyr Pro Arg Thr Gly Arg Pro Ala Ser Glu Phe Ser Ile His Gly
        50                  55                  60

Leu Trp Pro Asn Tyr Lys Thr Gly Lys Trp Pro Gln Phe Cys Gly Ser
65                  70                  75                  80

Ser Glu Glu Phe Asp Tyr Ser Lys Ile Ser Asp Leu Glu Glu Glu Leu
                85                  90                  95

Asn Arg Tyr Trp Gly Ser Leu Ser Cys Pro Ser Ser Asp Gly Gln Glu
            100                 105                 110

Phe Trp Gly His Glu Trp Glu Lys His Gly Thr Cys Ser Leu Asn Leu
        115                 120                 125

Asp Glu His Ser Tyr Phe Glu Lys Ala Leu Ser Leu Arg Gln Asn Ile
    130                 135                 140

Asp Ile Leu Gly Ala Leu Lys Thr Ala Gly Ile Lys Pro Asp Gly Ser
145                 150                 155                 160

Gln Tyr Ser Leu Ser Asp Ile Lys Glu Ala Ile Lys Gln Asn Thr Gly
                165                 170                 175

Gln Leu Pro Gly Ile Asp Cys Asn Thr Ser Ala Glu Gly Glu His Gln
            180                 185                 190

Leu Tyr Gln Val Tyr Val Cys Val Asp Lys Ser Asp Ala Ser Thr Val
        195                 200                 205

Ile Glu Cys Pro Ile Tyr Pro His Ser Asn Cys Pro Ser Met Val Val
    210                 215                 220

Phe Pro Pro Phe Gly Glu Asp Gln Glu Asp Arg Asp Gly Tyr Thr Glu
225                 230                 235                 240

Gly Met Tyr Glu Leu
                245

<210> SEQ ID NO 90
<211> LENGTH: 1323
<212> TYPE: DNA
<213> ORGANISM: Pinus radiata

<400> SEQUENCE: 90 acttttctc ttaatttgtg aatccattac aatgatggta tgcaggtgaa aggaatagga      60
gtgggattct tattaagcaa tggaaggtta cgctgcgaat aacgatgcag aacttctgag     120 caaaacccctt caagtggaac agaagttgtt ctatttcgat ctcaaggaaa accccgagg    180 tcaataccctt aaaatctctg agaagacctc cggctcacgg tctacaataa ttgtgcccat   240
tggtggagtt gcatggttcc tcgatctctt taattattat gtcgacggag atgacgagga    300
agttttgagc aaggaattgc agctggatgc caaggtattt tatttcgatg ttgggggtgaa   360 taaaagggt cggttcttga agatttctga agcatctaca tcctacagtc gcagcacaat    420
cattgtacct gtaggaaaca caagaaaaga tggttgggca gcatttagaa atattttagg    480
agagataaat gaagcttccc aacaagcttc tggcccatcc gaacatttgg gagggctttc    540
cgatgaagtt ggtgctggtt tcctatcagg tggaagtgga gaagcagcat ttgaggcaga    600
cacaactggt gacagagcca tgggtttaac tccagcagaa gatacgggtg aagcagttgt    660
ttcaaaagtg attcgagctg atcagaaacg tttcttttt gatcttgggt gtaacaaccg     720
gggccagttt cttagaattt ctgaggtgat aggtcctgac cgttcagcta ttattgttcc    780
```

```
tgtatctgct ttggagcagt ttcatgatgt gctaggccat tttgttgaca tcaccagaac    840
tcagggtctt gcagctgcaa gtggtgcaaa tgtgcgcaca gtagcagctg cacacagacg    900
aaatgaaaac tagattacct gcatataaac cgaaatgtga tttgattgga ctgatcatag    960
ggagcattgg aaatggtcaa tgacacttca caagtttatg actgtcattt gcggccattt   1020
catcatgcaa ataatcttct ttgttgccat cacattatgt gagtataacc tgtttgttga   1080
agtgctactg aagcacatga ccattataac ctttgctatt ggtggacttt tgaaggaaag   1140
gcaccaatga aacttcatgg gttatttgag gtttacatat atggttggcg gatctatatc   1200
acttaaggag agtttttatg caacagcatt tttgtttcta tcagaaggct gctttaatcc   1260
agaagccatt aaacaatttc aaaatgaaat aaatttgtct taaatttcaa aaaaaaaaa    1320 aaa                                                                 1323
```

<210> SEQ ID NO 91
<211> LENGTH: 344
<212> TYPE: DNA
<213> ORGANISM: Pinus radiata

<400> SEQUENCE: 91

```
aaattaatgg actcagcgag gtgaaaggaa taggagtggg attcttatta agcaatggaa     60
ggttacgctg cgaataacga tgcagaactt ctgagcaaaa cccttcaagt ggaacagaag    120
ttgttctatt tcgatctcaa ggaaaacccc cgtggtcaat accttaaaat ctctgagaag    180
acctccggct cacggtctac ataattgtg cccattggtg gagttgcatg gttcctcgat     240
ctctttaatt attatgtcga cggagatgac gaggaagttt tgagcaagga attgcagctg    300
gatgccaagg tattttattt cgatgttggg gtgaataaaa gggg                    344
```

<210> SEQ ID NO 92
<211> LENGTH: 1463
<212> TYPE: DNA
<213> ORGANISM: Eucalyptus grandis

<400> SEQUENCE: 92

```
cctcctcctc ctcctccttc ttccttcttc ttcctccaat cttcctcctt catagtcgtc     60
gtccatccat ggcgatcccg gccaccgccg ccgcggccct cctcctcttc tgcgccgtcg    120
ccgccgtcgc tgcggccgcg aggaccgacg aggaggtcat gggcatgtac gagctctggc    180
tcgccaagca cggcaaggcc tacaacggcc tcggcgagcg ggagcggcgg ttcgagatct    240
tccgcgacaa cctccggttc gtcgacgagc acaacgccct caaccggtcg tacaccctcg    300
ggatgaaccg gttcgccgac ctcaccaacg aggagtaccg cgccgtctac ctcggcaccc    360
ggagcgaccc catgcgccgg gtggcgaagg cggcgcgcgc gagcggccgc tacgccccc     420 gccccgacga catgctgccg gcagccgtcg actggaggac ccgtggcgcc gttaacaagg    480
tcaaggacca gggagcttgc ggaagctgct gggccttctc taccatagct gctgtggaag    540
gaatcaacca gatcgtcacc ggcgagttca tatccctctc cgagcaagag ctcgtggatt    600
gtgaccgggc ctacgatgcc ggttgcaatg gtgggctcat ggactatgcc ttccagttca    660
tcattgacaa tggtggcatt gacactgatg aggactactc ttacacggga gtcgatggaa    720
cctgtgatgc gtctaaggtt aactcaaagg tggtgagcat tgatgggtac gaggatgtcc    780
cggcctttga cgagagagcc ttgaagaagg ctgtggctca tcaacccgtg agtgttgcca    840
ttgaagctgg aggcagagat ttccaacttt atgaatccgg cgtgttcact ggagaatgtg    900
```

-continued

```
gaactgcact ggaccacggt gtgatcgcag ttggatacgg gaggcaacat ggtgctgact      960
actggcttgt aaggaactcg tggggctcct tgtggggcga gagcggatac atcaagatgg     1020
agaggaactt ggccaacaac tactttggca agtgcggtat cgcaatggag cttcttacc     1080 ctgtcaagac cactcagaac cctgctagta aatattcttc aatgggaagc agtggtggca     1140
tcgagctcgt cagcagttct tgaagcccgg aatagaggaa acttacaga aaggtgcaag     1200 attgattgtc tttgagttcg gggatcactc tggggttcaca taattgtgtt atattccttc    1260 ccggggggtcg gtttatggaa gggggaaagg aatatggatg cacatcgggc ggttttctta    1320
tgattctact gtaaatatct ttcatttcgt caacatttga attccgaaga attgcaccat     1380
aagaagcaat agttattgta actcgaactg cctagttcaa gtcttcaatt gaaactcctc     1440
tctttcacaa aaaaaaaaaa aaa                                             1463

<210> SEQ ID NO 93
<211> LENGTH: 330
<212> TYPE: DNA
<213> ORGANISM: Eucalyptus grandis

<400> SEQUENCE: 93
ccttcctcca atcttcctcc ttcatcgtcc ttgtccatcc atggcgatcc cggccgccgc       60
cgccgccgcc ctcctcctct tctccgccgt cgccgccgtc gccgccgccg ctgcgaggac     120
tgacgaggag gtcatgggca tgtacgagct ttggctcgtc aagcacggca aggcctacaa     180
cggcctcggc gagcgggagc ggcggttcga gatcttccgc gacaacctcc ggttcgtgga     240
cgagcacacc ggcctcaacc ggtcgtacgc cctcgggatg aaccggttcg ccgacctcac     300
caacgaggag taccgcgcca tctacctcgg                                      330

<210> SEQ ID NO 94
<211> LENGTH: 886
<212> TYPE: DNA
<213> ORGANISM: Eucalyptus grandis

<400> SEQUENCE: 94
cagatcgtca ccggtgagct catatccctc tctgagcaag agcttgtgga ttgtgaccgg       60
tcctatgatg ccggttgcaa tggtgggctc atggactatg ccttccagtt catcattgac     120
aatggtggca tcgacactga tgaggactac tcttacacgg gagtcgatgg aacctgtgat     180
gcgtccaagg ttaactcaaa ggtggtgagc attgatgggt acgaggatgt cccggccttt     240
gacgagagag ccttgaagaa ggctgtggct catcaacccg tgagtgttgc cattgaagct     300
ggaggcagag atttccaact ttatgaatcc ggcgtgttca ctggcgaatg tggaactgca     360
ctggaccacg gtgtgatcgc ggttggatac gggaggcaac atggtgctga ctactggctt     420
gtaaggaact cgtggggctc cttgtggggt gagagcggat acatcaagat ggagaggaac     480
ttggccaaca actactttgg caagtgcggc atcgcaatgg aggcttctta ccctgtcaag     540
acctcccaga accctgctag taaatattct tcaatgggaa gcagcggtgg catcgagctt     600
gtcagcagtt cttgaagccc ggaatagagg aaaacttaca gaaaggtgca agatcgattg     660
tctttgagtt cggggatcac tctggggttca cataattgtg ttatattcct tccgggggggt     720 cggtttatgg aagggggaaa ggaatatgga tgcacatcgg gcggttttct tatgattcta     780 ctgtaaaatat ctttcatttc atcaacattt gaattccgaa gaattgcacc ataagaagta     840
atagttattg taactcgaac tgcctagttc aagtcttcaa ttgaaa                    886
```

<210> SEQ ID NO 95
<211> LENGTH: 948
<212> TYPE: DNA
<213> ORGANISM: Pinus radiata

<400> SEQUENCE: 95

| | | | | | |
|---|---|---|---|---|---|
| acaaagtggt | caggcccttt | tgcttctctt | ggtcaatgcc | ctctctgcgt | taacatttcg | 60 |
| ttcgcagcaa | gccaccggga | aaggcctgat | ccagccaaaa | gaagtacgga | tctcgaggtg | 120 |
| gaagatctac | tgtagatatg | ggaattcttc | tgttctttgc | tctgctggca | atgttagcca | 180 |
| tggctggcaa | tgcatcaaga | gcggattttt | ccatcatcag | caacaaggat | ctgagagaag | 240 |
| atgacgcaat | catggagctc | tatgaactgt | ggcttgcaga | gcacaaaaaa | gcctacaatg | 300 |
| gtcttgacga | gaagcagaag | aggttcactg | tattcaaaga | caattttctg | tatattcacg | 360 |
| agcacaacca | ggggaatcgg | tcctacaaac | tgggtctgaa | ccagtttgca | gatctgagcc | 420 |
| acgaggaatt | caaggccaca | tatctgggtg | ccaagctgga | tactaagaaa | cgcttgctga | 480 |
| ggtctcccag | ccctcgatac | cagtattccg | acggcgagga | tttgccaaag | tccattgact | 540 |
| ggagagaaaa | gggagccgtg | gctcctgtga | aggaccaggt | tgcatgtgga | agttgttggg | 600 |
| cgttctcaac | tgtggcggcc | gttgaaggaa | tcaatcaaat | cgtgaccggc | gatttgattt | 660 |
| cgctgtccga | gcaagaactg | gtggactgtg | atacttctta | caaccaagga | tgcaacggtg | 720 |
| gcctcatgga | ttacgctttc | gagtttatca | taaacaatgg | tggacttgac | agcgaggagg | 780 |
| attacccta | cacggcctac | gatggatcat | gtgacgctta | caggaaaaat | gcccatgtgg | 840 |
| tgacaatcga | tgactacgaa | gatgtgcctg | aaaacgatga | gaaatcgttg | aagaaggctg | 900 |
| cggctaatca | gccaattagc | gttgccatcg | aagccagcgg | gagggagt | | 948 |

<210> SEQ ID NO 96
<211> LENGTH: 883
<212> TYPE: DNA
<213> ORGANISM: Pinus radiata

<400> SEQUENCE: 96

| | | | | | |
|---|---|---|---|---|---|
| gtggtcaggc | cctttgtcttc | ctcttggtca | atgccctctc | tgcgttagca | tttcgttcgc | 60 |
| agcaagccac | cgggaaaggc | ctgatccagc | caaaagaagt | acggatctcg | aggtggaaga | 120 |
| tctactgtag | atatgggaat | tcttctgttc | tttgctctgc | tggcaatgtc | agccatggct | 180 |
| ggcagtgcat | caagagcgga | tttttccatc | atcagcaaca | aggatctgag | agaagatgac | 240 |
| gcaatcatgg | agctctatga | actgtggctt | gcagagcaca | aaaagccta | caatggtctt | 300 |
| gacgagaagc | agaagaggtt | caccgtattc | aaagacaatt | ttctgtatat | tcacgagcac | 360 |
| aaccagggga | atcggtccta | caaactgggt | ctgaaccagt | ttgcagatct | gagccacgag | 420 |
| gaattcaagg | ccacatatct | gggtgccaag | ctggatacta | agaaacgctt | gctgaggtct | 480 |
| cccagccctc | gataccagta | ttccgacggc | gaggatttgc | caaagtccat | tgactggaga | 540 |
| gaaaagggag | ccgtggctcc | tgtgaaggac | cagggtgcat | gtggaagttg | ttgggcgttc | 600 |
| tcaactgtgg | cggccgttga | aggaatcaat | caaatcgtga | ccggcgattt | gatttcgctg | 660 |
| tccgagcaag | aactggtgga | ctgtgatact | tcttacaacc | aaggatgcaa | cggtggcctc | 720 |
| atggattacg | ctttcgagtt | tatcataaac | aatggtggac | ttgacagcga | ggaggattac | 780 |
| ccctacacgg | cctacgatgg | atcatgtgac | gcttacagga | aaaatgccca | tgtggtgaca | 840 |
| atcgatgact | acgaagatgt | gcctgaaaac | gatgagaaat | cgt | | 883 |

<210> SEQ ID NO 97

<211> LENGTH: 1066
<212> TYPE: DNA
<213> ORGANISM: Pinus radiata

<400> SEQUENCE: 97

| | | | | | |
|---|---|---|---|---|---|
| caggaacgcc | caccctttc | attttgaggg | tgactgcttt | gcttggtcca | tccatgtggc | 60 |
| tttgaatcct | ttgagagact | ggtttggttt | tcagcgaggg | ttacgcccag | accggtggag | 120 |
| agaaattccc | tatttgtgcc | caaatcagtc | aaaaactaag | attgtatcag | tatgggaatc | 180 |
| cttctgctgt | ttgctctgct | ggcactgttt | gccatggcag | gcagtgcttc | cagagcagat | 240 |
| ttttccatca | tcgggtatga | tagcaaagat | ctgagggaag | atgatgcgat | catggagctt | 300 |
| tatgaactgt | ggctcgctca | gcacaggaaa | gcctataatg | gccttgacga | gaaacagaag | 360 |
| aggttctctg | tatttaaaga | caattttctg | tatattcatc | agcacaacaa | ccaagggaac | 420 |
| ccatccttca | aaatgggct | gaaccagttt | gcagacctaa | gtcacgagga | attcaaggcc | 480 |
| acatatttgg | ggtgcgaact | ggataccaag | aaacgcttgt | ccaagtctcc | cagccctcga | 540 |
| taccagtatt | cggagggcga | gaatttgcca | gagtccgttg | actggagaga | aaagggagcc | 600 |
| gtggctgctg | ttaaggacca | gggctcctgc | ggaagttgtt | gggcgttctc | gacggtggct | 660 |
| gccgttgaag | gcatcaatca | aattgtgact | ggcaatttga | cttccctgtc | cgagcaggaa | 720 |
| ctggtggatt | gcgatacttc | ttacaaccaa | ggatgcaatg | gcgtctcat | ggattatgct | 780 |
| ttccagttta | tcatagacaa | cggtgggctt | gacagtgagg | atgattaccc | ttacatggcc | 840 |
| aacgatggca | gctgtgacgc | ttaccgaaaa | atgcccatg | tggtgacaat | tgatagctac | 900 |
| gaagatgtgc | ctgagaacga | tgagaagtcg | ctgaagaagg | ccgcggcgca | tcagccgatt | 960 |
| agcgttgcca | tcgaagccag | cggaagggcg | ttccagtttt | acgaatctgg | cgtgttcaca | 1020 |
| agcacctgcg | gaactcagct | ggaccacggt | gtcactctgg | tagggg | | 1066 |

<210> SEQ ID NO 98
<211> LENGTH: 1600
<212> TYPE: DNA
<213> ORGANISM: Eucalyptus grandis

<400> SEQUENCE: 98

| | | | | | |
|---|---|---|---|---|---|
| attttctctc | tctatacttc | tctctctctc | ctctgatgct | ccgatcggat | acgccgaagc | 60 |
| caagaagatg | gatctcaaat | cgccgccggc | ggcggccgcc | gtggccgtcc | tcgccctcgc | 120 |
| gctggccctg | acgacgatcg | cctccgccct | cgacatgtcc | atcgtcagct | acgatcgggc | 180 |
| ccacggcgac | cggtcctcct | cctcctcctc | ctcctggagg | tccgacgacg | aggtgatggc | 240 |
| cgtctacgag | agctggctcg | ccaagcacgg | caaggcctac | aacgccctgg | gcgagaagga | 300 |
| gaagcgcttc | caggtcttca | aggacaacct | ccggttcatc | gacgaccaca | cgccggcgg | 360 |
| ggaccggacc | tacacggtcg | gcctcaacca | gttcgccgac | ctcactaacg | aggagtaccg | 420 |
| gtccatgtac | ctgggcgcca | ggatggatcg | gtcgggcgg | cggctcggga | gggcccgcag | 480 |
| cgatcggtac | gccgtggccg | ccggggagga | gctgccggcg | tccgtcgatt | ggaggaagga | 540 |
| aggcgccgtt | gttgacgtca | aggaccaggg | aagctgcggg | agttgctggg | cgttctctac | 600 |
| aattgctgct | gtggagggga | taaacaagct | tgtgactggt | gatttgatct | ctctgtccga | 660 |
| gcaggaactt | gtggactgcg | atacatccta | caatgaagga | tgtaatggcg | ggctcatgga | 720 |
| ttatgccttt | gaattcatta | tcaacaacg | aggcattgat | accgaggaag | attatcccta | 780 |
| tagagctgta | gatagcactt | gtgaccaata | caggaagaac | gcaaaggttg | tgacgattga | 840 |
| cgattatgaa | gatgttccag | aaaatgatga | gaaagcattg | caaaaggcag | ttgctaatca | 900 |

```
accagtcagt gtggccattg aagcaggagg ccgggaattc cagttttatg attcgggtat    960
atttactggc aaatgtggga cagctctgga tcatggggtt actgcagtcg gatatggcac   1020
agaaaacgga gttgattact ggatagtgaa gaactcatgg ggcggtagct ggggagagca   1080
agggtacatc aaaatggcac gaaatgtggc caatagcccc actggcaaat gtggtatagc   1140
aatggaggcc tcctacccca tcaagaaagg ccaaaatcct cctaatcccg gcccatctcc   1200
tccatctcca gtgaagcccc caactgtctg cgacaattac tactcttgtc ccgagagcaa   1260
cacctgctgc tgtgtctatg agtatgcaaa ctactgcttt gcctggggat gctgccctct   1320
cgaggcagcc acctgttgtg aagaccacta tagttgctgc cctcaagact tcccggtctg   1380
caatgtaaac gctgggacct gccagatgag caaagacaat ccactaggag tcaaggcatt   1440
gaagcgcact cctgctaaat ttcactgggc ttttggaagt gatggacaga gagcagtgc    1500
ataaaaaaaa aacttgggat tgtatgctgt agatggagat tcttaaggag agtcaagaaa   1560
atcacagcga ctcatcttct cctcattctc attaaactgc                         1600
```

<210> SEQ ID NO 99
<211> LENGTH: 700
<212> TYPE: DNA
<213> ORGANISM: Pinus radiata

<400> SEQUENCE: 99

```
ggatcaaggc gactgtggaa gttgttgggc attctcggca gcggcagcta tggaagggat     60
taccatgatc aagaagggga agttggtgcc actctcagta caagaactcg tggattgtga    120
cgttgacgat aatggctgcc atggcgggct catggacagg gccttcaagt ttatcaagag    180
caagggcgga ctctcgactg aggcgaacta cccctaccag gcaaataacg gaacctgcaa    240
tacggccaag atggcaaacc ccgtggcctc aataactgga taccaggatg tgccggccaa    300
taacgaaaag gccctcttgc aggccgtggc aaaccagcca gtctcggtgg caattgaggg    360
gagcgggttc aatttccaat tctactcaag cggtgtgttc tctggctcgt gtggaaccag    420
tatcgaccat gccgtcacgg cggtcgggta tgggaagacc tccaggggaa ccaagtattg    480
gctgctgaag aattcatggg gcactggatg gggtgagagc gggtacatga ggatccagag    540
ggacgtgagt tctaacgctg gtctctgtgg ccttgccatg gaagcttctt atccaaccgc    600
atgaagaaag aagaagaaga aaaaatacag tatgagctta tataagtgat actggttctt    660
aggctctcta tacgtatgaa ataatgtcta gtgtctctgt                          700
```

<210> SEQ ID NO 100
<211> LENGTH: 739
<212> TYPE: DNA
<213> ORGANISM: Eucalyptus grandis

<400> SEQUENCE: 100

```
caattacttg aggacgaaca agctcctctc tctttccgag caagagctgg tggactgcga     60
caacacacaa aaccacgggt gcaacggcgg gctcatggat attgcattcg aattcatcaa    120
gcagaaggga ggcatcacgt ccgagtcgaa ttacccttac caagcaagca atgggacctg    180
tgacgctgcc aaggagaatt ccccggtggt gtcgatcgat ggacatgaaa atgttccgc     240
caacgacgag gatgcgttgc agaaggcggt cgctaatcag cctgtgtctg tggccataga    300
agcaagcggt gcagattttc aattctactc gagggtgta ttcactggaa gctgtggcac    360
acacctagat cacggagtcg cgattgtcgg ctacgggagc actctccagg ggaccaagta   420
```

```
ctggattgtg aggaactcct ggggtccaga atggggcgag aagggctacc taaggatgga    480
gcgtgggatc gaagctaagg aagggctgtg cggcatagcc atggaggcct catacccat    540 caagaactcc tcagataatc ccgccggagt ttcatctcct gtcaaggatg aactctaggc    600
aatgactcaa gattgactag tgatcacagt ttcttaggct ttcgtttgtg tcctctgctt    660
gatagtgtgc atgtcctgtg tccacataga cacaaataat gtctgctccc tatgattaca    720
cagtgaatgt ttatagggc                                                 739
```

```
<210> SEQ ID NO 101
<211> LENGTH: 1474
<212> TYPE: DNA
<213> ORGANISM: Eucalyptus grandis

<400> SEQUENCE: 101 aagcacagg gaagaagaaa agaatccgtg caaaatcatc tgctaaaaga aagttacaac      60
tcaccaagtc actccaattg tgtcctagac agtacccaga gcacgactat ggccaaacaa    120
aaccaattct cattcctcac atcagctgct cttttggtca ttatagtttc tgtttcggaa    180
acgctttgtc gccctcttga agaggaacag ttgttaaagc aacatgagga gtggatggca    240
atccacgggc gtgtctacaa ggacgcggtc gaaaaggcaa acggtatga gatatttaaa     300 gagaacgtta agcgcatcaa cgcctttaat aatggtaagg acgtggggta taaaatggct    360
gtgaataagt tcgcagacct aaccaatgag gagttccgcg cttcctacac cggctacaag    420
aggaggccca aagggtcct gtcctctggc gaaaaaaac cgttcaagta tgccaacttc      480
accgccattc cagctgcctt agactggcga accaagaagg ctgtgacacc tgttaaggat    540
caaggcggct gtggaagttg ttgggcattc tcggctgtgg cagctatgga agggattacc    600
atgatcaaga aggggaagtt ggtgccactc tcggtgcaag aactcgtgga ttgtgatgat    660
aacgatgaag gttgcagggg cgggctcatg gacagtgcct tcaagttcat tgtaagcaat    720
ggtggcctca cgactgaggc gaactatcct taccagggaa atgacgggac ctgcaatacg    780
gccaagacgg caaaccccgc agcctcaata actgggtatc aggatgtgcc ggccaacaac    840
gagaaggccc tcttgcaggc cgtggcaaac cagccagtct cggtggcaat tgagggggc     900 gggtataatt tccaattcta ctcaagcggc gtgttcacag gctcatgtgg gaccgacatc    960
gaccacgcgg tcacggcagt cgggtatggg aagacctctg gctctggcgg gaccaagtat   1020
tggctgatga agaattcgtg gggcaccggg tggggagaga aaggtacat gaggatccag    1080 aaggatgtga gctctaaggc tggtctctgt ggtcttgcca cggaagcttc ttatccagct   1140
gcatgaagaa ataagaagat gaaaaaataa attatgagtc catatatgtg atagtggttc   1200
ttgggctctc tatatgtatg aaatgtagtc tagcgtctct gtaaagaag caagttttaa    1260 gtgacagtac gtcactaggg ttggtgtgtc ctacaacaga aactaaatgt tgtaagcaaa   1320
attaggagcc tactaactaa acttggttct aagtgttcaa ataaatgtgt gggacaagat   1380
aaaagaacag tcccgtgaat gaatggaaca gtttcgtcag cgtaattta tagtaaaaaa    1440 aaaaaaaaaa aaaactcgag actaggtctc tctc                              1474
```

```
<210> SEQ ID NO 102
<211> LENGTH: 2167
<212> TYPE: DNA
<213> ORGANISM: Pinus radiata

<400> SEQUENCE: 102
aagaaaatcg tcttcccctt tctccacaca aattctcatt atctctctga attttgttgt     60
```

-continued

```
tatttcgtga tggcgagtgt ttcaaaggca accctgttac tcttccttgc gaccaccttg      120
tggactttat cagccaatgc ttcggattct tcccccggat ttacagatga agacctcaag      180
tctgaggaaa gtctgcgact cctttatgac aaatgggcac ttcggcatcg caccaccaga      240
agtttggatt cggatgagca tgccaaacga ttcgagatat tcaaagacaa tgtgaaatat      300
atcgactccg tgaatcagaa ggatggtcca tacaaacttg gattgaataa gtttacagat      360
ctgagtaacg aagaattcaa ggccatgcac atgacaacta gaatggagaa gcacaagagt      420
ctgcgccgag acagaggaac acacagtgga tcattcatgt accaaaactc cgacaacctg      480
ccagagtcta ttgattggag agaaaaggga gccgttaatc ctgtgaagaa ccaaggccaa      540
tgtggaagtt gttgggcatt ttcaactata gcttctgtag agggcattag ctatgtcaaa      600
acagggaagc tggtttcttt atccgagcaa cagttggtag attgcagtaa agagaacgca      660
ggctgcaacg gagggcttat ggacagcgcc ttccaatata tcatagataa tggtgggatc      720
gttgctgaag atgagtatcc atatactgct gaagccagcg aatgcagtcc ctccaaggtt      780
aaaccgaatg caatagcagc aactattgat ggttttgaag atgttcctgc taacaatgaa      840
aaagctctta agaagcagt gggccaccaa cctgtgtctg tcgccattga agcaagtggt      900
aaagattttc aattttattc aaaaggagta ttcactggtg aatgtggcac tgaacttgac      960
catggagttg tagccgttgg ttatggcaag tctcctgagg gaattaatta ttggatagtt     1020
aggaactctt ggggacctga atggggagaa gaagggtata taaaaatgca acgagatatt     1080
gaagcagtag aagggaagtg tggtattgcc atgcaagctt catatccgac gaagaaaaca     1140
caaggcattg atattgaact ggatgtcgct catgttagtg acgaactgtg aaaattgtct     1200
caacaaaaaa ttggtattgt gaattcaata atatgaagat tcgttcttca tttattagtt     1260
aaatttagtc attatactac attattgttc ataggtacgc gttccacgag cgccacgaga     1320
agaaacaaga cgaggaaacc gaggaagccg aaggtggccg caagcctcgc cacaatctct     1380
tctgaatttg gccatgcctc tctaatggtg gacttttgga gcaaaagcca attatagcag     1440
ttggtgatta ctatgttcag tgttaagtag taataaagtt atgtaatttt ttttcagtgg     1500
acttgttaca gtaaggtagt taggtgctgt cgttacttga gttacagttc agttgaattt     1560
gtgatatgta tctctgtata tgagtgaata taaagtacct cagatcactg tttgctttga     1620
cattgatgcc aatggtatcc tgaacgtctc tgctgaggat aaaacgacgg ggcagaaaaa     1680
caagatcacc attaccaatg acaagggcag gctaagcaag gatgagatag aaaagatggt     1740
tcaggatgca gagaaataca aggctgagga tgaagagctc aaattgaagg tagaagctaa     1800
aaattctcta gagaactatg catacaacat gaggaatacc atcaaagatg ataagattgc     1860
aggaaagttg gaccctgctg acaagaagaa aatcgaggat gcagttgatg gaattatcag     1920
ctggttggat ggaaaccagt tggccagaa ggaagagttt gaggataagt tgaaagagct     1980
ggagtctact tgcaatccta tcattgcaaa aatgtaccag ggtgaagggg gtgcgggatt     2040
tccaggtgct gatgcttttg gtggagcttc tggagctggt gacgagggtg caagtggccc     2100
tggtcccaag atcgaggaag tcgactagat atatttcttc atcacctcct acgtgttttt     2160
tttgtta                                                              2167
```

<210> SEQ ID NO 103
<211> LENGTH: 557
<212> TYPE: DNA
<213> ORGANISM: Eucalyptus grandis

<400> SEQUENCE: 103

```
gaagattatc cgtataaagc tgtcgatggc aaatgtgacc aatatcgaaa gaatgccaaa      60
gttgttacga tagatgatta tgaagatgtt ccagcgaacg atgagaaagc attgcaaaag     120
gcagttgcta atcaaccagt gagtgtggcc attgaagccg tggtcgggc atttcagttg      180
taccagtcgg gtgttttcag tggacgatgt ggtactgcac tggaccacgg agtgactgcc     240
gtaggatatg gcacagaaaa aggtatgaat tactggatcg taaagaactc ttggggcaaa     300
agctggggag agcagggtta catcagaatg gagcgtagct tgaccaatac tataactggc     360
aagtgtggga tcgcaatgga agcatcttac cccatcaaaa atggcccgaa tccccgaac      420
ccagggccat ctccccgtc tccaataaaa ccaccgacca cttgtgatcg ttattactct      480
tgtgctgaga gcacgacttg ctgctgcgtc tatcagtatg ccaactattg cttcgcctgg     540
ggatgctgcc cgcttga                                                    557
```

<210> SEQ ID NO 104
<211> LENGTH: 482
<212> TYPE: DNA
<213> ORGANISM: Eucalyptus grandis

<400> SEQUENCE: 104

```
catcaacacc caggaactcc tcccaagtca attctttcaa gtaccaaggt tcgaatagca      60
tcccagagag catcgattgg gtccaaaaag gtgctgtcaa ccctatcaaa taccaacgtc     120
aatgtggatc ttgctggtcg ttctccgtgg tggcggcagt agaagcaatc acacagatca     180
ccactggcgt gctaccgagc ctgtccgagc agcaactcat agactgcacc actgatggga     240
accacggctg tgaaggcggc tcaatggaca atggcttcga gtacatcatc aacaataacg     300
gcatcagctc cgagacgaac tacccatacg ttggggtcga cggcacctgc aatgtgcagg     360
cctcctctgt cgccgaggcc aaaatatcag accacaagga cgtcccctca acgaggatg      420
acatgctgaa ggccgtggcg atgcagccgg tgtcggcggc aatcgatgca acggagacg      480
tg                                                                    482
```

<210> SEQ ID NO 105
<211> LENGTH: 817
<212> TYPE: DNA
<213> ORGANISM: Eucalyptus grandis

<400> SEQUENCE: 105

```
agtcactcca attgtgtcct agatagtacc cacaccagta ctatggccaa acaaaaccaa      60
ctcccattcc tcacattagc cactcttttg gtcatcatag tttttgtttc ggaaacgctt     120
tgccgccccc ttggagagga acacctgtta aagcaacatg agcagtggat ggcggttcac     180
gggcgcgtgt acaaggatgc ggatgaaaaa gcgaaacggt atgagatatt caaacagaac     240
gttaaccgca tcaacgcctt taataatgat aaggacgcgg cgtataaact ggctgtgaac     300
aagttcgcgg acctaaccaa cgaggagttc cgcgcttcct tcaccggcta caagaggagg     360
tccacccgtg tcctgacctc tgtggacgag aaaccgttca gtacgcgaaa cttcaccgct     420
gctccacccg tcttggactg gcgaaccaag aaagctgtga catctgtcaa ggatcaaagc     480
agctgtgag cttgttgggc gttctcggct gtggcggcta tggaagggat taccatgctc     540
aagaagggga agttggtgtc actctcggag caagaactcg tggattgcga tgttaacggt     600
gtcaaccaag gctgcgaggg cgggctcatg gacagtgcct tccagttcat caaaagcaag     660
ggtggcctca cctccgaggc aaactaccct ttccagggga atgacgggac ctgcagaacg     720
```

```
gccaaggcgg cgaatatcgt ggcctcgata gcaggctacc aggatgtgcc ggccaacaat      780
gagaaggccc ttctgcaggc ccgtggcgaa ccagcca                               817

<210> SEQ ID NO 106
<211> LENGTH: 368
<212> TYPE: DNA
<213> ORGANISM: Eucalyptus grandis

<400> SEQUENCE: 106
agtcactcca attgtgtcct agatagtacc cacaccagta ctatggccaa acaaaaccaa       60
ctcccattcc tcacattagc cactcttttg gtcatcatag tttctgtttc ggaaacgctt      120
tgccgccctc tcggagagga acacctgtta aagcaacatg agcagtggat ggcggttcac      180
gggcgtgtgt acaaggacgc ggatgaaaaa gcgaacggt  atgagatatt caaacagaac      240
gttaaccgca tcaacgcctt taataatgat aaggacgcgg ggtataaact ggctgtgaac      300
aagttcgcgg acctaaccaa cgaggagttc cgcgcttcct tcaccggcta caagaggagg      360
tccacccg                                                              368

<210> SEQ ID NO 107
<211> LENGTH: 1407
<212> TYPE: DNA
<213> ORGANISM: Eucalyptus grandis

<400> SEQUENCE: 107
ccgacccaca tttcttggaa tccacagaga gagagagaga gagagagaga gagagaaatg       60
gctcgcgcga ggctcctgtg ctccgccgtc tcctcctcg  tcgccgtcgt cgtctccgcc      120
gcggcgtcga gcttcgagga gtccaacccc atccggctct tccccgacgg cggcctccgc      180
gacctcgagt cctccatcgt ccagatcgtc ggccgcaccc gccacgcctt ctccttcgcc      240
cgcttcgcca acaggtatgg gaagaggtac gagaccgcgg aggagatcaa gctgcggttc      300
gagatcttca gggagaatct caagttgatc cgatccacca caagaagggg cttgccctac      360
accctcggtg tcaataagtt tgctgattgg agctgggagg agttcaggag gcacagactg      420
ggagctgctc aaaactgctc tgccaccacc aagggcaacc acaagctcac cgacgaagct      480
cttcccgaga tgaaagactg gagagaaaag ggcattgtaa gcccaattaa agatcagggg      540
cactgtggat cttgctggac tttcagtacc actggagctc ttgaggctgc ttatcaccaa      600
gcattcggga acaaatctc  tctgtctgag cagcagctcg tggactgtgc tggggctttc      660
aacaactttg gatgtagtgg tggactgcca tcccaagcct ttgagtacgt caagtacaac      720
ggtggccttg ataccgagga agcatatcct tataccgcag tggatggtag ctgcaaattc      780
tcggctgata tgttggtgt  ccaagtgctc gactctgtta acatcacctt gggtgctgag      840
gatgaactaa agcatgcagt tgccttcgtc cggccagtga gtgtggcatt ccaggtcgtg      900
aaagacttca gattgtacaa gtcgggtgtc tacacgagcg atacatgcgg tagcacttcc      960
atggatgtga accatgctgt tctcgctgtt ggttatggag ttgaagatgg tgttccgttc     1020
tggctcatca agaattcctg gggagcagac tggggtgacc acggatactt caagatggag     1080
atgggaaaga acatgtgtgg agtcgctact tgtgcatcat accctgttgt ggcctagatt     1140
gtttccagag gatcaatggg ttcgtgtgcc aggtaattcg agatatatat atatttcgca     1200
tgaagaattg ctccgccctg agttggaatg ctatagtgtt agcacaaaag gggtttagctt    1260 agtgcaaaaa ataatcatca ggacagctgc aactccatat ggttattgtt atatgaacaa     1320
```

```
agaccttgta ataccttto tatgtttgtg tggcatggaa cgctatcttt gcaagaataa      1380
cgcatcaaat tcccaccaaa aaaaaaa                                         1407
```

<210> SEQ ID NO 108
<211> LENGTH: 388
<212> TYPE: DNA
<213> ORGANISM: Pinus radiata

<400> SEQUENCE: 108

```
agccatgcat atgaaaacca ggatggagaa gcacaggagc ctgcgcggag acagaggagt       60
gcagggtgga tcattcatgt atcaaaactc taagcacctg ccggcgtcta tcgattggag      120
aaaaaaggga gcggttactc cagtgaagaa tcaaggccaa tgcggaagtt gttgggcatt      180
ttcaactgta gcttcggtag agggcattaa ctatatcaaa acagggaagc tggtttcttt      240
atcagagcaa cagttggtag attgcagtaa agagaacgca ggttgcaacg gagggcttat      300
ggacaacgcc tttcaatata tcatagataa tggcgggatc gttagtgaag cagagtatcc      360
ttacactgcc gaagctaggg agtgcagt                                         388
```

<210> SEQ ID NO 109
<211> LENGTH: 1062
<212> TYPE: DNA
<213> ORGANISM: Eucalyptus grandis

<400> SEQUENCE: 109

```
gctcaaccca agttgagaga acatcatcat gggttcttct ccaagaactc atcatcaact       60
aggtcttgcc atcctcttct ttgcttccct cgcgcgcctg tctctgtcac acgcctctct      120
ccccagcgag tactcgatca tcggccatgg acaggacccg aatggcgccg tgtcggacga      180
acgtgccgtc gagctcttcc ggagatggca ggcgcagcac aagaaggtgt acaagcacgc      240
cggggaggcc gagaggcggc tcgagaactt caaaaggaac ctgaggtacg tgatggagag      300
aagccggagg gatggcggca agcagcatgg cgtgggctg aacaagttcg ccgacctgag      360
caacgaggag ttcaggcagc gctacctgtc caaggtgaag aagtcggtga accagaagtg      420
gagggccaag agggagagct tgatgaggaa caagaggaag ggagcggagt cctgcaaggc      480
gccgtcgtct ctggattgga ggaactacgg cattgtcacc ggcgtgaagg accagggaga      540
atgcggaagt tgctgggcgt tctcttcgac cggagcaatg gaaggaatca atgcgctcaa      600
gagcggggac ctgatcagcc tttccgagca agagctcgtg gactgcgaca ccaccaacga      660
cggctgcgac ggcggctaca tggactatgc gttcgagtgg gtcatcaaca acggcggtat      720
cgattcggaa gaagactatc cctacaccag cgtctttggc gagggtggta tctgcaacgt      780
caccaaggag gagaacaaca aggcggtcac cattgatggg tatgtggacg tttatccgtc      840
ggacgacggc cttctctgca cggtcatcca acagccgatt agcgtcggca tggacggctc      900
ggcgatagat ttccagctct acactggggg catctacgac ggtagctgtt cagcgaatcc      960
cgacgacatc gaccatgcgg tcctgatagt tggttatggc tccgaaggcg gcgaagatta     1020
ttggatcgtg aaagaactcc ttggggaaca gatttgggga gt                        1062
```

<210> SEQ ID NO 110
<211> LENGTH: 765
<212> TYPE: DNA
<213> ORGANISM: Eucalyptus grandis

<400> SEQUENCE: 110

```
caagctcaac ccaagttgag agaacatcat catgggttct tctccaagaa ctcatcatca       60
```

```
actaggtctt gccatcctcg tctttgcttc cctcgcgcgc ctgtctctgt cacacgcctc    120
tctccccagc gagtactcga tcatcggcca tggacaggac ccgaacggcg ccgtgtcgga    180
cgaacgagcc gtcgagctct ccggagatg gcaggcgcag cacaagaagg tgtacaagca     240
cgccggggag gccgagaggc ggctcgagaa cttcaaaagg aacctgaggt acgtgatgga    300
gagaagccag agggatggcg gcaagcagca tggcgtgggg ctgaacaagt tcgccgacct    360
gagcaacgag gagttcaggc agctctacct gtccaaggtg aagaagtcgg tgaaccagaa    420
gtggagggcc aagagggaga gcttgatgag gaacaagagg aagggagcgg agtcctgcaa    480
ggcgccgtcg tctctggact ggaggaacta cggcattgtc accggcgtga aggaccaggg    540
agaatgcgga agttgctggg cgttctcttc gaccggagca atggaaggaa tcaatgcgct    600
caagagcggt gacctgatca gcctttccga gcaagagctc gtggactgcg acaccaccaa    660
cgacgggtgc gacggcggct acatggacta tgccttcgag tgggtcatca acaacggcgg    720
tatcgattcg gaagaagact atccctacac cagcgtcttt ggcga                   765

<210> SEQ ID NO 111
<211> LENGTH: 677
<212> TYPE: DNA
<213> ORGANISM: Eucalyptus grandis

<400> SEQUENCE: 111
gagagagaga gagagaatgg ctggtgctag atttctgtgt tccttcctcc tcctcttgac     60
cgcttgctcc gccacagcag ctggcttcca gggcgccgac ctcgagtcct ccatcctcca    120
aaccgttggc cacggccgtc ccgccctctc cttcgtagac tttgccagca ggtacgagaa    180
gaggtacgag acagcggagg agatcaagtt gaggttcgat aattacaggg agaatctcaa    240
gctcattcga tccaccaacc agaagggctt gccttacact ctcgctgtta atcagtatgc    300
tgactggagc tgggaggagt tcaagacgca cagactggga gcttctcaag actgctctgc    360
caccaccaag ggcagccaca agctcaccga cgctgttctt cccaaaacga agactggag     420 aaaagagggc attgtaagcc cagttaaaaa tcaaggcggc tgtggatctt gctggagttt    480
cagcgccact ggagctctcg aggctgctta tcaccaagca cacgggaaag gaatctctct    540
gtctgagcag cagctcgtgg actgcgctac ggctttcaac aactttggat gcgatggcgg    600
gttgccgtca caagccttcg agtacatcaa gtacaacggt ggccttgaga ccgaggaagc    660
ttatccttat actgcac                                                   677

<210> SEQ ID NO 112
<211> LENGTH: 522
<212> TYPE: DNA
<213> ORGANISM: Eucalyptus grandis

<400> SEQUENCE: 112
cacagtttgt ggaaaccaca gggagagaga gagagagaga gaatggctgg tgctagattt     60
ctgtgttcct tcctcctcgt cgtgaccgct tgctccgccg cagcagctgg cttcgagggc    120
gctgaccttg agtcctccat cctccaaacc gtcgccacac ccgtccgc cctctccttc      180 gtagacttcg cccgcgggca cggaagact acaagacag cggaggagat caagttgagg     240
ttcgataatt acagggagaa tctcaagctc attcgatcca ccaaccagaa gggcttgcct    300
tacactctcg ctgttaatca gtatgctgac tggagctggg aggagttcaa gacgcacaga    360
ctgggagctt ctcaagactg ctctgccacc accaagggca gccacaagct caccgacgat    420
```

```
gttcttcccg aaacgaaaga ctgggagaga aaagggcatt gtaggcccca gttaaagatc    480
aaggcggctt gtggatcttg ctggagtttc agcgcaactg ga                       522
```

<210> SEQ ID NO 113
<211> LENGTH: 392
<212> TYPE: DNA
<213> ORGANISM: Eucalyptus grandis

<400> SEQUENCE: 113

```
ctggattggg tggcaaaagg agccgtaaat gccataaaag atcaaggtcg atgtggctct     60
tgctgggcct tctcagcggt agcggcaata gaatcgatta cccagatcaa gactggtaag    120
ttactggaac tatcagagca acaattggta gactgtacta tcgaaaacta tggctgcagt    180
gggggttgga tggacaccgc gttcgactac ataatacaaa atggaggcat ctcctctgaa    240
actaattatc cctacaattc atcggacgga acatgcaatg ctcacatggc gtccctgagc    300
gtggccaaaa ttgtgggtta tgaggatgtc cctgacaaca atgagggaga gatcttaaag    360
gccgtggcga tgcaaccggt ctcggtcgcc ct                                  392
```

<210> SEQ ID NO 114
<211> LENGTH: 835
<212> TYPE: DNA
<213> ORGANISM: Eucalyptus grandis

<400> SEQUENCE: 114

```
tcttcttctg cgcactcttc accaaccatg aatcgcttcc tctctctcct cgctctcttc     60
tccctcgcca tcgtctcggc ctacgcctcc tcggaggtcg acggcgatgc gctgatccgg    120
caggtcgtgg acgcgccgc cgccgatggc gacctctcga ccgaggacca ccgccacttc    180
tcgctcttca gaggcgtttt cggcaagtcg tacgcctccc aggaggagca cgatcaccga    240
ttcgcggtgt tcagggcgaa cctgcgccgc gcgaggaggc accaggagct cgatccctcg    300
gcggtccacg gcgtcactcg gttctccgac ctgacgccct ccgagttcag gaggagtcat    360
ttggggatca gaggcgggct ccggttgccg aaggacgcga atgaggcccc gctcctgccg    420
accgacgacc tgcccgagga tttcgattgg agagatcacg gagctgtcac cggtgtcaaa    480
aatcaaggct cgtgtgggtc atgctggagt ttcagcgcga caggagcact ggaaggcgcg    540
cattaccttg ctactggaga actagttagc ctcagcgagc aacaacttgt ggattgtgat    600
catgagtgtg atccagatga acccggttca tgtgactctg gatgcaatgg tggattgatg    660
aacagtgctt ttgagtacac tcttaaagca ggtgggctta tgcgagaggg tgactacccc    720
tacactggca ctgatcgcgg aacttgcaaa tttgacaagt ccaagattgc tgcatcagtg    780
tccaacttca gcgttgtttc ccttaatgaa gatcaaattg cagcaaatct tgtga         835
```

<210> SEQ ID NO 115
<211> LENGTH: 291
<212> TYPE: DNA
<213> ORGANISM: Pinus radiata

<400> SEQUENCE: 115

```
cttcgctctc cgagcaagag ctcatcgact gtgacacaac ttacaacaat gggtgcaatg     60
gcggtctcat ggactatgca ttctcttaca ttatctcaaa tggcgggctt cacaaggaag    120
aagactatcc ttacatcatg gaagaaggaa cctgcgagat gaccaaggac caatcggagg    180
tggtaactat cactggctac aaggatgtgc cggtggacaa tgagcagggc ctcttgaagg    240
cactcgccaa ccagccactc agtgttgcca tcgaagcctc gggcagagac t             291
```

<210> SEQ ID NO 116
<211> LENGTH: 445
<212> TYPE: DNA
<213> ORGANISM: Eucalyptus grandis

<400> SEQUENCE: 116

| | | | | | |
|---|---|---|---|---|---|
| aaaatgaccc | tcgaggcggc | ctcaaacctc | ccgacatctt | gttcaccccg | attattgcag | 60 |
| ttctccgacc | tgaccccgtc | ggagttccgg | aggacgcacc | tggggctccg | gaggaaggtc | 120 |
| aagctgccca | aggacgcgaa | cgaggcgccg | atcttgccca | cccaggatct | gccgaaagat | 180 |
| ttcgattgga | gagatcatgg | agccgtcacc | gcggtcaaga | atcagggttc | atgcggatcg | 240 |
| tgctggagtt | tcagcaccac | cggagccttg | aaggcgcaa | actaccttgc | aaccgggaaa | 300 |
| cttgtcagcc | tcagcgagca | acagcttgtg | gactgtgatc | acgagtgtga | tccagaagaa | 360 |
| ccaggttcct | gtgactcggg | ttgcaatggt | ggtttgatga | acagtgcctt | tgaatacact | 420 |
| ctcagtaccg | gtgtatgggt | agtct | | | | 445 |

<210> SEQ ID NO 117
<211> LENGTH: 360
<212> TYPE: DNA
<213> ORGANISM: Eucalyptus grandis

<400> SEQUENCE: 117

| | | | | | |
|---|---|---|---|---|---|
| ggcccaccag | ggtcctgtcc | tctgtggatg | tgaaaccgtt | caagtacgcg | aacttcaccg | 60 |
| ccattccagc | tgccttggat | tggcgaacca | agaaggccgt | gacgtctgtc | aaggatcaag | 120 |
| gcgtctgcgg | atgttgttgg | gcattctcgg | cagtggcagc | tatggaaggg | cttacccagc | 180 |
| tcaagaagag | gaagttggtg | ccactctcgg | tgcaagaact | tgtcgattgc | gatgttaatg | 240 |
| gtaaggataa | aggctgcagg | ggcggttaca | tggacagtgc | ctttgagttc | gtaataagca | 300 |
| acggcggcct | cacgactgag | gcagaatatc | cttaccaggg | aactgaccgg | acctgcaaca | 360 |

<210> SEQ ID NO 118
<211> LENGTH: 1428
<212> TYPE: DNA
<213> ORGANISM: Pinus radiata

<400> SEQUENCE: 118

| | | | | | |
|---|---|---|---|---|---|
| aattgctcaa | caatgggatc | ctccacgctg | ctgcttttgg | ctctctgtat | ttcctctgta | 60 |
| atttgccttt | cctcggccat | aaggcctgac | gatgacctta | ttcgtcaagt | gacggacgaa | 120 |
| gtagattcag | atccacagat | cctcgatgct | cggagcgccc | tgttcaacgc | tgaagcgcac | 180 |
| ttcaggcgct | tcatcaggcg | ctacgggaag | aagtactcgg | ggccggaaga | gcacgagcac | 240 |
| cgcttcggtg | tcttcaagag | caatttacta | agagccttgg | agcaccagaa | gctcgacccc | 300 |
| caggcctccc | atggcgtcac | agaattctct | gatttgacac | aagaggagtt | ccgacgacag | 360 |
| tatctagggc | tcagggcacc | accgatccga | gacgcccacg | atgctccaat | tttgcccaca | 420 |
| aacgatctgc | cggaggagtt | cgattggaga | gagaagggag | ccgtgaccga | ggttaagaat | 480 |
| cagggatcgt | gcggttcctg | ctgggctttc | agcacaaccg | gggcgctaga | gggcgcgaat | 540 |
| ttcctgaaga | cggggaagct | ggtgagcctg | agcgagcaac | aattggtgga | ctgcgatcac | 600 |
| gagtgcgatc | cttcggacgc | aagatcatgt | gattctggtt | gcaatggtgg | gctaatgacg | 660 |
| agtgcttatc | aatatgctct | gaaagctggt | ggattggaga | aggaagagga | ctacccatat | 720 |
| actggaaaag | acggaacttg | cagctttaac | aagaacaaaa | ttgtggcaca | ggtttcgaat | 780 |

-continued

```
ttcagcgttg tttctattga tgaagatcaa attgctgcaa atctggtgaa gaatggacct    840
ctatcagtgg gaatcaatgc tgcatttatg cagacatacg taggaggtgt atcttgccca    900
tacatctgca gcaagcgcat gttggatcat ggtgtgctcc tggtaggata tggttctgca    960
ggctttgctc ccattagaat gaaggacaaa ccctactgga tcataaagaa ctcatgggga   1020
cctaactggg gagaaaatgg attctacaaa cttttgcaggg gacataacgt ttgcggaatc   1080
aacaacatgg tttccactgt tgcagctatc tgagcattca aattagatca gtttcttgta   1140
tatacctgtt tctttagact ttggttgaaa ctatgttgtt gaatgcacat acatattcaa   1200
tatacattga atatagttta tcaagtata ctgaaggatt taagtattta aaggatttac   1260
aaatgaagca ctctgatgaa tactcttaag aatattaata tggtttgtgg ttcaaaaaac   1320
tgccagtcaa gggcttcaaa ctctggtttc caagtttgtt tgaggtgatg taaatatggg   1380
agtttatgat ttgtcataat atgggaaatt gtcgaatcaa aaaaaaaa               1428
```

<210> SEQ ID NO 119
<211> LENGTH: 413
<212> TYPE: DNA
<213> ORGANISM: Pinus radiata

<400> SEQUENCE: 119

```
ctcaacaatg ggatcctcca cgctgctgct tttggctctc tgtatttcct ctgtaatttg     60
cctttcctcg gccataaggc ctgacgatga ccttattcgt caagtgacgg acgaagtaga    120
ttcagaccca cagatcctcg atgctcggag cgccctgttc aacgctgaag cgcacttcag    180
gcgcttcatc aggcgctacg ataagaagta ctcggggccg aagagcacg agcatcgctt    240 cggtgtcttc aagagcaatt tactaagagc cttggagcac cagaagctcg accccaggc    300 ctcccatggc gtcacagaat tctctgattt gacacaagag gagttccgac gacagtatct    360
agggctcagg gcaccaccga tccgagacgc ccacgatgct ccaattttgc cca           413
```

<210> SEQ ID NO 120
<211> LENGTH: 475
<212> TYPE: DNA
<213> ORGANISM: Pinus radiata

<400> SEQUENCE: 120

```
caatcccaag tctctagagt ttgcggagtt cgctgtcaga tatggcaaga ggtacgattc     60
tgtccatcag cttgtgcata gattcaatgt ctttgtgaag aacgtggagc tgatcgagtc    120
aagaaacaga atgaagcttc cttatacttt ggcaataaat gagtttgctg acataacatg    180
ggaggaattc catggacaat atttgggtgc ttcacagaac tgttcggcta cccacagtaa    240
ccataagttg acgtatgccc agcttcctgc gaagaaagac tggagacaag aaggcatagt    300
gagtcctgta aaaaccaag cccattgtgg atcctgctgg acattcagca ctactggagc    360
actagaagct gcctatactc aggctacagg aaagactgtt atcctgtctg aacagcagct    420
ggttgactgt gctggagcat ttaacaactt tggttgcaat ggtggactgc catcc         475
```

<210> SEQ ID NO 121
<211> LENGTH: 399
<212> TYPE: DNA
<213> ORGANISM: Eucalyptus grandis

<400> SEQUENCE: 121

```
cagcggcgga gagatggaca ccgcgttttc cttcatccaa cgcaacggcg gcatcacttc     60
cgagtccgat tatccctacc gaggacggga cggatcttgc gacgcggcca tgctcaggag    120
```

```
tcacgcggcc acgattagcg gatacggcga tgtgccccc  aacgatgagc ggagcctgca    180
agccgcggtg gctcgccaac cgatctccgt ggccatcgac gcgggcggac tggaattcca    240
gctatactcc aggggatttt tcacgggcat atgcggatac gacttgaatc acgggtggc     300 ggcggtcggg tacggatccg agggctcgag aaattattgg atcgtgaaga attcgtgggg    360
gcgcgactgg ggcgaggacg gctacgtaag gatgctcaa                           399
```

<210> SEQ ID NO 122
<211> LENGTH: 441
<212> TYPE: DNA
<213> ORGANISM: Pinus radiata

<400> SEQUENCE: 122

```
acatacaagc ttggattgaa taaatttgca gatctgagta acgaagaatt caaagccatg     60
catatgacaa ccacgatgga gaaccacagg agtctgcgca gagatagagg agtgcagagt    120
ggatcattca tgtatcaaaa ttcgaagcat ttgccagcat ctattgattg gagaaaaaag    180
ggagctgtta ctccggtgaa gagtcaaggc caatgcggaa gttgttgggc attttcaact    240
gtagcttcgg tagagggcat taactatatc aaaacaggga agctggtttc tttatcagag    300
cacaggttgg tagattgcag taaagagaac gcaggttgca atggaggact tatggataac    360
gccttccaat atatcataga taatggcggg atcgttagtg aagcagagta tccttacact    420
gccgaagcga gcgagtgcag t                                              441
```

<210> SEQ ID NO 123
<211> LENGTH: 370
<212> TYPE: DNA
<213> ORGANISM: Pinus radiata

<400> SEQUENCE: 123

```
gatggcgagt gtttccaagg caaccctgtt actcttcctt gcgaccacct tgtggacttt     60
atcagcccat gcttcggatt cttccctgg atttacagat gaagacctca agtctgagga    120
aagtctgcga ctccttttatg acaaatgggc acttcggcat cgcaccacca gaagtttgga   180
ttcggatgag catgccaaac gattcgagat attcaaagac aatgtgaaat atatcgactc    240
cgtgaatcag aaggatggtc catacaaact tggattgaat aagtttacag atctgagtaa    300
cgaagaattc aaggccatgc acatgacaac tagaatggag aagcacaaga gtctgcgccg    360
agacagagga                                                          370
```

<210> SEQ ID NO 124
<211> LENGTH: 370
<212> TYPE: DNA
<213> ORGANISM: Pinus radiata

<400> SEQUENCE: 124

```
gatggcgagt gtttccaagg caaccctgtt actcttcctt gcgaccacct tgtggacttt     60
atcagcccat gcttcggatt cttccctgg atttacagat gaagacctca agtctgagga    120
aagtctgcga ctccttttatg acaaatgggc acttcggcat cgcaccacca gaagtttgga   180
ttcggatgag catgccaaac gattcgagat attcaaagac aatgtgaaat atatcgactc    240
cgtgaatcag aaggatggtc catacaaact tggattgaat aagtttacag atctgagtaa    300
cgaagaattc aaggccatgc acatgacaac tagaatggag aagcacaaga gtctgcgccg    360
agacagagga                                                          370
```

<210> SEQ ID NO 125
<211> LENGTH: 392
<212> TYPE: DNA
<213> ORGANISM: Eucalyptus grandis

<400> SEQUENCE: 125

| | | | | | |
|---|---|---|---|---|---|
| gcaaactata | agaatccatc | cacccccct | cctctctctc | tatctctaac | aaacttctgc | 60 |
| accagaagct | cgacccctcg | gccgcccacg | gcgtgacgca | gttctccgac | ctgaccccgt | 120 |
| cggagttccg | gaggacgcac | ctggggctcc | ggaggaaggt | caagctgccc | aaggacgcga | 180 |
| acgaggcgcc | gatcttgccc | acccaggatc | tgccgaaaga | tttcgattgg | agagatcatg | 240 |
| gagccgtcac | cgcggtcaag | aatcagggtt | catgcggatc | gtgctggagt | ttcagcacca | 300 |
| ccggagcctt | ggaaggcgca | aactaccttg | caaccgggaa | acttgtcagc | ctcagcgagc | 360 |
| aacagcttgt | ggactgtgat | cacgagtgtg | at | | | 392 |

<210> SEQ ID NO 126
<211> LENGTH: 452
<212> TYPE: DNA
<213> ORGANISM: Eucalyptus grandis

<400> SEQUENCE: 126

| | | | | | |
|---|---|---|---|---|---|
| ggcacgagct | taggcaactc | attgttcatt | gttaaccttc | tctcttcctt | gagaggaacc | 60 |
| ccaaaggagt | tacgaagtaa | tggcttcttc | ttcctccaag | gggcccaaaa | ggagttacga | 120 |
| tgcaatggct | tcttcttcct | ccaagaagcc | agaagaagt | tacgatgtct | tcctgagttt | 180 |
| cagaggtcca | gatgtccgca | atcactttct | cagtcatctc | tacgtagctc | tagatcaagc | 240 |
| agggatatcc | acttacatcg | acaaaaaaga | gctggggaag | ggagaacaaa | tatcacctgc | 300 |
| acttatgaaa | gcgatcgagg | aatcgcacat | cgcgatcgtg | gttttctctg | aggactacgc | 360 |
| ctcttcgtca | tggtgtttgg | aagagttaac | gaaaatcatg | gagtgcaagg | agcaaaaagg | 420 |
| cctcatggtc | tttccagtgt | tttacaaagt | ag | | | 452 |

<210> SEQ ID NO 127
<211> LENGTH: 452
<212> TYPE: DNA
<213> ORGANISM: Eucalyptus grandis

<400> SEQUENCE: 127

| | | | | | |
|---|---|---|---|---|---|
| gcaactcatt | gttcattgtt | aaccttctct | cttccttgag | aggaacccca | aaggagttac | 60 |
| gaagtaatgg | cttcttctcc | ctccaaggag | cccaaaagga | gttacgatgt | cttcctgagt | 120 |
| ttcagaggtc | cagatgtccg | caatcacttt | ctcagtcatc | tctacgcagc | tctagatcaa | 180 |
| gtagggatat | ccacttacat | cgacaatgaa | gagctgagga | agggagaaca | aatatcacct | 240 |
| gcacttatga | aagcgattga | ggaatcgcaa | attgcaattg | tggttttctc | tgagaactac | 300 |
| gcctcttcaa | catggtgttt | ggaagagata | tcgaaaatca | tggagtgcaa | ggagaaaaaa | 360 |
| ggcctcaagg | tccttccggt | gttttacaaa | gtagaaccaa | gagaagtgag | agggcagaaa | 420 |
| cagagctatg | gaaaagctat | ggatgagcat | ga | | | 452 |

<210> SEQ ID NO 128
<211> LENGTH: 3095
<212> TYPE: DNA
<213> ORGANISM: Pinus radiata

<400> SEQUENCE: 128

| | | | | | |
|---|---|---|---|---|---|
| agctggagct | cgcgcgcctg | caggtcgaca | ctagtggatc | caaagaattc | ggcacgaggc | 60 |

```
tgttttgttt tcaatcgtgt gcccaaacat tggggtgttg atacacacac aagaatagca    120
aaggcgcagc tggtaagttg cttgccctcc agaatctttc tgacgcaaat attgagtctc    180
accgcacttt ctccatctct gcaaaatatc ttcgatctta cttctctgtt attctgtatc    240
caatggcaaa cgttaacttt accccgccg cccgtgacgg aacatcctcc gcatccacct     300
cccagggcaa taccaacagc tatgtgtatc aagtgtttct gaatcaccgc ggtcctgacg    360
taaagaaagg actcgctacc cacatctacc atcgtcttaa agatctcgga ttatcagttt    420
ttctggacca gcaagaactg caaagaggag agaagttgga gccccaaatc gaaggggcta    480
ttcgaacagc ttctgttcat gtagcgatat tctcgccaaa ttatgctcaa tctagatggt    540
gtctggatga actcgtccag atgttggaga tgttggagtc agggtccaca ataattccag    600
tcttctacaa agtagatccc gcagatctcc ggtggacgcg cggaggaaaa ggagtttatg    660
ctagagattt gggcgagctt gaaggaaga gagcatctga ttctcaggaa ccacggtacg      720
accccgagac catagaaaaa tggaggaatg ctctttctgc tgtggcggat atagtcggtt    780
ttgagctgaa ggacaaggaa gagtcgcagc tcgtccagga ggtcgtccaa caagttgtga    840
aaaaggttcg caaaccgcct ctcaacgtcg ccaaatatcc tactggcctc gatgaaaaaa    900
ttgaagatgt ggacagaaca ttgtcactgc agcggcaaag cgagaaggct acaattttgg    960
gaattgtagg ttttggcggg gtcgggaagt ctaccctggc taaacaattc ttcaaccgag    1020
aaagatcaaa ttacgatcga tcttgcttct tatctgatat cagatccaaa tctttgcctt    1080
ccgtgcagag tagccttctt aaggatctga ttcaatcgga tgcacaaata aatagcgttg    1140
ctgaaggcat agagaagctc aaaagagttt ctcaacggtg tcttatcatt ttagatgata    1200
ttgatcatat tgatcaaatg gatgcattat atgcacccgt tataaggtct attcatgtag    1260
gtagcttaat tttaattaca tcccgtaata aggatgtgct tagaagcgca ggcattggag    1320
agtcatccat ttgcacactg aaaggtctca atggagagca ctcgcaagag ctcttttgct    1380
ggcatgcctt cggtcgaccc agtcctgttg taggatttga aaaagtggtt gagaagtttt    1440
tgaatgcctg caatggtttg cccctctcgc ttaaagtgct tggggcgctc cttcatggaa    1500
aagacgattt gaagctttgg aatgcgcaat tgcgcaaaac ctccaaagta cttccggaag    1560
atatacggag cacacttaga attagctatg atgctctaga taaagaggaa aagcaaatat    1620
ttttagatat cgcctgtttc tttataggga aaaacaggga tagtgctata agagtatggg    1680
atggatccaa ctgggaaggg ttgctgggtc tttggaagct ggaaaacaga tgcctcgtgg    1740
aggtggacag ttcgaactgt ctcagaatgc atgaccacct tcgagacata ggcagaggta    1800
tagctgaata tctagaatat ccccgtcgtc tttggcattt cgaagagaat tttccttgtaa   1860 gtattctgaa gctttcgacg gactttcaaa atagccccttt gttatcaaaa ttgtctgtca    1920
atttctaaat cttaaaacta acagcttggg gtgaacaatt cagatgcagg tgcatggaat    1980
tagcaggtcc aaccgaagca tgttgcagct gcttaggact gaaagtgact ctgttgaacg    2040
aatattcagc agtgaacagt taccgccgct tgtatatctg cactggaagc gctgtccgaa    2100 gtcctctta gctccctgga ttccattaaa taatttaagt gtgttacata taggggggga     2160
tcaactggaa acactctcac tctggcaaca tgaatttcag gcacctctgc aattgaggga    2220
gttgcatatt gatgctcccc tttcaaaggt tccagagtcc attggaaaac tgaagtacct    2280
tgaaaaagtt catctggaga gcaagcagct gcagacgcta ccagagtcga ttgggaacct    2340
gtcgggcctc caaagtcttg acctgatcgg gtgctccagt ctgcagacac tcccagactc    2400
```

-continued

| | |
|---|---|
| agtggggaac ctgtcgggcc tccaaagtct taaattggtc ttctgcttca gtctgcagac | 2460 |
| actcccagac tcagtgggga acctgtcggg cctccaaagt cttgacttga tcgggtgctc | 2520 |
| cagtctgcag acactcccag actcagtggg aacctgtcg ggcctccaaa gtcttaactt | 2580 |
| gaacatgtgc aggagtctgc agacactccc agactcagtg gtaacctgt cgggcctcca | 2640 |
| aagtcttaac ttgagcgggt gcaggagtct gcagacactc ccagactcaa tggggaacct | 2700 |
| gtcgggcctc caaagtcttg acttgagctg gtgcaaaaaa ctgcggacac tcccacactc | 2760 |
| actggagaac ctgtcgggcc tccaacgtcg cgacgatgat tatttgaatt ttgatcacaa | 2820 |
| aatccacaaa atctgataag tgattttatt gggagttgtc tataatgcga cttttggag | 2880 |
| attccggtga cggaatccgg cggatgtaat gaggttaaat cttgattttt agcagttaaa | 2940 |
| atggtttttt aactggattc agcgccctga aaaaccctg ggagcctttc attgtgcaga | 3000 |
| aactagctat caaacttggg attccaatga attgctgccg gattttacc ggaaaaatcg | 3060 |
| gccaaaaga ttttcaaaaa aaaaaaaaaa aaaaa | 3095 |

<210> SEQ ID NO 129
<211> LENGTH: 543
<212> TYPE: DNA
<213> ORGANISM: Pinus radiata

<400> SEQUENCE: 129

| | |
|---|---|
| gcatctgatt ctcagaaatc acggtacgac accgatacca tagaaaaatg gaggaatgct | 60 |
| ctttcttctg tggcggatat agtcggtttt gagctgaaag acaaggaaga gtcgcagctc | 120 |
| gtccaggagg tcgtccaaca agttgtgaaa aagtttccca accgcctct cgacgtcgcc | 180 |
| aaatatccta ctggcctcga cgaaaaaatt aaagatgtgg acagaacatt gtcactgcag | 240 |
| cggcaaagcg agaaggctac aattttggga attgtaggtt ttggcggggt cgggaagtct | 300 |
| accctggcta acaattctt caaccgagaa agatcaaatt acgatcgatc ttgcttctta | 360 |
| tttgatatca gatccaaatc tttgccttcc gtgcagagta gccttctcac ggatctgatt | 420 |
| caaccgaatg cacaaataaa caacgttgat gaaggcatag agaggctcaa acagtttct | 480 |
| caacggtgtc ttatcatttt agatgatatt gatcatattg atcaaatgga tgcattatat | 540 |
| gca | 543 |

<210> SEQ ID NO 130
<211> LENGTH: 397
<212> TYPE: DNA
<213> ORGANISM: Pinus radiata

<400> SEQUENCE: 130

| | |
|---|---|
| attgatcaac tggatgcatt atgtgcaccc gttatagata ctattgatgt aggtagctta | 60 |
| atttaatta catctcggaa taaggatgta cttagaagcg caggtattgg agagtcatcc | 120 |
| atttacacac tgaaaggtct caatggaaag cactcgcaag agctcttttg ctggcatgcc | 180 |
| ttcggtcaac ccagtcctgt tgtaggattt gaaaaagtgg ttgagaagtt tttgaatgtc | 240 |
| tgccatggtt tgcccctctc gcttaaagtg tttggggcgc ttcttcgtgg aaaagacgat | 300 |
| ttggagcttt ggaatgcgga attgcgcaaa acctccaaag tacttccgaa agatatacgg | 360 |
| agcacactta gaattagcta tgatgctcta gataagc | 397 |

<210> SEQ ID NO 131
<211> LENGTH: 3124
<212> TYPE: DNA
<213> ORGANISM: Pinus radiata

<400> SEQUENCE: 131

```
ggtctatata agcagagctg gtttagtgaa ccgtcagatc cgctagccgc aattacttgt      60
gagttagctc actcattagg cacccaggc tttacacttt atacttccgg ctcgtatatt     120
gtgtggaatt gtgagcggat aacaatttca cacaggaaac agctatgacc ttgattacgc    180
caagctcgaa attaaccctc actaaaggga acaaaagctg gagctcgcgc gcctgcaggt    240
cgacactagt ggatccaaag aattcggcac gagacccaat cttctacaat ttctctgcgc    300
ttttaaaaca gtgaatcgtc ccgttgcaga ctctgtgtct atagcatcca accattacta    360
ccttaatttc tgttttgatc tcggcaatgg catcatcttc atcctccacc ttctccagca    420
acaaatccca ccaagttttc ataaaccatc gcggggttga tgtgaagaaa accttcgcca    480
ggtctctata ccttcgcctt cgcgagaaag gattgacggc tttcctcgat gacgaagaga    540
tgcaagtcgg atatgaaatt tctcctcaac tcgcagacgc tattaggacg gcctccgttc    600
atgtggccat cttctctccg agatacgctg aatcagaatg gtgcctcaat gagctccttg    660
agatgttaaa gtcaaagaaa cctataattc ctgtatttta cggcatcagt ccggctgagg    720
ttcggtggat gcagggcgtc tatggtaaag ctctacaaac tcataaagag aagccgcgaa    780
atgatcccag cactattgaa gaatggagaa atgcactcca tcaagttgca acaggagcg    840
ggttcgagct ggacaagtac cctgggtaaa aactcaaacc ttcctctggc tgtatttat    900
attggataaa taggcataga cgtttgtttc tcactaggtc tacttaattt ctccagccag    960
gatttggtgc tggaactgct agataaggtg gttaaacatc tgttggaatt ggtgccaaag   1020
ccagatttgt acgtggcgga gtatccaacc ggcctcgatg acaaactgaa agattttgaa   1080
gatacagtcc tgttgaggca acaacaggc cgaaaacccc agatcttagg gattgtgggg   1140
ttaggtggtg tgggaaagac aacacttgcc acagcattct tcaataagaa gaaatcagct   1200
tatcatagaa gttgtttttt atgtgatgtc agagaaaata caaccaatag gtctttacat   1260
ttgttgcaga gtcaacttct taatagcttg actggcttca ataatcaggt aaacagtgag   1320
cgtgaaggta aggggatgct tatagagcct ctcaaatctt gtaaagccat aatgatcttt   1380
gatgatgttg acgatgtgga tcaggtgaag gcattttttgc cccaatctga tgtactcaat   1440
tcagagagct taatattgat tacaactaga gataggaatg ttttgagaag cttaaaagtt   1500
gaaaattcat caattatag cctatcagga cttaataaag agcactccct agaactcttt   1560
tgttcccatg ccttcagccc agcatttcct ctcccagaat ttaaatccct ggtagataag   1620
ttcatagatt attgtaatgg attgcccctg tctttaaaaa tatttgggggc acttctttat   1680
ggtaaagata tatctcagtg gaaagaagaa tgggagagtc ttagacaaat agctcccatt   1740
gccatacatg acacatttaa aataagctat gactccctca atcaagagga aaagatata   1800
ttcttagaca ttgcatgctt tttgcgatgt caccacagag atgccgcaat aagcatatgg   1860
aacaaatcgg gctggagagg aaatcggggg tttctaaatc tacaggacaa atctcttgtg   1920
gaagttgacg cctttaattg tatacagatg cacaaccacc taagggaccct gggaagacag   1980
gttgcagcgt cttcgttgcc tcctcgtctt ttaataacaa agaacctcat ccataatttg   2040
tcacaccaat catctgtaag tgttcagtca ttcaatcctt tgtttgttat tcactaaaag   2100
tcagagattg tttgttgaat gaagaagtaa taacgattgt ttttcaacaa tggacaggaa   2160
ataaccttcc gcggaattgg gatggttccc ggtgaatata gtgcccaaga tgatgatgat   2220
gatgatgtat ttggcgtcgt tgatactgaa aatgctgtct tggaacgcag tttcaggagt   2280
```

-continued

```
gtgcaaattc ttgaaatgga aggttgtcac ctggaaccca ttttgaggaa ggcaaagcca    2340
ccaaacctat catgcctcag ctggaacaga tgtcctcact cttccctgcc ttcctgggtt    2400
tcagtgaaga atttaaggat tctacatctg gagcaatgcg aactaaaggc attgtggcct    2460
tcccagtttt cagtgaagaa tttatgggct ctattgtggc actggaaaag tgaatcacag    2520
tcacctctgc agtttccgat atctttggag cagctggtgg tacgccaatg tgagaaattg    2580
agaagcataa ccgggttggt gcatgcgaca atcttcggg agctaaatgt ttctaactgc    2640
tctgagttag aagaactgtc tagtttggaa gcattggtat cgttggagca tttgcaggct    2700
gatggatgta agaaactgaa agccatacga gggttggtgc atgcgacaag cttagagta    2760 ctggatgttt ctaactgctc tgagttagaa gaacttccta gtttggaaac attggtatcg    2820
ttggagggtt tgtgggctga tggatgtaag aaactgaaag catacgagg tttagcccac    2880 gccacaaatc ttcggacgct aagtgttcgt gagtgctttg ccttggaaga attcagagat    2940
gtctctgaat gtcacaaatt gagtcacaaa ttggtgtggg aatagcggag cagttgtttg    3000
ggaatagtcg atgtctctga atgtcacaaa ttggtcctcc tgtccatcat gtatagtggt    3060
gtcatttaaa cacaactcca caaagaatt tataaattat ttgtactaaa aaaaaaaaaa    3120
aaaa                                                                 3124
```

<210> SEQ ID NO 132
<211> LENGTH: 1653
<212> TYPE: DNA
<213> ORGANISM: Pinus radiata

<400> SEQUENCE: 132

```
agacgaaaat attgaggttc accgctcatt cccaatctct gtaaacatc ttggatctcg      60 cttgcttctt tcttctctgt aaaacgtctt ggatctcgct tgcttctttc ttcttctgtg    120
tccgatggcg gaccataccg gggatatcac atgcatcgcc tcttcttcgt cttcatccac    180
caacactggc caggtttttg acgttttcct caaccaccgc ggtcccgaca caagaaagg    240 cctcgccagc catatctacc gtggcctat tgtccgtggg ttaagagtat ttctcgacca    300
gcccgagttg cgtaagggag aggacaacct ttctcaaatc aaagaggcta ttcgaaccgc    360
ctcagtgcat gttgcaatat tttctccaaa ctatgctcaa tcaagatggt gtcttgatga    420
gctggcacta atggtggaat ccgagtcgac aataattcca gtcttccatg atgtcgatcc    480
ctccgaactt cggtggcagc agagtggaga tggagtcgag agtatcatcc gctgtctctg    540
tccgtgtcta ctgggcggaa agggacggta tgctcgagac ctgcacatgc tccaaaagaa    600
gacaacattg gatcctcata ccaacaaaaa gaagccacga catgactcga gaactctgca    660
aaaatggagg aaagctctct ctgatgtctc caataaaagc ggttttatta tcaacgcata    720
caatggtgac gaagggcagc tagttgatgc ggtcgtcgaa gaagtgtggc gaaaggttga    780
gaaaacacct cttaatgtgg ccaaataccc tactggcctc gttgagaaaa tagaagacgt    840
gggaagaatg gtactcttgc agcatcaaag ccagaagact aaggttgtgg gaattgtggg    900
tcttggcggt gtagggaaaa cgacccttgc aaaagaattc ttcaacagac acagatcaaa    960
ttatgatcga tcttgttttc tgtttgatgt gagagaaacc gcagccaaga gctctttaag   1020
ttcattgcag acacaacttc ttaaacactt ggctcatttg caggacgagc aaataagaaa   1080
caccgatgaa gtcatagaga agctccgaaa gcatctctca tcctcccccc gatctctgat   1140
agtcttagat gatgttgatc atattgatca acttgacgca ttgttttcac cggtgataga   1200
taccattcag gccagtagtt taatcttagt tacttctcgc aatagggatg tacttataag   1260
```

```
ctcgggaatt ctagaggcgt ctatttacca gcaaacaggt cttaacccac aacagtccag     1320
agaactattc tgctcgcatg cctttgacca gagttgtcct gtgacgggat ttgaacaact     1380
ggttgaagat tttttggatt tctgtgatgg attgcccttta tctcttaagg tcatcggagc    1440
ggctattcgt ggaaaagatt ctgagttttg gataggacag ctagacaaaa acagaagaat    1500
acttcacacg gatattcata gcaagcttaa aattagctat gatggtctgg ataaagagga    1560
gcagcagatc tttttagacg tcgcttgttt ttttatagga gaaaacagag ataccgccat    1620
cagaagatgg aatggatctg acggtaagtg tac                                 1653
```

<210> SEQ ID NO 133
<211> LENGTH: 346
<212> TYPE: DNA
<213> ORGANISM: Pinus radiata

<400> SEQUENCE: 133

```
cagccatatc taccgtggcc ttattgtccg tgggttaaga gtatttctgg accagcccga      60
gttgcgtaag ggaaaggaca tcccttctca aatcaaagag gctattcgaa ccgactcagt     120
gcatgttgca atattttctc caacatatgc tcaatcaaga tggtgtcttg atgagctcgc     180
actaatggtg gaatccaagt cgacaattat tccagtcttc catgatgtcg atcccttcga     240
acttcggtgg ccgcagagtg gagatggagt cgagagtatc atccgctgtc tctgtccgtg     300
tctactgggc ggaaagggac ggtatgctcg agacctgcac atgctc                    346
```

<210> SEQ ID NO 134
<211> LENGTH: 1737
<212> TYPE: DNA
<213> ORGANISM: Pinus radiata

<400> SEQUENCE: 134

```
cttgtagaga tcgacagtga agggtgtata agaatgcacg accacctgcg cgatctcggc      60
agagatgtag cagaaaagga acatccgctt cggctttcgc gaccaaatgt caatcttctt     120
cgtactcttt cccctcatc gcctgtgcga ggaattagca tgaattatgg aaatggcggc     180
aaacaatttt tggaatacat tagggtcaac tgcaacctaa gcaggttgga actgcttagg    240
ggtgaaggtt cttttgttga agcatattc agtgcagggg agatacgaca actggtatat     300
ctccaatgga aggagtgtcc gatctcctca atatctttca caatcccaac aaggaattta    360
agcgtgttat acatacaggg ttatgctttg aaaacactct ggcaacatga atctcaggca    420
ccactacagt tgacggaatt gtatattgat gctaccctttcagaggttcc acagtctatt    480 ggtaaactga atcagctcga aagaattgtc ctgaaaaatg gttattttaa aactttacca    540
aatgaattct atgatatgca ttcattgaag catatcacgt tacaaaactg tgaacaaatg    600
atgttgctgc cggattcagt tgggatcttg acgggccgcc aaacgcacga cttttccggg    660
tgctccaacc tgcaagcgct cccagactcg gtggggcagc tgacgggcct caagacgctc    720
gacttggaag actgcaccag cctgcagggg ctcccagact cggtggggca gctgacgggc    780
ctccagagcc tcgacttgga acactgcacc agcctgcagg ggctcccaga ctcggtgggg    840
cagctgacgg gcctccagac actcgacttg cgtgggtgct ccagcctgca ggggctgcca    900
gactcggtgg ggcagctgac gggcctcgag ggactctact tgagcgggtg cttcagcctg    960
caagggctcc cagactcggt ggagcagctg acgggcctcg agggactcta cttgagcggg    1020
tgcttcagcc tgcaagggct cccagactcg gtggggcagc tgacgggcct ccagagcctc    1080
```

-continued

```
aacttggaat actgcaccag cctggagggg ctcccagact cggtggggca gctgacggac    1140
ctcccgatac tcgacttgaa tacgtgcatc agcctgcagg ggcttccaga ctcggtgggg    1200
cagctgaggg gcctccagaa cctcgacttg cgttggtgcg acagcctgca ggggctccca    1260
gactcggtgg ggcaactgac gggcctccag atactcgact tgagtgggtg caccagcttg    1320 cagggggctcc cagactccgt ggggcagctg acgggcctcc ggacgctcca cttggaaaac    1380
tgcaccagcc tgcaggggct cccagactca gtcgggaact taacgagtct caaatggctt    1440
aacttatctg ggtgttccaa tttacagatg ctgcccaatt ccgtcatttt gagctcgttg    1500
gaggagcttc acttgtctgg atgttccaat ttacagatgc cgcccaatgt tcagcatttg    1560
agctcgctgg tggagctttc tgtgtctcac tgttcaaaac tgcaatgggg tgctggagta    1620
gtcgagtccc tgcgccatcg actgggaaat ggcttcatcg aagaaggcgg cgaaaacatt    1680
gataaagaaa gttgggaaga aggcagcgaa aaagtgata aagaaagttg ggaagaa       1737
```

<210> SEQ ID NO 135
<211> LENGTH: 527
<212> TYPE: DNA
<213> ORGANISM: Pinus radiata

<400> SEQUENCE: 135

```
cggtcctcca gacactcgac ttgcgtaggt gctccagcct gcaggggctg ccagagtcgg     60
tggggcagct gacgggcctc cagagcctca acttggaaaa gtgcaccaga ctacaggggc    120
tgccagagtc ggtggggcag ctgacgggcc tccagacact cgacttgcgt aggtgctcca    180
gcctacaggg gctgccagag tcggtggggc agctgacggg cctccagagc tcaacttga     240 aagagtgcac tagcttgcag gggctcccaa actctctggg gcagctgacg ggcctccata    300
gcctctactt ggttgagtgc tccagcctgc aggggctccc agactcggtg gggcagctga    360
cgggcctcca gagcatcaac ttgcaaggct gctccagcct gcaggggctc ccagattcgg    420
tggggcagct gacgggcctc cacagcctca acttagaagg ctgctccaga ctgcaggggc    480
tcccagactt ggtggggcag ctgacaggcc tccagagcct caaattg                  527
```

<210> SEQ ID NO 136
<211> LENGTH: 485
<212> TYPE: DNA
<213> ORGANISM: Pinus radiata

<400> SEQUENCE: 136

```
tggaccgctg ctccagcctg caggggctcc cagactcggt ggggcagctg acgggcctcc     60
ggcaactcaa cttgaacggg tgctccagcc tgcaggggct cccagactcg gtggggcagc    120
tgacgggcct ctggatactc gacctgaccg ggtgctccag cctgcagggg ctcccagact    180
cggtgaggca gctgaggtgc ctccggggcg aagcggacg gcctgcgga cgggcagcgg     240 aagcaccagc ctacaatggc gggctgccag gcgggctcgc agaatcacga ttagcgagag    300
gctattggct taacttgtct gggtgttcca atttacagat gccgcccaat gttcagcatt    360
tgagctcgct gttgaagctt tatgtgtctc actgttcaaa actgcaatgg ggtgctggag    420
tagtcgagtc cctgcgccat cgactggaaa taacttcgtc gaagaaggcg gcgaaaacat    480
caatg                                                                485
```

<210> SEQ ID NO 137
<211> LENGTH: 918
<212> TYPE: DNA
<213> ORGANISM: Pinus radiata

<400> SEQUENCE: 137

```
ggggctccca gactcggtgg ggcagctgac gggcctccag acactcgact tgcgtgggtg      60
ctccagcctg caggggctgc cagactcggt ggggcagctg acgggcctcg agggactcta     120
cttgagcggg tgcttcagcc tgcaagggct cccagactcg gtggagcagc tgacgggcct     180
cgagggactc tacttgagcg gtgcttcag cctgcaaggc ctcccagact cggtggggca      240
gctgacgggc ctccagagcc tcaacttgga atactgcacc agcctggagg ggctcccaga     300
ctcggtgggg cagctgacgg acctcccgat actcgacttg aatacgtgca tcagcctgca     360
ggggcttcca gactcggtgg ggcagctgag gggcctccag aacctcgact tgcgttggtg     420
cgacagcctg caggggctcc cagactcggt ggggcaactg acgggcctcc agatactcga     480
cttgagtggg tgcaccagct tgcaggggct cccagactcc gtggggcagc tgacgggcct     540
ccggacgctc cacttggaaa actgcaccag cctgcagggg ctcccagact cagtcgggaa     600
cttaacgagt ctcaaatggc ttaacttatc tgggtgttcc aatttacaga tgctgcccaa     660
tttccgtcat ttgagctcgt tggaggagct tcacttgtct ggatgttcca atttacagat     720
gccgcccaat gttcagcatt tgagctcgct ggtggagctt tctgtgtctc actgttcaaa     780
actgcaatgg ggtgctggag tagtcgagtc cctgcgccat cgactgggaa atggcttcat     840
cgaagaaggc ggcgaaaaca ttgataaaga agttgggaa gaaggcagcg aaaaaagtga      900
taaagaaagt tgggaaga                                                   918
```

<210> SEQ ID NO 138
<211> LENGTH: 257
<212> TYPE: DNA
<213> ORGANISM: Pinus radiata

<400> SEQUENCE: 138

```
atgctgcccc atttttcggca tttgagcttg atggaggagc ttcacttgtc tggatgttcc     60
aatttacaga tgccgcccaa tgttcagcat ttgagctcgc tggtgaagct ttatgtgtct    120
cactgttcaa aactgcaatg gggtgctgga gtagtcgagt ccctgcgcca tcgactggga    180
aatggcttca tcgaagaagg cggagaaaac agtaatgaat acaactgcag cgagttgtat    240
aatataagag aacttct                                                    257
```

<210> SEQ ID NO 139
<211> LENGTH: 1166
<212> TYPE: DNA
<213> ORGANISM: Pinus radiata

<400> SEQUENCE: 139

```
tgaacagctg caccagcctg caggggctcc cagactcggt ggggcagctg acgggcctcc      60
ggacactcga cttgaacagc tgcaccagcc tgcaggggct cccagactcg gtggggcagc    120
tgacgggcct ccggacactc gacttgcaca gctgcaccag cctgcagggg ctcccagact    180
cggtggggca gctgacgggc ctcgagacac tcgacttgca agactgcacc agcctgcagg    240
ggctcccaga ctcggtgggg cagctgacgg gcctccaggt actctacttg agacggtgct    300
ccaacctgca ggggctccca gactcggtgg ggcagctgac gtgcctcaag gtactgtgct    360
tgagatggtg ctccaacctg caagcgctcc cagactcggt ggggcagcta acgggcctca    420
aggcactcaa cttgcaagac tgcaccagcc tgcaggggct cccagacttg gtggggcagc    480
tgacgggcct caaggcactc aacttgcaaa actgcaccag cctgcagggg ctcccagact    540
```

```
cggtggggca gctgaccggt ctccaggtac tctacttgag acagtgctcc aacctgcaag    600
cgctcccaga ctcagtgggg cagctgacgg gcctgaataa actctacttg aacgggtgct    660
ccagcctaca ggggctccca gactcagtcg agaacttaac gagactcaaa tggcttatat    720
tgtctgggtg ttccaatttta cagatgctgc ccaattttcg gcatttgagg tcgttggaga    780
ggcttcactt gtctggatgt tccaatttac agatgccgcc caatgttcag catttgagct    840
cgctggtgca gctttatgtg tctcactgtt caaaactgca atgggtgct ggagtagtcg     900 agtccctgcg ccatcgactg ggaaatggct tcatcgaaga aggcggcgaa acagtaatg    960 aataaagctg cagctagttg tataatataa gagaacttct taagatcaga tggccacggt    1020
gctcattaat cttcatagag ctgtaatcag aggcaaaatg aattacacaa tgtacagaat    1080
gctctacatt ttaaaaaaaa aaaaaaaaaa aaaactcgag agtacttcta gagcggccgc    1140
gggcccatcg attttccacc ccaggt                                         1166
```

<210> SEQ ID NO 140
<211> LENGTH: 1921
<212> TYPE: DNA
<213> ORGANISM: Pinus radiata

<400> SEQUENCE: 140

```
cttgcattat aggttgttct aaagtttctg aaactggttt gcaatttaca tcaatcattg     60
aaagctatcc atcgcttatt cggcaatggc atccaccgcc tccactgcca tcaacacaag    120
caattatcaa tacgacgtgt ttctgaatca tcgcggccgc gatacgaaga acgacttcgc    180
cggtcatctc tactctcgcc ttcgttcacg tggaatccgt gtctttctgg acaaggaaga    240
gatgcaagtg ggagacgatt taacttatca gataaaagcc gttattaaaa ccgcctctgt    300
ccatctggcc attttcagtg agaactacgc cgagtcaaag tggtgccttg atgagcttgt    360
gctgatggtc gagtcggagg ctaccatcat ccccgtcttt tttaaaaatg tggaacctga    420
tcatcttcag tggattggaa gccagactcg ggataccgag cagagcgggg ataccaagca    480
gagcggaagc cagactcggg aaaccgagca gagcggaagc caagcaaaca agaagccaca    540
gaagacaaag tttgctgatg gcttctggaa acttcaaaat aagacggata atgggcagcg    600
gcgacacaaa catgagacta ttggaaaatg ggcatctgct cttccaacag tttccgaaag    660
aacctgtttc aagctggcag cgtttaatgg gtgagaactc aatttcccctt ttcagtatgc    720 tacatagatg taaatggacg tttctcactt gttctattta ctctcttgtg aataaccagc    780
gacgaggtgg agctaatcga aagatcgtc cagtctgtgt tagaaaagt gaatagatct    840 tccttctatg tgcccaaata tgaggtcggt ttggatgaga atgtagaaaa gtttcgtaaa    900
aaggtaaaag aatggtcgca gcagcggcag aatgaaaaag ctcaggtcgt gggggatagtg    960 gggttggggtg atgttggaaa dcaacgcta gtaaaggaat tcttccctac agagagtcca    1020
gcataccgta acttctgctt ttaccctgtg aggcgaaatg gatgtataac acgtccagat    1080
tgtttgattg gagagctttt taagggctcg agtggtttgg tttcgtcacc aaccagcgtt    1140
gatgcagtta aaatattgcc ggacgcgtct aatccctcag tagacatgat tcgaaacaat    1200
ccctccttag tagttttaga tggagtagat aatgttgagg agaggagaa tctttttgaaa    1260 attcaagaaa ggctccactc caaaagtttta atattgatta catctaggga cccagaagtt    1320
ctgaggtgct cagaagttga aaagatttat cacttaaatg gccttaatga accgtgttcc    1380
cgaaagcttt ttttgcttcca tgccttccac caggcagctc cacttcaagg gtatgaatac    1440
ctggttgctt gggttttaag agtatgcgac ggattgcctt tattattgaa actgttgggg    1500
```

-continued

```
gcattacttt gtggaaataa tgacagattt tattgggaag acctatgtga tagtcttcaa    1560
gcaaaaaaga tagaggaaaa gcttaaagtt atttacgaca cgttgggaac agaggaacaa    1620 cagaccttt  tggacattgc ctgtaatttg gtgggtaaaa acgcagatat ttggttaaaa    1680
tcaggaaaga aagtattat  ttggtttcag attctactgg aaaagcgtct agtggaggtg    1740
gatagtgaaa attgtataca gatgcatgat cttcttaaaa atttgggagg agaaattgct    1800
aaggcaacaa atcgccgcg  tcctcttttt ttcggctgat tagtcgcaaa aatcccatgt    1860
aagtgtaata aaaatctgtg cagagttttt taattcttca tcatttttaa gcaaaaaact    1920
c                                                                    1921
```

<210> SEQ ID NO 141
<211> LENGTH: 278
<212> TYPE: PRT
<213> ORGANISM: Pinus radiata

<400> SEQUENCE: 141

```
Ala Met Glu Gly Tyr Ala Ala Asn Asn Asp Ala Glu Leu Leu Ser Lys
 1               5                  10                  15

Thr Leu Gln Val Glu Gln Lys Leu Phe Tyr Phe Asp Leu Lys Glu Asn
             20                  25                  30

Pro Arg Gly Gln Tyr Leu Lys Ile Ser Glu Lys Thr Ser Gly Ser Arg
         35                  40                  45

Ser Thr Ile Ile Val Pro Ile Gly Gly Val Ala Trp Phe Leu Asp Leu
     50                  55                  60

Phe Asn Tyr Tyr Val Asp Gly Asp Glu Glu Val Leu Ser Lys Glu
 65                  70                  75                  80

Leu Gln Leu Asp Ala Lys Val Phe Tyr Phe Asp Val Gly Val Asn Lys
                 85                  90                  95

Arg Gly Arg Phe Leu Lys Ile Ser Glu Ala Ser Thr Ser Tyr Ser Arg
            100                 105                 110

Ser Thr Ile Ile Val Pro Val Gly Asn Thr Arg Lys Asp Gly Trp Ala
        115                 120                 125

Ala Phe Arg Asn Ile Leu Gly Glu Ile Asn Glu Ala Ser Gln Gln Ala
    130                 135                 140

Ser Gly Pro Ser Glu His Leu Gly Gly Leu Ser Asp Glu Val Gly Ala
145                 150                 155                 160

Gly Phe Leu Ser Gly Gly Ser Gly Glu Ala Ala Phe Glu Ala Asp Thr
                165                 170                 175

Thr Gly Asp Arg Ala Met Gly Leu Thr Pro Ala Glu Asp Thr Gly Glu
            180                 185                 190

Ala Val Val Ser Lys Val Ile Arg Ala Asp Gln Lys Arg Phe Phe Phe
        195                 200                 205

Asp Leu Gly Cys Asn Asn Arg Gly Gln Phe Leu Arg Ile Ser Glu Val
    210                 215                 220

Ile Gly Pro Asp Arg Ser Ala Ile Ile Val Pro Val Ser Ala Leu Glu
225                 230                 235                 240

Gln Phe His Asp Val Leu Gly His Phe Val Asp Ile Thr Arg Thr Gln
                245                 250                 255

Gly Leu Ala Ala Ala Ser Gly Ala Asn Val Arg Thr Val Ala Ala Ala
            260                 265                 270

His Arg Arg Asn Glu Asn
        275
```

<210> SEQ ID NO 142
<211> LENGTH: 97
<212> TYPE: PRT
<213> ORGANISM: Pinus radiata

<400> SEQUENCE: 142

Ala Met Glu Gly Tyr Ala Ala Asn Asn Asp Ala Glu Leu Leu Ser Lys
 1               5                  10                  15

Thr Leu Gln Val Glu Gln Lys Leu Phe Tyr Phe Asp Leu Lys Glu Asn
             20                  25                  30

Pro Arg Gly Gln Tyr Leu Lys Ile Ser Glu Lys Thr Ser Gly Ser Arg
         35                  40                  45

Ser Thr Ile Ile Val Pro Ile Gly Gly Val Ala Trp Phe Leu Asp Leu
 50                  55                  60

Phe Asn Tyr Tyr Val Asp Gly Asp Glu Glu Val Leu Ser Lys Glu
65                  70                  75                  80

Leu Gln Leu Asp Ala Lys Val Phe Tyr Phe Asp Val Gly Val Asn Lys
                 85                  90                  95

Arg

<210> SEQ ID NO 143
<211> LENGTH: 386
<212> TYPE: PRT
<213> ORGANISM: Eucalyptus grandis

<400> SEQUENCE: 143

Ser Ser Ser Ser Ser Phe Phe Leu Leu Leu Pro Pro Ile Phe Leu Leu
 1               5                  10                  15

His Ser Arg Arg Pro Ser Met Ala Ile Pro Ala Thr Ala Ala Ala Ala
             20                  25                  30

Leu Leu Leu Phe Cys Ala Val Ala Ala Val Ala Ala Ala Ala Arg Thr
         35                  40                  45

Asp Glu Glu Val Met Gly Met Tyr Glu Leu Trp Leu Ala Lys His Gly
 50                  55                  60

Lys Ala Tyr Asn Gly Leu Gly Glu Arg Glu Arg Arg Phe Glu Ile Phe
65                  70                  75                  80

Arg Asp Asn Leu Arg Phe Val Asp Glu His Asn Ala Leu Asn Arg Ser
                 85                  90                  95

Tyr Thr Leu Gly Met Asn Arg Phe Ala Asp Leu Thr Asn Glu Glu Tyr
            100                 105                 110

Arg Ala Val Tyr Leu Gly Thr Arg Ser Asp Pro Met Arg Arg Val Ala
        115                 120                 125

Lys Ala Ala Arg Ala Ser Gly Arg Tyr Ala Pro Arg Pro Asp Asp Met
130                 135                 140

Leu Pro Ala Ala Val Asp Trp Arg Thr Arg Gly Ala Val Asn Lys Val
145                 150                 155                 160

Lys Asp Gln Gly Ala Cys Gly Ser Cys Trp Ala Phe Ser Thr Ile Ala
                165                 170                 175

Ala Val Glu Gly Ile Asn Gln Ile Val Thr Gly Glu Phe Ile Ser Leu
            180                 185                 190

Ser Glu Gln Glu Leu Val Asp Cys Asp Arg Ala Tyr Asp Ala Gly Cys
        195                 200                 205

Asn Gly Gly Leu Met Asp Tyr Ala Phe Gln Phe Ile Ile Asp Asn Gly
    210                 215                 220

Gly Ile Asp Thr Asp Glu Asp Tyr Ser Tyr Thr Gly Val Asp Gly Thr

```
                225                 230                 235                 240

Cys Asp Ala Ser Lys Val Asn Ser Lys Val Val Ser Ile Asp Gly Tyr
                245                 250                 255

Glu Asp Val Pro Ala Phe Asp Glu Arg Ala Leu Lys Lys Ala Val Ala
                260                 265                 270

His Gln Pro Val Ser Val Ala Ile Glu Ala Gly Gly Arg Asp Phe Gln
                275                 280                 285

Leu Tyr Glu Ser Gly Val Phe Thr Gly Glu Cys Gly Thr Ala Leu Asp
                290                 295                 300

His Gly Val Ile Ala Val Gly Tyr Gly Arg Gln His Gly Ala Asp Tyr
305                 310                 315                 320

Trp Leu Val Arg Asn Ser Trp Gly Ser Leu Trp Gly Glu Ser Gly Tyr
                325                 330                 335

Ile Lys Met Glu Arg Asn Leu Ala Asn Asn Tyr Phe Gly Lys Cys Gly
                340                 345                 350

Ile Ala Met Glu Ala Ser Tyr Pro Val Lys Thr Thr Gln Asn Pro Ala
                355                 360                 365

Ser Lys Tyr Ser Ser Met Gly Ser Ser Gly Gly Ile Glu Leu Val Ser
                370                 375                 380

Ser Ser
385

<210> SEQ ID NO 144
<211> LENGTH: 109
<212> TYPE: PRT
<213> ORGANISM: Eucalyptus grandis

<400> SEQUENCE: 144

Leu Pro Pro Ile Phe Leu Leu His Arg Pro Cys Pro Ser Met Ala Ile
1               5                   10                  15

Pro Ala Ala Ala Ala Ala Leu Leu Phe Ser Ala Val Ala Ala
                20                  25                  30

Val Ala Ala Ala Ala Arg Thr Asp Glu Glu Val Met Gly Met Tyr
            35                  40                  45

Glu Leu Trp Leu Val Lys His Gly Lys Ala Tyr Asn Gly Leu Gly Glu
    50                  55                  60

Arg Glu Arg Arg Phe Glu Ile Phe Arg Asp Asn Leu Arg Phe Val Asp
65                  70                  75                  80

Glu His Thr Gly Leu Asn Arg Ser Tyr Ala Leu Gly Met Asn Arg Phe
                85                  90                  95

Ala Asp Leu Thr Asn Glu Glu Tyr Arg Ala Ile Tyr Leu
                100                 105

<210> SEQ ID NO 145
<211> LENGTH: 204
<212> TYPE: PRT
<213> ORGANISM: Eucalyptus grandis

<400> SEQUENCE: 145

Gln Ile Val Thr Gly Glu Leu Ile Ser Leu Ser Glu Gln Glu Leu Val
1               5                   10                  15

Asp Cys Asp Arg Ser Tyr Asp Ala Gly Cys Asn Gly Gly Leu Met Asp
                20                  25                  30

Tyr Ala Phe Gln Phe Ile Ile Asp Asn Gly Gly Ile Asp Thr Asp Glu
            35                  40                  45

Asp Tyr Ser Tyr Thr Gly Val Asp Gly Thr Cys Asp Ala Ser Lys Val
```

```
              50                  55                  60
Asn Ser Lys Val Val Ser Ile Asp Gly Tyr Glu Asp Val Pro Ala Phe
 65                  70                  75                  80

Asp Glu Arg Ala Leu Lys Lys Ala Val Ala His Gln Pro Val Ser Val
                 85                  90                  95

Ala Ile Glu Ala Gly Gly Arg Asp Phe Gln Leu Tyr Glu Ser Gly Val
                100                 105                 110

Phe Thr Gly Glu Cys Gly Thr Ala Leu Asp His Gly Val Ile Ala Val
                115                 120                 125

Gly Tyr Gly Arg Gln His Gly Ala Asp Tyr Trp Leu Val Arg Asn Ser
130                 135                 140

Trp Gly Ser Leu Trp Gly Glu Ser Gly Tyr Ile Lys Met Glu Arg Asn
145                 150                 155                 160

Leu Ala Asn Asn Tyr Phe Gly Lys Cys Gly Ile Ala Met Glu Ala Ser
                165                 170                 175

Tyr Pro Val Lys Thr Ser Gln Asn Pro Ala Ser Lys Tyr Ser Ser Met
                180                 185                 190

Gly Ser Ser Gly Gly Ile Glu Leu Val Ser Ser Ser
                195                 200

<210> SEQ ID NO 146
<211> LENGTH: 286
<212> TYPE: PRT
<213> ORGANISM: Pinus radiata

<400> SEQUENCE: 146

Ser Ser Gln Lys Lys Tyr Gly Ser Arg Gly Gly Arg Ser Thr Val Asp
 1               5                  10                  15

Met Gly Ile Leu Leu Phe Phe Ala Leu Leu Ala Met Leu Ala Met Ala
                20                  25                  30

Gly Asn Ala Ser Arg Ala Asp Phe Ser Ile Ile Ser Asn Lys Asp Leu
                35                  40                  45

Arg Glu Asp Asp Ala Ile Met Glu Leu Tyr Glu Leu Trp Leu Ala Glu
 50                  55                  60

His Lys Lys Ala Tyr Asn Gly Leu Asp Glu Lys Gln Lys Arg Phe Thr
 65                  70                  75                  80

Val Phe Lys Asp Asn Phe Leu Tyr Ile His Glu His Asn Gln Gly Asn
                85                  90                  95

Arg Ser Tyr Lys Leu Gly Leu Asn Gln Phe Ala Asp Leu Ser His Glu
                100                 105                 110

Glu Phe Lys Ala Thr Tyr Leu Gly Ala Lys Leu Asp Thr Lys Lys Arg
                115                 120                 125

Leu Leu Arg Ser Pro Ser Pro Arg Tyr Gln Tyr Ser Asp Gly Glu Asp
130                 135                 140

Leu Pro Lys Ser Ile Asp Trp Arg Glu Lys Gly Ala Val Ala Pro Val
145                 150                 155                 160

Lys Asp Gln Gly Ala Cys Gly Ser Cys Trp Ala Phe Ser Thr Val Ala
                165                 170                 175

Ala Val Glu Gly Ile Asn Gln Ile Val Thr Gly Asp Leu Ile Ser Leu
                180                 185                 190

Ser Glu Gln Glu Leu Val Asp Cys Asp Thr Ser Tyr Asn Gln Gly Cys
                195                 200                 205

Asn Gly Gly Leu Met Asp Tyr Ala Phe Glu Phe Ile Ile Asn Asn Gly
210                 215                 220
```

```
Gly Leu Asp Ser Glu Glu Asp Tyr Pro Tyr Thr Ala Tyr Asp Gly Ser
225                 230                 235                 240

Cys Asp Ala Tyr Arg Lys Asn Ala His Val Val Thr Ile Asp Asp Tyr
                245                 250                 255

Glu Asp Val Pro Glu Asn Asp Glu Lys Ser Leu Lys Lys Ala Ala Ala
            260                 265                 270

Asn Gln Pro Ile Ser Val Ala Ile Glu Ala Ser Gly Arg Glu
        275                 280                 285

<210> SEQ ID NO 147
<211> LENGTH: 266
<212> TYPE: PRT
<213> ORGANISM: Pinus radiata

<400> SEQUENCE: 147

Ser Ser Gln Lys Lys Tyr Gly Ser Arg Gly Gly Arg Ser Thr Val Asp
1               5                   10                  15

Met Gly Ile Leu Leu Phe Phe Ala Leu Leu Ala Met Ser Ala Met Ala
            20                  25                  30

Gly Ser Ala Ser Arg Ala Asp Phe Ser Ile Ile Ser Asn Lys Asp Leu
        35                  40                  45

Arg Glu Asp Asp Ala Ile Met Glu Leu Tyr Glu Leu Trp Leu Ala Glu
    50                  55                  60

His Lys Lys Ala Tyr Asn Gly Leu Asp Glu Lys Gln Lys Arg Phe Thr
65                  70                  75                  80

Val Phe Lys Asp Asn Phe Leu Tyr Ile His Glu His Asn Gln Gly Asn
                85                  90                  95

Arg Ser Tyr Lys Leu Gly Leu Asn Gln Phe Ala Asp Leu Ser His Glu
            100                 105                 110

Glu Phe Lys Ala Thr Tyr Leu Gly Ala Lys Leu Asp Thr Lys Lys Arg
        115                 120                 125

Leu Leu Arg Ser Pro Ser Pro Arg Tyr Gln Tyr Ser Asp Gly Glu Asp
    130                 135                 140

Leu Pro Lys Ser Ile Asp Trp Arg Glu Lys Gly Ala Val Ala Pro Val
145                 150                 155                 160

Lys Asp Gln Gly Ala Cys Gly Ser Cys Trp Ala Phe Ser Thr Val Ala
                165                 170                 175

Ala Val Glu Gly Ile Asn Gln Ile Val Thr Gly Asp Leu Ile Ser Leu
            180                 185                 190

Ser Glu Gln Glu Leu Val Asp Cys Asp Thr Ser Tyr Asn Gln Gly Cys
        195                 200                 205

Asn Gly Gly Leu Met Asp Tyr Ala Phe Glu Phe Ile Ile Asn Asn Gly
    210                 215                 220

Gly Leu Asp Ser Glu Glu Asp Tyr Pro Tyr Thr Ala Tyr Asp Gly Ser
225                 230                 235                 240

Cys Asp Ala Tyr Arg Lys Asn Ala His Val Val Thr Ile Asp Asp Tyr
                245                 250                 255

Glu Asp Val Pro Glu Asn Asp Glu Lys Ser
            260                 265

<210> SEQ ID NO 148
<211> LENGTH: 302
<212> TYPE: PRT
<213> ORGANISM: Pinus radiata

<400> SEQUENCE: 148
```

```
Asp Cys Ile Ser Met Gly Ile Leu Leu Phe Ala Leu Leu Ala Leu
 1               5                  10                  15

Phe Ala Met Ala Gly Ser Ala Ser Arg Ala Asp Phe Ser Ile Ile Gly
             20                  25                  30

Tyr Asp Ser Lys Asp Leu Arg Glu Asp Asp Ala Ile Met Glu Leu Tyr
             35                  40                  45

Glu Leu Trp Leu Ala Gln His Arg Lys Ala Tyr Asn Gly Leu Asp Glu
 50                  55                  60

Lys Gln Lys Arg Phe Ser Val Phe Lys Asp Asn Phe Leu Tyr Ile His
 65                  70                  75                  80

Gln His Asn Asn Gln Gly Asn Pro Ser Phe Lys Met Gly Leu Asn Gln
                 85                  90                  95

Phe Ala Asp Leu Ser His Glu Gly Phe Lys Ala Thr Tyr Leu Gly Cys
             100                 105                 110

Glu Leu Asp Thr Lys Lys Arg Leu Ser Lys Ser Pro Ser Pro Arg Tyr
             115                 120                 125

Gln Tyr Ser Glu Gly Glu Asn Leu Pro Glu Ser Val Asp Trp Arg Glu
 130                 135                 140

Lys Gly Ala Val Ala Ala Val Lys Asp Gln Gly Ser Cys Gly Ser Cys
145                 150                 155                 160

Trp Ala Phe Ser Thr Val Ala Ala Val Glu Gly Ile Asn Gln Ile Val
                 165                 170                 175

Thr Gly Asn Leu Thr Ser Leu Ser Glu Gln Glu Leu Val Asp Cys Asp
             180                 185                 190

Thr Ser Tyr Asn Gln Gly Cys Asn Gly Gly Leu Met Asp Tyr Ala Phe
             195                 200                 205

Gln Phe Ile Ile Asp Asn Gly Gly Leu Asp Ser Glu Asp Asp Tyr Pro
 210                 215                 220

Tyr Met Ala Asn Asp Gly Ser Cys Asp Ala Tyr Arg Lys Asn Ala His
225                 230                 235                 240

Val Val Thr Ile Asp Ser Tyr Glu Asp Val Pro Glu Asn Asp Glu Lys
                 245                 250                 255

Ser Leu Lys Lys Ala Ala Ala His Gln Pro Ile Ser Val Ala Ile Glu
             260                 265                 270

Ala Ser Gly Arg Ala Phe Gln Phe Tyr Glu Ser Gly Val Phe Thr Ser
             275                 280                 285

Thr Cys Gly Thr Gln Leu Asp His Gly Val Thr Leu Val Gly
             290                 295                 300
```

<210> SEQ ID NO 149
<211> LENGTH: 500
<212> TYPE: PRT
<213> ORGANISM: Eucalyptus grandis

<400> SEQUENCE: 149

```
Phe Ser Leu Ser Ile Leu Leu Ser Leu Ser Ser Asp Ala Pro Ile Gly
 1               5                  10                  15

Tyr Ala Glu Ala Lys Lys Met Asp Leu Lys Ser Pro Ala Ala Ala
             20                  25                  30

Ala Val Ala Val Leu Ala Leu Ala Leu Ala Leu Thr Thr Ile Ala Ser
             35                  40                  45

Ala Leu Asp Met Ser Ile Val Ser Tyr Asp Arg Ala His Gly Asp Arg
 50                  55                  60

Ser Ser Ser Ser Ser Ser Trp Arg Ser Asp Asp Glu Val Met Ala
 65                  70                  75                  80
```

-continued

```
Val Tyr Glu Ser Trp Leu Ala Lys His Gly Lys Ala Tyr Asn Ala Leu
                85                  90                  95
Gly Glu Lys Glu Lys Arg Phe Gln Val Phe Lys Asp Asn Leu Arg Phe
                100                 105                 110
Ile Asp Asp His Asn Ala Gly Gly Asp Arg Thr Tyr Thr Val Gly Leu
                115                 120                 125
Asn Gln Phe Ala Asp Leu Thr Asn Glu Glu Tyr Arg Ser Met Tyr Leu
    130                 135                 140
Gly Ala Arg Met Asp Arg Ser Gly Arg Leu Gly Arg Ala Arg Ser
145                 150                 155                 160
Asp Arg Tyr Ala Val Ala Ala Gly Glu Glu Leu Pro Ala Ser Val Asp
                165                 170                 175
Trp Arg Lys Glu Gly Ala Val Val Asp Val Lys Asp Gln Gly Ser Cys
                180                 185                 190
Gly Ser Cys Trp Ala Phe Ser Thr Ile Ala Ala Val Glu Gly Ile Asn
                195                 200                 205
Lys Leu Val Thr Gly Asp Leu Ile Ser Leu Ser Glu Gln Glu Leu Val
    210                 215                 220
Asp Cys Asp Thr Ser Tyr Asn Glu Gly Cys Asn Gly Gly Leu Met Asp
225                 230                 235                 240
Tyr Ala Phe Glu Phe Ile Ile Asn Asn Gly Gly Ile Asp Thr Glu Glu
                245                 250                 255
Asp Tyr Pro Tyr Arg Ala Val Asp Ser Thr Cys Asp Gln Tyr Arg Lys
                260                 265                 270
Asn Ala Lys Val Val Thr Ile Asp Asp Tyr Glu Asp Val Pro Glu Asn
    275                 280                 285
Asp Glu Lys Ala Leu Gln Lys Ala Val Ala Asn Gln Pro Val Ser Val
290                 295                 300
Ala Ile Glu Ala Gly Gly Arg Glu Phe Gln Phe Tyr Asp Ser Gly Ile
305                 310                 315                 320
Phe Thr Gly Lys Cys Gly Thr Ala Leu Asp His Gly Val Thr Ala Val
                325                 330                 335
Gly Tyr Gly Thr Glu Asn Gly Val Asp Tyr Trp Ile Val Lys Asn Ser
                340                 345                 350
Trp Gly Gly Ser Trp Gly Glu Gln Gly Tyr Ile Lys Met Ala Arg Asn
                355                 360                 365
Val Ala Asn Ser Pro Thr Gly Lys Cys Gly Ile Ala Met Glu Ala Ser
                370                 375                 380
Tyr Pro Ile Lys Lys Gly Gln Asn Pro Pro Asn Pro Gly Pro Ser Pro
385                 390                 395                 400
Pro Ser Pro Val Lys Pro Pro Thr Val Cys Asp Asn Tyr Tyr Ser Cys
                405                 410                 415
Pro Glu Ser Asn Thr Cys Cys Val Tyr Glu Tyr Ala Asn Tyr Cys
                420                 425                 430
Phe Ala Trp Gly Cys Cys Pro Leu Glu Ala Ala Thr Cys Cys Glu Asp
                435                 440                 445
His Tyr Ser Cys Cys Pro Gln Asp Phe Pro Val Cys Asn Val Asn Ala
    450                 455                 460
Gly Thr Cys Gln Met Ser Lys Asp Asn Pro Leu Gly Val Lys Ala Leu
465                 470                 475                 480
Lys Arg Thr Pro Ala Lys Phe His Trp Ala Phe Gly Ser Asp Gly Gln
                485                 490                 495
```

Lys Ser Ser Ala
         500

<210> SEQ ID NO 150
<211> LENGTH: 200
<212> TYPE: PRT
<213> ORGANISM: Eucalyptus grandis

<400> SEQUENCE: 150

Asp Gln Gly Asp Cys Gly Ser Cys Trp Ala Phe Ser Ala Ala Ala Ala
1               5                   10                  15

Met Glu Gly Ile Thr Met Ile Lys Lys Gly Lys Leu Val Pro Leu Ser
            20                  25                  30

Val Gln Glu Leu Val Asp Cys Asp Val Asp Asp Asn Gly Cys His Gly
        35                  40                  45

Gly Leu Met Asp Arg Ala Phe Lys Phe Ile Lys Ser Lys Gly Gly Leu
    50                  55                  60

Ser Thr Glu Ala Asn Tyr Pro Tyr Gln Ala Asn Asn Gly Thr Cys Asn
65                  70                  75                  80

Thr Ala Lys Met Ala Asn Pro Val Ala Ser Ile Thr Gly Tyr Gln Asp
                85                  90                  95

Val Pro Ala Asn Asn Glu Lys Ala Leu Leu Gln Ala Val Ala Asn Gln
            100                 105                 110

Pro Val Ser Val Ala Ile Glu Gly Ser Gly Phe Asn Phe Gln Phe Tyr
        115                 120                 125

Ser Ser Gly Val Phe Ser Gly Ser Cys Gly Thr Ser Ile Asp His Ala
    130                 135                 140

Val Thr Ala Val Gly Tyr Gly Lys Thr Ser Arg Gly Thr Lys Tyr Trp
145                 150                 155                 160

Leu Leu Lys Asn Ser Trp Gly Thr Gly Trp Gly Glu Ser Gly Tyr Met
                165                 170                 175

Arg Ile Gln Arg Asp Val Ser Ser Asn Ala Gly Leu Cys Gly Leu Ala
            180                 185                 190

Met Glu Ala Ser Tyr Pro Thr Ala
        195                 200

<210> SEQ ID NO 151
<211> LENGTH: 198
<212> TYPE: PRT
<213> ORGANISM: Eucalyptus grandis

<400> SEQUENCE: 151

Asn Tyr Leu Arg Thr Asn Lys Leu Leu Ser Leu Ser Glu Gln Glu Leu
1               5                   10                  15

Val Asp Cys Asp Asn Thr Gln Asn His Gly Cys Asn Gly Gly Leu Met
            20                  25                  30

Asp Ile Ala Phe Glu Phe Ile Lys Gln Lys Gly Gly Ile Thr Ser Glu
        35                  40                  45

Ser Asn Tyr Pro Tyr Gln Ala Ser Asn Gly Thr Cys Asp Ala Ala Lys
    50                  55                  60

Glu Asn Ser Pro Val Val Ser Ile Asp Gly His Glu Asn Val Pro Ala
65                  70                  75                  80

Asn Asp Glu Asp Ala Leu Gln Lys Ala Val Ala Asn Gln Pro Val Ser
                85                  90                  95

Val Ala Ile Glu Ala Ser Gly Ala Asp Phe Gln Phe Tyr Ser Glu Gly
            100                 105                 110

```
Val Phe Thr Gly Ser Cys Gly Thr His Leu Asp His Gly Val Ala Ile
            115                 120                 125

Val Gly Tyr Gly Ser Thr Leu Gln Gly Thr Lys Tyr Trp Ile Val Arg
        130                 135                 140

Asn Ser Trp Gly Pro Glu Trp Gly Glu Lys Gly Tyr Leu Arg Met Glu
145                 150                 155                 160

Arg Gly Ile Glu Ala Lys Glu Gly Leu Cys Gly Ile Ala Met Glu Ala
            165                 170                 175

Ser Tyr Pro Ile Lys Asn Ser Ser Asp Asn Pro Ala Gly Val Ser Ser
            180                 185                 190

Pro Val Lys Asp Glu Leu
            195

<210> SEQ ID NO 152
<211> LENGTH: 381
<212> TYPE: PRT
<213> ORGANISM: Eucalyptus grandis

<400> SEQUENCE: 152

Lys Thr Gln Gly Arg Arg Lys Glu Ser Val Gln Asn His Leu Leu Lys
1               5                   10                  15

Glu Ser Tyr Asn Ser Pro Ser His Ser Asn Cys Val Leu Asp Ser Thr
            20                  25                  30

Gln Ser Thr Thr Met Ala Lys Gln Asn Gln Phe Ser Phe Leu Thr Ser
        35                  40                  45

Ala Ala Leu Leu Val Ile Ile Val Ser Val Ser Glu Thr Leu Cys Arg
    50                  55                  60

Pro Leu Glu Glu Glu Gln Leu Leu Lys Gln His Glu Glu Trp Met Ala
65                  70                  75                  80

Ile His Gly Arg Val Tyr Lys Asp Ala Val Glu Lys Ala Lys Arg Tyr
                85                  90                  95

Glu Ile Phe Lys Glu Asn Val Lys Arg Ile Asn Ala Phe Asn Asn Gly
            100                 105                 110

Lys Asp Val Gly Tyr Lys Met Ala Val Asn Lys Phe Ala Asp Leu Thr
        115                 120                 125

Asn Glu Glu Phe Arg Ala Ser Tyr Thr Gly Tyr Lys Arg Arg Pro Thr
    130                 135                 140

Arg Val Leu Ser Ser Gly Glu Lys Lys Pro Phe Lys Tyr Ala Asn Phe
145                 150                 155                 160

Thr Ala Ile Pro Ala Ala Leu Asp Trp Arg Thr Lys Lys Ala Val Thr
                165                 170                 175

Pro Val Lys Asp Gln Gly Gly Cys Gly Ser Cys Trp Ala Phe Ser Ala
            180                 185                 190

Val Ala Ala Met Glu Gly Ile Thr Met Ile Lys Lys Gly Lys Leu Val
        195                 200                 205

Pro Leu Ser Val Gln Glu Leu Val Asp Cys Asp Asp Asn Asp Glu Gly
    210                 215                 220

Cys Arg Gly Gly Leu Met Asp Ser Ala Phe Lys Phe Ile Val Ser Asn
225                 230                 235                 240

Gly Gly Leu Thr Thr Glu Ala Asn Tyr Pro Tyr Gln Gly Asn Asp Gly
                245                 250                 255

Thr Cys Asn Thr Ala Lys Thr Ala Asn Pro Ala Ala Ser Ile Thr Gly
            260                 265                 270

Tyr Gln Asp Val Pro Ala Asn Asn Glu Lys Ala Leu Leu Gln Ala Val
        275                 280                 285
```

-continued

```
Ala Asn Gln Pro Val Ser Val Ala Ile Glu Gly Gly Tyr Asn Phe
    290                 295                 300

Gln Phe Tyr Ser Ser Gly Val Phe Thr Gly Ser Cys Gly Thr Asp Ile
305                 310                 315                 320

Asp His Ala Val Thr Ala Val Gly Tyr Gly Lys Thr Ser Gly Ser Gly
                325                 330                 335

Gly Thr Lys Tyr Trp Leu Met Lys Asn Ser Trp Thr Gly Trp Gly
            340                 345                 350

Glu Lys Gly Tyr Met Arg Ile Gln Lys Asp Val Ser Ser Lys Ala Gly
            355                 360                 365

Leu Cys Gly Leu Ala Thr Glu Ala Ser Tyr Pro Ala Ala
    370                 375                 380
```

<210> SEQ ID NO 153
<211> LENGTH: 396
<212> TYPE: PRT
<213> ORGANISM: Pinus radiata

<400> SEQUENCE: 153

```
Lys Lys Ile Val Phe Pro Phe Leu His Thr Asn Ser His Tyr Leu Ser
1               5                   10                  15

Glu Phe Cys Cys Tyr Phe Val Met Ala Ser Val Ser Lys Ala Thr Leu
                20                  25                  30

Leu Leu Phe Leu Ala Thr Thr Leu Trp Thr Leu Ser Ala Asn Ala Ser
            35                  40                  45

Asp Ser Ser Pro Gly Phe Thr Asp Glu Asp Leu Lys Ser Glu Glu Ser
    50                  55                  60

Leu Arg Leu Leu Tyr Asp Lys Trp Ala Leu Arg His Arg Thr Thr Arg
65                  70                  75                  80

Ser Leu Asp Ser Asp Glu His Ala Lys Arg Phe Glu Ile Phe Lys Asp
                85                  90                  95

Asn Val Lys Tyr Ile Asp Ser Val Asn Gln Lys Asp Gly Pro Tyr Lys
                100                 105                 110

Leu Gly Leu Asn Lys Phe Thr Asp Leu Ser Asn Glu Glu Phe Lys Ala
            115                 120                 125

Met His Met Thr Thr Arg Met Glu Lys His Lys Ser Leu Arg Arg Asp
    130                 135                 140

Arg Gly Thr His Ser Gly Ser Phe Met Tyr Gln Asn Ser Asp Asn Leu
145                 150                 155                 160

Pro Glu Ser Ile Asp Trp Arg Glu Lys Gly Ala Val Asn Pro Val Lys
                165                 170                 175

Asn Gln Gly Gln Cys Gly Ser Cys Trp Ala Phe Ser Thr Ile Ala Ser
            180                 185                 190

Val Glu Gly Ile Ser Tyr Val Lys Thr Gly Lys Leu Val Ser Leu Ser
    195                 200                 205

Glu Gln Gln Leu Val Asp Cys Ser Lys Glu Asn Ala Gly Cys Asn Gly
    210                 215                 220

Gly Leu Met Asp Ser Ala Phe Gln Tyr Ile Ile Asp Asn Gly Gly Ile
225                 230                 235                 240

Val Ala Glu Asp Glu Tyr Pro Tyr Thr Ala Glu Ala Ser Glu Cys Ser
                245                 250                 255

Pro Ser Lys Val Lys Pro Asn Ala Ile Ala Ala Thr Ile Asp Gly Phe
            260                 265                 270

Glu Asp Val Pro Ala Asn Asn Glu Lys Ala Leu Lys Glu Ala Val Gly
```

```
                275                 280                 285
His Gln Pro Val Ser Val Ala Ile Glu Ala Ser Gly Lys Asp Phe Gln
            290                 295                 300
Phe Tyr Ser Lys Gly Val Phe Thr Gly Glu Cys Gly Thr Glu Leu Asp
305                 310                 315                 320
His Gly Val Val Ala Val Gly Tyr Gly Lys Ser Pro Glu Gly Ile Asn
                325                 330                 335
Tyr Trp Ile Val Arg Asn Ser Trp Pro Glu Trp Gly Glu Gly
            340                 345                 350
Tyr Ile Lys Met Gln Arg Asp Ile Glu Ala Val Glu Gly Lys Cys Gly
            355                 360                 365
Ile Ala Met Gln Ala Ser Tyr Pro Thr Lys Lys Thr Gln Gly Ile Asp
            370                 375                 380
Ile Glu Leu Asp Val Ala His Val Ser Asp Glu Leu
385                 390                 395

<210> SEQ ID NO 154
<211> LENGTH: 185
<212> TYPE: PRT
<213> ORGANISM: Eucalyptus grandis

<400> SEQUENCE: 154

Glu Asp Tyr Pro Tyr Lys Ala Val Asp Gly Lys Cys Asp Gln Tyr Arg
1               5                   10                  15
Lys Asn Ala Lys Val Val Thr Ile Asp Asp Tyr Glu Asp Val Pro Ala
            20                  25                  30
Asn Asp Glu Lys Ala Leu Gln Lys Ala Val Ala Asn Gln Pro Val Ser
        35                  40                  45
Val Ala Ile Glu Ala Gly Gly Arg Ala Phe Gln Leu Tyr Gln Ser Gly
    50                  55                  60
Val Phe Ser Gly Arg Cys Gly Thr Ala Leu Asp His Gly Val Thr Ala
65                  70                  75                  80
Val Gly Tyr Gly Thr Glu Lys Gly Met Asn Tyr Trp Ile Val Lys Asn
                85                  90                  95
Ser Trp Gly Lys Ser Trp Gly Glu Gln Gly Tyr Ile Arg Met Glu Arg
            100                 105                 110
Ser Leu Thr Asn Thr Ile Thr Gly Lys Cys Gly Ile Ala Met Glu Ala
        115                 120                 125
Ser Tyr Pro Ile Lys Asn Gly Pro Asn Pro Asn Pro Gly Pro Ser
    130                 135                 140
Pro Pro Ser Pro Ile Lys Pro Pro Thr Cys Asp Arg Tyr Tyr Ser
145                 150                 155                 160
Cys Ala Glu Ser Thr Thr Cys Cys Val Tyr Gln Tyr Ala Asn Tyr
                165                 170                 175
Cys Phe Ala Trp Gly Cys Cys Pro Leu
            180                 185

<210> SEQ ID NO 155
<211> LENGTH: 160
<212> TYPE: PRT
<213> ORGANISM: Eucalyptus grandis

<400> SEQUENCE: 155

Ser Thr Pro Arg Asn Ser Ser Gln Val Asn Ser Phe Lys Tyr Gln Gly
1               5                   10                  15
Ser Asn Ser Ile Pro Glu Ser Ile Asp Trp Val Gln Lys Gly Ala Val
```

```
            20                  25                  30
Asn Pro Ile Lys Tyr Gln Arg Gln Cys Gly Ser Cys Trp Ser Phe Ser
            35                  40                  45

Val Val Ala Ala Val Glu Ala Ile Thr Gln Ile Thr Thr Gly Val Leu
 50                  55                  60

Pro Ser Leu Ser Glu Gln Gln Leu Ile Asp Cys Thr Thr Asp Gly Asn
 65                  70                  75                  80

His Gly Cys Glu Gly Gly Ser Met Asp Asn Gly Phe Glu Tyr Ile Ile
                 85                  90                  95

Asn Asn Asn Gly Ile Ser Ser Glu Thr Asn Tyr Pro Tyr Val Gly Val
                100                 105                 110

Asp Gly Thr Cys Asn Val Gln Ala Ser Ser Val Ala Glu Ala Lys Ile
                115                 120                 125

Ser Asp His Lys Asp Val Pro Ser Asn Glu Asp Met Leu Lys Ala
                130                 135                 140

Val Ala Met Gln Pro Val Ser Ala Ala Ile Asp Ala Asn Gly Asp Val
145                 150                 155                 160

<210> SEQ ID NO 156
<211> LENGTH: 272
<212> TYPE: PRT
<213> ORGANISM: Eucalyptus grandis

<400> SEQUENCE: 156

Ser His Ser Asn Cys Val Leu Asp Ser Thr His Thr Ser Thr Met Ala
 1               5                  10                  15

Lys Gln Asn Gln Leu Pro Phe Leu Thr Leu Ala Thr Leu Leu Val Ile
                20                  25                  30

Ile Val Phe Val Ser Glu Thr Leu Cys Arg Pro Leu Gly Glu Glu His
                35                  40                  45

Leu Leu Lys Gln His Glu Gln Trp Met Ala Val His Gly Arg Val Tyr
 50                  55                  60

Lys Asp Ala Asp Glu Lys Ala Leu Arg Tyr Glu Ile Phe Lys Gln Asn
 65                  70                  75                  80

Val Asn Arg Ile Asn Ala Phe Asn Asn Asp Lys Asp Ala Ala Tyr Lys
                 85                  90                  95

Leu Ala Val Asn Lys Phe Ala Asp Leu Thr Asn Glu Glu Phe Arg Ala
                100                 105                 110

Ser Phe Thr Gly Tyr Lys Arg Arg Ser Thr Arg Val Leu Thr Ser Val
                115                 120                 125

Asp Glu Lys Pro Phe Lys Tyr Ala Asn Phe Thr Ala Ala Pro Pro Val
                130                 135                 140

Leu Asp Trp Arg Thr Lys Lys Ala Val Thr Ser Val Lys Asp Gln Ser
145                 150                 155                 160

Ser Cys Gly Ala Cys Trp Ala Phe Ser Ala Val Ala Ala Met Glu Gly
                165                 170                 175

Ile Thr Met Leu Lys Lys Gly Lys Leu Val Ser Leu Ser Glu Gln Glu
                180                 185                 190

Leu Val Asp Cys Asp Val Asn Gly Val Asn Gln Gly Cys Glu Gly Gly
                195                 200                 205

Leu Met Asp Ser Ala Phe Gln Phe Ile Lys Ser Lys Gly Gly Leu Thr
                210                 215                 220

Ser Glu Ala Asn Tyr Pro Phe Gln Gly Asn Asp Gly Thr Cys Arg Thr
225                 230                 235                 240
```

```
Ala Lys Ala Ala Asn Ile Val Ala Ser Ile Ala Gly Tyr Gln Asp Val
            245                 250                 255

Pro Ala Asn Asn Glu Lys Ala Leu Leu Gln Ala Arg Gly Glu Pro Ala
            260                 265                 270
```

<210> SEQ ID NO 157
<211> LENGTH: 122
<212> TYPE: PRT
<213> ORGANISM: Eucalyptus grandis

<400> SEQUENCE: 157

```
Ser His Ser Asn Cys Val Leu Asp Ser Thr His Thr Ser Thr Met Ala
  1               5                  10                  15

Lys Gln Asn Gln Leu Pro Phe Leu Thr Leu Ala Thr Leu Leu Val Ile
             20                  25                  30

Ile Val Ser Val Ser Glu Thr Leu Cys Arg Pro Leu Gly Glu Glu His
             35                  40                  45

Leu Leu Lys Gln His Glu Gln Trp Met Ala Val His Gly Arg Val Tyr
         50                  55                  60

Lys Asp Ala Asp Glu Lys Ala Lys Arg Tyr Glu Ile Phe Lys Gln Asn
 65                  70                  75                  80

Val Asn Arg Ile Asn Ala Phe Asn Asn Asp Lys Asp Ala Gly Tyr Lys
                 85                  90                  95

Leu Ala Val Asn Lys Phe Ala Asp Leu Thr Asn Glu Glu Phe Arg Ala
             100                 105                 110

Ser Phe Thr Gly Tyr Lys Arg Arg Ser Thr
             115                 120
```

<210> SEQ ID NO 158
<211> LENGTH: 378
<212> TYPE: PRT
<213> ORGANISM: Eucalyptus grandis

<400> SEQUENCE: 158

```
Pro Thr His Ile Ser Trp Asn Pro Gln Arg Glu Arg Glu Arg Glu Arg
  1               5                  10                  15

Glu Arg Glu Met Ala Arg Ala Arg Leu Leu Cys Ser Ala Val Leu Leu
             20                  25                  30

Leu Val Ala Val Val Ser Ala Ala Ser Ser Phe Glu Glu Ser
             35                  40                  45

Asn Pro Ile Arg Leu Phe Pro Asp Gly Gly Leu Arg Asp Leu Glu Ser
         50                  55                  60

Ser Ile Val Gln Ile Val Gly Arg Thr Arg His Ala Phe Ser Phe Ala
 65                  70                  75                  80

Arg Phe Ala Asn Arg Tyr Gly Lys Arg Tyr Glu Thr Ala Glu Glu Ile
                 85                  90                  95

Lys Leu Arg Phe Glu Ile Phe Arg Glu Asn Leu Lys Leu Ile Arg Ser
             100                 105                 110

Thr Asn Lys Lys Gly Leu Pro Tyr Thr Leu Gly Val Asn Lys Phe Ala
             115                 120                 125

Asp Trp Ser Trp Glu Glu Phe Arg Arg His Arg Leu Gly Ala Ala Gln
         130                 135                 140

Asn Cys Ser Ala Thr Thr Lys Gly Asn His Lys Leu Thr Asp Glu Ala
145                 150                 155                 160

Leu Pro Glu Met Lys Asp Trp Arg Glu Lys Gly Ile Val Ser Pro Ile
                 165                 170                 175
```

```
Lys Asp Gln Gly His Cys Gly Ser Cys Trp Thr Phe Ser Thr Thr Gly
            180                 185                 190

Ala Leu Glu Ala Ala Tyr His Gln Ala Phe Gly Lys Gln Ile Ser Leu
            195                 200                 205

Ser Glu Gln Gln Leu Val Asp Cys Ala Gly Ala Phe Asn Asn Phe Gly
            210                 215                 220

Cys Ser Gly Gly Leu Pro Ser Gln Ala Phe Glu Tyr Val Lys Tyr Asn
225                 230                 235                 240

Gly Gly Leu Asp Thr Glu Glu Ala Tyr Pro Tyr Thr Ala Val Asp Gly
            245                 250                 255

Ser Cys Lys Phe Ser Ala Asp Asn Val Gly Val Gln Val Leu Asp Ser
            260                 265                 270

Val Asn Ile Thr Leu Gly Ala Glu Asp Glu Leu Lys His Ala Val Ala
            275                 280                 285

Phe Val Arg Pro Val Ser Val Ala Phe Gln Val Val Lys Asp Phe Arg
            290                 295                 300

Leu Tyr Lys Ser Gly Val Tyr Thr Ser Asp Thr Cys Gly Ser Thr Ser
305                 310                 315                 320

Met Asp Val Asn His Ala Val Leu Ala Val Gly Tyr Gly Val Glu Asp
            325                 330                 335

Gly Val Pro Phe Trp Leu Ile Lys Asn Ser Trp Gly Ala Asp Trp Gly
            340                 345                 350

Asp His Gly Tyr Phe Lys Met Glu Met Gly Lys Asn Met Cys Gly Val
            355                 360                 365

Ala Thr Cys Ala Ser Tyr Pro Val Val Ala
            370                 375

<210> SEQ ID NO 159
<211> LENGTH: 129
<212> TYPE: PRT
<213> ORGANISM: Pinus radiata

<400> SEQUENCE: 159

Ala Met His Met Lys Thr Arg Met Glu Lys His Arg Ser Leu Arg Gly
1               5                   10                  15

Asp Arg Gly Val Gln Gly Gly Ser Phe Met Tyr Gln Asn Ser Lys His
            20                  25                  30

Leu Pro Ala Ser Ile Asp Trp Arg Lys Lys Gly Ala Val Thr Pro Val
            35                  40                  45

Lys Asn Gln Gly Gln Cys Gly Ser Cys Trp Ala Phe Ser Thr Val Ala
            50                  55                  60

Ser Val Glu Gly Ile Asn Tyr Ile Lys Thr Gly Lys Leu Val Ser Leu
65                  70                  75                  80

Ser Glu Gln Gln Leu Val Asp Cys Ser Lys Glu Asn Ala Gly Cys Asn
            85                  90                  95

Gly Gly Leu Met Asp Asn Ala Phe Gln Tyr Ile Ile Asp Asn Gly Gly
            100                 105                 110

Ile Val Ser Glu Ala Glu Tyr Pro Tyr Thr Ala Glu Ala Arg Glu Cys
            115                 120                 125

Ser

<210> SEQ ID NO 160
<211> LENGTH: 348
<212> TYPE: PRT
<213> ORGANISM: Eucalyptus grandis
```

```
<400> SEQUENCE: 160

Glu Asn Ile Ile Met Gly Ser Ser Pro Arg Thr His His Gln Leu Gly
 1               5                  10                  15

Leu Ala Ile Leu Phe Phe Ala Ser Leu Ala Arg Leu Ser Leu Ser His
             20                  25                  30

Ala Ser Leu Pro Ser Glu Tyr Ser Ile Ile Gly His Gly Gln Asp Pro
         35                  40                  45

Asn Gly Ala Val Ser Asp Glu Arg Ala Val Glu Leu Phe Arg Arg Trp
     50                  55                  60

Gln Ala Gln His Lys Lys Val Tyr Lys His Ala Gly Glu Ala Glu Arg
 65                  70                  75                  80

Arg Leu Glu Asn Phe Lys Arg Asn Leu Arg Tyr Val Met Glu Arg Ser
                 85                  90                  95

Arg Arg Asp Gly Gly Lys Gln His Gly Val Gly Leu Asn Lys Phe Ala
            100                 105                 110

Asp Leu Ser Asn Glu Glu Phe Arg Gln Arg Tyr Leu Ser Lys Val Lys
        115                 120                 125

Lys Ser Val Asn Gln Lys Trp Arg Ala Lys Arg Glu Ser Leu Met Arg
130                 135                 140

Asn Lys Arg Lys Gly Ala Glu Ser Cys Lys Ala Pro Ser Ser Leu Asp
145                 150                 155                 160

Trp Arg Asn Tyr Gly Ile Val Thr Gly Val Lys Asp Gln Gly Glu Cys
                165                 170                 175

Gly Ser Cys Trp Ala Phe Ser Ser Thr Gly Ala Met Glu Gly Ile Asn
            180                 185                 190

Ala Leu Lys Ser Gly Asp Leu Ile Ser Leu Ser Glu Gln Glu Leu Val
        195                 200                 205

Asp Cys Asp Thr Thr Asn Asp Gly Cys Asp Gly Gly Tyr Met Asp Tyr
    210                 215                 220

Ala Phe Glu Trp Val Ile Asn Asn Gly Gly Ile Asp Ser Glu Glu Asp
225                 230                 235                 240

Tyr Pro Tyr Thr Ser Val Phe Gly Glu Gly Ile Cys Asn Val Thr
                245                 250                 255

Lys Glu Asn Asn Lys Ala Val Thr Ile Asp Gly Tyr Val Asp Val
            260                 265                 270

Tyr Pro Ser Asp Asp Gly Leu Leu Cys Thr Val Ile Gln Gln Pro Ile
        275                 280                 285

Ser Val Gly Met Asp Gly Ser Ala Ile Asp Phe Gln Leu Tyr Thr Gly
    290                 295                 300

Gly Ile Tyr Asp Gly Ser Cys Ser Ala Asn Pro Asp Asp Ile Asp His
305                 310                 315                 320

Ala Val Leu Ile Val Gly Tyr Gly Ser Glu Gly Gly Glu Asp Tyr Trp
                325                 330                 335

Ile Val Lys Glu Leu Leu Gly Glu Gln Ile Trp Gly
            340                 345

<210> SEQ ID NO 161
<211> LENGTH: 248
<212> TYPE: PRT
<213> ORGANISM: Eucalyptus grandis

<400> SEQUENCE: 161

Glu Asn Ile Ile Met Gly Ser Ser Pro Arg Thr His His Gln Leu Gly
 1               5                  10                  15
```

-continued

```
Leu Ala Ile Leu Val Phe Ala Ser Leu Ala Arg Leu Ser Leu Ser His
             20                  25                  30

Ala Ser Leu Pro Ser Glu Tyr Ser Ile Ile Gly His Gly Gln Asp Pro
         35                  40                  45

Asn Gly Ala Val Ser Asp Glu Arg Ala Val Glu Leu Phe Arg Arg Trp
 50                  55                  60

Gln Ala Gln His Lys Lys Val Tyr Lys His Ala Gly Glu Ala Glu Arg
 65                  70                  75                  80

Arg Leu Glu Asn Phe Lys Arg Asn Leu Arg Tyr Val Met Glu Arg Ser
                 85                  90                  95

Arg Arg Asp Gly Gly Lys Gln His Gly Val Gly Leu Asn Lys Phe Ala
            100                 105                 110

Asp Leu Ser Asn Glu Glu Phe Arg Gln Leu Tyr Leu Ser Lys Val Lys
        115                 120                 125

Lys Ser Val Asn Gln Lys Trp Arg Ala Lys Arg Glu Ser Leu Met Arg
130                 135                 140

Asn Lys Arg Lys Gly Ala Glu Ser Cys Lys Ala Pro Ser Ser Leu Asp
145                 150                 155                 160

Trp Arg Asn Tyr Gly Ile Val Thr Gly Val Lys Asp Gln Gly Glu Cys
                165                 170                 175

Gly Ser Cys Trp Ala Phe Ser Ser Thr Gly Ala Met Glu Gly Ile Asn
            180                 185                 190

Ala Leu Lys Ser Gly Asp Leu Ile Ser Leu Ser Glu Gln Glu Leu Val
        195                 200                 205

Asp Cys Asp Thr Thr Asn Asp Gly Cys Asp Gly Gly Tyr Met Asp Tyr
    210                 215                 220

Ala Phe Glu Trp Val Ile Asn Asn Gly Gly Ile Asp Ser Glu Glu Asp
225                 230                 235                 240

Tyr Pro Tyr Thr Ser Val Phe Gly
                245

<210> SEQ ID NO 162
<211> LENGTH: 225
<212> TYPE: PRT
<213> ORGANISM: Eucalyptus grandis

<400> SEQUENCE: 162

Arg Glu Arg Glu Arg Met Ala Gly Ala Arg Phe Leu Cys Ser Phe Leu
 1               5                  10                  15

Leu Leu Leu Thr Ala Cys Ser Ala Thr Ala Ala Gly Phe Gln Gly Ala
             20                  25                  30

Asp Leu Glu Ser Ser Ile Leu Gln Thr Val Gly His Gly Arg Pro Ala
         35                  40                  45

Leu Ser Phe Val Asp Phe Ala Ser Arg Tyr Glu Lys Arg Tyr Glu Thr
 50                  55                  60

Ala Glu Glu Ile Lys Leu Arg Phe Asp Asn Tyr Arg Glu Asn Leu Lys
 65                  70                  75                  80

Leu Ile Arg Ser Thr Asn Gln Lys Gly Leu Pro Tyr Thr Leu Ala Val
                 85                  90                  95

Asn Gln Tyr Ala Asp Trp Ser Trp Glu Glu Phe Lys Thr His Arg Leu
            100                 105                 110

Gly Ala Ser Gln Asp Cys Ser Ala Thr Thr Lys Gly Ser His Lys Leu
        115                 120                 125

Thr Asp Ala Val Leu Pro Lys Thr Lys Asp Trp Arg Lys Glu Gly Ile
130                 135                 140
```

```
Val Ser Pro Val Lys Asn Gln Gly Gly Cys Gly Ser Cys Trp Ser Phe
145                 150                 155                 160

Ser Ala Thr Gly Ala Leu Glu Ala Ala Tyr His Gln Ala His Gly Lys
            165                 170                 175

Gly Ile Ser Leu Ser Glu Gln Gln Leu Val Asp Cys Ala Thr Ala Phe
            180                 185                 190

Asn Asn Phe Gly Cys Asp Gly Gly Leu Pro Ser Gln Ala Phe Glu Tyr
            195                 200                 205

Ile Lys Tyr Asn Gly Gly Leu Glu Thr Glu Ala Tyr Pro Tyr Thr
    210                 215                 220

Ala
225

<210> SEQ ID NO 163
<211> LENGTH: 174
<212> TYPE: PRT
<213> ORGANISM: Eucalyptus grandis

<400> SEQUENCE: 163

His Ser Leu Trp Lys Pro Gln Gly Glu Arg Glu Arg Glu Arg Met Ala
1               5                   10                  15

Gly Ala Arg Phe Leu Cys Ser Phe Leu Leu Val Val Thr Ala Cys Ser
            20                  25                  30

Ala Ala Ala Ala Gly Phe Glu Gly Ala Asp Leu Glu Ser Ser Ile Leu
            35                  40                  45

Gln Thr Val Gly His Thr Arg Pro Ala Leu Ser Phe Val Asp Phe Ala
    50                  55                  60

Arg Gly His Gly Lys Thr Tyr Lys Thr Ala Glu Ile Lys Leu Arg
65                  70                  75                  80

Phe Asp Asn Tyr Arg Glu Asn Leu Lys Leu Ile Arg Ser Thr Asn Gln
                85                  90                  95

Lys Gly Leu Pro Tyr Thr Leu Ala Val Asn Gln Tyr Ala Asp Trp Ser
            100                 105                 110

Trp Glu Glu Phe Lys Thr His Arg Leu Gly Ala Ser Gln Asp Cys Ser
        115                 120                 125

Ala Thr Thr Lys Gly Ser His Lys Leu Thr Asp Asp Val Leu Pro Glu
    130                 135                 140

Thr Lys Asp Trp Glu Arg Lys Gly His Cys Arg Pro Gln Leu Lys Ile
145                 150                 155                 160

Lys Ala Ala Cys Gly Ser Cys Trp Ser Phe Ser Ala Thr Gly
                165                 170

<210> SEQ ID NO 164
<211> LENGTH: 130
<212> TYPE: PRT
<213> ORGANISM: Eucalyptus grandis

<400> SEQUENCE: 164

Leu Asp Trp Val Ala Lys Gly Ala Val Asn Ala Ile Lys Asp Gln Gly
1               5                   10                  15

Arg Cys Gly Ser Cys Trp Ala Phe Ser Ala Val Ala Ala Ile Glu Ser
            20                  25                  30

Ile Thr Gln Ile Lys Thr Gly Lys Leu Leu Glu Leu Ser Glu Gln Gln
            35                  40                  45

Leu Val Asp Cys Thr Ile Glu Asn Tyr Gly Cys Ser Gly Gly Trp Met
    50                  55                  60
```

```
Asp Thr Ala Phe Asp Tyr Ile Ile Gln Asn Gly Gly Ile Ser Ser Glu
 65                  70                  75                  80

Thr Asn Tyr Pro Tyr Asn Ser Ser Asp Gly Thr Cys Asn Ala His Met
                 85                  90                  95

Ala Ser Leu Ser Val Ala Lys Ile Val Gly Tyr Glu Asp Val Pro Asp
            100                 105                 110

Asn Asn Glu Gly Glu Ile Leu Lys Ala Val Ala Met Gln Pro Val Ser
        115                 120                 125

Val Ala
    130

<210> SEQ ID NO 165
<211> LENGTH: 278
<212> TYPE: PRT
<213> ORGANISM: Eucalyptus grandis

<400> SEQUENCE: 165

Ser Ser Ser Ala His Ser Ser Pro Thr Met Asn Arg Phe Leu Ser Leu
  1               5                  10                  15

Leu Ala Leu Phe Ser Leu Ala Ile Val Ser Ala Tyr Ala Ser Ser Glu
             20                  25                  30

Val Asp Gly Asp Ala Leu Ile Arg Gln Val Val Asp Gly Ala Ala Ala
            35                  40                  45

Asp Gly Asp Leu Ser Thr Glu Asp His Arg His Phe Ser Leu Phe Lys
 50                  55                  60

Arg Arg Phe Gly Lys Ser Tyr Ala Ser Gln Glu Glu His Asp His Arg
 65                  70                  75                  80

Phe Ala Val Phe Arg Ala Asn Leu Arg Arg Ala Arg Arg His Gln Glu
                 85                  90                  95

Leu Asp Pro Ser Ala Val His Gly Val Thr Arg Phe Ser Asp Leu Thr
            100                 105                 110

Pro Ser Glu Phe Arg Arg Ser His Leu Gly Ile Arg Gly Gly Leu Arg
        115                 120                 125

Leu Pro Lys Asp Ala Asn Glu Ala Pro Leu Leu Pro Thr Asp Asp Leu
130                 135                 140

Pro Glu Asp Phe Asp Trp Arg Asp His Gly Ala Val Thr Gly Val Lys
145                 150                 155                 160

Asn Gln Gly Ser Cys Gly Ser Cys Trp Ser Phe Ser Ala Thr Gly Ala
                165                 170                 175

Leu Glu Gly Ala His Tyr Leu Ala Thr Gly Glu Leu Val Ser Leu Ser
            180                 185                 190

Glu Gln Gln Leu Val Asp Cys Asp His Glu Cys Asp Pro Asp Glu Pro
        195                 200                 205

Gly Ser Cys Asp Ser Gly Cys Asn Gly Gly Leu Met Asn Ser Ala Phe
210                 215                 220

Glu Tyr Thr Leu Lys Ala Gly Gly Leu Met Arg Glu Gly Asp Tyr Pro
225                 230                 235                 240

Tyr Thr Gly Thr Asp Arg Gly Thr Cys Lys Phe Asp Lys Ser Lys Ile
                245                 250                 255

Ala Ala Ser Val Ser Asn Phe Ser Val Val Ser Leu Asn Glu Asp Gln
            260                 265                 270

Ile Ala Ala Asn Leu Val
        275
```

```
<210> SEQ ID NO 166
<211> LENGTH: 96
<212> TYPE: PRT
<213> ORGANISM: Eucalyptus grandis

<400> SEQUENCE: 166

Ser Leu Ser Glu Gln Glu Leu Ile Asp Cys Asp Thr Thr Tyr Asn Asn
1               5                   10                  15

Gly Cys Asn Gly Gly Leu Met Asp Tyr Ala Phe Ser Tyr Ile Ile Ser
            20                  25                  30

Asn Gly Gly Leu His Lys Glu Glu Asp Tyr Pro Tyr Ile Met Glu Glu
        35                  40                  45

Gly Thr Cys Glu Met Thr Lys Asp Gln Ser Glu Val Val Thr Ile Thr
    50                  55                  60

Gly Tyr Lys Asp Val Pro Val Asp Asn Glu Gln Gly Leu Leu Lys Ala
65                  70                  75                  80

Leu Ala Asn Gln Pro Leu Ser Val Ala Ile Glu Ala Ser Gly Arg Asp
                85                  90                  95

<210> SEQ ID NO 167
<211> LENGTH: 148
<212> TYPE: PRT
<213> ORGANISM: Eucalyptus grandis

<400> SEQUENCE: 167

Lys Met Thr Leu Glu Ala Ala Ser Asn Leu Pro Thr Ser Cys Ser Pro
1               5                   10                  15

Arg Leu Leu Gln Phe Ser Asp Leu Thr Pro Ser Glu Phe Arg Arg Thr
            20                  25                  30

His Leu Gly Leu Arg Arg Lys Val Leu Pro Lys Asp Ala Asn Glu
        35                  40                  45

Ala Pro Ile Leu Pro Thr Gln Asp Leu Pro Lys Asp Phe Asp Trp Arg
    50                  55                  60

Asp His Gly Ala Val Thr Ala Val Lys Asn Gln Gly Ser Cys Gly Ser
65                  70                  75                  80

Cys Trp Ser Phe Ser Thr Thr Gly Ala Leu Glu Gly Ala Asn Tyr Leu
                85                  90                  95

Ala Thr Gly Lys Leu Val Ser Leu Ser Glu Gln Gln Leu Val Asp Cys
            100                 105                 110

Asp His Glu Cys Asp Pro Glu Glu Pro Gly Ser Cys Asp Ser Gly Cys
        115                 120                 125

Asn Gly Gly Leu Met Asn Ser Ala Phe Glu Tyr Thr Leu Ser Thr Gly
    130                 135                 140

Val Trp Val Val
145

<210> SEQ ID NO 168
<211> LENGTH: 119
<212> TYPE: PRT
<213> ORGANISM: Eucalyptus grandis

<400> SEQUENCE: 168

Pro Thr Arg Val Leu Ser Ser Val Asp Val Lys Pro Phe Lys Tyr Ala
1               5                   10                  15

Asn Phe Thr Ala Ile Pro Ala Ala Leu Asp Trp Arg Thr Lys Lys Ala
            20                  25                  30

Val Thr Ser Val Lys Asp Gln Gly Val Cys Gly Cys Cys Trp Ala Phe
        35                  40                  45
```

-continued

```
Ser Ala Val Ala Ala Met Glu Gly Leu Thr Gln Leu Lys Lys Arg Lys
    50                  55                  60

Leu Val Pro Leu Ser Val Gln Glu Leu Val Asp Cys Asp Val Asn Gly
 65                  70                  75                  80

Lys Asp Lys Gly Cys Arg Gly Gly Tyr Met Asp Ser Ala Phe Glu Phe
                 85                  90                  95

Val Ile Ser Asn Gly Gly Leu Thr Thr Glu Ala Glu Tyr Pro Tyr Gln
                100                 105                 110

Gly Thr Asp Arg Thr Cys Asn
            115

<210> SEQ ID NO 169
<211> LENGTH: 370
<212> TYPE: PRT
<213> ORGANISM: Pinus radiata

<400> SEQUENCE: 169

Asn Cys Ser Thr Met Gly Ser Ser Thr Leu Leu Leu Ala Leu Cys
  1               5                  10                  15

Ile Ser Ser Val Ile Cys Leu Ser Ser Ala Ile Arg Pro Asp Asp Asp
                 20                  25                  30

Leu Ile Arg Gln Val Thr Asp Glu Val Asp Ser Asp Pro Gln Ile Leu
             35                  40                  45

Asp Ala Arg Ser Ala Leu Phe Asn Ala Glu Ala His Phe Arg Arg Phe
 50                  55                  60

Ile Arg Arg Tyr Gly Lys Lys Tyr Ser Gly Pro Glu His Glu His
 65                  70                  75                  80

Arg Phe Gly Val Phe Lys Ser Asn Leu Leu Arg Ala Leu Glu His Gln
                 85                  90                  95

Lys Leu Asp Pro Gln Ala Ser His Gly Val Thr Glu Phe Ser Asp Leu
            100                 105                 110

Thr Gln Glu Glu Phe Arg Arg Gln Tyr Leu Gly Leu Arg Ala Pro Pro
            115                 120                 125

Ile Arg Asp Ala His Asp Ala Pro Ile Leu Pro Thr Asn Asp Leu Pro
130                 135                 140

Glu Glu Phe Asp Trp Arg Glu Lys Gly Ala Val Thr Glu Val Lys Asn
145                 150                 155                 160

Gln Gly Ser Cys Gly Ser Cys Trp Ala Phe Ser Thr Thr Gly Ala Leu
                165                 170                 175

Glu Gly Ala Asn Phe Leu Lys Thr Gly Lys Leu Val Ser Leu Ser Glu
            180                 185                 190

Gln Gln Leu Val Asp Cys Asp His Glu Cys Asp Pro Ser Asp Ala Arg
        195                 200                 205

Ser Cys Asp Ser Gly Cys Asn Gly Gly Leu Met Thr Ser Ala Tyr Gln
    210                 215                 220

Tyr Ala Leu Lys Ala Gly Gly Leu Glu Lys Glu Asp Tyr Pro Tyr
225                 230                 235                 240

Thr Gly Lys Asp Gly Thr Cys Ser Phe Asn Lys Asn Lys Ile Val Ala
                245                 250                 255

Gln Val Ser Asn Phe Ser Val Val Ser Ile Asp Glu Asp Gln Ile Ala
            260                 265                 270

Ala Asn Leu Val Lys Asn Gly Pro Leu Ser Val Gly Ile Asn Ala Ala
        275                 280                 285

Phe Met Gln Thr Tyr Val Gly Gly Val Ser Cys Pro Tyr Ile Cys Ser
```

-continued

```
                        290                 295                 300
Lys Arg Met Leu Asp His Gly Val Leu Leu Val Gly Tyr Gly Ser Ala
305                 310                 315                 320

Gly Phe Ala Pro Ile Arg Met Lys Asp Lys Pro Tyr Trp Ile Ile Lys
                325                 330                 335

Asn Ser Trp Gly Pro Asn Trp Gly Glu Asn Gly Phe Tyr Lys Leu Cys
                340                 345                 350

Arg Gly His Asn Val Cys Gly Ile Asn Asn Met Val Ser Thr Val Ala
        355                 360                 365

Ala Ile
    370

<210> SEQ ID NO 170
<211> LENGTH: 137
<212> TYPE: PRT
<213> ORGANISM: Pinus radiata

<400> SEQUENCE: 170

Ser Thr Met Gly Ser Ser Thr Leu Leu Leu Ala Leu Cys Ile Ser
1               5                   10                  15

Ser Val Ile Cys Leu Ser Ser Ala Ile Arg Pro Asp Asp Leu Ile
                20                  25                  30

Arg Gln Val Thr Asp Glu Val Asp Ser Asp Pro Gln Ile Leu Asp Ala
            35                  40                  45

Arg Ser Ala Leu Phe Asn Ala Glu Ala His Phe Arg Arg Phe Ile Arg
    50                  55                  60

Arg Tyr Asp Lys Lys Tyr Ser Gly Pro Glu Glu His Glu His Arg Phe
65                  70                  75                  80

Gly Val Phe Lys Ser Asn Leu Leu Arg Ala Leu Glu His Gln Lys Leu
                85                  90                  95

Asp Pro Gln Ala Ser His Gly Val Thr Glu Phe Ser Asp Leu Thr Gln
            100                 105                 110

Glu Glu Phe Arg Arg Gln Tyr Leu Gly Leu Arg Ala Pro Pro Ile Arg
        115                 120                 125

Asp Ala His Asp Ala Pro Ile Leu Pro
    130                 135

<210> SEQ ID NO 171
<211> LENGTH: 158
<212> TYPE: PRT
<213> ORGANISM: Pinus radiata

<400> SEQUENCE: 171

Asn Pro Lys Ser Leu Glu Phe Ala Glu Phe Ala Val Arg Tyr Gly Lys
1               5                   10                  15

Arg Tyr Asp Ser Val His Gln Leu Val His Arg Phe Asn Val Phe Val
                20                  25                  30

Lys Asn Val Glu Leu Ile Glu Ser Arg Asn Arg Met Lys Leu Pro Tyr
            35                  40                  45

Thr Leu Ala Ile Asn Glu Phe Ala Asp Ile Thr Trp Glu Glu Phe His
    50                  55                  60

Gly Gln Tyr Leu Gly Ala Ser Gln Asn Cys Ser Ala Thr His Ser Asn
65                  70                  75                  80

His Lys Leu Thr Tyr Ala Gln Leu Pro Ala Lys Lys Asp Trp Arg Gln
                85                  90                  95

Glu Gly Ile Val Ser Pro Val Lys Asn Gln Ala His Cys Gly Ser Cys
```

```
                  100                 105                 110
Trp Thr Phe Ser Thr Thr Gly Ala Leu Glu Ala Ala Tyr Thr Gln Ala
            115                 120                 125

Thr Gly Lys Thr Val Ile Leu Ser Glu Gln Gln Leu Val Asp Cys Ala
        130                 135                 140

Gly Ala Phe Asn Asn Phe Gly Cys Asn Gly Gly Leu Pro Ser
145                 150                 155
```

<210> SEQ ID NO 172
<211> LENGTH: 132
<212> TYPE: PRT
<213> ORGANISM: Eucalyptus grandis

<400> SEQUENCE: 172

```
Ser Gly Gly Glu Met Asp Thr Ala Phe Ser Phe Ile Gln Arg Asn Gly
  1               5                  10                  15

Gly Ile Thr Ser Glu Ser Asp Tyr Pro Tyr Arg Gly Arg Asp Gly Ser
             20                  25                  30

Cys Asp Ala Ala Met Leu Arg Ser His Ala Ala Thr Ile Ser Gly Tyr
         35                  40                  45

Gly Asp Val Pro Pro Asn Asp Glu Arg Ser Leu Gln Ala Ala Val Ala
     50                  55                  60

Arg Gln Pro Ile Ser Val Ala Ile Asp Ala Gly Gly Leu Glu Phe Gln
 65                  70                  75                  80

Leu Tyr Ser Arg Gly Ile Phe Thr Gly Ile Cys Gly Tyr Asp Leu Asn
                 85                  90                  95

His Gly Val Ala Ala Val Gly Tyr Gly Ser Glu Gly Ser Arg Asn Tyr
            100                 105                 110

Trp Ile Val Lys Asn Ser Trp Gly Arg Asp Trp Gly Glu Asp Gly Tyr
        115                 120                 125

Val Arg Met Leu
    130
```

<210> SEQ ID NO 173
<211> LENGTH: 147
<212> TYPE: PRT
<213> ORGANISM: Pinus radiata

<400> SEQUENCE: 173

```
Thr Tyr Lys Leu Gly Leu Asn Lys Phe Ala Asp Leu Ser Asn Glu Glu
  1               5                  10                  15

Phe Lys Ala Met His Met Thr Thr Met Glu Asn His Arg Ser Leu
             20                  25                  30

Arg Arg Asp Arg Gly Val Gln Ser Gly Ser Phe Met Tyr Gln Asn Ser
         35                  40                  45

Lys His Leu Pro Ala Ser Ile Asp Trp Arg Lys Lys Gly Ala Val Thr
     50                  55                  60

Pro Val Lys Ser Gln Gly Gln Cys Gly Ser Cys Trp Ala Phe Ser Thr
 65                  70                  75                  80

Val Ala Ser Val Glu Gly Ile Asn Tyr Ile Lys Thr Gly Lys Leu Val
                 85                  90                  95

Ser Leu Ser Glu His Arg Leu Val Asp Cys Ser Lys Glu Asn Ala Gly
            100                 105                 110

Cys Asn Gly Gly Leu Met Asp Asn Ala Phe Gln Tyr Ile Ile Asp Asn
        115                 120                 125

Gly Gly Ile Val Ser Glu Ala Glu Tyr Pro Tyr Thr Ala Glu Ala Ser
```

```
              130                 135                 140

Glu Cys Ser
145

<210> SEQ ID NO 174
<211> LENGTH: 123
<212> TYPE: PRT
<213> ORGANISM: Pinus radiata

<400> SEQUENCE: 174

Met Ala Ser Val Ser Lys Ala Thr Leu Leu Leu Phe Leu Ala Thr Thr
 1               5                  10                  15

Leu Trp Thr Leu Ser Ala His Ala Ser Asp Ser Ser Pro Gly Phe Thr
            20                  25                  30

Asp Glu Asp Leu Lys Ser Glu Glu Ser Leu Arg Leu Leu Tyr Asp Lys
        35                  40                  45

Trp Ala Leu Arg His Arg Thr Thr Arg Ser Leu Asp Ser Asp Glu His
 50                  55                  60

Ala Lys Arg Phe Glu Ile Phe Lys Asp Asn Val Lys Tyr Ile Asp Ser
 65                  70                  75                  80

Val Asn Gln Lys Asp Gly Pro Tyr Lys Leu Gly Leu Asn Lys Phe Thr
            85                  90                  95

Asp Leu Ser Asn Glu Glu Phe Lys Ala Met His Met Thr Thr Arg Met
            100                 105                 110

Glu Lys His Lys Ser Leu Arg Arg Asp Arg Gly
            115                 120

<210> SEQ ID NO 175
<211> LENGTH: 123
<212> TYPE: PRT
<213> ORGANISM: Pinus radiata

<400> SEQUENCE: 175

Met Ala Ser Val Ser Lys Ala Thr Leu Leu Leu Phe Leu Ala Thr Thr
 1               5                  10                  15

Leu Trp Thr Leu Ser Ala His Ala Ser Asp Ser Ser Pro Gly Phe Thr
            20                  25                  30

Asp Glu Asp Leu Lys Ser Glu Glu Ser Leu Arg Leu Leu Tyr Asp Lys
        35                  40                  45

Trp Ala Leu Arg His Arg Thr Thr Arg Ser Leu Asp Ser Asp Glu His
 50                  55                  60

Ala Lys Arg Phe Glu Ile Phe Lys Asp Asn Val Lys Tyr Ile Asp Ser
 65                  70                  75                  80

Val Asn Gln Lys Asp Gly Pro Tyr Lys Leu Gly Leu Asn Lys Phe Thr
            85                  90                  95

Asp Leu Ser Asn Glu Glu Phe Lys Ala Met His Met Thr Thr Arg Met
            100                 105                 110

Glu Lys His Lys Ser Leu Arg Arg Asp Arg Gly
            115                 120

<210> SEQ ID NO 176
<211> LENGTH: 127
<212> TYPE: PRT
<213> ORGANISM: Eucalyptus grandis

<400> SEQUENCE: 176

Glu Ser Ile His Pro Pro Ser Ser Leu Ser Ile Ser Asn Lys Leu Leu
 1               5                  10                  15
```

```
His Gln Lys Leu Asp Pro Ser Ala Ala His Gly Val Thr Gln Phe Ser
            20                  25                  30

Asp Leu Thr Pro Ser Glu Phe Arg Arg Thr His Leu Gly Leu Arg Arg
        35                  40                  45

Lys Val Lys Leu Pro Lys Asp Ala Asn Glu Ala Pro Ile Leu Pro Thr
    50                  55                  60

Gln Asp Leu Pro Lys Asp Phe Asp Trp Arg Asp His Gly Ala Val Thr
65                  70                  75                  80

Ala Val Lys Asn Gln Gly Ser Cys Gly Ser Cys Trp Ser Phe Ser Thr
                85                  90                  95

Thr Gly Ala Leu Glu Gly Ala Asn Tyr Leu Ala Thr Gly Lys Leu Val
            100                 105                 110

Ser Leu Ser Glu Gln Gln Leu Val Asp Cys Asp His Glu Cys Asp
        115                 120                 125
```

<210> SEQ ID NO 177
<211> LENGTH: 133
<212> TYPE: PRT
<213> ORGANISM: Eucalyptus grandis

<400> SEQUENCE: 177

```
Glu Glu Pro Gln Arg Ser Tyr Glu Val Met Ala Ser Ser Ser Ser Lys
1               5                   10                  15

Gly Pro Lys Arg Ser Tyr Asp Ala Met Ala Ser Ser Ser Lys Lys
            20                  25                  30

Pro Arg Arg Ser Tyr Asp Val Phe Leu Ser Phe Arg Gly Pro Asp Val
        35                  40                  45

Arg Asn His Phe Leu Ser His Leu Tyr Val Ala Leu Asp Gln Ala Gly
    50                  55                  60

Ile Ser Thr Tyr Ile Asp Lys Lys Glu Leu Gly Lys Gly Glu Gln Ile
65                  70                  75                  80

Ser Pro Ala Leu Met Lys Ala Ile Glu Glu Ser His Ile Ala Ile Val
                85                  90                  95

Val Phe Ser Glu Asp Tyr Ala Ser Ser Ser Trp Cys Leu Glu Glu Leu
            100                 105                 110

Thr Lys Ile Met Glu Cys Lys Glu Gln Lys Gly Leu Met Val Phe Pro
        115                 120                 125

Val Phe Tyr Lys Val
        130
```

<210> SEQ ID NO 178
<211> LENGTH: 137
<212> TYPE: PRT
<213> ORGANISM: Eucalyptus grandis

<400> SEQUENCE: 178

```
Glu Glu Pro Gln Arg Ser Tyr Glu Val Met Ala Ser Ser Pro Ser Lys
1               5                   10                  15

Glu Pro Lys Arg Ser Tyr Asp Val Phe Leu Ser Phe Arg Gly Pro Asp
            20                  25                  30

Val Arg Asn His Phe Leu Ser His Leu Tyr Ala Ala Leu Asp Gln Val
        35                  40                  45

Gly Ile Ser Thr Tyr Ile Asp Asn Glu Glu Leu Arg Lys Gly Glu Gln
    50                  55                  60

Ile Ser Pro Ala Leu Met Lys Ala Ile Glu Glu Ser Gln Ile Ala Ile
65                  70                  75                  80
```

-continued

```
Val Val Phe Ser Glu Asn Tyr Ala Ser Ser Thr Trp Cys Leu Glu Glu
                85                  90                  95
Ile Ser Lys Ile Met Glu Cys Lys Glu Lys Gly Leu Lys Val Leu
                100                 105                 110
Pro Val Phe Tyr Lys Val Glu Pro Arg Glu Val Arg Gly Gln Lys Gln
                115                 120                 125
Ser Tyr Gly Lys Ala Met Asp Glu His
        130                 135

<210> SEQ ID NO 179
<211> LENGTH: 608
<212> TYPE: PRT
<213> ORGANISM: Pinus radiata

<400> SEQUENCE: 179

Tyr Thr His Lys Asn Ser Lys Gly Ala Ala Gly Lys Leu Leu Ala Leu
 1               5                  10                  15
Gln Asn Leu Ser Asp Ala Asn Ile Glu Ser His Arg Thr Phe Ser Ile
                20                  25                  30
Ser Ala Lys Tyr Leu Arg Ser Tyr Phe Ser Val Ile Leu Tyr Pro Met
                35                  40                  45
Ala Asn Val Asn Phe Thr Pro Ala Ala Arg Asp Gly Thr Ser Ser Ala
        50                  55                  60
Ser Thr Ser Gln Gly Asn Thr Asn Ser Tyr Val Tyr Gln Val Phe Leu
65                  70                  75                  80
Asn His Arg Gly Pro Asp Val Lys Lys Gly Leu Ala Thr His Ile Tyr
                85                  90                  95
His Arg Leu Lys Asp Leu Gly Leu Ser Val Phe Leu Asp Gln Gln Glu
                100                 105                 110
Leu Gln Arg Gly Glu Lys Leu Glu Pro Gln Ile Glu Gly Ala Ile Arg
                115                 120                 125
Thr Ala Ser Val His Val Ala Ile Phe Ser Pro Asn Tyr Ala Gln Ser
        130                 135                 140
Arg Trp Cys Leu Asp Glu Leu Val Gln Met Leu Glu Met Leu Glu Ser
145                 150                 155                 160
Gly Ser Thr Ile Ile Pro Val Phe Tyr Lys Val Asp Pro Ala Asp Leu
                165                 170                 175
Arg Trp Thr Arg Gly Gly Lys Gly Val Tyr Ala Arg Asp Leu Gly Glu
                180                 185                 190
Leu Glu Arg Lys Arg Ala Ser Asp Ser Gln Glu Pro Arg Tyr Asp Pro
                195                 200                 205
Glu Thr Ile Glu Lys Trp Arg Asn Ala Leu Ser Ala Val Ala Asp Ile
        210                 215                 220
Val Gly Phe Glu Leu Lys Asp Lys Glu Glu Ser Gln Leu Val Gln Glu
225                 230                 235                 240
Val Val Gln Gln Val Val Lys Lys Val Arg Lys Pro Pro Leu Asn Val
                245                 250                 255
Ala Lys Tyr Pro Thr Gly Leu Asp Glu Lys Ile Glu Asp Val Asp Arg
                260                 265                 270
Thr Leu Ser Leu Gln Arg Gln Ser Glu Lys Ala Thr Ile Leu Gly Ile
                275                 280                 285
Val Gly Phe Gly Gly Val Gly Lys Ser Thr Leu Ala Lys Gln Phe Phe
        290                 295                 300
Asn Arg Glu Arg Ser Asn Tyr Asp Arg Ser Cys Phe Leu Ser Asp Ile
```

```
305                 310                 315                 320
Arg Ser Lys Ser Leu Pro Ser Val Gln Ser Ser Leu Lys Asp Leu
                325                 330                 335

Ile Gln Ser Asp Ala Gln Ile Asn Ser Val Ala Glu Gly Ile Glu Lys
            340                 345                 350

Leu Lys Arg Val Ser Gln Arg Cys Leu Ile Ile Leu Asp Asp Ile Asp
            355                 360                 365

His Ile Asp Gln Met Asp Ala Leu Tyr Ala Pro Val Ile Arg Ser Ile
        370                 375                 380

His Val Gly Ser Leu Ile Leu Ile Thr Ser Arg Asn Lys Asp Val Leu
385                 390                 395                 400

Arg Ser Ala Gly Ile Gly Glu Ser Ser Ile Cys Thr Leu Lys Gly Leu
                405                 410                 415

Asn Gly Glu His Ser Gln Glu Leu Phe Cys Trp His Ala Phe Gly Arg
            420                 425                 430

Pro Ser Pro Val Val Gly Phe Glu Lys Val Val Glu Lys Phe Leu Asn
            435                 440                 445

Ala Cys Asn Gly Leu Pro Leu Ser Leu Lys Val Leu Gly Ala Leu Leu
        450                 455                 460

His Gly Lys Asp Asp Leu Lys Leu Trp Asn Ala Gln Leu Arg Lys Thr
465                 470                 475                 480

Ser Lys Val Leu Pro Glu Asp Ile Arg Ser Thr Leu Arg Ile Ser Tyr
                485                 490                 495

Asp Ala Leu Asp Lys Glu Lys Gln Ile Phe Leu Asp Ile Ala Cys
            500                 505                 510

Phe Phe Ile Gly Lys Asn Arg Asp Ser Ala Ile Arg Val Trp Asp Gly
            515                 520                 525

Ser Asn Trp Glu Gly Leu Leu Gly Leu Trp Lys Leu Glu Asn Arg Cys
530                 535                 540

Leu Val Glu Val Asp Ser Ser Asn Cys Leu Arg Met His Asp His Leu
545                 550                 555                 560

Arg Asp Ile Gly Arg Gly Ile Ala Glu Tyr Leu Glu Tyr Pro Arg Arg
                565                 570                 575

Leu Trp His Phe Glu Glu Asn Phe Leu Val Ser Ile Leu Lys Leu Ser
            580                 585                 590

Thr Asp Phe Gln Asn Ser Pro Leu Leu Ser Lys Leu Ser Val Asn Phe
            595                 600                 605

<210> SEQ ID NO 180
<211> LENGTH: 181
<212> TYPE: PRT
<213> ORGANISM: Pinus radiata

<400> SEQUENCE: 180

Ala Ser Asp Ser Gln Lys Ser Arg Tyr Asp Thr Asp Thr Ile Glu Lys
1               5                   10                  15

Trp Arg Asn Ala Leu Ser Ser Val Ala Asp Ile Val Gly Phe Glu Leu
            20                  25                  30

Lys Asp Lys Glu Glu Ser Gln Leu Val Gln Glu Val Gln Gln Val
        35                  40                  45

Val Lys Lys Phe Pro Lys Pro Pro Leu Asp Val Ala Lys Tyr Pro Thr
    50                  55                  60

Gly Leu Asp Glu Lys Ile Lys Asp Val Asp Arg Thr Leu Ser Leu Gln
65                  70                  75                  80
```

-continued

```
Arg Gln Ser Glu Lys Ala Thr Ile Leu Gly Ile Val Gly Phe Gly Gly
                 85                  90                  95

Val Gly Lys Ser Thr Leu Ala Lys Gln Phe Phe Asn Arg Glu Arg Ser
            100                 105                 110

Asn Tyr Asp Arg Ser Cys Phe Leu Phe Asp Ile Arg Ser Lys Ser Leu
            115                 120                 125

Pro Ser Val Gln Ser Ser Leu Leu Thr Asp Leu Ile Gln Pro Asn Ala
        130                 135                 140

Gln Ile Asn Asn Val Asp Glu Gly Ile Glu Arg Leu Lys Thr Val Ser
145                 150                 155                 160

Gln Arg Cys Leu Ile Ile Leu Asp Asp Ile Asp His Ile Asp Gln Met
                165                 170                 175

Asp Ala Leu Tyr Ala
            180

<210> SEQ ID NO 181
<211> LENGTH: 132
<212> TYPE: PRT
<213> ORGANISM: Pinus radiata

<400> SEQUENCE: 181

Ile Asp Gln Leu Asp Ala Leu Cys Ala Pro Val Ile Asp Thr Ile Asp
1                5                  10                  15

Val Gly Ser Leu Ile Leu Ile Thr Ser Arg Asn Lys Asp Val Leu Arg
            20                  25                  30

Ser Ala Gly Ile Gly Glu Ser Ser Ile Tyr Thr Leu Lys Gly Leu Asn
        35                  40                  45

Gly Lys His Ser Gln Glu Leu Phe Cys Trp His Ala Phe Gly Gln Pro
    50                  55                  60

Ser Pro Val Val Gly Phe Glu Lys Val Glu Lys Phe Leu Asn Val
65                  70                  75                  80

Cys His Gly Leu Pro Leu Ser Leu Lys Val Phe Gly Ala Leu Leu Arg
                85                  90                  95

Gly Lys Asp Asp Leu Glu Leu Trp Asn Ala Glu Leu Arg Lys Thr Ser
            100                 105                 110

Lys Val Leu Pro Lys Asp Ile Arg Ser Thr Leu Arg Ile Ser Tyr Asp
        115                 120                 125

Ala Leu Asp Lys
    130

<210> SEQ ID NO 182
<211> LENGTH: 395
<212> TYPE: PRT
<213> ORGANISM: Pinus radiata

<400> SEQUENCE: 182

Ile Gly Ile Asp Val Cys Phe Ser Leu Gly Leu Leu Asn Phe Ser Ser
1                5                  10                  15

Gln Asp Leu Val Leu Glu Leu Leu Asp Lys Val Val Lys His Leu Leu
            20                  25                  30

Glu Leu Val Pro Lys Pro Asp Leu Tyr Val Ala Glu Tyr Pro Thr Gly
        35                  40                  45

Leu Asp Asp Lys Leu Lys Asp Phe Glu Asp Thr Val Leu Leu Arg Gln
    50                  55                  60

Gln Gln Gly Arg Lys Pro Gln Ile Leu Gly Ile Val Gly Leu Gly Gly
65                  70                  75                  80
```

```
Val Gly Lys Thr Thr Leu Ala Thr Ala Phe Asn Lys Lys Ser
              85                  90                  95

Ala Tyr His Arg Ser Cys Phe Leu Cys Asp Val Arg Glu Asn Thr Thr
                    100                 105                 110

Asn Arg Ser Leu His Leu Leu Gln Ser Gln Leu Leu Asn Ser Leu Thr
            115                 120                 125

Gly Phe Asn Asn Gln Val Asn Ser Glu Arg Glu Gly Lys Gly Met Leu
            130                 135                 140

Ile Glu Pro Leu Lys Ser Cys Lys Ala Ile Met Ile Phe Asp Val
145                 150                 155                 160

Asp Asp Val Asp Gln Val Lys Ala Phe Leu Pro Gln Ser Asp Val Leu
                165                 170                 175

Asn Ser Glu Ser Leu Ile Leu Ile Thr Thr Arg Asp Arg Asn Val Leu
            180                 185                 190

Arg Ser Leu Lys Val Glu Asn Ser Ser Ile Tyr Ser Leu Ser Gly Leu
            195                 200                 205

Asn Lys Glu His Ser Leu Glu Leu Phe Cys Ser His Ala Phe Ser Pro
210                 215                 220

Ala Phe Pro Leu Pro Glu Phe Lys Ser Leu Val Asp Lys Phe Ile Asp
225                 230                 235                 240

Tyr Cys Asn Gly Leu Pro Leu Ser Leu Lys Ile Phe Gly Ala Leu Leu
                245                 250                 255

Tyr Gly Lys Asp Ile Ser Gln Trp Lys Glu Glu Trp Glu Ser Leu Arg
                260                 265                 270

Gln Ile Ala Pro Ile Ala Ile His Asp Thr Phe Lys Ile Ser Tyr Asp
                275                 280                 285

Ser Leu Asn Gln Glu Glu Lys Asp Ile Phe Leu Asp Ile Ala Cys Phe
            290                 295                 300

Leu Arg Cys His His Arg Asp Ala Ala Ile Ser Ile Trp Asn Lys Ser
305                 310                 315                 320

Gly Trp Arg Gly Asn Arg Gly Phe Leu Asn Leu Gln Asp Lys Ser Leu
                325                 330                 335

Val Glu Val Asp Ala Phe Asn Cys Ile Gln Met His Asn His Leu Arg
                340                 345                 350

Asp Leu Gly Arg Gln Val Ala Ala Ser Ser Leu Pro Pro Arg Leu Leu
            355                 360                 365

Ile Thr Lys Asn Leu Ile His Asn Leu Ser His Gln Ser Ser Val Ser
370                 375                 380

Val Gln Ser Phe Asn Pro Leu Phe Val Ile His
385                 390                 395

<210> SEQ ID NO 183
<211> LENGTH: 523
<212> TYPE: PRT
<213> ORGANISM: Pinus radiata

<400> SEQUENCE: 183

Asn Val Leu Asp Leu Ala Cys Phe Phe Leu Leu Cys Pro Met Ala
 1               5                  10                  15

Asp His Thr Gly Asp Ile Thr Cys Ile Ala Ser Ser Ser Ser Ser
                20                  25                  30

Thr Asn Thr Gly Gln Val Phe Asp Val Phe Leu Asn His Arg Gly Pro
            35                  40                  45

Asp Thr Lys Lys Gly Leu Ala Ser His Ile Tyr Arg Gly Leu Ile Val
50                  55                  60
```

```
Arg Gly Leu Arg Val Phe Leu Asp Gln Pro Glu Leu Arg Lys Gly Glu
 65                  70                  75                  80

Asp Asn Leu Ser Gln Ile Lys Glu Ala Ile Arg Thr Ala Ser Val His
                 85                  90                  95

Val Ala Ile Phe Ser Pro Asn Tyr Ala Gln Ser Arg Trp Cys Leu Asp
            100                 105                 110

Glu Leu Ala Leu Met Val Glu Ser Glu Ser Thr Ile Ile Pro Val Phe
        115                 120                 125

His Asp Val Asp Pro Ser Glu Leu Arg Trp Gln Gln Ser Gly Asp Gly
    130                 135                 140

Val Glu Ser Ile Ile Arg Cys Leu Cys Pro Cys Leu Leu Gly Gly Lys
145                 150                 155                 160

Gly Arg Tyr Ala Arg Asp Leu His Met Leu Gln Lys Lys Thr Thr Leu
                165                 170                 175

Asp Pro His Thr Asn Lys Lys Pro Arg His Asp Ser Arg Thr Leu
            180                 185                 190

Gln Lys Trp Arg Lys Ala Leu Ser Asp Val Ser Asn Lys Ser Gly Phe
        195                 200                 205

Ile Ile Asn Ala Tyr Asn Gly Asp Glu Gly Gln Leu Val Asp Ala Val
    210                 215                 220

Val Glu Glu Val Trp Arg Lys Val Glu Lys Thr Pro Leu Asn Val Ala
225                 230                 235                 240

Lys Tyr Pro Thr Gly Leu Val Glu Lys Ile Glu Asp Val Gly Arg Met
                245                 250                 255

Val Leu Leu Gln His Gln Ser Gln Lys Thr Lys Val Val Gly Ile Val
            260                 265                 270

Gly Leu Gly Gly Val Gly Lys Thr Thr Leu Ala Lys Glu Phe Phe Asn
        275                 280                 285

Arg His Arg Ser Asn Tyr Asp Arg Ser Cys Phe Leu Phe Asp Val Arg
    290                 295                 300

Glu Thr Ala Ala Lys Ser Ser Leu Ser Ser Leu Gln Thr Gln Leu Leu
305                 310                 315                 320

Lys His Leu Ala His Leu Gln Asp Glu Gln Ile Arg Asn Thr Asp Glu
                325                 330                 335

Val Ile Glu Lys Leu Arg Lys His Leu Ser Ser Ser Pro Arg Ser Leu
            340                 345                 350

Ile Val Leu Asp Asp Val Asp His Ile Asp Gln Leu Asp Ala Leu Phe
        355                 360                 365

Ser Pro Val Ile Asp Thr Ile Gln Ala Ser Ser Leu Ile Leu Val Thr
370                 375                 380

Ser Arg Asn Arg Asp Val Leu Ile Ser Ser Gly Ile Leu Glu Ala Ser
385                 390                 395                 400

Ile Tyr Gln Gln Thr Gly Leu Asn Pro Gln Gln Ser Arg Glu Leu Phe
                405                 410                 415

Cys Ser His Ala Phe Asp Gln Ser Cys Pro Val Thr Gly Phe Glu Gln
            420                 425                 430

Leu Val Glu Asp Phe Leu Asp Phe Cys Asp Gly Leu Pro Leu Ser Leu
        435                 440                 445

Lys Val Ile Gly Ala Ala Ile Arg Gly Lys Asp Ser Glu Phe Trp Ile
    450                 455                 460

Gly Gln Leu Asp Lys Asn Arg Arg Ile Leu His Thr Asp Ile His Ser
465                 470                 475                 480
```

-continued

Lys Leu Lys Ile Ser Tyr Asp Gly Leu Asp Lys Glu Glu Gln Gln Ile
              485                 490                 495

Phe Leu Asp Val Ala Cys Phe Phe Ile Gly Glu Asn Arg Asp Thr Ala
              500                 505                 510

Ile Arg Arg Trp Asn Gly Ser Asp Gly Lys Cys
              515                 520

<210> SEQ ID NO 184
<211> LENGTH: 115
<212> TYPE: PRT
<213> ORGANISM: Pinus radiata

<400> SEQUENCE: 184

Ser His Ile Tyr Arg Gly Leu Ile Val Arg Gly Leu Arg Val Phe Leu
 1               5                  10                  15

Asp Gln Pro Glu Leu Arg Lys Gly Lys Asp Ile Pro Ser Gln Ile Lys
              20                  25                  30

Glu Ala Ile Arg Thr Asp Ser Val His Val Ala Ile Phe Ser Pro Thr
              35                  40                  45

Tyr Ala Gln Ser Arg Trp Cys Leu Asp Glu Leu Ala Leu Met Val Glu
         50                  55                  60

Ser Lys Ser Thr Ile Ile Pro Val Phe His Asp Val Asp Pro Phe Glu
 65                  70                  75                  80

Leu Arg Trp Pro Gln Ser Gly Asp Gly Val Glu Ser Ile Ile Arg Cys
                  85                  90                  95

Leu Cys Pro Cys Leu Leu Gly Gly Lys Gly Arg Tyr Ala Arg Asp Leu
              100                 105                 110

His Met Leu
     115

<210> SEQ ID NO 185
<211> LENGTH: 579
<212> TYPE: PRT
<213> ORGANISM: Pinus radiata

<400> SEQUENCE: 185

Leu Val Glu Ile Asp Ser Glu Gly Cys Ile Arg Met His Asp His Leu
 1               5                  10                  15

Arg Asp Leu Gly Arg Asp Val Ala Glu Lys Glu His Pro Leu Arg Leu
              20                  25                  30

Ser Arg Pro Asn Val Asn Leu Leu Arg Thr Leu Ser Pro Ser Ser Pro
              35                  40                  45

Val Arg Gly Ile Ser Met Asn Tyr Gly Asn Gly Lys Gln Phe Leu
         50                  55                  60

Glu Tyr Ile Arg Val Asn Cys Asn Leu Ser Arg Leu Glu Leu Leu Arg
 65                  70                  75                  80

Gly Glu Gly Ser Phe Val Glu Ser Ile Phe Ser Ala Gly Glu Ile Arg
                  85                  90                  95

Gln Leu Val Tyr Leu Gln Trp Lys Glu Cys Pro Ile Ser Ser Ile Ser
              100                 105                 110

Phe Thr Ile Pro Thr Arg Asn Leu Ser Val Leu Tyr Ile Gln Gly Tyr
              115                 120                 125

Ala Leu Lys Thr Leu Trp Gln His Glu Ser Gln Ala Pro Leu Gln Leu
         130                 135                 140

Thr Glu Leu Tyr Ile Asp Ala Thr Leu Ser Glu Val Pro Gln Ser Ile
145                 150                 155                 160

-continued

```
Gly Lys Leu Asn Gln Leu Glu Arg Ile Val Leu Lys Asn Gly Tyr Phe
                165                 170                 175
Lys Thr Leu Pro Asn Glu Phe Tyr Asp Met His Ser Leu Lys His Ile
            180                 185                 190
Thr Leu Gln Asn Cys Glu Gln Met Met Leu Leu Pro Asp Ser Val Gly
        195                 200                 205
Ile Leu Thr Gly Arg Gln Thr His Asp Phe Ser Gly Cys Ser Asn Leu
    210                 215                 220
Gln Ala Leu Pro Asp Ser Val Gly Gln Leu Thr Gly Leu Lys Thr Leu
225                 230                 235                 240
Asp Leu Glu Asp Cys Thr Ser Leu Gln Gly Leu Pro Asp Ser Val Gly
                245                 250                 255
Gln Leu Thr Gly Leu Gln Ser Leu Asp Leu Glu His Cys Thr Ser Leu
            260                 265                 270
Gln Gly Leu Pro Asp Ser Val Gly Gln Leu Thr Gly Leu Gln Thr Leu
        275                 280                 285
Asp Leu Arg Gly Cys Ser Ser Leu Gln Gly Leu Pro Asp Ser Val Gly
    290                 295                 300
Gln Leu Thr Gly Leu Glu Gly Leu Tyr Leu Ser Gly Cys Phe Ser Leu
305                 310                 315                 320
Gln Gly Leu Pro Asp Ser Val Glu Gln Leu Thr Gly Leu Glu Gly Leu
                325                 330                 335
Tyr Leu Ser Gly Cys Phe Ser Leu Gln Gly Leu Pro Asp Ser Val Gly
            340                 345                 350
Gln Leu Thr Gly Leu Gln Ser Leu Asn Leu Glu Tyr Cys Thr Ser Leu
        355                 360                 365
Glu Gly Leu Pro Asp Ser Val Gly Gln Leu Thr Asp Leu Pro Ile Leu
    370                 375                 380
Asp Leu Asn Thr Cys Ile Ser Leu Gln Gly Leu Pro Asp Ser Val Gly
385                 390                 395                 400
Gln Leu Arg Gly Leu Gln Asn Leu Asp Leu Arg Trp Cys Asp Ser Leu
                405                 410                 415
Gln Gly Leu Pro Asp Ser Val Gly Gln Leu Thr Gly Leu Gln Ile Leu
            420                 425                 430
Asp Leu Ser Gly Cys Thr Ser Leu Gln Gly Leu Pro Asp Ser Val Gly
        435                 440                 445
Gln Leu Thr Gly Leu Arg Thr Leu His Leu Glu Asn Cys Thr Ser Leu
    450                 455                 460
Gln Gly Leu Pro Asp Ser Val Gly Asn Leu Thr Ser Leu Lys Trp Leu
465                 470                 475                 480
Asn Leu Ser Gly Cys Ser Asn Leu Gln Met Leu Pro Asn Phe Arg His
                485                 490                 495
Leu Ser Ser Leu Glu Glu Leu His Leu Ser Gly Cys Ser Asn Leu Gln
            500                 505                 510
Met Pro Pro Asn Val Gln His Leu Ser Ser Leu Val Glu Leu Ser Val
        515                 520                 525
Ser His Cys Ser Lys Leu Gln Trp Gly Ala Gly Val Val Glu Ser Leu
    530                 535                 540
Arg His Arg Leu Gly Asn Gly Phe Ile Glu Glu Gly Gly Glu Asn Ile
545                 550                 555                 560
Asp Lys Glu Ser Trp Glu Glu Gly Ser Glu Lys Ser Asp Lys Glu Ser
                565                 570                 575
Trp Glu Glu
```

```
<210> SEQ ID NO 186
<211> LENGTH: 175
<212> TYPE: PRT
<213> ORGANISM: Pinus radiata

<400> SEQUENCE: 186

Val Leu Gln Thr Leu Asp Leu Arg Arg Cys Ser Ser Leu Gln Gly Leu
1               5                   10                  15

Pro Glu Ser Val Gly Gln Leu Thr Gly Leu Gln Ser Leu Asn Leu Glu
            20                  25                  30

Lys Cys Thr Arg Leu Gln Gly Leu Pro Glu Ser Val Gly Gln Leu Thr
        35                  40                  45

Gly Leu Gln Thr Leu Asp Leu Arg Arg Cys Ser Ser Leu Gln Gly Leu
    50                  55                  60

Pro Glu Ser Val Gly Gln Leu Thr Gly Leu Gln Ser Leu Asn Leu Lys
65                  70                  75                  80

Glu Cys Thr Ser Leu Gln Gly Leu Pro Asn Ser Leu Gly Gln Leu Thr
                85                  90                  95

Gly Leu His Ser Leu Tyr Leu Val Glu Cys Ser Ser Leu Gln Gly Leu
            100                 105                 110

Pro Asp Ser Val Gly Gln Leu Thr Gly Leu Gln Ser Ile Asn Leu Gln
        115                 120                 125

Gly Cys Ser Ser Leu Gln Gly Leu Pro Asp Ser Val Gly Gln Leu Thr
    130                 135                 140

Gly Leu His Ser Leu Asn Leu Glu Gly Cys Ser Arg Leu Gln Gly Leu
145                 150                 155                 160

Pro Asp Leu Val Gly Gln Leu Thr Gly Leu Gln Ser Leu Lys Leu
                165                 170                 175

<210> SEQ ID NO 187
<211> LENGTH: 161
<212> TYPE: PRT
<213> ORGANISM: Pinus radiata

<400> SEQUENCE: 187

Asp Arg Cys Ser Ser Leu Gln Gly Leu Pro Asp Ser Val Gly Gln Leu
1               5                   10                  15

Thr Gly Leu Arg Gln Leu Asn Leu Asn Gly Cys Ser Ser Leu Gln Gly
            20                  25                  30

Leu Pro Asp Ser Val Gly Gln Leu Thr Gly Leu Trp Ile Leu Asp Leu
        35                  40                  45

Thr Gly Cys Ser Ser Leu Gln Gly Leu Pro Asp Ser Val Arg Gln Leu
    50                  55                  60

Arg Cys Leu Arg Gly Gly Ser Gly Arg Ala Cys Gly Arg Ala Ala Glu
65                  70                  75                  80

Ala Pro Ala Tyr Asn Gly Gly Leu Pro Gly Gly Leu Ala Glu Ser Arg
                85                  90                  95

Leu Ala Arg Gly Tyr Trp Leu Asn Ser Gly Cys Ser Asn Leu Gln
            100                 105                 110

Met Pro Pro Asn Val Gln His Leu Ser Ser Leu Leu Lys Leu Tyr Val
        115                 120                 125

Ser His Cys Ser Lys Leu Gln Trp Gly Ala Gly Val Val Glu Ser Leu
    130                 135                 140

Arg His Arg Leu Glu Ile Thr Ser Ser Lys Lys Ala Ala Lys Thr Ser
145                 150                 155                 160
```

Met

<210> SEQ ID NO 188
<211> LENGTH: 305
<212> TYPE: PRT
<213> ORGANISM: Pinus radiata

<400> SEQUENCE: 188

```
Gly Leu Pro Asp Ser Val Gly Gln Leu Thr Gly Leu Gln Thr Leu Asp
 1               5                  10                  15

Leu Arg Gly Cys Ser Ser Leu Gln Gly Leu Pro Asp Ser Val Gly Gln
            20                  25                  30

Leu Thr Gly Leu Glu Gly Leu Tyr Leu Ser Gly Cys Phe Ser Leu Gln
        35                  40                  45

Gly Leu Pro Asp Ser Val Glu Gln Leu Thr Gly Leu Glu Gly Leu Tyr
    50                  55                  60

Leu Ser Gly Cys Phe Ser Leu Gln Gly Leu Pro Asp Ser Val Gly Gln
65                  70                  75                  80

Leu Thr Gly Leu Gln Ser Leu Asn Leu Glu Tyr Cys Thr Ser Leu Glu
                85                  90                  95

Gly Leu Pro Asp Ser Val Gly Gln Leu Thr Asp Leu Pro Ile Leu Asp
            100                 105                 110

Leu Asn Thr Cys Ile Ser Leu Gln Gly Leu Pro Asp Ser Val Gly Gln
        115                 120                 125

Leu Arg Gly Leu Gln Asn Leu Asp Leu Arg Trp Cys Asp Ser Leu Gln
    130                 135                 140

Gly Leu Pro Asp Ser Val Gly Gln Leu Thr Gly Leu Gln Ile Leu Asp
145                 150                 155                 160

Leu Ser Gly Cys Thr Ser Leu Gln Gly Leu Pro Asp Ser Val Gly Gln
                165                 170                 175

Leu Thr Gly Leu Arg Thr Leu His Leu Glu Asn Cys Thr Ser Leu Gln
            180                 185                 190

Gly Leu Pro Asp Ser Val Gly Asn Leu Thr Ser Leu Lys Trp Leu Asn
        195                 200                 205

Leu Ser Gly Cys Ser Asn Leu Gln Met Leu Pro Asn Phe Arg His Leu
    210                 215                 220

Ser Ser Leu Glu Glu Leu His Leu Ser Gly Cys Ser Asn Leu Gln Met
225                 230                 235                 240

Pro Pro Asn Val Gln His Leu Ser Ser Leu Val Glu Leu Ser Val Ser
                245                 250                 255

His Cys Ser Lys Leu Gln Trp Gly Ala Gly Val Val Glu Ser Leu Arg
            260                 265                 270

His Arg Leu Gly Asn Gly Phe Ile Glu Glu Gly Gly Glu Asn Ile Asp
        275                 280                 285

Lys Glu Ser Trp Glu Glu Gly Ser Glu Lys Ser Asp Lys Glu Ser Trp
    290                 295                 300

Glu
305
```

<210> SEQ ID NO 189
<211> LENGTH: 85
<212> TYPE: PRT
<213> ORGANISM: Pinus radiata

<400> SEQUENCE: 189

```
Met Leu Pro His Phe Arg His Leu Ser Leu Met Glu Glu Leu His Leu
 1               5                  10                  15

Ser Gly Cys Ser Asn Leu Gln Met Pro Pro Asn Val Gln His Leu Ser
             20                  25                  30

Ser Leu Val Lys Leu Tyr Val Ser His Cys Ser Lys Leu Gln Trp Gly
             35                  40                  45

Ala Gly Val Val Glu Ser Leu Arg His Arg Leu Gly Asn Gly Phe Ile
 50                  55                  60

Glu Glu Gly Gly Glu Asn Ser Asn Glu Tyr Asn Cys Ser Glu Leu Tyr
 65                  70                  75                  80

Asn Ile Arg Glu Leu
             85

<210> SEQ ID NO 190
<211> LENGTH: 320
<212> TYPE: PRT
<213> ORGANISM: Pinus radiata

<400> SEQUENCE: 190

Asn Ser Cys Thr Ser Leu Gln Gly Leu Pro Asp Ser Val Gly Gln Leu
 1               5                  10                  15

Thr Gly Leu Arg Thr Leu Asp Leu Asn Ser Cys Thr Ser Leu Gln Gly
             20                  25                  30

Leu Pro Asp Ser Val Gly Gln Leu Thr Gly Leu Arg Thr Leu Asp Leu
             35                  40                  45

His Ser Cys Thr Ser Leu Gln Gly Leu Pro Asp Ser Val Gly Gln Leu
     50                  55                  60

Thr Gly Leu Glu Thr Leu Asp Leu Gln Asp Cys Thr Ser Leu Gln Gly
 65                  70                  75                  80

Leu Pro Asp Ser Val Gly Gln Leu Thr Gly Leu Gln Val Leu Tyr Leu
             85                  90                  95

Arg Arg Cys Ser Asn Leu Gln Gly Leu Pro Asp Ser Val Gly Gln Leu
             100                 105                 110

Thr Cys Leu Lys Val Leu Cys Leu Arg Trp Cys Ser Asn Leu Gln Ala
             115                 120                 125

Leu Pro Asp Ser Val Gly Gln Leu Thr Gly Leu Lys Ala Leu Asn Leu
             130                 135                 140

Gln Asp Cys Thr Ser Leu Gln Gly Leu Pro Asp Leu Val Gly Gln Leu
145                 150                 155                 160

Thr Gly Leu Lys Ala Leu Asn Leu Gln Asn Cys Thr Ser Leu Gln Gly
             165                 170                 175

Leu Pro Asp Ser Val Gly Gln Leu Thr Gly Leu Gln Val Leu Tyr Leu
             180                 185                 190

Arg Gln Cys Ser Asn Leu Gln Ala Leu Pro Asp Ser Val Gly Gln Leu
             195                 200                 205

Thr Gly Leu Asn Lys Leu Tyr Leu Asn Gly Cys Ser Ser Leu Gln Gly
             210                 215                 220

Leu Pro Asp Ser Val Glu Asn Leu Thr Arg Leu Lys Trp Leu Ile Leu
225                 230                 235                 240

Ser Gly Cys Ser Asn Leu Gln Met Leu Pro Asn Phe Arg His Leu Arg
             245                 250                 255

Ser Leu Glu Arg Leu His Leu Ser Gly Cys Ser Asn Leu Gln Met Pro
             260                 265                 270

Pro Asn Val Gln His Leu Ser Ser Leu Val Gln Leu Tyr Val Ser His
             275                 280                 285
```

```
Cys Ser Lys Leu Gln Trp Gly Ala Gly Val Val Glu Ser Leu Arg His
        290                 295                 300

Arg Leu Gly Asn Gly Phe Ile Glu Glu Gly Gly Glu Asn Ser Asn Glu
305                 310                 315                 320

<210> SEQ ID NO 191
<211> LENGTH: 355
<212> TYPE: PRT
<213> ORGANISM: Pinus radiata

<400> SEQUENCE: 191

Ile Thr Ser Asp Glu Val Glu Leu Ile Glu Lys Ile Val Gln Ser Val
  1               5                  10                  15

Leu Glu Lys Val Asn Arg Ser Ser Phe Tyr Val Pro Lys Tyr Glu Val
             20                  25                  30

Gly Leu Asp Glu Asn Val Glu Lys Phe Arg Lys Val Lys Glu Trp
             35                  40                  45

Ser Gln Gln Arg Gln Asn Glu Lys Ala Gln Val Val Gly Ile Val Gly
         50                  55                  60

Leu Gly Asp Val Gly Lys Thr Thr Leu Val Lys Glu Phe Phe Pro Thr
 65                  70                  75                  80

Glu Ser Pro Ala Tyr Arg Asn Phe Cys Phe Tyr Pro Val Arg Arg Asn
                 85                  90                  95

Gly Cys Ile Thr Arg Pro Asp Cys Leu Ile Gly Glu Leu Phe Lys Gly
                100                 105                 110

Ser Ser Gly Leu Val Ser Ser Pro Thr Ser Val Asp Ala Val Lys Ile
            115                 120                 125

Leu Pro Asp Ala Ser Asn Pro Ser Val Asp Met Ile Arg Asn Asn Pro
        130                 135                 140

Ser Leu Val Val Leu Asp Gly Val Asp Asn Val Glu Glu Arg Glu Asn
145                 150                 155                 160

Leu Leu Lys Ile Gln Glu Arg Leu His Ser Lys Ser Leu Ile Leu Ile
                165                 170                 175

Thr Ser Arg Asp Pro Glu Val Leu Arg Cys Ser Glu Val Glu Lys Ile
            180                 185                 190

Tyr His Leu Asn Gly Leu Asn Glu Pro Cys Ser Arg Lys Leu Phe Cys
        195                 200                 205

Phe His Ala Phe His Gln Ala Ala Pro Leu Gln Gly Tyr Glu Tyr Leu
    210                 215                 220

Val Ala Trp Val Leu Arg Val Cys Asp Gly Leu Pro Leu Leu Leu Lys
225                 230                 235                 240

Leu Leu Gly Ala Leu Leu Cys Gly Asn Asn Asp Arg Phe Tyr Trp Glu
                245                 250                 255

Asp Leu Cys Asp Ser Leu Gln Ala Lys Lys Ile Glu Glu Lys Leu Lys
            260                 265                 270

Val Ile Tyr Asp Thr Leu Gly Thr Glu Glu Gln Thr Phe Leu Asp
        275                 280                 285

Ile Ala Cys Asn Leu Val Gly Lys Asn Ala Asp Ile Trp Leu Lys Ser
    290                 295                 300

Gly Lys Lys Gly Ile Ile Trp Phe Gln Ile Leu Leu Glu Lys Arg Leu
305                 310                 315                 320

Val Glu Val Asp Ser Glu Asn Cys Ile Gln Met His Asp Leu Leu Lys
                325                 330                 335

Asn Leu Gly Gly Glu Ile Ala Lys Ala Thr Lys Ser Pro Arg Pro Leu
```

Phe Phe Gly
355

<210> SEQ ID NO 192
<211> LENGTH: 433
<212> TYPE: DNA
<213> ORGANISM: Pinus radiata

<400> SEQUENCE: 192

```
ctgaggaaga aggcgtaagt ttctttaaaa gttttcattt tggtttttat ccccgagctt      60
aaatctttga ttttctcctc taaatggtta gcatttgcag agcattgcaa atgtaggaaa     120
aagtaagaaa aaaactttca atacagttcg tgcattcttc tactgggtta ctaaagagga     180
aggatcattt gattggttca agggagtcat gaatgaagtg gcagaaattg atcaaagggg    240
cataattgag ttgcacaact attgcacaag tgtttatgaa gagggtgatg ctcgatcagc     300
attgatcgct atgttgcagg cactaaatca tgccaaacat ggtgttgata ttgtatcggg     360
caccagggtt tgcacacact ttgccaagcc taattggaga acgcttcaa gagtattgct      420
ctcatgcaca aag                                                        433
```

<210> SEQ ID NO 193
<211> LENGTH: 431
<212> TYPE: DNA
<213> ORGANISM: Eucalyptus grandis

<400> SEQUENCE: 193

```
agacccctta cgtgagaaga gaattaagag aattcacaaa gccttagact ccgatgatat      60
tgaacttgtt acgcttctct tgagcgagtc caatatcaac ttagatgaag cctatggctt    120
acattatgct gcagcttact gtgaccccaa ggttgtctct gagttgcttg gtttgggctt    180
ggctaacgtc aaccttcgga acccaagggg atacactgtg ctccatgttg ctgcaatgag    240
gaaggagact aagatcatag tctcattgtt gtcaaaaggt gcttgtgcat cggaattgac    300
acctgatgga cagaatgctg tcagcatctg ccgaaggttg acaaggccta aggattataa    360
tgctaaaaca gagcagtgcc aggaagcaaa caaggacagg ctatgcatag atgtactgga    420
gagggaattg t                                                         431
```

<210> SEQ ID NO 194
<211> LENGTH: 427
<212> TYPE: DNA
<213> ORGANISM: Eucalyptus grandis

<400> SEQUENCE: 194

```
tcaataagat catcgatacc ggtgacttgt catggctggg aactgttggt gatgacactc      60
cagaggaaca acttcgtaag aagcaaaggc atatggaagt tgaagaacag atgactgaag    120
cttatactca agacaaagag gagactgata agtctagtat attgtcttct tcatcgtcga    180
cttcaatgag tttccttaag cctaatggta aattaacgac aagtgaccag cagcggcact    240
gcgagattta agatgccaaa agacatcttt ctcattgtac aatattccaa ttttttccca    300
tgtgatgtat ctttatagcc agtcgtttgt aagtactcat ctacacagca aatagatgag    360
gagtgatata cgtacatgca gatgattgtc ttaatagaaa atcatttctc ttaaaaaaaa    420
aaaaaaa                                                              427
```

<210> SEQ ID NO 195

<211> LENGTH: 306
<212> TYPE: DNA
<213> ORGANISM: Eucalyptus grandis

<400> SEQUENCE: 195

```
cacaggtgct tgttggcggc tcggagccag tttcttcacg agtttttcaa gcagggaggc      60
ggcgacaatg caagggaagg aaagccgagg tatcccattt cggacttagt gaaaaagggt     120
catgttggat gtgaggcttt taaatatgtg ttgagataca tgtacacggg aagctcaag     180
ctatttccag cggaggtgtc gacatgcgtg gacagcagtt gcgcacatga cgtgtgcggc     240
cctgctatta attatgccgt ggagttgatg tatgcctcgg ccacttttga gatagcagag     300
ttagtg                                                                306
```

<210> SEQ ID NO 196
<211> LENGTH: 114
<212> TYPE: PRT
<213> ORGANISM: Pinus radiata

<400> SEQUENCE: 196

```
His Leu Gln Ser Ile Ala Asn Val Gly Lys Ser Lys Lys Thr Phe
  1               5                  10                  15

Asn Thr Val Arg Ala Phe Phe Tyr Trp Val Thr Lys Glu Glu Gly Ser
             20                  25                  30

Phe Asp Trp Phe Lys Gly Val Met Asn Glu Val Ala Glu Ile Asp Gln
         35                  40                  45

Lys Gly Ile Ile Glu Leu His Asn Tyr Cys Thr Ser Val Tyr Glu Glu
     50                  55                  60

Gly Asp Ala Arg Ser Ala Leu Ile Ala Met Leu Gln Ala Leu Asn His
 65                  70                  75                  80

Ala Lys His Gly Val Asp Ile Val Ser Gly Thr Arg Val Cys Thr His
                 85                  90                  95

Phe Ala Lys Pro Asn Trp Arg Asn Ala Ser Arg Val Leu Leu Ser Cys
            100                 105                 110

Thr Lys
```

<210> SEQ ID NO 197
<211> LENGTH: 143
<212> TYPE: PRT
<213> ORGANISM: Eucalyptus grandis

<400> SEQUENCE: 197

```
Asp Pro Leu Arg Glu Lys Arg Ile Lys Arg Ile His Lys Ala Leu Asp
  1               5                  10                  15

Ser Asp Asp Ile Glu Leu Val Thr Leu Leu Ser Glu Ser Asn Ile
             20                  25                  30

Asn Leu Asp Glu Ala Tyr Gly Leu His Tyr Ala Ala Tyr Cys Asp
         35                  40                  45

Pro Lys Val Val Ser Glu Leu Leu Gly Leu Gly Leu Ala Asn Val Asn
     50                  55                  60

Leu Arg Asn Pro Arg Gly Tyr Thr Val Leu His Val Ala Ala Met Arg
 65                  70                  75                  80

Lys Glu Thr Lys Ile Ile Val Ser Leu Leu Ser Lys Gly Ala Cys Ala
                 85                  90                  95

Ser Glu Leu Thr Pro Asp Gly Gln Asn Ala Val Ser Ile Cys Arg Arg
            100                 105                 110

Leu Thr Arg Pro Lys Asp Tyr Asn Ala Lys Thr Glu Gln Cys Gln Glu
```

```
                    115                 120                 125
Ala Asn Lys Asp Arg Leu Cys Ile Asp Val Leu Glu Arg Glu Leu
    130                 135                 140
```

<210> SEQ ID NO 198
<211> LENGTH: 82
<212> TYPE: PRT
<213> ORGANISM: Eucalyptus grandis

<400> SEQUENCE: 198

```
Asn Lys Ile Ile Asp Thr Gly Asp Leu Ser Trp Leu Gly Thr Val Gly
  1               5                  10                  15

Asp Asp Thr Pro Glu Glu Gln Leu Arg Lys Lys Gln Arg His Met Glu
             20                  25                  30

Val Glu Glu Gln Met Thr Glu Ala Tyr Thr Gln Asp Lys Glu Glu Thr
         35                  40                  45

Asp Lys Ser Ser Ile Leu Ser Ser Ser Ser Thr Ser Met Ser Phe
     50                  55                  60

Leu Lys Pro Asn Gly Lys Leu Thr Thr Ser Asp Gln Gln Arg His Cys
 65                  70                  75                  80

Glu Ile
```

<210> SEQ ID NO 199
<211> LENGTH: 102
<212> TYPE: PRT
<213> ORGANISM: Eucalyptus grandis

<400> SEQUENCE: 199

```
His Arg Cys Leu Leu Ala Ala Arg Ser Gln Phe Leu His Glu Phe Phe
  1               5                  10                  15

Lys Gln Gly Gly Gly Asp Asn Ala Arg Glu Gly Lys Pro Arg Tyr Pro
             20                  25                  30

Ile Ser Asp Leu Val Lys Lys Gly His Val Gly Cys Glu Ala Phe Lys
         35                  40                  45

Tyr Val Leu Arg Tyr Met Tyr Thr Gly Lys Leu Lys Leu Phe Pro Ala
     50                  55                  60

Glu Val Ser Thr Cys Val Asp Ser Ser Cys Ala His Asp Val Cys Gly
 65                  70                  75                  80

Pro Ala Ile Asn Tyr Ala Val Glu Leu Met Tyr Ala Ser Ala Thr Phe
                 85                  90                  95

Glu Ile Ala Glu Leu Val
            100
```

<210> SEQ ID NO 200
<211> LENGTH: 1425
<212> TYPE: DNA
<213> ORGANISM: Pinus radiata

<400> SEQUENCE: 200

```
atcattttgt gtgaaaataa gcgatgggtt ggttccacag gtgttttgga ttcattagaa      60
agaagaagaa gcagaaaagc ccaaaatctg agcctccgtc tcgtgaacat ttactgaagt     120
ccacacaaga agaattcgag aatacaaagg gagctcaata caaatatcac cgcagatttc     180
ctgctgttag ggataaaacc gagcaggttg cgacgcgatc atttggggat tggatggag      240 cttcactaat agaaactcct ggcagagaaa ccctccaaat tgttataaca gagtgcccaa     300
atactcgtac agtatgttct ggatgtaaat ccaggttaag caactggtgt ccgtcctgca     360
```

-continued

```
gatgcaacct tggaaatttt aggtgcttag ctcctgaaac ggagacatca tctcaagaac    420
ttacttgcat gtatcaaagc tatggttgtg aggatatgta tccttactac agtgaattaa    480
gacatgaagc tcactgcaat tttaggccat acaactgtcc ctatgctggc tccgaatgca    540
agctagttgg agatattccc ttttggtgg ctcatttaag agatgatcac aaagtttata    600
tgcataatag ttgcaccttt gatcatcgat atgtaaagtc aaatccactc gaggttgaga    660
atgctatttg gatgccaact gtaatcaatt gttttgggca attcttttgt ctacattttg    720
aagcgtttct attagacatg gcccctgtat atatagcttt tctgattttc atgggagatg    780
ataatgaagc taaaaacttt agctattgcc tcgagactgg aggcaatggt cggaaactga    840
tttggcatgg ggttcctcga agcatcagag attgtcacag gaaagttcat gacagtagtg    900
acggactaat tatacaaaga gatgtggcac tcttttctc aggtggtgac ataaatgaat    960
tgaatcttag attgacagga cacatattga aggaacaata atatatgcac ttttcaaaga   1020
tctatggact aggaaaagta agtcatatct cctgttattt atcttctcct ttgctgctga   1080
ttaatattgt aaaggttcag atcctttcag tagcaagctg tcattgccag aacaacgaga   1140
gagaaaaatc atatctagaa agtgtatagg ttgaccacgg cacaggtgta tgccattttc   1200
tcatgtaaag acattctcct aattgctaaa gaatgtactt gaattgaatt gaatgccctt   1260
tatttatgga ttgtctgatc gtaatcatgg agagaatatt tgttgttgtt taccactgcc   1320
aacaatacta cgagcgggag aggatttggg tggtagtggt tgtgtaggaa ttaagaatcc   1380
ggactcaaag gttttgataa taaggtttga atcttaaaaa aaaaa                   1425
```

<210> SEQ ID NO 201
<211> LENGTH: 325
<212> TYPE: PRT
<213> ORGANISM: Pinus radiata

<400> SEQUENCE: 201

```
Met Gly Trp Phe His Arg Cys Phe Gly Phe Ile Arg Lys Lys Lys
  1               5                  10                  15

Gln Lys Ser Pro Lys Ser Glu Pro Pro Ser Arg Glu His Leu Leu Lys
             20                  25                  30

Ser Thr Gln Glu Glu Phe Glu Asn Thr Lys Gly Ala Gln Tyr Lys Tyr
         35                  40                  45

His Arg Arg Phe Pro Ala Val Arg Asp Lys Thr Glu Gln Val Ala Thr
     50                  55                  60

Arg Ser Phe Gly Asp Leu Asp Gly Ala Ser Leu Ile Glu Thr Pro Gly
 65                  70                  75                  80

Arg Glu Thr Leu Gln Ile Val Ile Thr Glu Cys Pro Asn Thr Arg Thr
                 85                  90                  95

Val Cys Ser Gly Cys Lys Ser Arg Leu Ser Asn Trp Cys Pro Ser Cys
            100                 105                 110

Arg Cys Asn Leu Gly Asn Phe Arg Cys Leu Ala Pro Glu Thr Glu Thr
        115                 120                 125

Ser Ser Gln Glu Leu Thr Cys Met Tyr Gln Ser Tyr Gly Cys Glu Asp
    130                 135                 140

Met Tyr Pro Tyr Tyr Ser Glu Leu Arg His Glu Ala His Cys Asn Phe
145                 150                 155                 160

Arg Pro Tyr Asn Cys Pro Tyr Ala Gly Ser Glu Cys Lys Leu Val Gly
                165                 170                 175

Asp Ile Pro Phe Leu Val Ala His Leu Arg Asp Asp His Lys Val Tyr
            180                 185                 190
```

```
Met His Asn Ser Cys Thr Phe Asp His Arg Tyr Val Lys Ser Asn Pro
            195                 200                 205
Leu Glu Val Glu Asn Ala Ile Trp Met Pro Thr Val Ile Asn Cys Phe
    210                 215                 220
Gly Gln Phe Phe Cys Leu His Phe Glu Ala Phe Leu Leu Asp Met Ala
225                 230                 235                 240
Pro Val Tyr Ile Ala Phe Leu Ile Phe Met Gly Asp Asp Asn Glu Ala
                245                 250                 255
Lys Asn Phe Ser Tyr Cys Leu Glu Thr Gly Gly Asn Gly Arg Lys Leu
                260                 265                 270
Ile Trp His Gly Val Pro Arg Ser Ile Arg Asp Cys His Arg Lys Val
            275                 280                 285
His Asp Ser Ser Asp Gly Leu Ile Ile Gln Arg Asp Val Ala Leu Phe
        290                 295                 300
Phe Ser Gly Gly Asp Ile Asn Glu Leu Asn Leu Arg Leu Thr Gly His
305                 310                 315                 320
Ile Leu Lys Glu Gln
                325
```

<210> SEQ ID NO 202
<211> LENGTH: 1474
<212> TYPE: DNA
<213> ORGANISM: Pinus radiata

<400> SEQUENCE: 202

```
gaattcggca cgagaaaacg tccatagctt ccttgccaac tgcaagcaat acagtacaag      60
agccagacga tcgaatcctg tgaagtggtt ctgaagtgat gggaagcttg gaatctgaaa     120
aaactgttac aggatatgca gctcgggact ccagtggcca cttgtcccct tacacttaca     180
atctcagaaa gaaaggacct gaggatgtaa ttgtaaaggt catttactgc ggaatctgcc     240
actctgattt agttcaaatg cgtaatgaaa tggacatgtc tcattaccca atggtccctg     300
ggcatgaagt ggtggggatt gtaacagaga ttggcagcga ggtgaagaaa ttcaaagtgg     360
gagagcatgt aggggttggt tgcattgttg ggtcctgtcg cagttgcggt aattgcaatc     420
agagcatgga acaatactgc agcaagagga tttggaccta caatgatgtg aaccatgacg     480
gcacacctac tcagggcgga tttgcaagca gtatggtggt tgatcagatg tttgtggttc     540
gaatcccgga gaatcttcct ctggaacaag cggcccctct gttatgtgca ggggttacag     600
ttttcagccc aatgaagcat tcgccatga cagagcccgg gaagaaatgt gggattttgg      660
gtttaggagg cgtggggcac atgggtgtca agattgccaa agcctttgga ctccacgtga     720
cggttatcag ttcgtctgat aaaagaaag aagaagccat ggaagtcctc ggcgccgatg      780
cttatcttgt tagcaaggat actgaaaaga tgatggaagc agcagagagc ctagattaca     840
taatggacac cattccagtt gctcatcctc tggaaccata tcttgccctt ctgaagacaa     900
atggaaagct agtgatgctg gcgttgttc cagagccgtt gcacttcgtg actcctctct      960
taatacttgg gagaaggagc atagctggaa gtttcattgg cagcatggag gaaacacagg    1020
aaactctaga tttctgtgca gagaagaagg tatcatcgat gattgaggtt gtgggcctgg    1080
actacatcaa cacggccatg gaaaggttgg agaagaacga tgtccgttac agatttgtgg    1140
tggatgttgc tagaagcaag ttggataatt agtctgcaat caatcaatca gatcaatgcc    1200
tgcatgcaag atgaatagat ctggactagt agcttaacat gaaagggaaa ttaaattttt    1260
atttaggaac tcgatactgg tttttgttac tttagtttag cttttgtgag gttgaaacaa    1320
```

-continued

```
ttcagatgtt tttttaactt gtatatgtaa agatcaattt ctcgtgacag taaataataa    1380
tccaatgtct tctgccaaat taatatatgt attcgtattt ttatatgaaa aaaaaaaaaa    1440
aaaaaaaaaa aaaaaaaaaa aaaaaaaaaa aaaa                                1474

<210> SEQ ID NO 203
<211> LENGTH: 414
<212> TYPE: DNA
<213> ORGANISM: Eucalyptus grandis

<400> SEQUENCE: 203
cacgctcgac gaattcggta ccccgggttc gaaatcgata agcttggatc caaagcaaca      60
cattgaactc tctctctctc tctctctctc tctctctctc tcccccaccc ccccttccca    120
accccaccca catacagaca agtagatacg cgcacacaga agaagaaaag atgggggttt    180
caatgcagtc aatcgcacta gcgacggttc tggccgtcct aacgacatgg gcgtggaggg    240
cggtgaactg ggtgtggctg aggccgaaga ggctcgagag gcttctgaga cagcaaggtc    300
tctccggcaa gtcctacacc ttcctggtcg gcgacctcaa ggagaacctg cggatgctca    360
aggaagccaa gtccaagccc atcgccgtct ccgatgacat caagcctcgt ctct          414

<210> SEQ ID NO 204
<211> LENGTH: 755
<212> TYPE: DNA
<213> ORGANISM: Pinus radiata

<400> SEQUENCE: 204
ggcggccgtt cctaaggctc caatggcgat gggtgggagt gcagccaagg atgtggcaga      60
ttccattgat tgggaggtta ggcctggagg aatgctggtt atgtggcaga ttccattgat    120
tgggaggtta ggcctggagg aatgctggtt caaggtcaga gtcacctacg gctcttcctt    180
gcatgaagtt tctgtcagta tgcagaccac atttggtgag ttgaaaaaac tacttgctcc    240
tgagactgga ttagaaccac aagatcaaaa gcttatcttt agaggaaaag aaagggatgg    300
caaggacttc ttagatttag caggtgtgaa agacaagtca aagatcgtgc ttatggaaga    360
tccgatgagt cgagaaaaga agtacattga aatgaggaag aatgcaaaaa ttgagagggc    420
gaccagagct attgctgacg tgagcctaga ggtggataaa cttgcagcac agttgtcttc    480
cctggaagca ctgattgtta aaggcaaaag agtagctgaa aatgatttgg ttgacctcat    540
tgaaatgctt atgagacaac tagtaaaatt agatagcatc ccagctgatg gagatgccaa    600
attgcagaga agaatgcagg ttagaagggt gcaaaagtat gtcgagacat tggatgttct    660
gaaggttccc aatgctacac agaactcatc atctcaacaa cctgtagtgg tgacaacaaa    720
gtgggaaacc ttcgaaactt aattgccacc atgga                                755

<210> SEQ ID NO 205
<211> LENGTH: 246
<212> TYPE: PRT
<213> ORGANISM: Pinus radiata

<400> SEQUENCE: 205

Ala Ala Val Pro Lys Ala Pro Met Ala Met Gly Gly Ser Ala Ala Lys
 1               5                  10                  15

Asp Val Ala Asp Ser Ile Asp Trp Glu Val Arg Pro Gly Gly Met Leu
            20                  25                  30

Val Met Trp Gln Ile Pro Leu Ile Gly Arg Leu Gly Leu Glu Glu Cys
        35                  40                  45
```

-continued

```
Trp Phe Lys Val Arg Val Thr Tyr Gly Ser Ser Leu His Glu Val Ser
    50                  55                  60

Val Ser Met Gln Thr Thr Phe Gly Glu Leu Lys Lys Leu Leu Ala Pro
65                  70                  75                  80

Glu Thr Gly Leu Glu Pro Gln Asp Gln Lys Leu Ile Phe Arg Gly Lys
                85                  90                  95

Glu Arg Asp Gly Lys Asp Phe Leu Asp Leu Ala Gly Val Lys Asp Lys
                100                 105                 110

Ser Lys Ile Val Leu Met Glu Asp Pro Met Ser Arg Glu Lys Lys Tyr
            115                 120                 125

Ile Glu Met Arg Lys Asn Ala Lys Ile Glu Arg Ala Thr Arg Ala Ile
        130                 135                 140

Ala Asp Val Ser Leu Glu Val Asp Lys Leu Ala Ala Gln Leu Ser Ser
145                 150                 155                 160

Leu Glu Ala Leu Ile Val Lys Gly Lys Arg Val Ala Glu Asn Asp Leu
                165                 170                 175

Val Asp Leu Ile Glu Met Leu Met Arg Gln Leu Val Lys Leu Asp Ser
                180                 185                 190

Ile Pro Ala Asp Gly Asp Ala Lys Leu Gln Arg Arg Met Gln Val Arg
            195                 200                 205

Arg Val Gln Lys Tyr Val Glu Thr Leu Asp Val Leu Lys Val Pro Asn
    210                 215                 220

Ala Thr Gln Asn Ser Ser Ser Gln Gln Pro Val Val Val Thr Thr Lys
225                 230                 235                 240

Trp Glu Thr Phe Glu Thr
                245
```

<210> SEQ ID NO 206
<211> LENGTH: 347
<212> TYPE: DNA
<213> ORGANISM: Pinus radiata

<400> SEQUENCE: 206

```
taccottgga gttgtcgatt cctacgtgtt caagagcaac gtagtgaagc tagacgtata      60
agacgttgag catggttcga cttctagtag ctagacatac accagatgcg tcaagagtgc     120
cgtcaacacg tccaacagat ctaccgttat caacctagta aaggaaagtt acgaaaagaa     180
agtcctcaag atagaacgtg ccccagtcga cacgaacgtc aaacaaacgc ctacgttcag     240
ttgtttcttt tgttccttaa gttcctagag ggaggtcttt ctctaaacgt ctaaaacaaa     300
acacgttaga acatgaagtg aaccactatt acttgaagga tccaatc                   347
```

US 6,451,604 B1

COMPOSITIONS AFFECTING PROGRAMMED CELL DEATH AND THEIR USE IN THE MODIFICATION OF FORESTRY PLANT DEVELOPMENT

FIELD OF INVENTION

This invention involves the modification of plant developmental responses. Specifically, this invention relates to polynucleotides and polypeptides that affect programmed cell death. These polynucleotides and polypeptides, and genetic constructs comprising such polynucleotides and polypeptides may be used to modulate programmed cell death and thereby alter the developmental cycle of forestry plant cells, hence altering plant development.

BACKGROUND OF THE INVENTION

Programmed cell death (PCD) refers to an active process, in which gene expression is intimately associated with the events leading to cell death. The plant life cycle contains many instances of such cell death. During plant reproduction and early embryogenesis, events such as organ ablation during unisexual flower development, tapetum degeneration during pollen development and suspensor degeneration during embryo development all involve an active cell death process. During plant morphogenesis and maturation, aleurone cell degradation, the terminal phase of tracheary element differentiation in xylem, leaf blade development in some plants (e.g. genus Monstera), leaf/organ senescence, root cap cell differentiation and the hypersensitive response in plant/pathogen interactions provide further examples of the role of cell death programs in plant developmental cycles.

Most of the scientific investigation relating to programmed cell death to date has involved PCD in mammalian cells. PCD in these cells is evidenced by distinct morphological characteristics, such as cytoplasmic condensation, membrane blebbing, DNA fragmentation, condensation and fragmentation of the nucleus, and finally cell corpse engulfment. In mammalian cells, PCD provides a mechanism for removing unwanted cells, as well as for removing pathogens or pathogen-infected cells. It is also believed that a breakdown in normal PCD mechanisms plays an important role in many disease states, including many malignancies.

The role of PCD in plant systems has not been studied extensively. Preliminary comparisons between plant and mammalian PCD mechanisms suggest some similarities in the mechanisms. The potential similarities include: an oxygen requirement; activation by hydrogen peroxide; a role for calcium in the activation process; a transcription requirement; a dephosphorylation requirement; proteolytic and nucleolytic enzyme involvement and cell condensation and shrinkage. Modulation of the PCD mechanism in any one or more of these areas may affect plant development.

SUMMARY OF THE INVENTION

Briefly, the present invention provides isolated polypeptides, and the polynucleotides encoding the isolated polypeptides, having activity in PCD pathways and various developmental pathways in forestry plant species. Genetic constructs comprising such polynucleotides and methods for the use of such genetic constructs to modulate PCD and various developmental pathways in forestry plants are also provided. Transgenic cells and plants incorporating such genetic constructs and exhibiting a modified content of the polynucleotides and/or polypeptides of the present invention compared to a wild-type plant, are also provided. Methods for modulating plant cell death,. as well as for modulating various forestry plant species developmental pathways, using the polynucleotides and/or polypeptides of the present invention, are disclosed.

In mammalian PCD, regulation of cell cycle entry appears to be important, and it has been suggested that cell cycle checkpoint regulators may be involved in the commitment of a cell to death. For example, the known tumor suppressor p45 is capable of mediating cell cycle arrest and can trigger PCD. One of the key genes involved in p45 mediated responses is the retinoblastoma gene (RB). This tumor suppressor can bind and inhibit the transcription factors that initiate entry into the cell cycle. In addition, RB plays a regulatory role in the cell death process, depending on its phosphorylation status. The regulation of RB proteolysis by phosphorylation status, and the consequent RB levels in the cells are important in the determination of cellular fates. Two polynucleotides encoding retinoblastoma-related polypeptides (SEQ ID NOS: 36, 37) have been isolated from forestry species. Retinoblastoma-related polypeptides encoded by the polynucleotides are identified as SEQ ID NOS: 80, 81.

Another tumor suppressor gene, prohibitin, can also arrest the cell cycle. In rat B lymphocytes, the association of prohibitin with membrane-bound IgM has been suggested as a mediator of PCD in these cells. Furthermore, in yeast, the deletion of prohibitin homologs resulted in a decreased replicative lifespan, leading to successive decreases in cell cycle time, ageing and cellular senescence. While the above studies have been conducted in non-plant systems, it is likely that similar cell cycle modulators are effective in plant systems. Several polynucleotides encoding prohibitin-related polypeptides (SEQ ID NOS: 22–26) have been isolated from forestry species. Prohibitin-related polypeptides encoded by the polynucleotides are identified as SEQ ID NOS: 67–71.

Polynucleotides associated with cellular housekeeping functions are necessary for cell health and survival, and their loss may lead to cell death. One such polynucleotide, initially identified in temperature-sensitive mutant hamster cell lines, was DAD1 (Defender Against Cell Death 1). Cells in temperature-sensitive mutant hamster cell lines undergo PCD at restrictive temperatures, and it has been shown that the Arabidopsis DAD1 can rescue the hamster temperature-sensitive mutant. The presence of DAD1 can also reduce cell death in the developing embryo of the worm *Caenorhabditis elegans*, which undergoes developmentally-regulated cell death. DAD1 has been shown to be a component of oligosaccharyltransferase, involved in N-linked glycosylation. The induction of cell death by DAD1 inactivation, as well as the ability of DAD1 to reduce PCD during development illustrates the essential role of this housekeeping gene. Several polynucleotides encoding DAD1-related polypeptides (SEQ ID NOS: 6–9) have been isolated from forestry species. DAD1-related polypeptides encoded by the polynucleotides are identified as SEQ ID NOS: 51–54.

Another housekeeping polynucleotide which may be used to control cell survival and cell death is the TATA Box Binding Protein (TFIID). TFIID is the most important general factor required for gene transcription by RNA Polymerase II. TFIID binds to the TATA box and participates in the first steps of transcription factor assembly, which is important for the control of gene expression. The ability to developmentally or tissue-specifically knock-out TFIID activity provides a method of specifically inducing cell death. Attempts at TFIID knock-out have not been reported for plants. Polynucleotides encoding TFIID-related transcription initiation factors (SEQ ID NOS: 41, 42) have been isolated from forestry species. TFIID-related transcription initiation factors encoded by the polynucleotides are identified as SEQ ID NOS: 85, 86.

Another transcription factor involved in the control of mammalian cell death is pur-alpha. Pur-alpha is a single-stranded DNA binding protein, which has been shown to play a role in both DNA replication and transcriptional regulation. Pur-alpha is able to suppress PCD of mammalian cells by two mechanisms. The first is the transcriptional repression of Fas (CD-95), a receptor which transduces a cell death signal by interaction with its ligand, and the second is the protection of mammalian cells against cell death mediated by p53. Polynucleotides encoding allelic variants of plant pur-alpha have been isolated (SEQ ID NOS: 90–91) from forestry species. The corresponding amino acid sequences of the pur-alpha polypeptides encoded by the polynucleotides are identified as SEQ ID NOS: 141–142.

The actual process of cell death involves the degradation of proteins and nucleic acids, mediated by proteases and nucleases. Experimental work done with mammalian systems suggests that proteases may be an important trigger of cell death. In animals, the caspase family of cysteine proteases are major effectors of this process. Cysteine proteases have been identified in plants which are up-regulated and specifically associated with aleurone and tracheary element cell death. Polynucleotides encoding cysteine proteases in forestry species have been identified as SEQ ID NOS: 92–125. The corresponding amino acid sequences of polypeptides encoded by the polynucleotides are identified by SEQ ID NOS: 143–176. In addition, an aspartic nuclease, nucellin, has been shown to be specifically associated with nucellar cell death. Polynucleotides encoding a nucellin-like aspartic protease (SEQ ID NOS: 15–16) have been isolated from forestry species. The corresponding amino acid sequences of the aspartic nuclease encoded by the polynucleotides are identified in SEQ ID NOS: 60–61.

In addition to actual protease activity, targeting of proteins for proteolytic degradation via the ubiquitin-proteosome pathway is up-regulated during PCD. Human homologs to the Drosophila SINA (Seven In Absentia) gene are activated during PCD. SINA has been shown to target specific proteins for ubiquitination and degradation in both humans and Drosophila. Polynucleotides encoding SINA-related polypeptides (SEQ ID NOS: 38–40, and 200) have been isolated from forestry species. SINA-related polypeptides encoded by the polynucleotides are identified as SEQ ID NOS:. 82–84, and 201.

Nuclear DNA cleavage, nuclear fragmentation and RNA degradation are active processes that occur during PCD in animals and plants. Specific plant DNases and RNases have been identified during PCD in plant aleurone cells, tracheary elements, cells undergoing a hypersensitive response to a pathogen, as well as during salt stress-induced cell death. Polynucleotides encoding a plant DNase (SEQ ID NO: 10) and xylogenic RNase (SEQ ID NO: 45) have been isolated from forestry species. The corresponding amino acid sequences of the DNase and RNase encoded by the polynucleotides are identified in SEQ ID NOS: 55 and 89, respectively.

In mammalian systems, caspase activation can be inhibited by proteins such as Bcl-2, providing protection against cell death. However, other members of the Bcl-2 family, such as Bax, are antagonistic towards the protective effect of Bcl-2 and promote cell death, due to their ability to interact with Bcl-2 and inhibit its protective ability. A recently discovered gene, BI-1 (Bax Inhibitor-1), was found to inhibit Bax-induced cell death. This gene is identical to a previously identified human gene identified as TEGT (Testis Enhanced Gene Transcript). is Polynucleotides encoding TEGT polypeptides isolated from forestry species are identified as SEQ ID NOS: 43–44. The corresponding amino acid sequences of the TEGT polypeptides encoded by the polynucleotides are identified as SEQ ID NOS:87–88.

Another protein involved in inhibition of PCD is BAG-1 (Bcl-2-Associated-athanoGene), a multifunctional protein that blocks apoptosis and interacts with several types of proteins, including Bcl-2 family proteins, the kinase Raf-1, certain tyrosine kinase growth factor receptors, and steroid hormone receptors in mammalian cells. It is identical to a hormone-receptor binding protein RAP46. BAG-1 binds to and potentiates the effect of the anti-apoptotic protein Bcl-2, to make cells more resistant to apoptosis. Human BAG-1 is overexpressed in human leukemias, colon, cervical, breast, prostate and lung cancer cell lines. A polynucleotide encoding a BAG-1 polypeptide isolated from forestry species is identified as SEQ ID NO: 204. The corresponding amino acid sequence of the BAG-1 polypeptide encoded by the polynucleotide is identified as SEQ ID NO: 205. The isolated polynucleotide sequence encoding BAG-1 contains a PROSITE motif for a ubiquitin-like domain that is also present in the human and mouse BAG-1 proteins.

Numerous studies of mammalian systems have shown that treatments that induce PCD also cause oxidative stress, suggesting a role for oxidative stress in PCD. This has been confirmed by observations that the addition of ROS (Reactive Oxygen Species) or a depletion of cellular antioxidants can cause PCD. PCD can be associated with ROS induction, and PCD can be blocked by the addition of compounds with antioxidant properties. Reactive oxygen species such as superoxide, the hydroxyl radical and hydrogen peroxide can react with and damage cell macromolecules. Additionally, they may set in motion chain reactions in which free radicals are passed from one molecule to another, resulting in extensive cell damage and toxicity.

Plants also exhibit ROS induction during PCD, such as during osmotic stress-mediated death, the hypersensitive response and the terminal stages of tracheary element differentiation. In animal cells, the membrane bound NADPH oxidase complex leads to the generation of superoxide, which is then converted to other ROS. In addition, the small cytosolic protein rac2 is required for activation of the oxidase. When a constitutively active rac2 mutant was inserted into mice, a significant enhancement of PCD occurred compared to wild type mice. Biochemical and immunochemical studies have shown that NADPH oxidase and rac2 are present in plant cells and interact during hypersensitive response PCD. Furthermore, the NADPH oxidase is active during osmotic stress-mediated cell death and during the terminal phase of tracheary element differentiation. The gp 91 NADPH oxidase subunit has been cloned from rice and Arabidopsis. Polynucleotides encoding polypeptides relating to Rac2 (SEQ ID NOS: 28–35) and the gp 91 NADPH oxidase subunit (SEQ ID NO 192) have been isolated from forestry species. The corresponding predicted amino acid sequences for the Rac2-related polypeptides encoded by the polynucleotides given in SEQ ID NOS: 28 and 30–45 are given in SEQ ID NOS: 73 and 74–79. The corresponding predicted amino acid sequence for the gp 91 NADPH oxidase subunit related polypeptide is given in SEQ ID NO: 196.

The role of superoxide compounds in plant cell death was illustrated with the discovery of the lesion simulating cell death (lsd1) mutant in Arabidopsis. In this mutant, superoxide was necessary and sufficient to induce and propagate cell death. Lsd1 in wild type plants is believed to serve as a monitor to a superoxide-dependent signal and to act as a negative regulator of a plant cell death pathway. Polynucleotides encoding lsd1-related polypeptides (SEQ ID NOS: 13 and 14) have been isolated from forestry species. Lsd1-related polypeptides encoded by the polynucleotides are identified as SEQ ID NOS: 58 and 59.

ATL2 was identified as an Arabidopsis cDNA which was toxic when overexpressed in yeast. The nucleotide sequences of five ATL2 variants isolated from forestry species are given in SEQ ID NOS: 1–5 and the corresponding predicted amino acid sequences in SEQ ID NOS: 46–50.

Another gene, lls1, identified from a maize mutant, is also required to limit the spread of cell death in a developmental manner in leaves. Polynucleotides encoding lethal leaf spot protein lls1-related polypeptides; (SEQ ID NOS: 11–12) have been isolated from forestry species. Polypeptides encoded by the polynucleotides are identified as SEQ ID NOS: 56–57.

Another plant protein from Arabidopsis (oxy5) has been shown to be a member of the annexin family of proteins and protect bacterial cells from oxidative stress. Oxy5 has also been shown to protect mammalian cells from tumor necrosis factor-induced cell death. The involvement of oxidative stress in the various instances of PCD in plants suggests that oxy5 plays a protective role. The annexin sequences show good homology to oxy5, and hence are expected to provide the same function or similar function. The nucleotide sequences of annexin-like proteins isolated from forestry species are given in SEQ ID NOS: 17–21 and the corresponding predicted amino acid sequences in SEQ ID NOS: 62–66.

The most actively investigated example of PCD in plants concerns the hypersensitive response (HR) to pathogens. The HR is found in most responses mediated by disease resistance (R) genes. The HR is invoked by the association of a pathogen avirulence gene product with a receptor. This sets in motion a cascade of events involving ion fluxes, kinase/phosphatase actions and an oxidative burst leading to localized cell death and the induction of systemic acquired resistance (SAR), in which other parts of the plants develop an acquired resistance to the pathogen. A wide range of plant disease receptors have been identified, including polypeptides that span the cell membrane and contain an extracellular and cytoplasmic domain, as well as polypeptides that are strictly cytoplasmic and do not contain an extracellular domain.

Of the cytoplasmic polypeptide receptors involved in the HR, three families are of primary interest. The first is the RPS2-like polypeptide family, in which the polypeptides include an amino-terminal leucine zipper region, a nucleotide-binding site, an internal hydrophobic domain and a carboxy-terminal leucine-rich repeat. The second is the RPP5-like polypeptide family, in which the polypeptides include an amino-terminal Toll-like domain, a nucleotide-binding site, an internal hydrophobic domain and a carboxy-terminal leucine-rich repeat region. The nucleotide sequences of RPP5-like proteins isolated from forestry species are given in SEQ ID NOS:126–140, and the corresponding predicted amino acid sequences in SEQ ID NOS: 177–191.

The third family of cytoplasmic receptors involved in the HR is the PTO-like family, in which the polypeptides include, a serine-threonine kinase domain. The exact mechanisms by which the HR cell death signals are transduced are not known, although protein-protein interactions and kinase reactions have been shown to be involved in the PTO-like family, with several PTO-interacting protein genes identified.

Downstream of the initial avirulence/receptor interaction, the development of SAR occurs, which involves the NPR1 gene. Mutations in the NPR1 gene increase the susceptibility of plants to pathogen infection and prevent the development of HR PCD and SAR. The expression of R genes in transgenic plants has allowed the development of HR PCD and resistance to specific pathogens. In addition, the expression of PTO-like family members, such as Fen, can lead to PCD in the absence of a pathogen. The nucleotide sequences encoding NPR1-like proteins isolated from forestry species are given in SEQ ID NOS: 193–195 and the corresponding predicted amino acid sequences in SEQ ID NOS: 197–199. The nucleotide sequence encoding a Fen-like protein isolated from forestry species is given in SEQ ID-NO: 27, and the corresponding predicted amino acid sequence in SEQ ID NO: 72. Little is known about the roles of these genes in other cases of plant PCD. An interesting point comes from the realisation that members of the plant R gene families and NPR1 show similarity to several proteins that are involved in animal development and defense. The discovery of a shared pathway linking developmental processes and disease resistance suggests that there may be roles for HR-associated genes in other plant PCD and developmental pathways.

In a first aspect, the present invention provides isolated polynucleotide sequences identified in the attached Sequence Listing as SEQ ID NOS: 1–45, 90–140, 192–195, 200, 202 and 206; variants of those sequences; extended sequences comprising the sequences set out in SEQ ID NOS: 1–45, 90–140, 192–195, 200, 202 and 206, and their variants; probes and primers corresponding to the sequences set out in SEQ ID NOS: 1–45, 90–140, 192–195, 200, 202 and 206, and their variants; polynucleotides comprising at least a specified number of contiguous residues of any of the polynucleotides identified as SEQ ID NOS: 1–45, 90–140, 192–195, 200, 202 and 206 (x-mers); and extended sequences comprising portions of the sequences set out in SEQ ID NOS: 1–45, 90–140, 192–195, 200, 202 and 206; all of which are referred to herein, collectively, as "polynucleotides of the present invention." The present invention also provides isolated polypeptide sequences identified in the attached Sequence Listing as SEQ ID NOS: 46–89, 141–191, 196–199, 201 and 205; polypeptide variants of those sequences; and polypeptides comprising the isolated polypeptide sequences and variants of those sequences.

The polynucleotide sequences identified as SEQ ID NOS: 1–45, 90–140, 192–195, 200, 202 and 206, were derived from forestry plant sources, namely from *Eucalyptus grandis* and *Pinus radiata*. Some of the polynucleotides of the present invention are "partial" sequences, in that they do not represent a full length gene encoding a full length polypeptide. Such partial sequences may be extended by analyzing and sequencing various DNA libraries using primers and/or probes and well known hybridization and/or PCR techniques. Partial sequences may be extended until an open reading frame encoding a polypeptide, a full length polynucleotide and/or gene capable of expressing a polypeptide, or another useful portion of the genome is identified. Such extended sequences, including full length polynucleotides and genes, are described as "corresponding to" a sequence identified as one of the sequences of SEQ ID NOS: 1–45, 90–140, 192–195, 200, 202 and 206, or a variant thereof, or a portion of one of the sequences of SEQ ID NOS: 1–45, 90–140, 192–195, 200, 202 and 206, or a variant thereof, when the extended polynucleotide comprises an identified sequence or its variant, or an identified contiguous portion (x-mer) of one of the sequences of SEQ ID NOS: 1–45, 90–140, 192–195, 200, 202 and 206, or a variant thereof. Similarly, RNA sequences, reverse sequences, complementary sequences, antisense sequences, and the like, corresponding to the polynucleotides of the present invention, may be routinely ascertained and obtained using the cDNA sequences identified as SEQ ID NOS: 1–45, 90–140, 192–195, 200, 202 and 206.

The polynucleotides identified as SEQ ID NOS: 1–45, 90–140, 192–195, 200, 202 and 206, may contain open reading frames ("ORFs") or partial open reading frames encoding polypeptides. Additionally, open reading frames encoding polypeptides may be identified in extended or full length sequences corresponding to the sequences set out as SEQ ID NOS: 1–45, 90–140, 192–195, 200, 202 and 206. Open reading frames may be identified using techniques that are well known in the art. These techniques include, for example, analysis for the location of known start and stop codons, most likely reading frame identification based on codon frequencies, etc. Suitable tools and software for ORF analysis are available for example, on the Internet. Open reading frames and portions of open reading frames may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, open reading frames encoding polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

Polypeptides encoded by the pplynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

The present invention also contemplates methods for modulating the polynucleotide and/or polypeptide content and composition of a forestry species, such methods involving stably incorporating into the genome of the organism a genetic construct comprising one or more polynucleotides of the present invention. In one embodiment, the target organism is a forestry species, preferably a woody plant, more preferably a woody plant of the Pinus or Eucalyptus species, and most preferably *Eucalyptus grandis* or *Pinus radiata*. In a related aspect, a method for producing a forestry plant having an altered genotype or phenotype is provided, the method comprising transforming a plant cell with a genetic construct of the present invention to provide a transgenic cell, and cultivating the transgenic cell under conditions conducive to regeneration and mature plant growth. Forestry plants having an altered genotype or phenotype as a consequence of modulation of the level or content of a polynucleotide or polypeptide of the present invention compared to a wild-type organism, as well as components (seeds, etc.) of such forestry plants, and the progeny of such forestry plants, are contemplated by and encompassed within the present invention.

The isolated polynucleotides of the present invention also have utility in genome mapping, in physical mapping, and in positional cloning of genes. Additionally, the polynucleotide sequences identified as SEQ ID NOS: 1–45, 90–140, 192–195, 200, 204 and 206, and their variants, may be used to design oligonucleotide probes and primers. Oligonucleotide probes and primers have sequences that are substantially complementary to the polynucleotide of interest over a certain portion of the polynucleotide. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology used by Synteni (Palo Alto, Calif.).

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

The polypeptides of the present invention and the polynucleotides encoding the polypeptides have activity in PCD and various developmental pathways in plants. The polynucleotides were putatively identified by DNA and polypeptide similarity searches. In the attached Sequence Listing, SEQ ID NOS. 1–28, 30–45, 90–140, 192–195, 200 and 204, are polynucleotide sequences that encode the polypeptides listed in SEQ ID NOS. 46–73, 74–89, 141–191, 196–199, 201 and 205, respectively. The polynucleotides and polypeptides of the present invention have demonstrated similarity to the following polypeptides that are known to be involved in PCD and/or plant developmental processes:

TABLE 1

| POLYPEPTIDE IDENTITY | Polynucleotide SEQ ID NO. | Polypeptide SEQ ID NO. |
|---|---|---|
| ATL2 | 1–5 | 46–50 |
| DAD1 (Defender Against Cell Death) | 6–9 | 51–54 |
| DNase | 10 | 55 |
| lls (lethal leaf spot) | 11, 12 | 56, 57 |
| lsd1 (lesion stimulating death) | 13, 14 | 58, 59 |
| Nucellin-like aspartic protease | 15, 16 | 60, 61 |
| Annexin | 17–21 | 62–66 |
| Prohibitin | 22–26 | 67–71 |
| Fen-like protein | 27 | 72 |
| Rac2 | 28–35 | 73, 74–79 |
| Retinoblastoma-related Protein | 36, 37 | 80, 81 |
| SINA (Seven in absentia) | 38–40, 200 | 82–84, 201 |
| TFIID (Transcription Initiation Factor) | 41, 42 | 85, 86 |
| TEGT (Testis Enhanced Gene Transcript) | 43, 44 | 87, 88 |
| Xylogenic RNase | 45 | 89 |

TABLE 1-continued

| POLYPEPTIDE IDENTITY | Polynucleotide SEQ ID NO. | Polypeptide SEQ ID NO. |
|---|---|---|
| Pur-alpha | 90, 91 | 141, 142 |
| Cysteine proteases | 92–125 | 143–176 |
| RPP5-like proteins | 126–140 | 177–191 |
| gp 91 NADPH oxidase subunit | 192 | 196 |
| NPR-like proteins | 193–195 | 197–199 |
| BAG-1 | 204 | 205 |

In one embodiment, isolated polynucleotides of the present invention comprise a sequence selected from the group consisting of: (a) sequences recited in SEQ ID NOS: 1–45, 90–140, 192–195, 200, 204 and 206; (b) complements of the sequences recited in SEQ ID NOS: 1–45, 90–140, 192–195, 200, 204 and 206; (c) reverse complements of the sequences recited in SEQ ID NOS: 1–45,;90–140, 192–195, 200, 204 and 206; (d) reverse sequences of the sequences recited in SEQ ID NOS: 1–45, 90–140, 192–195, 200, 204 and 206; and (e) sequences having at least 50%, 75%, 90%, or 98% identity, as defined herein, to a sequence of (a)–(d) or a specified region of a sequence of (a)–(d).

In a further aspect, isolated polypeptides encoded by the polynucleotides of the present invention are provided. In one embodiment, such polypeptides comprise an amino acid sequence recited in SEQ ID NOS: 46–89, 141–191, 196–199, 201 and 205, and variants thereof, as well as polypeptides expressed by polynucleotides of the present invention, including polynucleotides comprising a sequence of SEQ ID NOS: 1–45, 90–140, 192–195, 200 and 204.

In another aspect, the invention provides genetic constructs comprising a polynucleotide of the present invention, either alone, in combination with one or more additional polynucleotides of the present invention, or in combination with one or more known polynucleotides, together with cells and target organisms comprising such constructs.

In a related aspect, the present invention provides genetic constructs comprising, in the 5'-3' direction, a gene promoter sequence, an open reading frame coding for at least a functional portion of a polypeptide encoded by a polynucleotide of the present invention, and a gene termination sequence. The open reading frame may be oriented in either a sense or antisense direction. Genetic constructs comprising a gene promoter sequence, a polynucleotide of the present invention, and a gene termination sequence are also contemplated, as are genetic constructs comprising a gene promoter sequence, an untranslated region of a polynucleotide of the present invention, or a nucleotide sequence complementary to an untranslated region, and a gene termination sequence. The genetic construct may further include a marker for the identification of transformed cells.

The gene promoter and termination sequences are preferably functional in a host plant and, most preferably, are those native to the host plant. Promoter and termination sequences that are generally used in the art, such as the Cauliflower Mosaic Virus (CMV) promoter, with or without enhancers such as the Kozak sequence or Omega enhancer, and *Agrobacterium tumefaciens* nopaline synthase terminator, are useful. Tissue-specific promoters may be employed in order to target expression to one or more desired tissues.

In a further aspect, methods for producing forestry plants having a modified content of a polynucleotide or polypeptide of the present invention compared to a native organism are provided. The methods involve transforming a target forestry plant with a genetic construct of the present invention to provide a transgenic cell, and cultivating the transgenic cell under conditions conducive to regeneration and mature plant growth. Cells comprising the genetic constructs of the present invention are provided, together with tissues and forestry plants comprising such transgenic cells; and fruits, seeds and other products, derivatives, or progeny of such forestry plants.

In yet another aspect of the present invention, methods for modulating PCD, and for modulating various developmental pathways of forestry plants are provided, such methods including stably incorporating into the genome of a forestry plant a genetic construct of the present invention. More specifically, methods for modulating developmental pathways, including wood development, senescence and reproductive development, as well as methods for modulating stress responses in forestry plants, are provided. Preferred forestry plants include woody plants, preferably selected from the group consisting of eucalyptus, pine, acacia, poplar, sweetgum, teak and mahogany species, more preferably from the group consisting of pine and eucalyptus species, and most preferably from the group consisting of *Eucalyptus grandis* and *Pinus radiata*.

The above-mentioned and additional features of the present invention and the manner of obtaining them will become apparent, and the invention will be best understood by reference to the following more detailed description.

DESCRIPTION OF PREFERRED EMBODIMENTS

Figure 1:
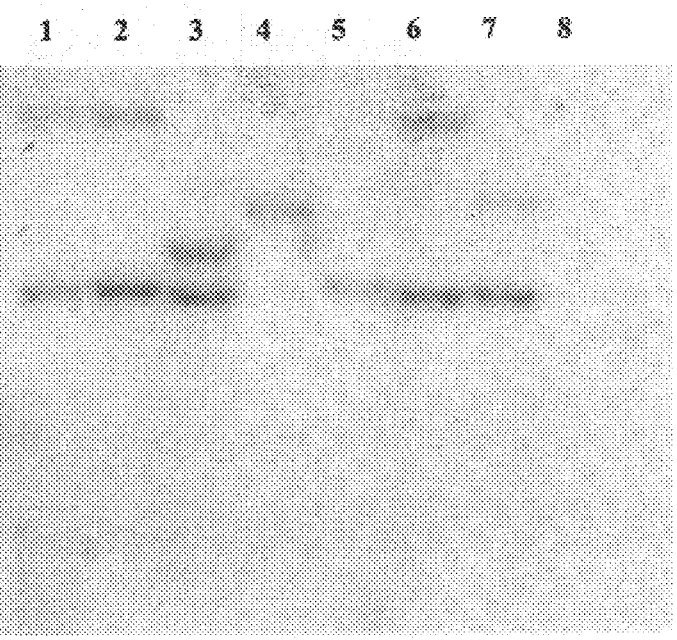
FIG. 1 shows a Southern blot analysis of tobacco plants transformed with an antisense sequence of a *Pinus radiata* DAD1 gene (SEQ ID NO: 8).

Using the methods and materials of the present invention, PCD and/or specific developmental pathways may be modulated in a forestry plant by modifying the polynucleotide and/or polypeptide content of the target organism, for example, by incorporating sense or antisense copies of polynucleotides of the present invention that encode polypeptides involved in the PCD and/or specific developmental pathways into the genome of the forestry plant. In addition, the number of copies and combination of polynucleotides of the present invention may be manipulated in a forestry plant, to modify the relative amounts of polypeptides synthesized, thereby producing biological materials having an altered composition and/or developmental metabolism.

According to one embodiment, the present invention provides isolated polynucleotides encoding, or partially encoding, polypeptides involved in PCD and/or specific developmental pathways in forestry plants. The polynucleotides of the present invention were isolated from eucalyptus and pine species, but they may alternatively be synthesized using conventional synthesis techniques. Specifically, isolated polynucleotides of the present invention include polynucleotides comprising a sequence selected from the group consisting of sequences identified as SEQ ID NOS: 1–45, 90–140, 192–195, 200, 204 and 206; complements of the sequences identified as SEQ ID NOS: 1–45, 90–140, 192–195, 200, 204 and 206; reverse sequences of the sequences identified as SEQ ID NOS: 1–45, 90–140, –192–195, 200, 204 and 206; reverse complements of the sequences identified as SEQ ID NOS: 1–45, 90–140, 192–195, 200, 204 and 206; at least a specified number of contiguous residues (x-mers) of any of the above-mentioned polynucleotides; antisense sequences corresponding to any of the above polynucleotides; and variants of any of the above polynucleotides, as that term is described in this specification.

The isolated polynucleotides recited in SEQ ID NOS: 1–45, 90–140, 192–195, 200, and 204, encode, or partially encode, polypeptides recited in SEQ ID NOS: 46–89, 141–191, 196–199, 201 and 205, respectively, that are involved in PCD and/or developmental processes, as identified in Table 1 above. Using methods and materials of the present invention, the polynucleotide and/or polypeptide content of a target organism, such as a forestry plant, may be increased or reduced, thereby modulating PCD in the organism or in a tissue of the organism, or modulating a developmental pathway in the organism or a tissue by incorporating various polynucleotides of the present invention, including untranslated portions of such polynucleotides and antisense copies of such polynucleotides.

In another embodiment, the present invention provides isolated polypeptides encoded by the DNA sequences of SEQ ID NOS: 1–45, 90–140, 192–195, 200and 204. The predicted amino acid sequences corresponding to the polynucleotides set out in SEQ ID NOS: 1–28, 30–45, 90–140, 192–195, 200 and 204, based on the information available at the time of filing this application, are provided in SEQ ID NOS: 46–73, 74–89, 141–191, 196–199, 201 and 205, respectively.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and antisense strands, and comprehends cDNA, genomic, DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. A gene is a DNA sequence that codes for a functional protein or RNA molecule. Operable antisense polynucleotides may comprise a fragment of the corresponding polynucleotide, and the definition of "polynucleotide" therefore includes all such operable antisense fragments. Antisense polynucleotides and techniques involving antisense polynucleotides are well known in the art and are described, for example, in Robinson-Benion, et al., "Antisense techniques," *Methods in Enzymol.* 254(23): 363–375 (1995); and Kawasaki, et al., *Artific. Organs* 20(8):836–848 (1996). Polynucleotides of the present invention also encompass polynucleotide sequences that differ from the disclosed sequences but which, as a result of the degeneracy of the genetic code, encode a polypeptide which is the same as that encoded by a DNA sequence disclosed herein.

The definitions of the terms "complement", "reverse complement" and "reverse sequence", as used herein, are best illustrated by the following examples. For the sequence 5' AGGACC 3', the complement, reverse complement and reverse sequences are as follows:

| complement | 3' TCCTGG 5' |
| reverse complement | 3' GGTCCT 5' |
| reverse sequence | 5' CCAGGA 3'. |

Identification of genomic DNA and heterologous species DNAs can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and protein sequences can be used to amplify and identify genomic and cDNA sequences. Synthetic DNA corresponding to the identified sequences and variants may be produced by conventional synthesis methods. All of the polynucleotides described herein are isolated and purified, as those terms are commonly used in the art.

In another aspect, the present invention provides isolated polypeptides encoded, or partially encoded, by the above polynucleotides. As used herein, the term "polypeptide" encompasses amino acid chains of any length, including full length proteins, wherein the amino acid residues are linked by covalent peptide bonds. The term "polypeptide encoded by a polynucleotide" as used herein, includes polypeptides encoded by a polynucleotide which comprises an isolated DNA sequence or variant provided herein. In specific embodiments, the inventive polypeptides comprise an amino acid sequence selected from the group consisting of sequences provided in SEQ ID NOS: 46–89, 141–191, 196–199, 201 and 205, as well as variants of such sequences.

Polypeptides of the present invention may be produced recombinantly by inserting a DNA sequence that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, insect, yeast or a mammalian cell line such as COS or CHO. The DNA sequences expressed in this manner may encode naturally occurring polypeptides, portions of naturally occurring polypeptides, or other variants thereof.

In a related aspect, polypeptides are provided that comprise at least a functional portion of a polypeptide having an amino acid sequence selected from the group consisting of sequences provided in SEQ ID NOS: 46–89, 141–191, 196–199, 201 and 205, and variants thereof. As used herein, the "functional. portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity.

Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below.

A functional portion comprising an active site may be made up of separate portions present on one or more polypeptide chains and generally exhibits high substrate specificity. The term "polypeptide encoded by a polynucleotide" as used herein, includes polypeptides encoded by a polynucleotide comprising a partial isolated polynucleotide of the present invention.

Portions and other variants of the inventive polypeptides may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85: 2149–2146, 1963. Equipment for automated synthesis of polypeptides is commercially available from suppliers such as Perkin Elmer/Applied Biosystems, Inc. (Foster City, Calif.), and may be operated, according to the manufacturer's instructions. Variants of a native polypeptide may be prepared using standard mutagenesis techniques, such as oligonucleotide-directed site-specific mutagensis (Kunkel, T., *Proc. Natl. Acad. Sci. USA* 82: 488–492, 1985). Sections of DNA sequences may also be removed using standard techniques to permit preparation of truncated polypeptides.

In general, the polypeptides disclosed herein are prepared in an isolated, substantially pure form. Preferably, the polypeptides are at least about 80% pure; more preferably at least about 90% pure; and most preferably, at least about 99% pure. In certain preferred embodiments, described in detail below, the isolated polypeptides are incorporated into pharmaceutical compositions or vaccines for use in the treatment of skin disorders.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%; more preferably, at least 75%; and most preferably, at least 90% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotide and polypeptide sequences may be aligned, and percentage of identical nucleotides in a specified region may be determined against another polynucleotide, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The, similarity of polypeptide sequences may be examined using the BLASTP algorithm. The BLASTN, BLASTX and BLASTP programs are available on the NCBI anonymous FTP server under/blast/executables/. The BLASTN algorithm version 2.0.4 [Feb-24-1998] and version 2.0.6 [Sep-16-1998], set to the default parameters described in the documentation and distributed with the algorithm, are preferred for use in the determination of polynucleotide variants according to the present invention. The BLASTP algorithm, set to the default parameters described in the documentation and distributed with the program, is preferred for use in the determination of polypeptide variants according to the present invention. The use of the BLAST family of algorithms, including BLASTN, BLASTP, and BLASTX, is described at NCBI's website and in the publication of Altschul, Stephen F., et al., "Gapped BLAST and PSI-BLAST: a new generation of protein database search programs," *Nucleic Acids Res.* 25: 3389–3402, 1997.

The computer algorithm FASTA is available on the Internet. Version 2.0u4, February 1996, set to the default parameters described in the documentation and distributed with the algorithm, may be used in the determination of variants according to the present invention. The use of the FASTA algorithm is described in Pearson, W R and Lipman D J, "Improved Tools for Biological Sequence Analysis," *Proc. Natl. Acad. Sci. USA* 85: 2444–2448, 1988; and W. R. Pearson, "Rapid and Sensitive Sequence Comparison with FASTP and FASTA," *Methods in Enzymology* 183: 63–98, 1990.

The following running parameters are preferred for determination of alignments and similarities using BLASTN that contribute to the E values and percentage identity for polynucleotide sequences: Unix running command: blastall -p blastn -d embldb -e 10 -G0 -E0 -r 1 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; and -o BLAST report Output File [File Out] Optional. The following running parameters are preferred for determination of alignments and similarities using BLASTP that contribute to the E values and percentage identity of polypeptide sequences: blastall -p blastp -d swissprotdb -e 10 -G 0 -E 0 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional. The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA, and BLASTP algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides and polypeptides, with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA, or BLASTP algorithms set at parameters described above. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at parameters described above. Similarly, according to a preferred embodiment, a variant polypeptide is a sequence having the same number or fewer amino acids than a polypeptide of the present invention that has at least a 99% probability of being the same as a polypeptide of the present invention, measured as having an E value of 0.01 or less using the BLASTP algorithm set at the parameters described above.

Alternatively, variant polynucleotides or polypeptides of the present invention comprise a sequence exhibiting at least 50%; more preferably at least 75%; more preferably yet at least 90%; and most preferably at least 98% similarity to a polynucleotide or polypeptide of the present invention, determined as described below. The percentage similarity is determined by aligning sequences using one of the BLASTN, FASTA, or BLASTP algorithms, set at the running parameters described above, and identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage similarity. For example, a polynucleotide of the present invention having 220 nucleic acids has a hit to a polynucleotide sequence in the EMBL database having 520 nucleic acids over a stretch of 23 nucleotides in the alignment produced by the BLASTN algorithm-using the parameters described above. The 23 nucleotide hit includes 21 identical nucleotides, one gap and one different nucleotide. The percentage similarity of the polynucleotide of the present invention to the hit in the EMBL library is thus 21/220 times 100, or 9.5%. The polynucleotide sequence in the EMBL database is thus not a variant of a polynucleotide of the present invention.

Alternatively, variant polynucleotides of the present invention hybridize to the polynucleotide sequences recited in SEQ ID NOS: 1–45, 90–140, 192–195, 200, 204 and 206, or complements, reverse sequences, or reverse complements of those sequences under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity as a polypeptide encoded by a polynucleotide of the present invention. Thus, polynucleotides comprising sequences that differ from the polynucleotide sequences recited in SEQ ID NOS: 1–45, 90–140, 192–195, 200, 204 and 206, or complements, reverse sequences, or reverse complements of those sequences as a result of conservative substitutions are contemplated by and encompassed within the present invention. Additionally, polynucleotides comprising sequences that differ from the polynucleotide sequences recited in SEQ ID NOS: 1–45, 90–140, 192–195, 200, 204 and 206, or complements, reverse complements, or reverse sequences as a result of deletions and/or insertions totaling less than 10% of the total sequence length are also contemplated by and encompassed within the present invention. Similarly, polypeptides comprising sequences that differ from the polypeptide sequences recited in SEQ ID NOS: 46–89, 141–191, 196–199, 201 and 205 as a result of amino acid substitutions, insertions, and/or deletions totalling less than 10% of the total sequence length are contemplated by an encompassed within the present invention, provided the variant polypeptide has activity in a PCD or plant developmental pathway.

The polynucleotides of the present invention may be isolated from various libraries, or may be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

Some of the polynucleotides identified as SEQ ID NOS: 1–45, 90–140, 192–195, 200, 204 and 206, are referred to as "partial" sequences, in that they do not represent the full coding portion of a gene encoding a naturally occurring polypeptide. The partial polynucleotide sequences disclosed herein may be employed to obtain the corresponding full length genes for various species and organisms by, for example, screening DNA expression libraries using hybridization probes based on the polynucleotides of the present invention, or using PCR amplification with primers based upon the polynucleotides of the present invention. In this way one can, using methods well known in the art, extend a polynucleotide of the present invention upstream and downstream of the corresponding mRNA, as well as identify the corresponding genomic DNA, including the promoter and enhancer regions, of the complete gene. The present invention thus comprehends isolated polynucleotides comprising a sequence identified in SEQ ID NOS: 1–45, 90–140, 192–195, 200, 204 and 206, or a variant of one of the specified sequences, that encode a functional polypeptide, including full length genes. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Polynucleotides of the present invention also comprehend polynucleotides comprising at least a specified number of contiguous residues (x-mers) of any of the polynucleotides identified as SEQ ID NO: 1–45, 90–140, 192–195, 200, 204 and 206, complements, reverse sequences, and reverse complements of such sequences, and their variants. Similarly, polypeptides of the present invention comprehend polypeptides comprising at least a specified number of contiguous residues (x-mers) of any of the polypeptides identified as SEQ ID NOS: 46–89, 141–191, 196–199, 201, and 205, and their variants. As used herein, the term "x-mer," with reference to a specific value of "x," refers to a sequence comprising at least a specified number ("x") of contiguous residues of any of the polynucleotides identified as SEQ ID NO: 1–45, 90–140, 192–195, 200, 204 and 206, or the polypeptides identified as SEQ ID NOS: 46–89, 141–191, 196–199, 201 and 205. According to preferred embodiments, the value of x is preferably at least 20; more preferably, at least 40; more preferably yet, at least 60; and most preferably, at least 80. Thus, polynucleotides and polypeptides of the present invention comprise a 20-mer, a 40-mer, a 60-mer, an 80-mer, a 100-mer, a 120-mer, a 150-mer, a 180-mer, a 220-mer, a 250-mer, or a 300-mer, 400-mer, 500-mer or 600-mer of a polynucleotide or polypeptide identified as SEQ ID NOS: 1–201, and 204–206, and variants thereof.

Polynucleotide probes and primers complementary to and/or corresponding to SEQ ID NOS: 1–45, 90–140, 192–195, 200, 204 and 206, and variants of those sequences, are also comprehended by the present invention. Such oligonucleotide probes and primers are substantially complementary to the polynucleotide of interest. As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

An oligonucleotide probe or primer is described as "corresponding to" a polynucleotide of the present invention, including one of the sequences set out as SEQ ID NOS: 1–45, 90–140, 192–195, 200, 204 and 206, or a variant, if the oligonucleotide probe or primer, or its complement, is contained within one of the sequences set out as SEQ ID NOS: 1–45, 90–140, 192–195, 200, 204 and 206, or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. The DNA from plants or samples or products containing plant material can be either genomic DNA or DNA derived by preparing cDNA from the RNA present in the sample.

In addition to DNA—DNA hybridization, DNA-RNA or RNA—RNA hybridization assays are also possible. In the first case, the mRNA from expressed genes would then be detected instead of genomic DNA or cDNA derived from mRNA of the sample. In the second case, RNA probes could be used. In addition, artificial analogs of DNA hybridizing specifically to target sequences could also be used.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA—DNA hybridization stringency, annealing and melting temperatures, and potential for formation of loops and other factors, which are well known in the art. Tools and software suitable for designing probes, and especially suitable for designing PCR primers, are available on the Internet, for example, at URL http://www.horizonpress.com/pcr/. Preferred techniques for designing PCR primers are also disclosed in Dieffenbach, C W and Dyksler, G S, *PCR Primer: a laboratory manual*, CSHL Press: Cold Spring Harbor, N.Y., 1995.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a is polynucleotide of the present invention, including a polynucleotide sequence identified in SEQ ID NOS: 1–45, 90–140, 192–195, 200, 204 and 206.

In one embodiment useful for high-throughput assays, the oligonucleotide probe kits of the present invention comprise multiple probes in an array format, wherein each probe is immobilized at a predefined, spatially addressable location on the surface of a solid substrate. Array formats which may be usefully employed in the present invention are disclosed, for example, in U.S. Pat. Nos. 5,412,087, 5,545,451, and PCT Publication No. WO 95/00450, the disclosures of which are hereby incorporated by reference.

Probes, preferably in the form of an array, may be employed to screen for differences in organisms or samples or products containing genetic material using high-throughput screening techniques that are well known in the art. The significance of using probes in high-throughput screening systems is apparent for applications such as plant breeding and quality control operations in which there is a need to identify large numbers of seed lots and plant seedlings, to examine samples or products for unwanted plant materials, to identify plants or samples or products containing plant material for quarantine purposes, etc., or to ascertain the true origin of plants or samples or products containing plant material. Screening for the presence or absence of polynucleotides of the present invention used as identifiers for tagging plants is valuable for later detecting the amount of gene flow in plant breeding, introgression of genes via dispersed pollen, etc.

In this manner, oligonucleotide probe kits of the present invention may be employed to examine the presence/absence (or relative amounts in case of mixtures) of polynucleotides in different samples or products containing different materials rapidly and in a cost-effective manner. Examples of plant species, which may be examined using the present invention include forestry species, such as pine and eucalyptus species, other tree species, and even agricultural and horticultural plants.

For applications where modulation of PCD and/or a developmental pathway is desired, an open reading frame may be inserted into a genetic construct in a sense or antisense orientation, such that transformation of a forestry plant with the genetic construct produces a change in the copy number of a polynucleotide or the expression level of a polypeptide compared to the polynucleotide copy number and/or polypeptide expression level in a wild-type organism. Transformation with a genetic construct comprising an open reading frame in a sense orientation will generally result in an increased expression level of the polypeptide encoded by the selected polynucleotide, while transformation with a genetic construct comprising an open reading frame in an antisense orientation will generally result in reduced expression of the polypeptide encoded by the selected polynucleotide. A forestry plant transformed with a genetic construct comprising an open reading frame of the present invention in either a sense or antisense orientation may be screened for increased or reduced copy numbers of the selected polynucleotide, or increased or reduced expression of the polypeptide of interest using techniques well known to those of skill in the art. Plants having the desired alterations may thus be identified and isolated. In general, an increase or reduction in the expression level of a polypeptide of interest of at least 25%, compared to expression levels in a corresponding wild-type organism, are significant.

Transformation of a target organism with a genetic construct of the present invention results in a modification in the polypeptide synthesis or content or structure in the target organism, producing a modification from the wild-type plant in the area of PCD or in a developmental pathway. Methods of the present invention involve modulating, generally promoting, and inhibiting, PCD in a forestry species. For example, transformation of a target organism with a genetic construct having an open reading frame coding for a polypeptide encoded by a polynucleotide of the present invention wherein the open reading frame is in a sense orientation and the polypeptide contributes to an increased level of PCD, generally produces a significant increase in the amount or expression of the polypeptide in the target organism and, consequently, a significant increase in PCD. Similarly, transformation of a target organism with a genetic construct having an open reading frame coding for a polypeptide encoded by a polynucleotide of the present invention wherein the open reading frame is in a sense orientation and the polypeptide contributes to a reduced level of PCD, generally produces a significant reduction in the amount or expression of the polypeptide in the target organism and, consequently, a significant reduction in PCD. Transformation of a target organism with a genetic construct comprising an open reading frame in an antisense orientation or an untranslated region of a polynucleotide generally produces a decrease in the level of the corresponding polypeptide, thereby producing a corresponding increase or reduction in PCD, depending on the role of the specific polypeptide. It will be recognized that transformation with other genetic constructs of the present invention will produce changes in the content, composition and/or metabolism of various polypeptides that play a role in PCD and/or plant developmental pathways, thereby producing changes in the content, composition, and/or metabolism of the forestry plant.

More specifically, methods of the present invention contemplate selectively promoting PCD in a forestry plant or cell population by: (1) introducing or increasing the copy number of a polynucleotide comprising a sequence selected from the group consisting of the sequences recited in SEQ ID NOS: 1–5, 10, 15, 16, 27–35, 38–40, 45, 92–140, 192–195, and 200, and variants of such sequences; (2) introducing, or increasing the expression level of, or activating a polypeptide encoded by a polynucleotide comprising a sequence selected from the group of sequences recited in SEQ ID NOS: 1–5, 10, 15, 16, 27–35, 38–40, 45, 92–140, 192–195, and 200, and variants of such sequences; (3) introducing, or increasing the expression level of, or activating a polypeptide comprising a sequence selected from the group consisting of the sequences recited in SEQ ID NOS: 46–50, 55, 60, 61, 72–79, 82–84, 89, 143–191, 196–199, and 201, and variants of such sequences; (4) reducing the copy number of a polynucleotide comprising a sequence selected from the group consisting of the sequences recited in SEQ ID NOS: 6–9, 11–14, 17–26, 36, 37, 41–44, 90, 91 and 204, and variants of such sequences; (5) reducing the expression level of or inactivating a polypeptide encoded by a polynucleotide comprising a sequence selected from the group of sequences recited in SEQ ID NOS: 6–9, 11–14, 17–26, 36, 37, 41–44, 90, 91 and 204, and variants of such sequences; or (6) reducing the expression level of or inactivating a polypeptide comprising a sequence selected from the group consisting of the sequences recited in SEQ ID NOS: 51–54, 56–59, 62–71, 80, 81, 85–88, 141, 142, and 205 and variants of such sequences. Methods of the present invention also contemplate selectively inhibiting PCD in a forestry plant or cell population by: (1) introducing or increasing the copy number of a polynucleotide comprising a sequence selected from the group consisting of the sequences recited in SEQ ID NOS: 6–9, 11–14, 17–26, 36, 37, 41–44, 90, 91 and 204, and variants of such sequences; (2) introducing, or increasing the expression level of, or activating a polypeptide encoded by a polynucleotide comprising a sequence selected from the group of sequences recited in SEQ ID NOS: 6–9, 11–14, 17–26, 36, 376 41–44, 90, 91 and 204, and variants of such sequences; (3) introducing, or increasing the expression level of, or activating a polypeptide comprising a sequence selected from the group consisting of the sequences recited in SEQ ID NOS: 51–54, 56–59, 62–71, 80, 81, 85–88, 141, 142 and 205, and variants of such sequences; (4) reducing the copy number of a polynucleotide comprising a sequence selected from the group consisting of the sequences recited in SEQ ID NOS: 1–5, 10, 15, 16, 27–35, 38–40, 45, 92–140, 192–195, and 200, and variants of such sequences; (5) reducing the expression level or inactivating a polypeptide encoded by a polynucleotide comprising a sequence selected from the group of sequences recited in SEQ ID NOS: 1–5, 10, 15, 16, 27–35, 38–40, 4, 92–140, 192–195, and 200, and variants of such sequences; or (6) reducing the expression level of or inactivating a polypeptide comprising a sequence selected from the group consisting of the sequences recited in SEQ ID NOS: 46–50, 55, 60, 61, 72–79, 82–84, 90, 143–191, 196–199, and 201, and variants of such sequences.

Expression of a polynucleotide involved in PCD or a selected developmental pathway may be inhibited by inserting a portion of an open reading frame of the present invention, in either sense or antisense orientation, in the genetic construct. Such portions need not be full-length but preferably comprise at least 25 and more preferably at least 50 residues of a polynucleotide of the present invention. A much longer portion, or even the full length polynucleotide corresponding to the complete open reading frame, may be employed. The portion of the open reading frame does not need to be precisely the same as the endogenous sequence, provided that there is sufficient sequence similarity to achieve inhibition of the target polynucleotide. Thus a sequence derived from one species may be used to inhibit expression of a polypeptide in a different species.

According to another embodiment, the genetic constructs of the present invention comprise a polynucleotide including an untranslated region of a polynucleotide coding for a polypeptide encoded by a polynucleotide of the present invention, or a polynucleotide complementary to such an untranslated region. Examples of untranslated regions that may be usefully employed in such constructs include introns and 5'-non-coding leader sequences. Transformation of a forestry plant with such a genetic construct generally produces a reduction in the expression level of the polypeptide by the process of cosuppression; in a manner similar to that discussed, for example, by Napoli, et al., *Plant Cell* 2: 279–290, 1990; and de Carvalho Niebel, et al., *Plant Cell* 7: 347–358, 1995.

Alternatively, regulation may be achieved by inserting appropriate sequences or subsequences (e.g. DNA or RNA) in ribozyme constructs (McIntyre C L, Manners J M, "Strategies for the suppression of peroxidase gene expression in tobacco: designing efficient ribozymes," *Transgenic Res.* 5(4): 257–262, 1966). Ribozymes are synthetic RNA molecules that comprise a hybridizing region complementary to two regions, each of which comprises at least 5 contiguous nucleotides in a mRNA molecule encoded by one of the inventive polynucleotides. Ribozymes possess highly specific endonuclease activity, which autocatalytically cleaves the mRNA.

The genetic constructs of the present invention may further comprise a gene promoter sequence and a gene termination sequence, operably linked to the polynucleotide and capable of controlling expression of the polypeptide. The gene promoter sequence is generally positioned at the 5' end of a polynucleotide to be transcribed, and is employed to initiate transcription of the polynucleotide. Gene promoter sequences are generally found in the 5' untranslated region of a gene, but they may exist downstream of the open reading frame or in introns (Luehrsen, K R, *Mol. Gen. Genet.* 225: 81–93, 1991), or in the coding region, as for. example in a plant defense gene (Douglas, et al., *EMBO J.* 10: 1767–1775, 1991).

Numerous gene promoter sequences that may be usefully employed in genetic constructs of the present invention are well known in the art. The gene promoter sequence, and also the gene termination sequence, may be endogenous to the target host or may be exogenous, provided the promoter is functional in the target host. For example, the promoter and termination sequences used when the target organism is a plant, may be from other plant species, plant viruses, bacterial plasmids and the like. In preferred embodiments, the gene promoter and termination sequences are common to those of the polynucleotide being introduced.

Factors influencing the choice of promoter include the desired tissue specificity of the construct, and the timing of transcription and translation. For example, constitutive promoters, such as the 35S Cauliflower Mosaic Virus (CaMV 35S) promoter with or without enhancers, such as the Kozak sequence or the Omega enhancer, and *Agrobacterium tumefaciens* nopaline synthase terminator, may be usefully employed in the present invention. Use of a tissue specific promoter will result in production of the desired sense or antisense RNA only in the tissue of interest. With genetic constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the gene in question, or promoters from a specific tissue-targeted gene in the organism to be transformed, such as eucalyptus or pine are used. Other examples of gene promoters which may be usefully employed in the present invention include mannopine synthase (mas), octopine synthase (ocs) and those reviewed by Chua et al. (*Science* 244: 174–181, 1989).

The gene termination sequence, which is located 3' to the polynucleotide to be transcribed, may come from the same gene as the gene promoter sequence or may be from a different gene. Many gene termination sequences known in the art may be usefully employed in the present invention, such as the 3' end of the Agrobacterium tumefaciens nopaline synthase gene. However, preferred gene terminator sequences are those from the original polynucleotide, or from the target species to be transformed.

The genetic constructs of the present invention may also contain a selection marker that is effective in target cells, such as forestry plant cells, to facilitate the detection of transformed cells containing the genetic construct. Such markers, which are well known in the art, typically confer resistance to one or more toxins. One example of such a marker is the NPTII gene, whose expression results in resistance to kanamycin or hygromycin, antibiotics which are usually toxic to plant cells at a moderate concentration (Rogers et al. in Weissbach, A and Weissbach, H, eds., *Methods for Plant Molecular Biology*, Academic Press: San Diego, Calif., 1988). Transformed cells can thus be identified by their ability to grow in media containing the antibiotic in question. Alternatively, the presence of the desired construct in transformed cells can be determined by means of other techniques that are well known in the art, such as Southern and Western blots.

Techniques for operatively linking the components of the genetic constructs of the present invention are well known in the art and include the use of synthetic linkers containing one or more restriction endonuclease sites as described, for example, by Sambrook, et al., *Molecular Cloning: A Laboratory Manual*, CSHL: Cold Spring Harbor, N.Y., 1989). Genetic constructs of the present invention may be linked to a vector having at least one replication system, for example *E. coli*, whereby after each manipulation, the resulting construct can be cloned and sequenced, and the correctness of the manipulation determined.

The genetic constructs of the present invention are used to transform forestry plants, including gymnosperms (e.g. Scots pine (Aronen, *Finnish Forest Res. Papers* v.595, 1996), white spruce (Ellis et al., *Biotechnology* 11:94–92, 1993), and larch (Huang et al., *In Vitro Cell* 27:201–207, 1991). In one preferred embodiment, the genetic constructs of the present invention are employed to transform woody plants, herein defined as a perennial tree or shrub whose stem increases in diameter each year by the addition of woody tissue. Preferred forestry plants are selected from the group consisting of eucalyptus and pine species, most preferably from the group consisting of *Eucalyptus grandis* and *Pinus radiata*. Other species which may be usefully transformed with the DNA constructs of the present invention include, but are not limited to: pines such as *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana*; other gymnosperm such as *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata*; and Eucalypts such as *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus novaanglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo, Eucalyptus youmanni*.

Techniques for stably incorporating genetic constructs into the genome of specific target organisms are well known in the art. Techniques that are suitable for transforming plants include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by Agrobacterium Ti plasmid technology, as described, for example by Bevan, *Nucl. Acid Res.* 12:8711–8721, 1984. Targets for the introduction of the genetic constructs of the present invention include tissues, such as leaf tissue, dissociated cells, protoplasts, seeds, embryos, meristematic regions; cotyledons, hypocotyls, and the like. The preferred method for transforming eucalyptus and pine is via *Agrobacterium tumefaciens* using adventitious shoot induction or somatic embryogenesis.

Target cells having non-native genetic constructs incorporated in their genome may be selected by means of a marker, such as the kanamycin resistance marker discussed above. Transgenic cells may then be cultured in an appropriate medium to regenerate whole plants, using techniques that are well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., "Somatic embryogenesis in woody plants," pp. 471–450 in Thorpe, T A, ed., "In vitro embryogenesis of plants," (Vol. 20 of *Current Plant Science and Biotechnology in Agriculture*). Specific protocols for the regeneration of spruce are discussed by Roberts et al., "Somatic Embryogenesis of Spruce," pp. 427–449, in Redenbaugh, K, ed., *Synseed: applications of synthetic seed to crop improvement*, CRC Press, 1993). The resulting transformed plants may be reproduced sexually or asexually, using methods well known in the art, to give successive generations of transgenic plants.

As discussed above, the production of RNA in target plant cells may be controlled by the choice of an appropriate promoter sequence, or by selecting the number of functional copies or the site of integration of the polynucleotides incorporated into the genome of the target host. A target host organism may be transformed with more than one genetic constructs of the present invention, thereby modulating the concentration or activity of more than one polypeptide, affecting more than one tissue, or affecting more than one expression time. Similarly, a genetic construct may be assembled containing more than one open reading frame encoded by a polynucleotide of the present invention or more than one untranslated region of a polynucleotide. The polynucleotides of the present inventive may also be employed in combination with other known sequences encoding various polypeptides.

Additionally, the polynucleotides of the present invention may be used as non-disruptive tags for marking organisms, particularly plants. Genetic constructs comprising polynucleotides of the present invention may be stably introduced into an organism as heterologous, non-functional, non-disruptive tags. It is then possible to identify the origin or source of the organism at a later date by determining the presence or absence of the tag(s) in a sample of material. Organisms other than plants may also be tagged with the polynucleotides of the present invention, including commercially valuable animals, fish, bacteria and yeasts.

Detection of the tag(s) may be accomplished using a variety of conventional techniques, and generally involves the use of nucleic acid probes. Sensitivity in assaying for the presence of probe may be usefully increased by using branched oligonucleotides, as described by Horn, T, Chang, C A, and Urdea, M S, "Chemical synthesis and characterization of branched oligo-deoxyribonucleotides (bDNA) for use as signal amplifiers in nucleic acid quantification assays," *Nucleic Acids Research* 25(23): 4842–4849, 1997, enabling detection of as few as 50 DNA molecules in the sample.

The following examples are offered by way of illustration and not by way of limitation.

EXAMPLE 1

Isolation and Characterization of cDNA Clones from *Pinus radiata* and *Eucalyptus grandis*

*Pinus radiata* and *Eucalyptus grandis* cDNA libraries were constructed using non-subtracted or subtracted methods and screened as follows. Total RNA was extracted from the plant tissue using the protocol of Chang et al., *Plant Molecular Biology Reporter* 11:113–116, 1993. mRNA was isolated from the total RNA preparation using a Poly(A) Quik mRNA Isolation Kit (Stratagene, La Jolla, Calif.) or Dynal Oligo (dT)$_{25}$ Beads (Dynal, Skogen, Norway). Non-subtracted cDNA libraries were constructed from the purified mRNA by reverse transcriptase synthesis followed by insertion of the resulting cDNA clones in Lambda ZAP using a ZAP Express cDNA Synthesis Kit (Stratagene, La Jolla Calif.) or a SuperScript Choice System (Gibco BRL Life Technologies, Gaithersburg Md.), according to the manufacturer's protocol. The resulting cDNAs were packaged using a Gigapack II Packaging Extract (Stratagene) employing 1 μl of sample DNA from the 5 μl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Subtracted *Pinus radiata* cDNA libraries (developed using early wood xylem [tester DNA] subtracted against late wood xylem [driver DNA] or late wood xylem [tester DNA] subtracted against early wood xylem [driver DNA] were constructed as follows. mRNA isolated using Dynal Beads (see above) was used to generate cDNA using manufacturer's instructions from the Clontech PCR-Select™ cDNA Subtraction Kit (Clontech Laboratories Inc, Palo Alto, Calif.). Both the tester and driver double-stranded cDNA preparations were digested with restriction endonuclease RsaI and then only the digested tester cDNA population used to generate. two distinct tester populations each with different adaptors ligated. The first round of hybridization, using both tester cDNA populations and the driver cDNA population combined, was performed to allow for equalization and enrichment of differentially expressed sequences. This was followed by a second round of hybridization to generate the templates for PCR amplification. Using suppression PCR, differentially expressed sequences were favourably amplified exponentially. This resultant population of cDNAs was then used in a second round of PCR amplification to remove background and further enrich for differentially expressed sequences. PCR products were -ligated to T-tailed pBluescript II SK+ (constructed according to the method of Khan et al., TIG 10:7, July 1994; or Hadjeb and Berkowitz, *Biotechniques*, January 1996). Electro-competent XLI-Blue *E. coli* cells were electroporated with recombinant plasmids and cells plated onto. LB-ampicillin plates containing X-gal and IPTG.

Colonies containing cDNA inserts were cultured in NZY broth with the appropriate antibiotic and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

Polynucleotides for positive clones were obtained using a Perkin Elmer/Applied Biosystems Division Prism 377 sequencer. cDNA clones were sequenced first from the 5' end and, in some cases, also from the 3' end. For some clones, internal sequences were obtained using subcloned fragments, exonuclease III deletions, or by direct sequencing using gene-specific primers designed to identified regions of the gene of interest. Subcloning was performed using standard procedures of restriction mapping and subcloning to pBluescript II SK+ vector (Stratagene) and other standard sequencing vectors.

The determined cDNA sequences, including the polynucleotides of the present invention, were compared to and aligned with known sequences in the EMBL database (as updated to end of August, 1998). Specifically, the polynucleotides identified in SEQ ID NOS. 1–45, 90–140, 192–195, 200, 202–204 and 206, were compared to polynucleotides in the EMBL database using the BLASTN algorithm version 2.0.4 [Feb-24-1998] and version 2.0.6 [Sep-16-1998] set to the preferred parameters described above. Specifically, running parameters used for determination of alignments and similarities using BLASTN that contribute to the E values and percentage identity were as follows: Unix running command: blastall -p blastn -d embldb -e 10 -G0 -E0 -r 1 -v 30 -b 30 -i queryseq -o results. Multiple alignments of redundant sequences were used to build up reliable consensus sequences. Based on similarity to known sequences from other plant or non-plant species, the isolated polynucleotides of the present invention identified as SEQ ID NOS. 1–45, 90–140, 192–195, 200 and 204, were putatively identified as encoding polypeptides having similarity to the polypeptides shown in Table 1, above.

The isolated cDNA sequences were compared to sequences in the EMBL DNA database using the computer algorithm BLASTN. The corresponding predicted protein sequences (DNA translated to protein in each of six reading frames) were compared to sequences in the SwissProt database using the computer algorithm BLASTP. Comparisons of DNA sequences provided in SEQ ID NOS: 1–45, 90–140, 192–195, 200, 204 and 206, to sequences in the EMBL DNA database (using BLASTN) and amino acid sequences provided in SEQ ID NOS: 46–89, 141–191, 196–199, 201 and 205, to sequences in the SwissProt database (using BLASTP) were made as of March, 1999. Analysis of the amino acid sequences against the EMBL DNA database dynamically translated in all six reading frames (both strands) was. conducted using the TBLASTN algorithm. Analysis of six-frame translations of the polynucleotides of SEQ ID NOS: 1–45, 90–140, 192–195 200, 204 and 206, were also compared to and aligned with the six-frame translations of polynucleotides in the EMBL database using the TBLASTX program.

BLASTN Polynucleotide Analysis

The cDNA sequences of SEQ ID NOS: 1–7, 10–18, 20–31, 35–40, 43, 44, 90–94, 98–107, 109, 110, 112–118, 120, 121, 123–140, 192–195, 200, 204, and 206, were determined to have less than 50% identity, determined as described above, to sequences in the EMBL database using the computer algorithm BLASTN, as described above. The cDNA sequences of SEQ ID NOS: 8, 9, 33, 34, 41, 42, 96, 108, and 111 were determined to have less than 75% identity, determined as described above, to sequences in the EMBL database using BLASTN, as described above. The cDNA sequences of SEQ ID NOS: 32, 95, 97, 119, and 122, were determined to have less than 90% identity, determined as described above, to sequences in the EMBL database using BLASTN, as described above. The cDNA sequence of SEQ ID NO: 9 was determined to have less than 98% identity, determined as described above, to sequences in the EMBL database using BLASTN, as described above.

BLASTP Amino Acid Analysis

The predicted amino acid sequences of SEQ ID NOS: 46, 48–50, 55, 58, 60, 61, 80, 81, 87–89, 141, 142, 144, 156, 157, 160, 161, 173, 174, 177, 179, 180, 182–191, 198 and 205, were determined to have less than 50% identity, determined as described above, to sequences in the SwissProt database using the BLASTP computer algorithm as described above. The predicted amino acid sequences of SEQ ID NOS: 49, 57, 59, 66, 67, 72, 82–84, 143, 145, 149, 150, 152–155, 159, 162–173, 178, 181, 196, 197, 199, and 201, were determined to have less than 75% identity, determined as described above, to sequences in the SwissProt database using the computer algorithm BLASTP, as described above. The predicted amino acid sequences of SEQ ID NOS: 51–54, 56, 62–65, 68–71, 73, 74, 79, 146, 147, 151, 158, and 176, were determined to have less than 90% identity, determined as described above, to sequences in the SwissProt database using the computer algorithm BLASTP, as described above. The predicted amino acid sequences of SEQ ID NOS: 75, 78, 85, 86, and 148, were determined to have less than 98% identity, determined as described above, to sequences in the SwissProt database using the computer algorithm BLASTP, as described above.

TBLASTN and TBLASTX Analysis

The predicted amino acid sequences of SEQ ID NOS: 46, 47, 49, 50, 58, 60, 61, 80, 83, 87, 89, 141, 157, 160, 161, 174, 175, 177, 179–180, 182–191, and 197–199, were determined to have less than 50% identity, determined as described above, to predicted amino acids dynamically translated in all six reading frames (both strands of polynucleotides) in the EMBL database. The predicted amino acid sequences of SEQ ID NOS: 48, 55, 57, 59, 66, 67, 69, 71, 72, 81, 82, 88, 142–145, 149, 150, 152, 153, 155, 156, 162–165, 167–172, 176, 178, 181 and 205, were determined to have less than 75% identity, determined as described above, to predicted amino acids dynamically translated in all six reading frames (both strands of polynucleotides) in the EMBL database. The predicted amino acid sequences of SEQ ID NOS: 51, 52, 56, 62–65, 68, 73, 74, 84, 146, 147, 151, 154, 158, 159, 166, 173, and 196, were determined to have less than 90% identity; and the predicted amino acid sequences of SEQ ID NOS: 53, 75, 78, 79, 85, 86, and 148, were determined to have less than 98% identity; all to dynamic translations in all six reading frames of sequences in the EMBL DNA database using the TBLASTN algorithm version 2.0.6 [Sept-16-1998] set to the following parameters: Unix running command: blastall -p blastn -d embldb -e10 -G0 -E0 -v30 -b30 -i queryseq -o results.

Finally, the six-frame translations of the polynucleotide sequences of SEQ ID NOS: 1–45, 90–140, 192–195, 200, 204 and 206 were compared to and aligned with six-frame translations of polynucleotides in the EMBL database using the TBLASTX program version 2.0.6 [Sept-16-1998] set to the following running parameters: Unix running command: blastall -p blastn -d embldb -e 10 -G 0 -E 0 -v 30 -b 30 -i queryseq -o results. The translations of the polynucleotides of SEQ ID NOS: 1–8, 10, 12–16, 18, 20–22, 24–27, 31, 34–40, 42–45, 90–140, 192–195, 204, and 206, were determined to have less than 50% identity, determined as described above, to translations of polynucleotides in the EMBL database using the computer algorithm TBLASTX. The translations of the polynucleotides of SEQ ID NOS: 17, 28–30, and 41, were determined to have less than 75% identity, determined as described above, to translations of polynucleotides in the EMBL database using the computer algorithm TBLASTX. The translations of the polynucleotide sequences of SEQ ID NOS: 11, 19, and 23, were determined to have less than 90% identity, determined as described above, to translations of polynucleotides in the EMBL database using the computer algorithm TBLASTX. The translations of the polynucleotide sequence of SEQ ID NO: 9 were determined to have less than 98% identity, determined as described above, to translations of polynucleotides in the EMBL database using is the computer algorithm TBLASTX.

EXAMPLE 2

Use of a DAD1 Gene to Modify Tobacco

Transformation of Tobacco Plants with a *Pinus radiata* DAD1 Gene

A genetic construct comprising the antisense nucleotide of a polynucleotide comprising the coding region of DAD1 (SEQ ID NO: 8) from *P. radiata* was constructed and inserted into *Agrobacterium tumefaciens* by direct transformation using published methods (See An G, Ebert P R, Mitra A, Ha S B, "Binary Vectors," in Gelvin SB, Schilperoort R A (eds). *Plant Molecular Biology Manual*, Kluwer Academic Publishers: Dordrecht, 1988). The nucleotide sequence of the antisense nucleotide is given in SEQ ID NO: 206. General methods for plant transformation are described in Horsch R, Fry J, Hofman N, Eichholtz N, Rogers S and Fraley R, "A simple and general method for transferring genes into plants," *Science* 227:1229–1231, 1985.) The antisense DNA construct was made by PCR amplification of the open reading frame for the cDNA, followed by purification and cloning of the PCR product into pART7 plasmid. The plasmid was then digested with restriction endonuclease NotI and the 35S promoter-Insert-OCS 3'UTR cloned into the pART27 plant expression vector (See Gleave A, "A versatile binary vector system with a T-DNA organizational structure conducive to efficient integration of cloned DNA into the plant genome," *Plant Molecular Biology* 20:1203–1207, 1992). The presence, integrity and orientation of the transgenic construct was verified by restriction digestion and DNA sequencing.

Tobacco (*Nicotiana tabacum* cv. Samsun) leaf sections were transformed with the antisense construct using the method of Horsch et al. (*Science* 227:1229–1231, 1985). Multiple independent transformed plant .lines were established for the sense construct. Transformed plants containing the appropriate gene construct were verified using Southern blot experiments.

FIG. 1 illustrates genomic DNA isolated from seven DAD1 transgenic tobacco lines (lanes 1–7) and from a non-DAD1 control tobacco plant (lane 8). As can be seen, plants 1–7 contain DNA which hybridizes with the pine DAD1 sequence (Final wash conditions: 1×SSC, 0.1% SDS at 65° C.), while the control tobacco plant does not. This demonstrates that the antisense polynucleotides corresponding to DAD1 were successfully transformed into target plants.

Figure 2:
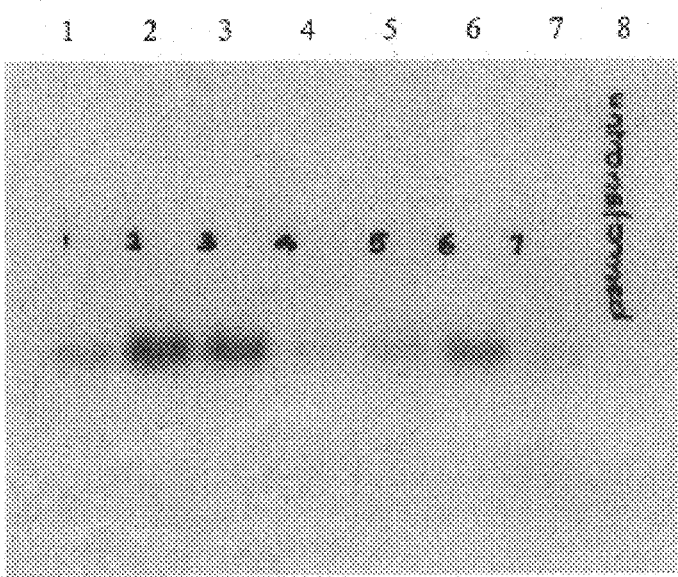
FIG. 2 shows a Northern blot analysis of tobacco plants transformed with an antisense sequence of *Pinus radiata* DAD1 gene (SEQ ID NO: 8).

Total RNA was isolated from each of the seven DAD1 antisense transformed tobacco plant lines, and from a control (non DAD1-containing) tobacco line. The RNA samples were analysed in a Northern blot experiment to determine the level of expression in each line. mRNA was hybridized with a pine DAD1 probe (Final wash conditions: 0.1×SSC, 0.1% SDS at 65° C.). FIG. 2 illustrates the presence of the pine DAD1 antisense mRNA in all seven transgenic tobacco lines (lanes 1–7), but not in the control tobacco line (lane 8).

EXAMPLE 3

Demonstration of the Presence/Absence of Unique Sequence Identifiers in Plants

Transgenic tobacco plants were created using unique identifier sequences which are not found in tobacco. The unique identifier sequences inserted were isolated from *Pinus radiata*, SEQ ID NO: 202, and *Eucalyptus grandis*, SEQ ID NO: 203. The unique identifier sequences were inserted into *Agrobacterium tumefaciens* LBA4301 (provided as a gift by Dr. C. Kado, University of California, Davis, Calif.) by direct transformation using published methods (See, An G, Ebert P R, Mitra A, Ha S B, "Binary Vectors," in Gelvin S B, Schilperoort R A (eds), *Plant Molecular Biology Manual*, Kluwer Academic Publishers: Dordrecht, 1988). The presence and integrity of the unique identifier sequences in the Agrobacterium transgenic constructs were verified by restriction digestion and DNA sequencing.

Tobacco (*Nicotiana tabacum* cv. Samsun) leaf sections were transformed using the method of Horsch et al. (Science, 227:1229–1231, 1985). Three independent transformed plant lines were established for each unique sequence identifier used. Two empty-vector control plant lines were established using an empty gene transfer vector that lacked a unique sequence identifier.

The uniqueness of the sequence identifiers was assayed using Southern blot analyses to test for the presence of the sequence identifier in the genome of the plants. If the sequence identifier is unique and therefore useful as a tag, then the sequence identifier should be clearly absent in plants which have not been tagged and it should be clearly present in plants which have been tagged. In the present example, the unique identifiers would be expected to be absent in the empty-vector transformed control plants. The unique identifier would be expected to be present in the transgenic plants transformed with the unique sequence identifiers.

Genomic DNA was prepared from empty-vector transformed control plants and plants transformed with unique sequence identifiers using the cetyltrimethyl-ammonium bromide (CTAB) extraction method of Murray and Thompson (*Nucleic Acids Research* 8:4321–4325, 1980). The DNA samples were digested with the restriction enzyme EcoRI in the case of the plants transformed with the Pinus unique sequence identifier (SEQ ID NO: 202) and the restriction enzyme XbaI in the case of the plants transformed with the Eucalyptus unique sequence identifier (SEQ ID NO: 203). The DNA fragments produced in the restriction digests were resolved on a 1% agarose-gel.

After the agarose gel electrophoresis step, the DNA samples were transferred to Hybond-N+ brand nylon membranes (Amersham Life Science, Little Chalfont, Buckinghamshire, England) using methods established by Southern (*J. Mol. Biol*. 98: 503–517). The nylon membranes were probed with radioactively-labeled probes for the unique sequence identifiers identified above and washed at high stringency (final wash: 0.5×salt sodium citrate buffer (SSC) plus 0.1% sodium dodecyl sulfate (SDS), 15 minutes at 65° C.). The hybridisation of the probes to complementary sequences in the genomic DNA samples was detected using auto-radiography.

Figure 3:
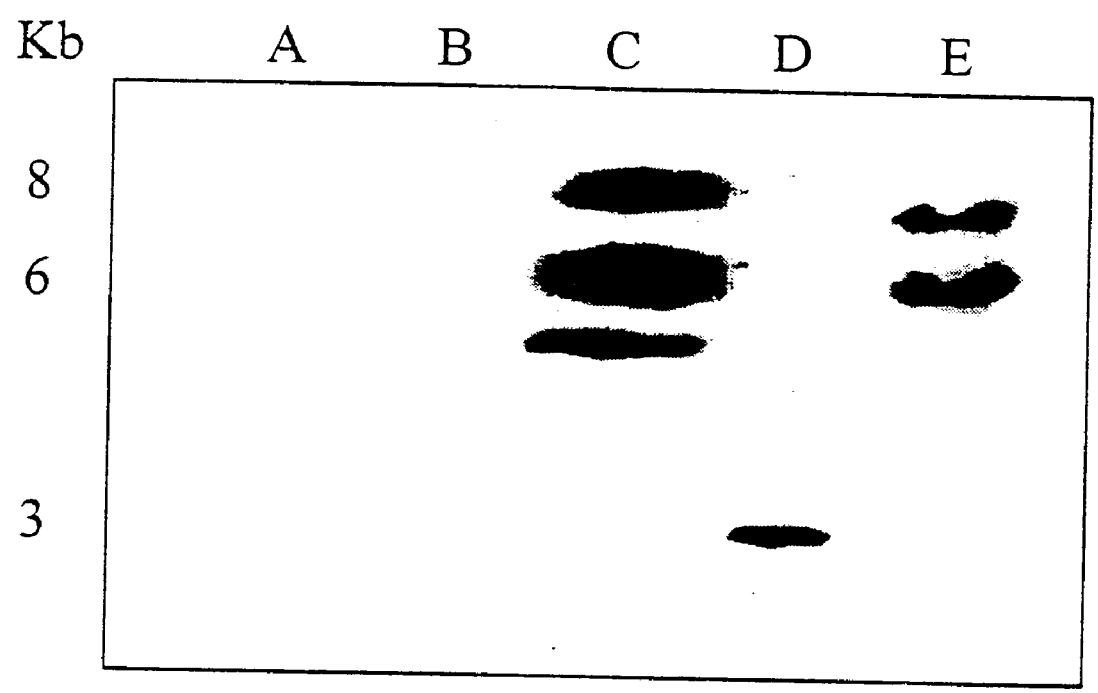
FIG. 3 illustrates detection of a Pinus unique sequence identifier in transformed tobacco plants. Lanes A and B show the hybridization of a probe from SEQ ID NO: 202 to the genomic DNA of tobacco plants which lack the Pinus unique sequence identifier (empty-vector transformed control plants or wild type). Lanes C–E show the hybridization of the probe to the. genomic DNA of tobacco plants containing one to three copies of the Pinus unique sequence identifier.
Figure 4:
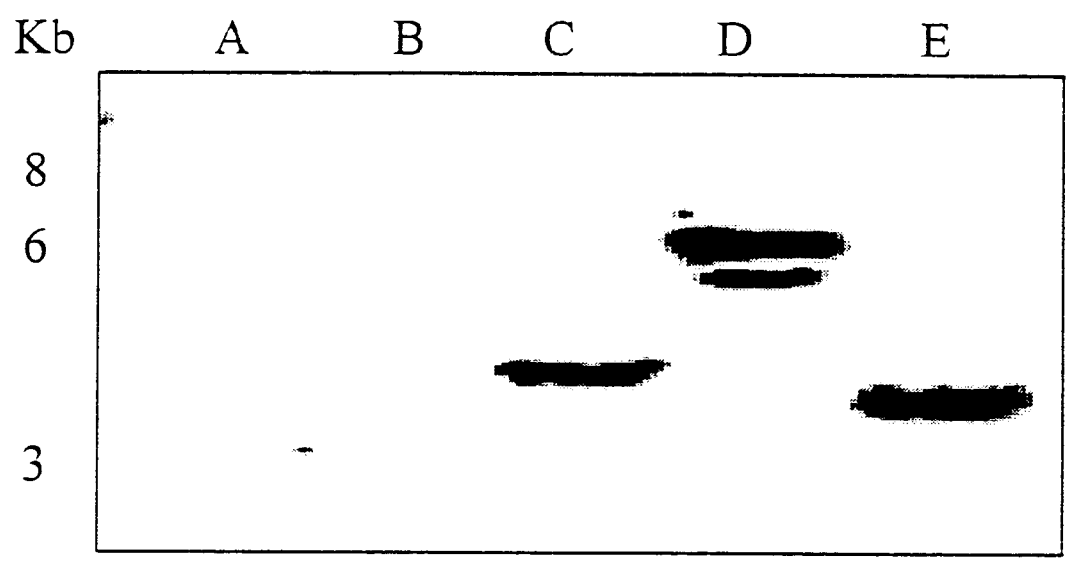
FIG. 4 illustrates detection of a Eucalyptus unique sequence identifier in transformed tobacco plants. Lanes A and B show the hybridization of a probe from SEQ ID NO: 203 to the genomic DNA of tobacco plants which lack the Eucalyptus unique sequence identifier (empty-vector transformed control plants. or wild type). Lanes C–E show the hybridization of the probe to the genomic DNA of tobacco plants containing one to two copies of the Eucalyptus unique sequence identifier.

The results are shown in FIGS. 3 and 4.

FIG. 3 shows the hybridisation pattern detected in the Southern blot analysis using a probe derived from the Pinus sequence identifier (SEQ ID NO: 202). Lanes A–B contain DNA samples from empty-vector transformed control plants and lanes C–E contain DNA from plants transformed with SEQ ID NO: 202. There is no hybridization in lanes A–B indicating that SEQ ID NO: 202 is not present in empty-vector transformed tobacco plants; that is, SEQ ID NO: 202 is a unique tag suitable for unambiguous marking of tobacco plants. There is strong hybridisation in lanes C–E, indicating that the plants which received SEQ ID NO: 202 via transformation have been clearly and unambiguously tagged with the unique sequence contained in SEQ ID NO: 202.

FIG. 4 shows the hybridization pattern detected in the Southern blot analysis using a probe derived from the Eucalyptus sequence identifier (SEQ ID NO: 203). Lanes A–B contain DNA samples from empty-vector transformed control plants and lanes C–E contain DNA from plants transformed with SEQ ID NO: 203. There is no hybridisation in lanes A–B indicating that SEQ ID NO: 203 is not present in empty-vector transformed tobacco plants; that is, SEQ ID NO: 203 is a unique tag suitable for unambiguous marking of tobacco plants. There is strong hybridisation in lanes C–E indicating that the plants which received SEQ ID NO: 203 via transformation have been clearly and unambiguously tagged with the unique sequence contained in SEQ ID NO: 203.

The data clearly demonstrates the utility of the sequences disclosed in this specification for the purposes of unambiguously tagging transgenic materials. A unique sequence was selected from a large number of potential tags and shown to be absent in the genome of the organism to be tagged. The tag was inserted into the genome of the organism to be tagged and a well-established DNA detection method was used to clearly detect the unique sequence identifier used as the tag.

Because of the sequence-specific detection methods used in the example, a user of the invention disclosed in this specification has both a high likelihood of finding a sequence identifier, among the list which has been disclosed, which will be useful for tagging any given organism and an unequivocal method for demonstrating that a tagged organism could only have acquired a given tag through the deliberate addition of the unique sequence to the genome of the organism to be tagged. If the user of this invention maintains the precise sequence of the tag used in a given organism as a secret, then any disputes as to the origin and history of the organism can be unambiguously resolved using the tag detection techniques demonstrated in the present example.

SEQ ID NOS: 1–206 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties. While in the foregoing specification, this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

We claim:

1. An isolated polynucleotide comprising a nucleotide sequence selected from the group consisting of: (1) the sequence recited in SEQ ID NO: 98; and (2) the complement of the sequence recited in SEQ ID NO: 98.

2. An isolated polynucleotide comprising a nucleotide sequence having at least 90% identity to the nucleotide sequence recited in SEQ ID NO:98, wherein the nucleotide sequence encodes a cysteine protease.

3. An isolated polynucleotide comprising a nucleotide sequence that hybridizes to the polynucleotide of claim 1 under stringent hybridization conditions.

4. A genetic construct comprising at least one polynucleotide described in any one of claims 1, 2 or 3.

5. A transgenic forestry plant cell comprising at least one genetic construct according to claim 4.

6. A genetic construct comprising, in the 5'-3' direction:

(a) a gene promoter sequence;

(b) a polynucleotide sequence comprising a polynucleotide of claim 1, 2, or 3; and (c) a gene termination sequence.

7. The construct of claim 6, wherein the polynucleotide is in a sense orientation.

8. The construct of claim 6, wherein the polynucleotide is in an antisense orientation.

9. The construct of claim 6, wherein the gene promoter sequence and gene termination sequences are functional in a forestry plant host.

10. A forestry plant cell comprising a construct of claim 6.

11. The forestry plant cell of claim 10, wherein the polynucleotide is in a sense orientation.

12. The forestry plant cell of claim 10, wherein the polynucleotide is in an antisense orientation.

13. A forestry plant comprising a forestry plant cell according to claim 10.

14. The forestry plant of claim 13, wherein the forestry plant is a woody plant.

15. The forestry plant of claim 14, wherein the plant is selected from the group consisting of eucalyptus and pine species.

16. A method for modulating a plant cell death pathway in a forestry plant, comprising stably incorporating into the genome of the forestry plant a construct of claim 4.

17. The method of claim 16, wherein the construct incorporated into the genome of the forestry plant comprises a polynucleotide encoding a cysteine protease that is not present in a native form of the forestry plant.

18. A method for modulating a cell death pathway in a forestry plant, comprising stably incorporating into the genome of the forestry plant a construct of claim 6.

19. A method for producing a forestry plant having an altered cell death pathway, comprising:
   (a) transforming a plant cell with a construct of claim 4 to provide a transgenic plant cell; and
   (b) cultivating the transgenic plant cell under conditions conducive to regeneration and mature plant growth.

* * * * *